United States Patent
Kuwabara et al.

(10) Patent No.: US 10,559,757 B2
(45) Date of Patent: Feb. 11, 2020

(54) HOST MATERIAL FOR DELAYED FLUORESCENT MATERIALS, ORGANIC LIGHT-EMITTING DEVICE AND COMPOUND

(71) Applicant: KYUSHU UNIVERSITY, NATIONAL UNIVERSITY CORPORATION, Fukuoka-shi, Fukuoka (JP)

(72) Inventors: Hirokazu Kuwabara, Tokyo (JP); Takumi Shibata, Tokyo (JP); Takehiro Takahashi, Tokyo (JP); William John Potscavage, Jr., Fukuoka (JP); Chihaya Adachi, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 150 days.

(21) Appl. No.: 15/508,236

(22) PCT Filed: Sep. 2, 2015

(86) PCT No.: PCT/JP2015/074901
§ 371 (c)(1),
(2) Date: Mar. 2, 2017

(87) PCT Pub. No.: WO2016/035803
PCT Pub. Date: Mar. 10, 2016

(65) Prior Publication Data
US 2017/0288146 A1 Oct. 5, 2017

(30) Foreign Application Priority Data
Sep. 3, 2014 (JP) .................. 2014-179589

(51) Int. Cl.
| | | |
|---|---|---|
| H01L 51/54 | (2006.01) | |
| C09K 11/06 | (2006.01) | |
| H01L 51/00 | (2006.01) | |
| C07C 49/788 | (2006.01) | |
| C07C 15/38 | (2006.01) | |
| C09K 11/02 | (2006.01) | |
| H01L 51/50 | (2006.01) | |

(52) U.S. Cl.
CPC .......... *H01L 51/0058* (2013.01); *C07C 15/38* (2013.01); *C07C 49/788* (2013.01); *C09K 11/025* (2013.01); *C09K 11/06* (2013.01); *H01L 51/006* (2013.01); *H01L 51/0054* (2013.01); *C09K 2211/1007* (2013.01); *C09K 2211/1011* (2013.01); *C09K 2211/1014* (2013.01); *H01L 51/0052* (2013.01); *H01L 51/0067* (2013.01); *H01L 51/0072* (2013.01); *H01L 51/5012* (2013.01); *H01L 51/5016* (2013.01); *H01L 2251/5384* (2013.01)

(58) Field of Classification Search
CPC ... C09K 11/025; C09K 11/06; C09K 2211/00; C09K 2211/10; C09K 2211/1007; C09K 2211/1011; C09K 2211/1014; C07C 15/38; C07C 49/788; H01L 51/0032; H01L 51/005; H01L 51/0058; H01L 51/006; H01L 51/0052; H01L 51/0054; H01L 51/0067; H01L 51/0072; H01L 51/5012; H01L 51/5016; H01L 2251/5384
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | | |
|---|---|---|---|---|
| 2006/0280965 A1* | 12/2006 | Kwong | ................... | C07C 13/62 428/690 |
| 2013/0009136 A1* | 1/2013 | Hong | ..................... | C09K 11/06 257/40 |
| 2014/0158992 A1 | 6/2014 | Xia et al. | | |

FOREIGN PATENT DOCUMENTS

| | | |
|---|---|---|
| CN | 102648268 A | 8/2012 |
| JP | 2008-543086 A | 11/2008 |
| JP | 2014-96586 A | 11/2008 |
| JP | 2012-104509 A | 5/2012 |
| JP | 2013-116975 A | 6/2013 |
| JP | 2013-253121 A | 12/2013 |
| JP | 2013-256490 A | 12/2013 |
| JP | 2014-9224 A | 1/2014 |
| WO | 2006/130598 A2 | 12/2006 |
| WO | 2013/011954 A1 | 1/2013 |
| WO | 2013/011955 A1 | 1/2013 |
| WO | 2013/081088 A1 | 6/2013 |
| WO | 2013/133359 A1 | 9/2013 |

(Continued)

OTHER PUBLICATIONS

Office Action dated Jan. 29, 2018 issued in the corresponding European/Japanese/ Koran/ Chinese patent application No. 201580047176.5 with its English Machine Translation.

(Continued)

*Primary Examiner* — Andrew K Bohaty
(74) *Attorney, Agent, or Firm* — Browdy and Neimark, PLLC

(57) ABSTRACT

A compound represented by $(Tr)_n$-Z is useful as a host material for delayed fluorescent materials. Tr represents a substituted or unsubstituted triphenylenyl group, and plural Tr's existing in the general formula (1) may be the same as or different from each other. Z represents a carbonyl group or a substituted or unsubstituted, n-valent aromatic hydrocarbon group. n represents an integer of 2 to 6, but when Z is a carbonyl group, n is 2.

15 Claims, 3 Drawing Sheets

(56) References Cited

FOREIGN PATENT DOCUMENTS

WO   2013/154064 A1   10/2013
WO   2013/161437 A1   10/2013

OTHER PUBLICATIONS

International Preliminary Report on Patentability for corresponding PCT International Application No. PCT/JP2015/074901, dated Mar. 16, 2017, with English translation.
International Search Report for corresponding PCT International Application No. PCT/JP2015/074901.
Office Action dated Sep. 25, 2018 issued in the corresponding Japanese patent application No. 2014-179589 with its English Machine Translation.

* cited by examiner

HOST MATERIAL FOR DELAYED FLUORESCENT MATERIALS, ORGANIC LIGHT-EMITTING DEVICE AND COMPOUND

TECHNICAL FIELD

The present invention relates to a compound useful as a host material for delayed fluorescent materials, and to an organic light-emitting device using the compound.

BACKGROUND ART

Studies are being actively performed for enhancing the light emission efficiency of organic light-emitting devices such as an organic electroluminescence devices (organic EL devices), etc. For example, regarding the light-emitting material for use in a light-emitting layer, development of delayed fluorescent materials is under way as those that can efficiently utilize the excitation energy thereof for light emission. A delayed fluorescent material is a light-emitting material that radiates fluorescence directly from the excited singlet state and radiates fluorescence (delayed fluorescence) also from the excited singlet state formed through reverse intersystem crossing from the excited triplet state, and the excited triplet state can also be made to contribute toward fluorescence emission along with the excited singlet state. As an application of the delayed fluorescent material, there are seen some publications describing an organic electroluminescence device having therein a light-emitting layer formed by a combination of a delayed fluorescent material and a host material.

For example, PTL 1 describes an example of producing an organic EL device having a light-emitting layer that contains 1,3-bis(carbazol-9-yl)benzene (mCP) and a delayed fluorescent material.

PTL 2 describes an example of producing an organic EL device having a light-emitting layer that contains 4,4'-bis (N-carbazolyl)biphenyl (CBP) and a delayed fluorescent material.

CITATION LIST

Patent Literature

PTL 1: JP-A 2013-253121
PTL 2: JP-A 2013-256490

SUMMARY OF INVENTION

Technical Problem

As described above, PTL 1 describes formation of a light-emitting layer by combining a delayed fluorescent material and mCP, and PTL 2 describes formation of a light-emitting layer by combining a delayed fluorescent material and CBP. Here, mCP and CBP employed in these publications have heretofore been generally used as a host material for a fluorescent material and a phosphorescent material. However, the present inventors have actually investigated the organic EL devices having the host material as combined with a delayed fluorescent material, and have found that the device lifetime is only 50 hours or so and is short, and the devices are impracticable. This is considered to be because a delayed fluorescent material differs from an ordinary fluorescent material or phosphorescent material in point of the light emission mechanism and, in addition, a delayed fluorescent material greatly differs from an ordinary light-emitting material in point of the characteristics necessary for host materials and the preferred structures of the materials. However, there exists no literature that investigates the characteristics and the structures of host materials to be combined with delayed fluorescent materials, and no one could expect what type of compound would be useful as a host material for delayed fluorescent materials, and the situation is such that no one could sufficiently utilize the characteristics of delayed fluorescent materials.

Given the situation, the present inventors have made assiduous studies of investigating the usefulness of various materials as a host material for delayed fluorescent materials. With that, the inventors have hit on a general formula of a compound useful as a host material for delayed fluorescent materials, and have further promoted assiduous investigations for generalizing the constitution of an organic light-emitting device having a high light emission efficiency and a long device lifetime.

Solution to Problem

As a result of assiduous studies, the present inventors have found that, by using a compound having a structure where plural triphenylenyl groups bond via a carbonyl group or an aromatic hydrocarbon group as a host material for delayed fluorescent materials, not only the device lifetime can be more greatly prolonged than in the case of using a carbazole-type host material but also high efficiency and low-voltage driving can be expected. Based on these findings, the present inventors have now reached providing the present invention as described below as a means for solving the above-mentioned problems.

[1] A host material for delayed fluorescent materials, containing a compound represented by the following general formula (1):

$$(Tr)_n\text{-}Z \quad \text{General Formula (1)}$$

[In the general formula (1), Tr represents a substituted or unsubstituted triphenylenyl group, and plural Tr's existing in the general formula (1) may be the same as or different from each other. Z represents a carbonyl group or a substituted or unsubstituted, n-valent aromatic hydrocarbon group. n represents an integer of 2 to 6, but when Z is a carbonyl group, n is 2.]

[2] The host material for delayed fluorescent materials according to [1], wherein Z is a substituted or unsubstituted, n-valent aromatic hydrocarbon group.

[3] The host material for delayed fluorescent materials according to [2], wherein Z is an n-valent benzene residue.

[4] The host material for delayed fluorescent materials according to [3], wherein Tr bonds to at least the 1-position and the 3-position of the benzene residue.

[5] The host material for delayed fluorescent materials according to [2], wherein Z is an n-valent biphenyl residue.

[6] The host material for delayed fluorescent materials according to [2], wherein Z is an n-valent aromatic hydrocarbon group substituted with a substituted or unsubstituted alkyl group or a substituted or unsubstituted aryl group.

[7] The host material for delayed fluorescent materials according to [1], wherein Z is a carbonyl group.

[8] The host material for delayed fluorescent materials according to [7], wherein at least one Tr has a substituent represented by the following general formula (2):

$$Tr^4\text{-CO—} \quad \text{General Formula (2)}$$

[In the general formula (2), $Tr^4$ represents a substituted or unsubstituted triphenylenyl group.]

[9] The host material for delayed fluorescent materials according to [8], wherein two Tr's have, in total, 1 to 5 substituents each represented by the general formula (2).

[10] The host material for delayed fluorescent materials according to any one of [7] to [9], which contains a partial structure with a carbonyl group bonding to the 2-position, the 3-position, the 6-position, the 7-position, the 10-position or the 11-position of the triphenylene ring inside the molecule.

[11] The host material for delayed fluorescent materials according to [10], wherein all the carbonyl groups bonding to the triphenylene ring existing inside the molecule bond to the 2-position, the 3-position, the 6-position, the 7-position, the 10-position or the 11-position of the triphenylene ring.

[12] The host material for delayed fluorescent materials according to any one of [1] to [11], wherein at least one Tr in the general formula (1) is a triphenylenyl group substituted with a substituted or unsubstituted alkyl group or a substituted or unsubstituted aryl group.

[13] An organic light-emitting device comprising a layer that contains the host material of any one of [1] to [12] and a delayed fluorescent material.

[14] The organic light-emitting device according to [13], comprising a layer that contains the host material of any one of [1] to [12] and any other host material other than that host material, and a delayed fluorescent material.

[15] The organic light-emitting device according to [13] or [14], which is an organic electroluminescence device.

[16] A compound represented by the following general formula (3):

$Tr^1$-CO-$Tr^2$                General Formula (3)

[In the general formula (3), $Tr^1$ and $Tr^2$ each independently represent a substituted or unsubstituted triphenylenyl group, and $Tr^1$ and $Tr^2$ may be the same as or different from each other.]

[17] A compound represented by the following general formula (4):

$(Tr^3)_{n1}$-$Z^1$                General Formula (4)

[In the general formula (4), $Tr^3$ represents a substituted or unsubstituted triphenylenyl group, and plural $Tr^3$'s existing in the general formula (4) may be the same as or different from each other. $Z^1$ represents a substituted or unsubstituted n-valent aromatic hydrocarbon group. n1 represents an integer of 2 to 6. At least one of $Tr^3$ and $Z^1$ is substituted with a substituted or unsubstituted alkyl group or a substituted or unsubstituted aryl group. When $Tr^3$ is unsubstituted, $Z^1$ is a benzene ring residue substituted with a phenyl group or a methyl group and bonds to $Tr^3$ at least at the 1-position and the 3-position, or is a biphenyl residue substituted with a phenyl group.]

Advantageous Effects of Invention

The compound of the present invention is useful as a host material for delayed fluorescent materials. In addition, the organic light-emitting device using the compound of the present invention as a host material for delayed fluorescent materials requires a low driving voltage and realizes a high light emission efficiency, and has a long device lifetime.

DESCRIPTION OF EMBODIMENTS

Figure 1:
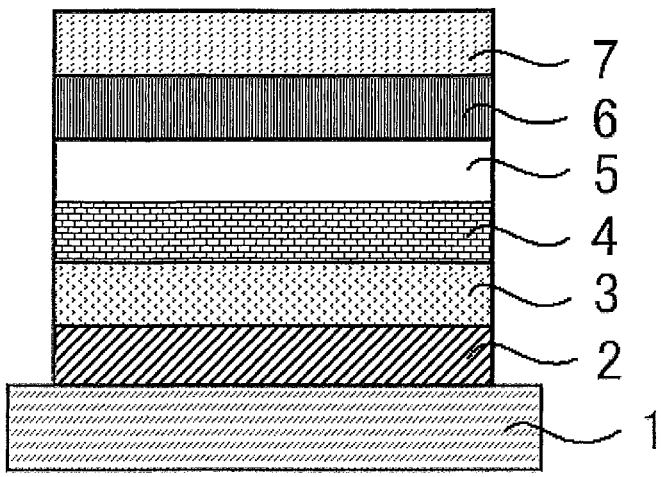
FIG. 1 This is a schematic cross-sectional view showing an example of a layer configuration of an organic electroluminescence device.

The contents of the present invention are described in detail hereinunder. The constitutional elements may be described below with reference to representative embodiments and specific examples of the invention, but the invention is not limited to the embodiments and the examples. In the description, a numerical range expressed with reference to the expressions, an upper limit or less and/or a lower limit or more, means a range that includes the upper limit and/or the lower limit.

[Compound Represented by General Formula (1)]

The host material for delayed fluorescent materials of the present invention contains a compound represented by the following general formula (1):

$(Tr)_n$-Z                General Formula (1)

In the general formula (1), Z represents a carbonyl group or a substituted or unsubstituted, n-valent aromatic hydrocarbon group.

The aromatic ring of the aromatic hydrocarbon group that Z represents may be a single-ring aromatic ring, or may be an aromatic ring of a ring-assembly structure where two or more aromatic rings bond via a single bond, such as a biphenyl ring, or may also be an aromatic ring of a polycyclic condensed structure where two or more aromatic rings are condensed such as naphthalene. Specifically, the aromatic hydrocarbon group is preferably an aromatic hydrocarbon group having a ring skeleton carbon number of 6 to 18. Preferably, the group is a residue of a benzene ring, a biphenyl ring, a naphthalene ring or a fluorene ring, more preferably a benzene residue or a biphenyl residue, and even more preferably a benzene residue.

When Z is a carbonyl group, n is 2.

When Z is an aromatic hydrocarbon group, n is 2 to 6, preferably 2 to 3. The bonding position of Tr in the aromatic hydrocarbon group is not specifically defined, but when Z is a benzene residue, preferably, Tr bonds to at least the 1-position and the 3-position of the residue. In the methine group and the methylene group of the aromatic hydrocarbon group to which Tr does not bond, the hydrogen atom may be substituted with a substituent, or may not be substituted. The substituent that may substitute in the aromatic hydrocarbon group includes those selected from a group of the substituents to be mentioned hereinunder, and among these, a substituted or unsubstituted alkyl group or a substituted or unsubstituted aryl group is preferred. With that, the stability of the compound represented by the general formula (1) may tend to increase. The alkyl group is preferably an alkyl group having 1 to 18 carbon atoms, and is more preferably a methyl group. For the description and the preferred range of the aromatic ring that constitutes the aryl group, the description and the preferred range of the aromatic ring of the aromatic hydrocarbon group that Z may represent may be referred to. Among these, the aryl group that may substitute in the aromatic hydrocarbon group is preferably a biphenyl residue, or a benzene residue (a phenyl group), and is more preferably a phenyl group.

Tr represents a substituted or unsubstituted triphenylenyl group. The bonding position of the triphenylenyl group to Z is not specifically defined, but is preferably the 2-position. In the methine group of the triphenylenyl group that does not bond to Z, the hydrogen atom may be substituted with a substituent, or may not be substituted. The substituting position in the case where the triphenylenyl group is substituted with a substituent is preferably at least one of the 6-position, the 7-position, the 10-position and the 11-position.

The substituent that may substitute in the triphenylenyl group includes those selected from a group of the substituents to be mentioned hereinunder. Here, at least one Tr is preferably substituted with a substituted or unsubstituted alkyl group or a substituted or unsubstituted aryl group. With that, the stability of the compound represented by the general formula (1) may tend to increase. The alkyl group is preferably an alkyl group having 1 to 18 carbon atoms, and is more preferably a methyl group. For the description and the preferred range of the aromatic ring that constitutes the aryl group, the description and the preferred range of the aromatic ring of the aromatic hydrocarbon group that Z may represent may be referred to. Among these, the aryl group that may substitute in the triphenylenyl group is preferably a biphenyl residue, or a benzene residue (a phenyl group), and is more preferably a phenyl group.

Preferably, at least one Tr has a substituent represented by the following general formula (2). Among plural Tr's, one or more may have the substituent represented by the general formula (2), but preferably two of them have the substituent. When two Tr's have a group represented by the general formula (2), the total of the groups represented by the general formula (2) is preferably 1 to 5, more preferably 1 to 4, even more preferably 1 to 3.

$Tr^4$-CO—          General Formula (2)

In the general formula (2), $Tr^4$ represents a substituted or unsubstituted triphenylenyl group. The bonding position to the carbonyl group (—CO—) in the triphenylenyl group is not specifically defined, but is preferably the 2-position. In the methine group not bonding to the carbonyl group in the triphenylenyl group, the hydrogen atom may be substituted with a substituent, or may not be substituted. For the description and the preferred range of the substituent that may substitute in the triphenylenyl group, the description and the preferred range of the substituent that may substitute in the triphenylenyl group of Tr may be referred to.

When plural Tr's exist inside the molecule of the compound represented by the general formula (1), the plural Tr's may be the same as or different from each other, but are preferably the same. When plural $Tr^4$'s represented by the general formula (2) exist inside the molecule of the compound represented by the general formula (1), the plural $Tr^4$'s may be the same as or different from each other, but are preferably the same.

The compound represented by the general formula (1) preferably contains 1 to 6 carbonyl groups, more preferably 1 to 3 carbonyl groups. Further, the compound represented by the general formula (1) preferably has a partial structure with a carbonyl group bonding to the 2-position, the 3-position, the 6-position, the 7-position, the 10-position or the 11-position of the triphenylene ring inside the molecule, and more preferably, all the carbonyl groups bonding to the triphenylene ring existing inside the molecule bond to the 2-position, the 3-position, the 6-position, the 7-position, the 10-position or the 11-position of the triphenylene ring.

Examples of the substituent of the aromatic hydrocarbon group that Z may represent, the substituent that may substitute in the triphenylenyl group of Tr and $Tr^4$, and the substituent of the substituted alkyl group and the substituted aryl group that may substitute in the aromatic hydrocarbon group of the triphenylenyl group include a hydroxy group, a halogen atom, a cyano group, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an acyl group having 2 to 20 carbon atoms, an aryl group having 6 to 40 carbon atoms, a heteroaryl group having 3 to 40 carbon atoms, an alkenyl group having 2 to 10 carbon atoms, an alkynyl group having 2 to 10 carbon atoms, an alkoxycarbonyl group having 2 to 10 carbon atoms, an alkylsulfonyl group having 1 to 10 carbon atoms, a haloalkyl group having 1 to 10 carbon atoms, an amide group, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, trialkylsilylalkynyl group having 5 to 20 carbon atoms, a nitro group, a substituent represented by the above-mentioned general formula (2), etc. Among these examples, the substituents that may be further substituted with a substituent may be substituted. More preferred substituents include a halogen atom, a cyano group, a substituted or unsubstituted alkyl group having 1 to 20 carbon atoms, an alkoxy group having 1 to 20 carbon atoms, a substituted or unsubstituted aryl group having 6 to 40 carbon atoms, a substituted or unsubstituted heteroaryl group having 3 to 40 carbon atoms, and a dialkyl-substituted amino group having 1 to 20 carbon atoms. Even more preferred substituents include a fluorine atom, a chlorine atom, a cyano group, a substituted or unsubstituted alkyl group having 1 to 10 carbon atoms, a substituted or unsubstituted alkoxy group having 1 to 10 carbon atoms, a substituted or unsubstituted aryl group having 6 to 15 carbon atoms, a substituted or unsubstituted heteroaryl group having 3 to 12 carbon atoms, and a substituent represented by the general formula (2).

In the following, specific examples of the compound represented by the general formula (1) are exemplified. However, the compound represented by the general formula (1) that is usable in the present invention should not be interpreted in a limited way by these examples. In the compounds represented by the following formulae, R represents a methyl group, a phenyl group, a benzoyl group, a triphenylenyl group or a triphenylenylcarbonyl group. Plural R's each representing the substituent may be the same as or different from each other.

[Chem. 1]
Compound 1
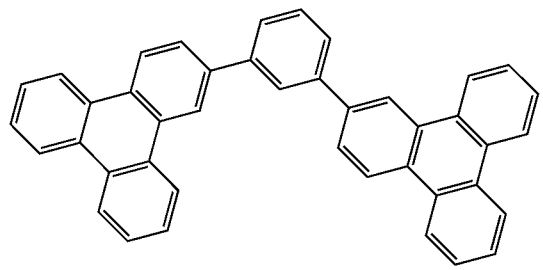
Compound 2
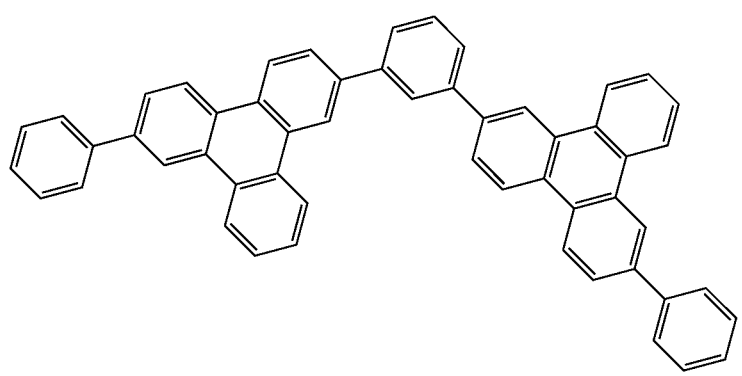
Compound 3
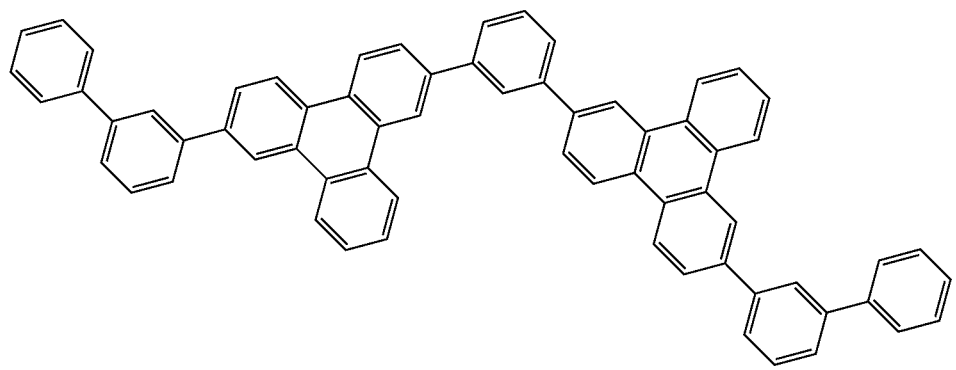
Compound 4
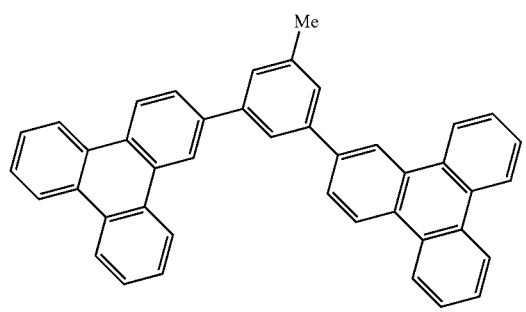
Compound 5
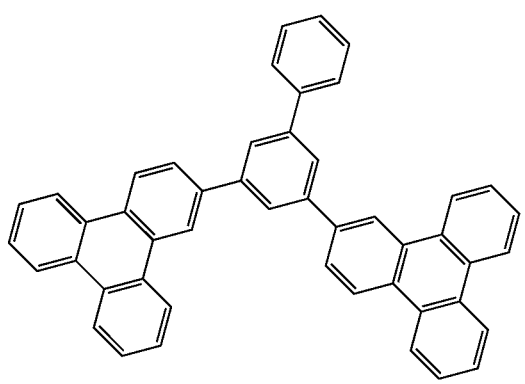

-continued
Compound 6
Compound 7
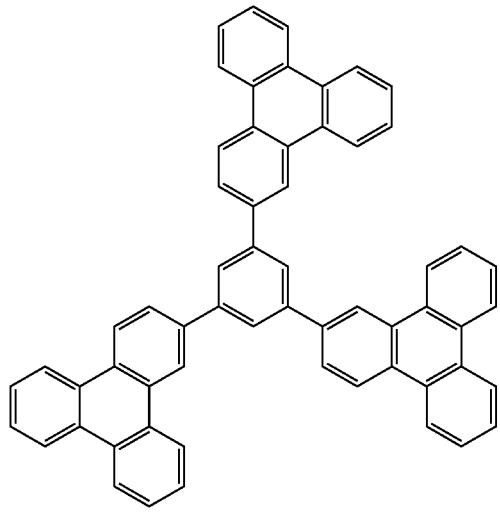
Compound 8
Compound 9

[Chem. 2]

Compound 10

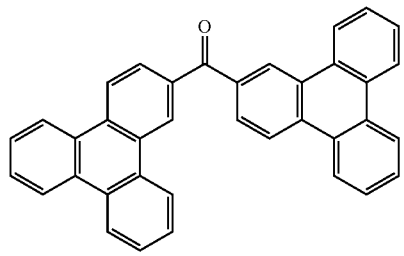

Compound 11

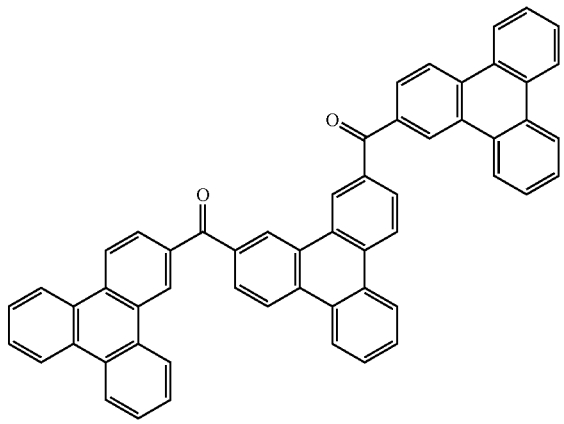

Compound 12

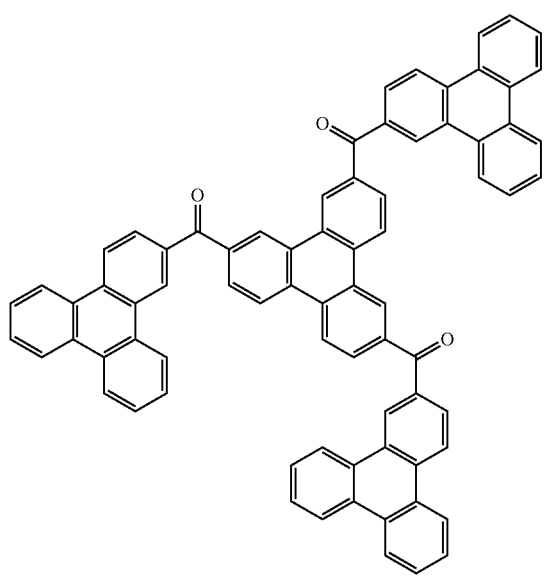

Compound 13

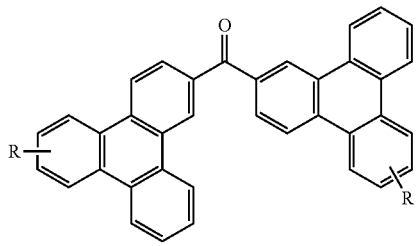

Compound 14

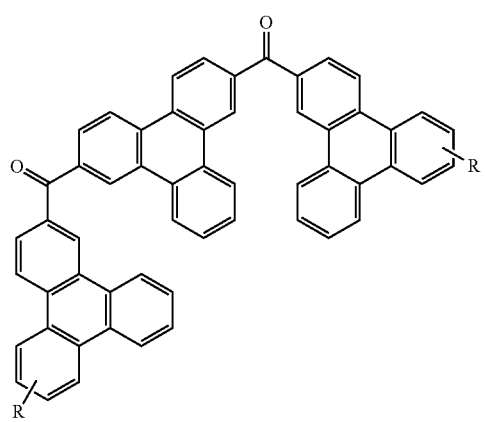

The molecular weight of the compound represented by the general formula (1) is, for example, in the case of using it by forming an organic layer that contains a compound represented by the general formula (1) according to a vapor deposition method, preferably 1500 or less, more preferably 1200 or less, even more preferably 1000 or less, still more preferably 800 or less. The lower limit of the molecular weight is the molecular weight of the smallest compound represented by the general formula (1).

The compound represented by the general formula (1) may be formed into a film according to a coating method irrespective of the molecular weight thereof. According to a coating method, even a compound having a relatively large molecular weight can be formed into a film.

By applying the present invention, it may be taken into consideration to use a compound containing plural structures represented by the general formula (1) in the molecule thereof, as a host material for delayed fluorescent materials.

For example, a polymerizable group is previously introduced in the structure represented by the general formula (1), and it may be taken into consideration to use a polymer obtained through polymerization of the polymerizable group as a host material for delayed fluorescent materials. Specifically, a monomer containing a polymerizable functional group in any of Tr and Z in the general formula (1) is prepared, and this is homo-polymerized singly or copolymerized with any other monomer to give a polymer having a repeating unit, and use of the polymer as a host material for delayed fluorescent materials may be taken into consideration. Alternatively, compounds each having a structure represented by the general formula (1) are coupled to give a dimer or a trimer, and use of these as a host material for delayed fluorescent materials may be taken into consideration.

Examples of the polymer having a repeating unit that contains a structure represented by the general formula (1) include polymers containing a structure represented by the following general formula (5) or (6).

[Chem. 3]

General Formula (5)

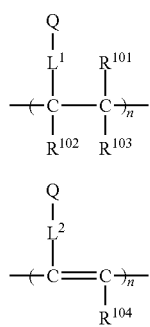

General Formula (6)

In the general formulae (5) and (6), Q represents a group containing the structure represented by the general formula (1), and $L^1$ and $L^2$ each represent a linking group. The carbon number of the linking group is preferably 0 to 20, more preferably 1 to 15, even more preferably 2 to 10. The linking group preferably has a structure represented by —$X^{11}$-$L^{11}$-. Here, $X^{11}$ represents an oxygen atom or a sulfur atom, and is preferably an oxygen atom. $L^{11}$ represents a linking group, and is preferably a substituted or unsubstituted alkylene group or a substituted or unsubstituted arylene group, more preferably a substituted or unsubstituted alkylene group having 1 to 10 carbon atoms or a substituted or unsubstituted phenylene group.

In the general formulae (5) and (6), $R^{101}$, $R^{102}$, $R^{103}$ and $R^{104}$ each independently represent a substituent. Preferably, they each are a substituted or unsubstituted alkyl group having 1 to 6 carbon atoms, a substituted or unsubstituted alkoxy group having 1 to 6 carbon atoms, or a halogen atom, more preferably an unsubstituted alkyl group having 1 to 3 carbon atoms, an unsubstituted alkoxy group having 1 to 3 carbon atoms, a fluorine atom or a chlorine atom, and even more preferably an unsubstituted alkyl group having 1 to 3 carbon atoms, or an unsubstituted alkoxy group having 1 to 3 carbon atoms.

The linking group represented by $L^1$ and $L^2$ may bond to any of Tr and Z in the structure of the general formula (1) that constitutes Q, or to $Tr^4$ in the general formula (2). Two or more linking groups may bond to one Q to form a crosslinked structure or a network structure.

Specific structural examples of the repeating unit include structures represented by the following formulae (7) to (10).

[Chem. 4]

Formula (7)

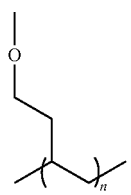

Formula (8)

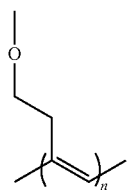

Formula (9)

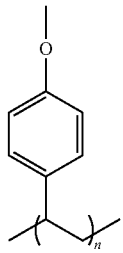

Formula (10)

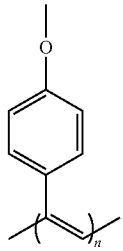

Polymers having a repeating unit of the formulae (7) to (10) may be synthesized by previously introducing a hydroxy group into any of Tr and Z in a structure of the general formula (1), then introducing a polymerizable group into the structure through reaction with any of the following compounds via the hydroxy group serving as a linker, and polymerizing the polymerizable group.

[Chem. 5]

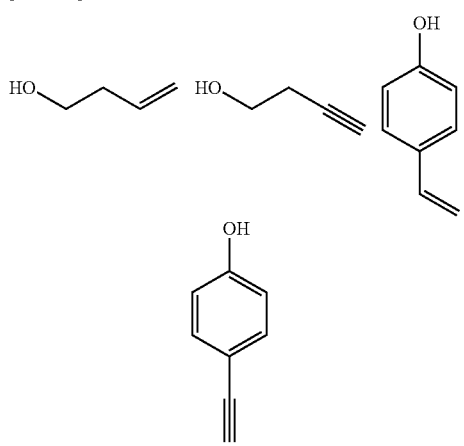

The polymer having a structure represented by the general formula (1) in the molecule may be a polymer containing a repeating unit alone having a structure represented by the general formula (1) or may be a polymer containing a repeating unit having any other structure. The repeating unit having a structure represented by the general formula (1) contained in the polymer may be one type alone or may contain two or more types of repeating units. A repeating unit not having a structure represented by the general formula (1) includes those derived from monomers to be used in ordinary copolymerization. For example, there are mentioned repeating units derived from monomers having an ethylenic unsaturated bond such as ethylene, styrene, etc.

[Compound Represented by General Formula (3)]

Among the compounds represented by the general formula (1), compounds represented by the following general formula (3) are novel compounds.

[Chem. 6]

$Tr^1\text{-}CO\text{-}Tr^2$    General Formula (3)

In the general formula (3), $Tr^1$ and $Tr^2$ each independently represent a substituted or unsubstituted triphenylenyl group, and $Tr^1$ and $Tr^2$ may be the same as or different from each other.

For the description and the preferred range of $Tr^1$ and $Tr^2$ in the general formula (3), the description of Tr in the general formula (1) may be referred to.

[Synthesis Method for Compound Represented by General Formula (3)]

The compound represented by the general formula (3) may be synthesized by combining known reactions. For example, the compound of the general formula (3) where $Tr^1$ and $Tr^2$ are unsubstituted triphenylenyl groups may be synthesized according to the reaction shown by the following formula.

[Chem. 7]

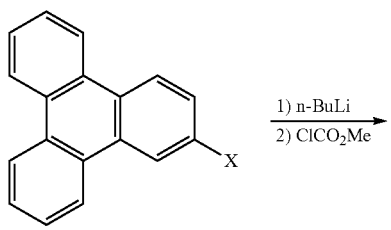

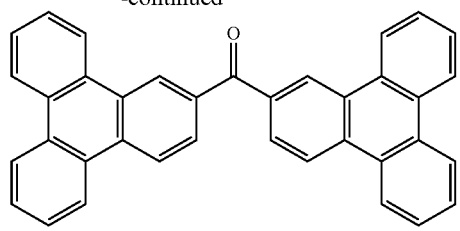

X in the above reaction formula represents a halogen atom, including a fluorine atom, a chlorine atom, a bromine atom and an iodine atom, and is preferably a chlorine atom, a bromine atom or an iodine atom.

For the details of the reaction, Synthesis Examples to be given hereinunder may be referred to.

In addition, the compound represented by the general formula (3) may also be synthesized by combining any other known synthesis reactions.

[Compound Represented by General Formula (4)]

Among the compounds represented by the general formula (1), compounds represented by the following general formula (4) are also novel compounds.

$(Tr^3)_{n1}\text{-}Z^1$    General Formula (4)

In the general formula (4), $Tr^3$ represents a substituted or unsubstituted triphenylenyl group, and plural $Tr^3$'s existing in the general formula (4) may be the same as or different from each other. $Z^1$ represents a substituted or unsubstituted n-valent aromatic hydrocarbon group. n1 represents an integer of 2 to 6. For the description and the preferred range of $Tr^3$, $Z^1$ and n1 in the general formula (4), the description of Tr, Z and n in the general formula (1) may be referred to. However, at least one of $Tr^3$ and $Z^1$ is substituted with a substituted or unsubstituted alkyl group or a substituted or unsubstituted aryl group. Among $Tr^3$ and $Z^1$, one or more $Tr^3$'s or one $Z^1$ alone, or one or more $Tr^3$'s and $Z^1$ may be substituted with a substituted or unsubstituted alkyl group or a substituted or unsubstituted aryl group. Here, when all $Tr^3$'s are unsubstituted, $Z^1$ is a benzene ring residue substituted with a phenyl group or a methyl group and bonds to $Tr^3$ at least at the 1-position and the 3-position, or is a biphenyl residue substituted with a phenyl group.

[Synthesis Method for Compound Represented by General Formula (4)]

The compound represented by the general formula (4) may be synthesized by combining known reactions. For example, a compound represented by the general formula (4) where $Tr^3$ is an unsubstituted triphenylenyl group, $Z^1$ is a benzene residue with a methyl group substituting in the 5-position, and $Z^1$ bonds to $Tr^3$ at the 1-position and the 3-position may be synthesized according to the reaction shown by the following formula.

[Chem. 8]

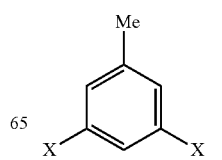

-continued

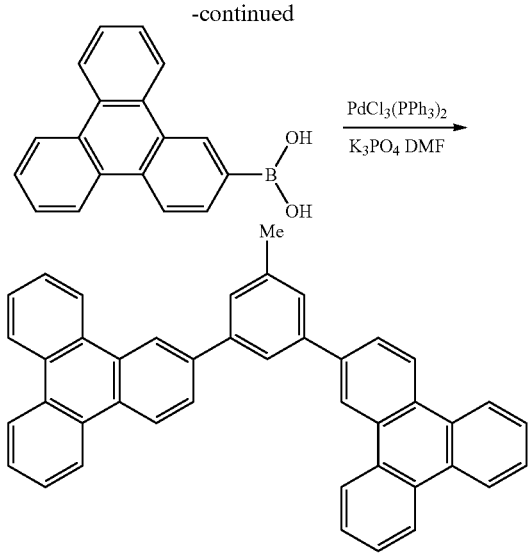

X in the above reaction formula represents a halogen atom, including a fluorine atom, a chlorine atom, a bromine atom and an iodine atom, and is preferably a chlorine atom, a bromine atom or an iodine atom.

For the details of the reaction, Synthesis Examples to be given hereinunder may be referred to. In addition, the compound represented by the general formula (4) may also be synthesized by combining any other known synthesis reactions.

Triphenylene derivatives (halide derivatives, borate derivatives) that are the starting materials for synthesizing the compounds represented by the general formulae (3) and (4) can be synthesized according to the method described in PCT Int. Appl., 2013085243, PCT Int. Appl., 2013073896, PCT Int. Appl., 2012002221, or are available as commercial products.

[Organic Light-Emitting Device]

The compound represented by the general formula (1) of the invention is useful as a host material for a delayed fluorescent material in an organic light emitting device. Accordingly, the compound represented by the general formula (1) of the invention may be effectively used as host material in an organic light-emitting device that uses a delayed fluorescent material as a light-emitting material therein. For example, it is presumed that, in an organic light-emitting device having a light-emitting layer that contains a host material of the compound represented by the general formula (1) and a delayed fluorescent material, the energy generated inside the molecule of the compound represented by the general formula (1) can be efficiently transferred to the delayed fluorescent material, and accordingly, the delayed fluorescent material can efficiently radiate delayed fluorescence. Consequently, the driving voltage for the organic light-emitting device of the type is low and the device can realize a high light emission efficiency. Further, the organic light-emitting device is almost free from a problem of brightness reduction with the lapse of driving time, and can realize a long lifetime. This is presumed because the compound represented by the general formula (1) could have high stability as compared with a host material having a carbazole ring such as CBP.

Here, in order that the organic light-emitting device can express a high light emission efficiency, it is important to use a delayed fluorescent material as a light-emitting material, as combined with the compound represented by the general formula (1) of the present invention. The principle of realizing a high light emission efficiency by the use of a delayed fluorescent material may be described as follows for an organic electroluminescence device as an example.

In an organic electroluminescence device, carriers are injected from an anode and a cathode to a light emitting material to form an excited state for the light emitting material, with which light is emitted. In the case of a carrier injection type organic electroluminescence device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy use efficiency. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescence device. In the case where a delayed fluorescent material is used in an organic electroluminescence device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

By using the compound represented by the general formula (1) of the invention as a host material for a delayed fluorescent material, there can be provided excellent organic light-emitting devices such as organic photoluminescence devices (organic PL devices), organic electroluminescence devices (organic EL devices), etc. An organic photoluminescence device has a structure that contains a substrate having formed thereon at least a light-emitting layer. An organic electroluminescence device has a structure containing at least an anode, a cathode and an organic layer formed between the anode and the cathode. The organic layer contains at least a light-emitting layer, and may be formed only of a light-emitting layer, or may have one or more organic layer in addition to the light-emitting layer. Examples of the organic layer include a hole transport layer, a hole injection layer, an electron barrier layer, a hole barrier layer, an electron injection layer, an electron transport layer and an exciton barrier layer. The hole transport layer may be a hole injection and transport layer having a hole injection function, and the electron transport layer may be an electron injection and transport layer having an electron injection function. A specific structural example of an organic electroluminescence device is shown in FIG. 1. In FIG. 1, the numeral 1 denotes a substrate, 2 denotes an anode, 3 denotes a hole injection layer, 4 denotes a hole transport layer, 5 denotes a light-emitting layer, 6 denotes an electron transport layer, and 7 denotes a cathode.

The members and the layers of the organic electroluminescence device will be described below. The descriptions for the substrate and the light-emitting layer may also be applied to the substrate and the light-emitting layer of the organic photoluminescence device.

(Substrate)

The organic electroluminescence device of the invention is preferably supported by a substrate. The substrate is not particularly limited and may be those that have been commonly used in an organic electroluminescence device, and examples thereof used include those formed of glass, transparent plastics, quartz and silicon.

(Anode)

The anode of the organic electroluminescence device used is preferably formed of as an electrode material include a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness thereof may be generally selected from a range of from 10 to 1,000 nm, and preferably from 10 to 200 nm, while depending on the material used.

(Cathode)

The cathode is preferably formed of as an electrode material including a metal having a small work function (4 eV or less) (referred to as an electron injection metal), an alloy or an electroconductive compound, or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 μm, and preferably from 50 to 200 nm. For transmitting the emitted light, any one of the anode and the cathode of the organic electroluminescence device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

(Light-Emitting Layer)

The light-emitting layer is a layer, in which holes and electrons injected from the anode and the cathode, respectively, are recombined to form excitons, and the layer contains a delayed fluorescent material and a host material for the delayed fluorescent material. As the host material for the delayed fluorescent material, one kind or two or more kinds selected from the group of compounds represented by the general formula (1) of the invention can be used. In order that the organic electroluminescence device and the organic photoluminescence device of the invention exhibit a high light emission efficiency, it is important that the singlet excitons and the triplet excitons generated in the delayed fluorescent material are confined in the delayed fluorescent material. Accordingly, as the host material for the delayed fluorescent material, those of the compounds represented by the general formula (1) are preferably so selected that at least any one of the excited singlet energy and the excited triplet energy thereof could be higher than that of the delayed fluorescent material. Consequently, the singlet excitons and the triplet excitons generated in the delayed fluorescent material can be confined in the molecule of the delayed fluorescent material, thereby eliciting the light emission efficiency of the material sufficiently.

In addition, the light-emitting layer may contain any other host material along with the host material for the delayed fluorescent material of the present invention. As the other host material, a compound having carrier transportability and excited energy transferability is preferably used. Accordingly, electrons and holes can be readily injected into the light-emitting layer and the probability of recombining the holes and the electrons increases. In addition, the excited energy formed by recombination of holes and electrons can be readily transferred to the delayed fluorescent material and the delayed fluorescent material can be thereby efficiently excited. As a result, the device can realize a high brightness at a low driving voltage. The host material having carrier transportability and excited energy transferability may be suitably selected from known host materials, and for the same reason as that for the compound represented by the general formula (1), it is desirable to select those of such that at least any one of the excited singlet energy and the excited triplet energy thereof is higher than that of the delayed fluorescent material. Specifically, as the other host material, a compound having a carbazole ring such as CBP or the like can be used.

In the organic light-emitting device or the organic electroluminescence device of the present invention, light emission forms from the delayed fluorescent material contained in the light-emitting layer. The light emission includes both fluorescence emission and delayed fluorescence emission. However, the light emission may partly include light emission from the compound represented by the general formula (1) as a part thereof.

The content of the delayed fluorescent material in the light-emitting layer is preferably 0.1 to 50% by mass, more preferably 0.1 to 20% by mass, even more preferably 0.5 to 5% by mass.

In the case where the host material for delayed fluorescent materials of the present invention is combined with any other host material for use herein, the ratio by mass of the two may be any arbitrary ratio, but is preferably 90/10 to 10/90, more preferably 75/25 to 25/75, even more preferably 66/33 to 33/66.

(Injection Layer)

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transport layer and between the cathode and the light-emitting layer or the electron transport layer. The injection layer may be provided depending on necessity.

(Barrier Layer)

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transport layer, and inhibits electrons from passing through the light-emitting layer toward the hole transport layer. Similarly, the hole barrier layer may be disposed between the light-emitting layer and the electron transport layer, and inhibits holes from passing through the light-emitting layer toward the electron transport layer. The barrier layer may also be used for inhibiting excitons from being diffused outside the light-emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

(Hole Barrier Layer)

The hole barrier layer has the function of an electron transport layer in a broad sense. The hole barrier layer has a function of inhibiting holes from reaching the electron transport layer while transporting electrons, and thereby enhances the recombination probability of electrons and holes in the light-emitting layer. As the material for the hole barrier layer, the materials for the electron transport layer described later may be used depending on necessity.

(Electron Barrier Layer)

The electron barrier layer has the function of transporting holes in a broad sense. The electron barrier layer has a function of inhibiting electrons from reaching the hole transport layer while transporting holes, and thereby enhances the recombination probability of electrons and holes in the light-emitting layer.

(Exciton Barrier Layer)

The exciton barrier layer is a layer for inhibiting excitons generated through recombination of holes and electrons in the light-emitting layer from being diffused to the charge transport layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transport layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transport layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the delayed fluorescent material, respectively.

(Hole Transport Layer)

The hole transport layer is formed of a hole transporting material having a function of transporting holes, and the hole transport layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transport Layer

The electron transport layer is formed of a material having a function of transporting electrons, and the electron transport layer may be provided as a single layer or plural layers.

The electron transporting material (which may also function as a hole barrier material in some cases) needs only to have a function of transporting electrons, which are injected from the cathode, to the light-emitting layer. Examples of the electron transport layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescence device, the compound represented by the general formula (1) may be used not only in the light-emitting layer but also in the other layers than the light-emitting layer. In this case, the compound represented by the general formula (1) used in the light-emitting layer and the compound represented by the general formula (1) used in the other layers than the light-emitting layer may be the same as or different from each other. For example, the compound represented by the general formula (1) may be used in the injection layer, the barrier layer, the hole barrier layer, the electron barrier layer, the exciton barrier layer, the hole transport layer, the electron transport layer and the like described above. The film forming method of the layers are not particularly limited, and the layers may be produced by any of a dry process and a wet process.

Specific examples of preferred materials that may be used in the organic electroluminescence device are shown below, but the materials that may be used in the invention are not construed as being limited to the example compounds. The compound that is shown as a material having a particular function may also be used as a material having another function. In the structural formulae of the example compounds shown below, R, R' and $R_1$ to $R_{10}$ each independently represent a hydrogen atom or a substituent. X represents a carbon atom or a hetero atom to form a ring skeleton, n represents an integer of 3 to 5, Y represents a substituent, and m represents an integer of 0 or more.

The delayed fluorescent material to be combined with the host material for delayed fluorescent materials that contains the compound represented by the general formula (1) is a compound capable of radiating delayed fluorescence. Preferred examples of the delayed fluorescent material are shown below, however, the delayed fluorescent material to be employed in the present invention is not limited to those shown below.

As a preferred delayed fluorescent material, a compound represented by the following general formula can be mentioned. The entire description of WO 2013/154064 including the paragraphs 0008 to 0048 and 0095 to 0133 is incorporated herein by reference as a part of the description of the present application.

[Chem. 9]

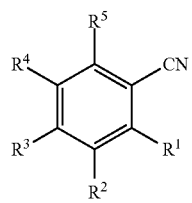

General Formula (101)

[In the general formula (101), at least one of $R^1$ to $R^5$ represents a cyano group, at least one of $R^1$ to $R^5$ represents a group represented by the following general formula (111), and the balance of $R^1$ to $R^5$ each represent a hydrogen atom or a substituent.]

[Chem. 10]

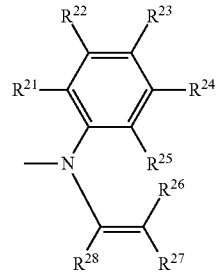

General Formula (111)

[In the general formula (111), $R^{21}$ to $R^{28}$ each independently represent a hydrogen atom or a substituent, provided that at least one of the following conditions <A> and <B> is satisfied:

<A> $R^{25}$ and $R^{26}$ together form a single bond, and

<B> $R^{27}$ and $R^{28}$ each represent an atomic group necessary for forming a substituted or unsubstituted benzene ring as combined together.]

Here, at least one of $R^1$ to $R^5$ preferably represents a group represented by any one of the following general formulae (112) to (115).

[Chem. 11]

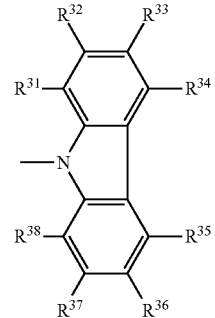

General Formula (112)

[In the general formula (112), $R^{31}$ to $R^{38}$ each independently represent a hydrogen atom or a substituent.]

[Chem. 12]

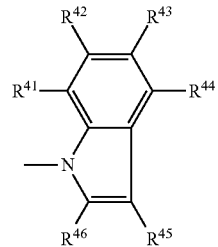

General Formula (113)

[In the general formula (113), $R^{41}$ to $R^{46}$ each independently represent a hydrogen atom or a substituent.]

[Chem. 13]

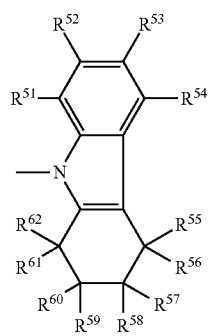

General Formula (114)

[In the general formula (114), $R^{51}$ to $R^{62}$ each independently represent a hydrogen atom or a substituent.]

[Chem. 14]

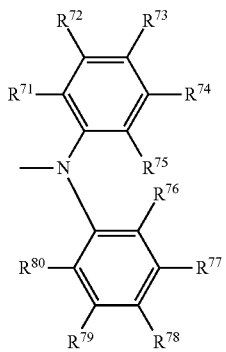

General Formula (115)

[In the general formula (115), $R^{71}$ to $R^{80}$ each independently represent a hydrogen atom or a substituent.]

Specific examples of the compounds include the compounds shown in the following tables. In the case where two or more groups represented by any one of the general formulae (112) to (115) are present in the molecule of the following example compounds, all the groups have the same structure. The formulae (121) to (124) in the tables represent the following formulae, respectively, and n represents the number of the repeating units.

[Chem. 15]

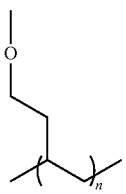

Formula (121)

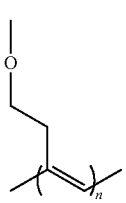

Formula (122)

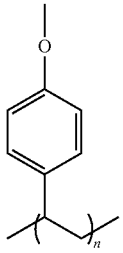

Formula (123)

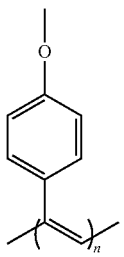

Formula (124)

TABLE 1

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 1' | General formula (112) | General formula (112) | CN | General formula (112) | General formula (112) | H | H | H | H |
| 2' | General formula (112) | General formula (112) | CN | General formula (112) | General formula (112) | H | $CH_3$ | H | H |
| 3' | General formula (112) | General formula (112) | CN | General formula (112) | General formula (112) | H | $CH_3O$ | H | H |
| 4' | General formula (112) | General formula (112) | CN | General formula (112) | General formula (112) | H | H | $CH_3$ | H |
| 5' | General formula (112) | General formula (112) | CN | General formula (112) | General formula (112) | H | H | $CH_3O$ | H |
| 6' | General formula (112) | General formula (112) | CN | General formula (112) | General formula (112) | H | H | $t\text{-}C_4H_9$ | H |
| 7' | General formula (112) | General formula (112) | CN | General formula (112) | General formula (112) | H | H | Cl | H |
| 8' | General formula (112) | General formula (112) | CN | General formula (112) | General formula (112) | H | H | F | H |
| 9' | General formula (112) | General formula (112) | CN | General formula (112) | General formula (112) | H | H | H | $CH_3$ |

TABLE 1-continued

| Compound No. | General formula (101) R¹ | R² | R³ | R⁴ | R⁵ | General formula (112) $R^{31}, R^{38}$ | $R^{32}, R^{37}$ | $R^{33}, R^{36}$ | $R^{34}, R^{35}$ |
|---|---|---|---|---|---|---|---|---|---|
| 10' | General formula (112) | General formula (112) | CN | General formula (112) | General formula (112) | H | H | H | CH₃O |
| 11' | General formula (112) | General formula (112) | CN | General formula (112) | H | H | H | H | H |
| 12' | General formula (112) | General formula (112) | CN | General formula (112) | H | H | CH₃ | H | H |
| 13' | General formula (112) | General formula (112) | CN | General formula (112) | H | H | CH₃O | H | H |
| 14' | General formula (112) | General formula (112) | CN | General formula (112) | H | H | H | CH₃ | H |
| 15' | General formula (112) | General formula (112) | CN | General formula (112) | H | H | H | CH₃O | H |
| 16' | General formula (112) | General formula (112) | CN | General formula (112) | H | H | H | t-C₄H₉ | H |
| 17' | General formula (112) | General formula (112) | CN | General formula (112) | H | H | H | Cl | H |
| 18' | General formula (112) | General formula (112) | CN | General formula (112) | H | H | H | F | H |
| 19' | General formula (112) | General formula (112) | CN | General formula (112) | H | H | H | H | CH₃ |
| 20' | General formula (112) | General formula (112) | CN | General formula (112) | H | H | H | H | CH₃O |
| 21' | General formula (112) | General formula (112) | CN | H | H | H | H | H | H |
| 22' | General formula (112) | General formula (112) | CN | H | H | H | CH₃ | H | H |
| 23' | General formula (112) | General formula (112) | CN | H | H | H | CH₃O | H | H |
| 24' | General formula (112) | General formula (112) | CN | H | H | H | H | CH₃ | H |
| 25' | General formula (112) | General formula (112) | CN | H | H | H | H | CH₃O | H |
| 26' | General formula (112) | General formula (112) | CN | H | H | H | H | t-C₄H₉ | H |
| 27' | General formula (112) | General formula (112) | CN | H | H | H | H | Cl | H |
| 28' | General formula (112) | General formula (112) | CN | H | H | H | H | F | H |
| 29' | General formula (112) | General formula (112) | CN | H | H | H | H | H | CH₃ |
| 30' | General formula (112) | General formula (112) | CN | H | H | H | H | H | CH₃O |
| 31' | General formula (112) | H | CN | General formula (112) | H | H | H | H | H |
| 32' | General formula (112) | H | CN | General formula (112) | H | H | CH₃ | H | H |
| 33' | General formula (112) | H | CN | General formula (112) | H | H | CH₃O | H | H |
| 34' | General formula (112) | H | CN | General formula (112) | H | H | H | CH₃ | H |
| 35' | General formula (112) | H | CN | General formula (112) | H | H | H | CH₃O | H |
| 36' | General formula (112) | H | CN | General formula (112) | H | H | H | t-C₄H₉ | H |
| 37' | General formula (112) | H | CN | General formula (112) | H | H | H | Cl | H |
| 38' | General formula (112) | H | CN | General formula (112) | H | H | H | F | H |
| 39' | General formula (112) | H | CN | General formula (112) | H | H | H | H | CH₃ |
| 40' | General formula (112) | H | CN | General formula (112) | H | H | H | H | CH₃O |
| 41' | General formula (112) | H | CN | H | General formula (112) | H | H | H | H |
| 42' | General formula (112) | H | CN | H | General formula (112) | H | CH₃ | H | H |
| 43' | General formula (112) | H | CN | H | General formula (112) | H | CH₃O | H | H |
| 44' | General formula (112) | H | CN | H | General formula (112) | H | H | CH₃ | H |
| 45' | General formula (112) | H | CN | H | General formula (112) | H | H | CH₃O | H |
| 46' | General formula (112) | H | CN | H | General formula (112) | H | H | t-C₄H₉ | H |
| 47' | General formula (112) | H | CN | H | General formula (112) | H | H | Cl | H |

TABLE 1-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 48' | General formula (112) | H | CN | H | General formula (112) | H | H | F | H |
| 49' | General formula (112) | H | CN | H | General formula (112) | H | H | H | CH$_3$ |
| 50' | General formula (112) | H | CN | H | General formula (112) | H | H | H | CH$_3$O |
| 51' | General formula (112) | H | CN | H | H | H | H | H | H |
| 52' | General formula (112) | H | CN | H | H | H | CH$_3$ | H | H |
| 53' | General formula (112) | H | CN | H | H | H | CH$_3$O | H | H |
| 54' | General formula (112) | H | CN | H | H | H | H | CH$_3$ | H |
| 55' | General formula (112) | H | CN | H | H | H | H | CH$_3$O | H |
| 56' | General formula (112) | H | CN | H | H | H | H | t-C$_4$H$_9$ | H |
| 57' | General formula (112) | H | CN | H | H | H | H | Cl | H |
| 58' | General formula (112) | H | CN | H | H | H | H | F | H |
| 59' | General formula (112) | H | CN | H | H | H | H | H | CH$_3$ |
| 60' | General formula (112) | H | CN | H | H | H | H | H | CH$_3$O |
| 61' | General formula (112) | General formula (112) | CN | General formula (112) | F | H | H | H | H |
| 62' | General formula (112) | General formula (112) | CN | General formula (112) | F | H | CH$_3$ | H | H |
| 63' | General formula (112) | General formula (112) | CN | General formula (112) | F | H | CH$_3$O | H | H |
| 64' | General formula (112) | General formula (112) | CN | General formula (112) | F | H | H | CH$_3$ | H |
| 65' | General formula (112) | General formula (112) | CN | General formula (112) | F | H | H | CH$_3$O | H |
| 66' | General formula (112) | General formula (112) | CN | General formula (112) | F | H | H | t-C$_4$H$_9$ | H |
| 67' | General formula (112) | General formula (112) | CN | General formula (112) | F | H | H | Cl | H |
| 68' | General formula (112) | General formula (112) | CN | General formula (112) | F | H | H | F | H |
| 69' | General formula (112) | General formula (112) | CN | General formula (112) | F | H | H | H | CH$_3$ |
| 70' | General formula (112) | General formula (112) | CN | General formula (112) | F | H | H | H | CH$_3$O |
| 71' | General formula (112) | General formula (112) | CN | F | F | H | H | H | H |
| 72' | General formula (112) | General formula (112) | CN | F | F | H | CH$_3$ | H | H |
| 73' | General formula (112) | General formula (112) | CN | F | F | H | CH$_3$O | H | H |
| 74' | General formula (112) | General formula (112) | CN | F | F | H | H | CH$_3$ | H |
| 75' | General formula (112) | General formula (112) | CN | F | F | H | H | CH$_3$O | H |
| 76' | General formula (112) | General formula (112) | CN | F | F | H | H | t-C$_4$H$_9$ | H |
| 77' | General formula (112) | General formula (112) | CN | F | F | H | H | Cl | H |
| 78' | General formula (112) | General formula (112) | CN | F | F | H | H | F | H |
| 79' | General formula (112) | General formula (112) | CN | F | F | H | H | H | CH$_3$ |
| 80' | General formula (112) | General formula (112) | CN | F | F | H | H | H | CH$_3$O |
| 81' | General formula (112) | F | CN | General formula (112) | F | H | H | H | H |
| 82' | General formula (112) | F | CN | General formula (112) | F | H | CH$_3$ | H | H |
| 83' | General formula (112) | F | CN | General formula (112) | F | H | CH$_3$O | H | H |
| 84' | General formula (112) | F | CN | General formula (112) | F | H | H | CH$_3$ | H |
| 85' | General formula (112) | F | CN | General formula (112) | F | H | H | CH$_3$O | H |

TABLE 1-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}$, $R^{38}$ | $R^{32}$, $R^{37}$ | $R^{33}$, $R^{36}$ | $R^{34}$, $R^{35}$ |
| 86' | General formula (112) | F | CN | General formula (112) | F | H | H | t-C$_4$H$_9$ | H |
| 87' | General formula (112) | F | CN | General formula (112) | F | H | H | Cl | H |
| 88' | General formula (112) | F | CN | General formula (112) | F | H | H | F | H |
| 89' | General formula (112) | F | CN | General formula (112) | F | H | H | H | CH$_3$ |
| 90' | General formula (112) | F | CN | General formula (112) | F | H | H | H | CH$_3$O |
| 91' | General formula (112) | F | CN | F | General formula (112) | H | H | H | H |
| 92' | General formula (112) | F | CN | F | General formula (112) | H | CH$_3$ | H | H |
| 93' | General formula (112) | F | CN | F | General formula (112) | H | CH$_3$O | H | H |
| 94' | General formula (112) | F | CN | F | General formula (112) | H | H | CH$_3$ | H |
| 95' | General formula (112) | F | CN | F | General formula (112) | H | H | CH$_3$O | H |
| 96' | General formula (112) | F | CN | F | General formula (112) | H | H | t-C$_4$H$_9$ | H |
| 97' | General formula (112) | F | CN | F | General formula (112) | H | H | Cl | H |
| 98' | General formula (112) | F | CN | F | General formula (112) | H | H | F | H |
| 99' | General formula (112) | F | CN | F | General formula (112) | H | H | H | CH$_3$ |
| 100' | General formula (112) | F | CN | F | General formula (112) | H | H | H | CH$_3$O |
| 101' | General formula (112) | F | CN | F | F | H | H | H | H |
| 102' | General formula (112) | F | CN | F | F | H | CH$_3$ | H | H |
| 103' | General formula (112) | F | CN | F | F | H | CH$_3$O | H | H |
| 104' | General formula (112) | F | CN | F | F | H | H | CH$_3$ | H |
| 105' | General formula (112) | F | CN | F | F | H | H | CH$_3$O | H |
| 106' | General formula (112) | F | CN | F | F | H | H | t-C$_4$H$_9$ | H |
| 107' | General formula (112) | F | CN | F | F | H | H | Cl | H |
| 108' | General formula (112) | F | CN | F | F | H | H | F | H |
| 109' | General formula (112) | F | CN | F | F | H | H | H | CH$_3$ |
| 110' | General formula (112) | F | CN | F | F | H | H | H | CH$_3$O |
| 111' | General formula (112) | General formula (112) | CN | General formula (112) | OH | H | H | H | H |
| 112' | General formula (112) | General formula (112) | CN | General formula (112) | OH | H | CH$_3$ | H | H |
| 113' | General formula (112) | General formula (112) | CN | General formula (112) | OH | H | CH$_3$O | H | H |
| 114' | General formula (112) | General formula (112) | CN | General formula (112) | OH | H | H | CH$_3$ | H |
| 115' | General formula (112) | General formula (112) | CN | General formula (112) | OH | H | H | CH$_3$O | H |
| 116' | General formula (112) | General formula (112) | CN | General formula (112) | OH | H | H | t-C$_4$H$_9$ | H |
| 117' | General formula (112) | General formula (112) | CN | General formula (112) | OH | H | H | Cl | H |
| 118' | General formula (112) | General formula (112) | CN | General formula (112) | OH | H | H | F | H |
| 119' | General formula (112) | General formula (112) | CN | General formula (112) | OH | H | H | H | CH$_3$ |
| 120' | General formula (112) | General formula (112) | CN | General formula (112) | OH | H | H | H | CH$_3$O |
| 121' | General formula (112) | General formula (112) | CN | OH | OH | H | H | H | H |
| 122' | General formula (112) | General formula (112) | CN | OH | OH | H | CH$_3$ | H | H |
| 123' | General formula (112) | General formula (112) | CN | OH | OH | H | CH$_3$O | H | H |

TABLE 1-continued

| Compound No. | General formula (101) R¹ | R² | R³ | R⁴ | R⁵ | General formula (112) $R^{31}, R^{38}$ | $R^{32}, R^{37}$ | $R^{33}, R^{36}$ | $R^{34}, R^{35}$ |
|---|---|---|---|---|---|---|---|---|---|
| 124' | General formula (112) | General formula (112) | CN | OH | OH | H | H | $CH_3$ | H |
| 125' | General formula (112) | General formula (112) | CN | OH | OH | H | H | $CH_3O$ | H |
| 126' | General formula (112) | General formula (112) | CN | OH | OH | H | H | $t-C_4H_9$ | H |
| 127' | General formula (112) | General formula (112) | CN | OH | OH | H | H | Cl | H |
| 128' | General formula (112) | General formula (112) | CN | OH | OH | H | H | F | H |
| 129' | General formula (112) | General formula (112) | CN | OH | OH | H | H | H | $CH_3$ |
| 130' | General formula (112) | General formula (112) | CN | OH | OH | H | H | H | $CH_3O$ |
| 131' | General formula (112) | OH | CN | General formula (112) | OH | H | H | H | H |
| 132' | General formula (112) | OH | CN | General formula (112) | OH | H | $CH_3$ | H | H |
| 133' | General formula (112) | OH | CN | General formula (112) | OH | H | $CH_3O$ | H | H |
| 134' | General formula (112) | OH | CN | General formula (112) | OH | H | H | $CH_3$ | H |
| 135' | General formula (112) | OH | CN | General formula (112) | OH | H | H | $CH_3O$ | H |
| 136' | General formula (112) | OH | CN | General formula (112) | OH | H | H | $t-C_4H_9$ | H |
| 137' | General formula (112) | OH | CN | General formula (112) | OH | H | H | Cl | H |
| 138' | General formula (112) | OH | CN | General formula (112) | OH | H | H | F | H |
| 139' | General formula (112) | OH | CN | General formula (112) | OH | H | H | H | $CH_3$ |
| 140' | General formula (112) | OH | CN | General formula (112) | OH | H | H | H | $CH_3O$ |
| 141' | General formula (112) | OH | CN | OH | General formula (112) | H | H | H | H |
| 142' | General formula (112) | OH | CN | OH | General formula (112) | H | $CH_3$ | H | H |
| 143' | General formula (112) | OH | CN | OH | General formula (112) | H | $CH_3O$ | H | H |
| 144' | General formula (112) | OH | CN | OH | General formula (112) | H | H | $CH_3$ | H |
| 145' | General formula (112) | OH | CN | OH | General formula (112) | H | H | $CH_3O$ | H |
| 146' | General formula (112) | OH | CN | OH | General formula (112) | H | H | $t-C_4H_9$ | H |
| 147' | General formula (112) | OH | CN | OH | General formula (112) | H | H | Cl | H |
| 148' | General formula (112) | OH | CN | OH | General formula (112) | H | H | F | H |
| 149' | General formula (112) | OH | CN | OH | General formula (112) | H | H | H | $CH_3$ |
| 150' | General formula (112) | OH | CN | OH | General formula (112) | H | H | H | $CH_3O$ |
| 151' | General formula (112) | OH | CN | OH | OH | H | H | H | H |
| 152' | General formula (112) | OH | CN | OH | OH | H | $CH_3$ | H | H |
| 153' | General formula (112) | OH | CN | OH | OH | H | $CH_3O$ | H | H |
| 154' | General formula (112) | OH | CN | OH | OH | H | H | $CH_3$ | H |
| 155' | General formula (112) | OH | CN | OH | OH | H | H | $CH_3O$ | H |
| 156' | General formula (112) | OH | CN | OH | OH | H | H | $t-C_4H_9$ | H |
| 157' | General formula (112) | OH | CN | OH | OH | H | H | Cl | H |
| 158' | General formula (112) | OH | CN | OH | OH | H | H | F | H |
| 159' | General formula (112) | OH | CN | OH | OH | H | H | H | $CH_3$ |
| 160' | General formula (112) | OH | CN | OH | OH | H | H | H | $CH_3O$ |
| 161' | General formula (112) | General formula (112) | CN | General formula (112) | Cl | H | H | H | H |

TABLE 1-continued

| Compound No. | General formula (101) | | | | | General formula (112) | | | |
|---|---|---|---|---|---|---|---|---|---|
| | R¹ | R² | R³ | R⁴ | R⁵ | R³¹, R³⁸ | R³², R³⁷ | R³³, R³⁶ | R³⁴, R³⁵ |
| 162' | General formula (112) | General formula (112) | CN | General formula (112) | Cl | H | CH₃ | H | H |
| 163' | General formula (112) | General formula (112) | CN | General formula (112) | Cl | H | CH₃O | H | H |
| 164' | General formula (112) | General formula (112) | CN | General formula (112) | Cl | H | H | CH₃ | H |
| 165' | General formula (112) | General formula (112) | CN | General formula (112) | Cl | H | H | CH₃O | H |
| 166' | General formula (112) | General formula (112) | CN | General formula (112) | Cl | H | H | t-C₄H₉ | H |
| 167' | General formula (112) | General formula (112) | CN | General formula (112) | Cl | H | H | Cl | H |
| 168' | General formula (112) | General formula (112) | CN | General formula (112) | Cl | H | H | F | H |
| 169' | General formula (112) | General formula (112) | CN | General formula (112) | Cl | H | H | H | CH₃ |
| 170' | General formula (112) | General formula (112) | CN | General formula (112) | Cl | H | H | H | CH₃O |
| 171' | General formula (112) | General formula (112) | CN | General formula (112) | F | H | H | H | H |
| 172' | General formula (112) | General formula (112) | CN | General formula (112) | F | H | CH₃ | H | H |
| 173' | General formula (112) | General formula (112) | CN | General formula (112) | F | H | CH₃O | H | H |
| 174' | General formula (112) | General formula (112) | CN | General formula (112) | F | H | H | CH₃ | H |
| 175' | General formula (112) | General formula (112) | CN | General formula (112) | F | H | H | CH₃O | H |
| 176' | General formula (112) | General formula (112) | CN | General formula (112) | F | H | H | t-C₄H₉ | H |
| 177' | General formula (112) | General formula (112) | CN | General formula (112) | F | H | H | Cl | H |
| 178' | General formula (112) | General formula (112) | CN | General formula (112) | F | H | H | F | H |
| 179' | General formula (112) | General formula (112) | CN | General formula (112) | F | H | H | H | CH₃ |
| 180' | General formula (112) | General formula (112) | CN | General formula (112) | F | H | H | H | CH₃O |
| 181' | General formula (112) | General formula (112) | CN | General formula (112) | CH₃O | H | H | H | H |
| 182' | General formula (112) | General formula (112) | CN | General formula (112) | CH₃O | H | CH₃ | H | H |
| 183' | General formula (112) | General formula (112) | CN | General formula (112) | CH₃O | H | CH₃O | H | H |
| 184' | General formula (112) | General formula (112) | CN | General formula (112) | CH₃O | H | H | CH₃ | H |
| 185' | General formula (112) | General formula (112) | CN | General formula (112) | CH₃O | H | H | CH₃O | H |
| 186' | General formula (112) | General formula (112) | CN | General formula (112) | CH₃O | H | H | t-C₄H₉ | H |
| 187' | General formula (112) | General formula (112) | CN | General formula (112) | CH₃O | H | H | Cl | H |
| 188' | General formula (112) | General formula (112) | CN | General formula (112) | CH₃O | H | H | F | H |
| 189' | General formula (112) | General formula (112) | CN | General formula (112) | C₂H₅O | H | H | H | CH₃ |
| 190' | General formula (112) | General formula (112) | CN | General formula (112) | C₂H₅O | H | H | H | CH₃O |
| 191' | General formula (112) | General formula (112) | CN | General formula (112) | C₂H₅O | H | H | H | H |
| 192' | General formula (112) | General formula (112) | CN | General formula (112) | C₂H₅O | H | CH₃ | H | H |
| 193' | General formula (112) | General formula (112) | CN | General formula (112) | C₂H₅O | H | CH₃O | H | H |
| 194' | General formula (112) | General formula (112) | CN | General formula (112) | C₂H₅O | H | H | CH₃ | H |
| 195' | General formula (112) | General formula (112) | CN | General formula (112) | C₂H₅O | H | H | CH₃O | H |
| 196' | General formula (112) | General formula (112) | CN | General formula (112) | C₂H₅O | H | H | t-C₄H₉ | H |
| 197' | General formula (112) | General formula (112) | CN | General formula (112) | C₂H₅O | H | H | Cl | H |
| 198' | General formula (112) | General formula (112) | CN | General formula (112) | C₂H₅O | H | H | F | H |
| 199' | General formula (112) | General formula (112) | CN | General formula (112) | C₂H₅O | H | H | H | CH₃ |

TABLE 1-continued

| Compound | General formula (101) | | | | | General formula (112) | | | |
|---|---|---|---|---|---|---|---|---|---|
| No. | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 200' | General formula (112) | General formula (112) | CN | General formula (112) | $C_2H_5O$ | H | H | H | $CH_3O$ |
| 201' | General formula (112) | General formula (112) | CN | General formula (112) | $C_6H_5O$ | H | H | H | H |
| 202' | General formula (112) | General formula (112) | CN | General formula (112) | $C_6H_5O$ | H | $CH_3$ | H | H |
| 203' | General formula (112) | General formula (112) | CN | General formula (112) | $C_6H_5O$ | H | $CH_3O$ | H | H |
| 204' | General formula (112) | General formula (112) | CN | General formula (112) | $C_6H_5O$ | H | H | $CH_3$ | H |
| 205' | General formula (112) | General formula (112) | CN | General formula (112) | $C_6H_5O$ | H | H | $CH_3O$ | H |
| 206' | General formula (112) | General formula (112) | CN | General formula (112) | $C_6H_5O$ | H | H | $t-C_4H_9$ | H |
| 207' | General formula (112) | General formula (112) | CN | General formula (112) | $C_6H_5O$ | H | H | Cl | H |
| 208' | General formula (112) | General formula (112) | CN | General formula (112) | $C_6H_5O$ | H | H | F | H |
| 209' | General formula (112) | General formula (112) | CN | General formula (112) | $C_6H_5O$ | H | H | H | $CH_3$ |
| 210' | General formula (112) | General formula (112) | CN | General formula (112) | $C_6H_5O$ | H | H | H | $CH_3O$ |
| 211' | General formula (112) | General formula (112) | CN | General formula (112) | Formula (121) | H | H | H | H |
| 212' | General formula (112) | General formula (112) | CN | General formula (112) | Formula (121) | H | $CH_3$ | H | H |
| 213' | General formula (112) | General formula (112) | CN | General formula (112) | Formula (121) | H | $CH_3O$ | H | H |
| 214' | General formula (112) | General formula (112) | CN | General formula (112) | Formula (121) | H | H | $CH_3$ | H |
| 215' | General formula (112) | General formula (112) | CN | General formula (112) | Formula (121) | H | H | $CH_3O$ | H |
| 216' | General formula (112) | General formula (112) | CN | General formula (112) | Formula (121) | H | H | $t-C_4H_9$ | H |
| 217' | General formula (112) | General formula (112) | CN | General formula (112) | Formula (121) | H | H | Cl | H |
| 218' | General formula (112) | General formula (112) | CN | General formula (112) | Formula (121) | H | H | F | H |
| 219' | General formula (112) | General formula (112) | CN | General formula (112) | Formula (121) | H | H | H | $CH_3$ |
| 220' | General formula (112) | General formula (112) | CN | General formula (112) | Formula (121) | H | H | H | $CH_3O$ |
| 221' | General formula (112) | General formula (112) | CN | General formula (112) | Formula (122) | H | H | H | H |
| 222' | General formula (112) | General formula (112) | CN | General formula (112) | Formula (122) | H | $CH_3$ | H | H |
| 223' | General formula (112) | General formula (112) | CN | General formula (112) | Formula (122) | H | $CH_3O$ | H | H |
| 224' | General formula (112) | General formula (112) | CN | General formula (112) | Formula (122) | H | H | $CH_3$ | H |
| 225' | General formula (112) | General formula (112) | CN | General formula (112) | Formula (122) | H | H | $CH_3O$ | H |
| 226' | General formula (112) | General formula (112) | CN | General formula (112) | Formula (122) | H | H | $t-C_4H_9$ | H |
| 227' | General formula (112) | General formula (112) | CN | General formula (112) | Formula (122) | H | H | Cl | H |
| 228' | General formula (112) | General formula (112) | CN | General formula (112) | Formula (122) | H | H | F | H |
| 229' | General formula (112) | General formula (112) | CN | General formula (112) | Formula (122) | H | H | H | $CH_3$ |
| 230' | General formula (112) | General formula (112) | CN | General formula (112) | Formula (122) | H | H | H | $CH_3O$ |
| 231' | General formula (112) | General formula (112) | CN | General formula (112) | Formula (123) | H | H | H | H |
| 232' | General formula (112) | General formula (112) | CN | General formula (112) | Formula (123) | H | $CH_3$ | H | H |
| 233' | General formula (112) | General formula (112) | CN | General formula (112) | Formula (123) | H | $CH_3O$ | H | H |
| 234' | General formula (112) | General formula (112) | CN | General formula (112) | Formula (123) | H | H | $CH_3$ | H |
| 235' | General formula (112) | General formula (112) | CN | General formula (112) | Formula (123) | H | H | $CH_3O$ | H |
| 236' | General formula (112) | General formula (112) | CN | General formula (112) | Formula (123) | H | H | $t-C_4H_9$ | H |
| 237' | General formula (112) | General formula (112) | CN | General formula (112) | Formula (123) | H | H | Cl | H |

TABLE 1-continued

| Compound No. | General formula (101) R¹ | R² | R³ | R⁴ | R⁵ | General formula (112) $R^{31}, R^{38}$ | $R^{32}, R^{37}$ | $R^{33}, R^{36}$ | $R^{34}, R^{35}$ |
|---|---|---|---|---|---|---|---|---|---|
| 238' | General formula (112) | General formula (112) | CN | General formula (112) | Formula (123) | H | H | F | H |
| 239' | General formula (112) | General formula (112) | CN | General formula (112) | Formula (123) | H | H | H | $CH_3$ |
| 240' | General formula (112) | General formula (112) | CN | General formula (112) | Formula (123) | H | H | H | $CH_3O$ |
| 241' | General formula (112) | General formula (112) | CN | General formula (112) | Formula (124) | H | H | H | H |
| 242' | General formula (112) | General formula (112) | CN | General formula (112) | Formula (124) | H | $CH_3$ | H | H |
| 243' | General formula (112) | General formula (112) | CN | General formula (112) | Formula (124) | H | $CH_3O$ | H | H |
| 244' | General formula (112) | General formula (112) | CN | General formula (112) | Formula (124) | H | H | $CH_3$ | H |
| 245' | General formula (112) | General formula (112) | CN | General formula (112) | Formula (124) | H | H | $CH_3O$ | H |
| 246' | General formula (112) | General formula (112) | CN | General formula (112) | Formula (124) | H | H | $t-C_4H_9$ | H |
| 247' | General formula (112) | General formula (112) | CN | General formula (112) | Formula (124) | H | H | Cl | H |
| 248' | General formula (112) | General formula (112) | CN | General formula (112) | Formula (124) | H | H | F | H |
| 249' | General formula (112) | General formula (112) | CN | General formula (112) | Formula (124) | H | H | H | $CH_3$ |
| 250' | General formula (112) | General formula (112) | CN | General formula (112) | Formula (124) | H | H | H | $CH_3O$ |
| 251' | General formula (112) | General formula (112) | CN | General formula (112) | General formula (112) | H | $C_6H_5$ | H | H |
| 252' | General formula (112) | General formula (112) | CN | General formula (112) | General formula (112) | H | H | $C_6H_5$ | H |
| 253' | General formula (112) | General formula (112) | CN | General formula (112) | H | H | $C_6H_5$ | H | H |
| 254' | General formula (112) | General formula (112) | CN | General formula (112) | H | H | H | $C_6H_5$ | H |
| 255' | General formula (112) | General formula (112) | CN | H | H | H | $C_6H_5$ | H | H |
| 256' | General formula (112) | General formula (112) | CN | H | H | H | H | $C_6H_5$ | H |
| 257' | General formula (112) | H | CN | General formula (112) | H | H | $C_6H_5$ | H | H |
| 258' | General formula (112) | H | CN | General formula (112) | H | H | H | $C_6H_5$ | H |
| 259' | General formula (112) | H | CN | H | General formula (112) | H | $C_6H_5$ | H | H |
| 260' | General formula (112) | H | CN | H | General formula (112) | H | H | $C_6H_5$ | H |
| 261' | General formula (112) | H | CN | H | H | H | $C_6H_5$ | H | H |
| 262' | General formula (112) | H | CN | H | H | H | H | $C_6H_5$ | H |
| 263' | General formula (112) | General formula (112) | CN | General formula (112) | F | H | $C_6H_5$ | H | H |
| 264' | General formula (112) | General formula (112) | CN | General formula (112) | F | H | H | $C_6H_5$ | H |
| 265' | General formula (112) | General formula (112) | CN | F | F | H | $C_6H_5$ | H | H |
| 266' | General formula (112) | General formula (112) | CN | F | F | H | H | $C_6H_5$ | H |
| 267' | General formula (112) | F | CN | General formula (112) | F | H | $C_6H_5$ | H | H |
| 268' | General formula (112) | F | CN | General formula (112) | F | H | H | $C_6H_5$ | H |
| 269' | General formula (112) | F | CN | F | General formula (112) | H | $C_6H_5$ | H | H |
| 270' | General formula (112) | F | CN | F | General formula (112) | H | H | $C_6H_5$ | H |
| 271' | General formula (112) | F | CN | F | F | H | $C_6H_5$ | H | H |
| 272' | General formula (112) | F | CN | F | F | H | H | $C_6H_5$ | H |
| 273' | General formula (112) | General formula (112) | CN | General formula (112) | OH | H | $C_6H_5$ | H | H |
| 274' | General formula (112) | General formula (112) | CN | General formula (112) | OH | H | H | $C_6H_5$ | H |
| 275' | General formula (112) | General formula (112) | CN | OH | OH | H | $C_6H_5$ | H | H |

TABLE 1-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 276' | General formula (112) | General formula (112) | CN | OH | OH | H | H | $C_6H_5$ | H |
| 277' | General formula (112) | OH | CN | General formula (112) | OH | H | $C_6H_5$ | H | H |
| 278' | General formula (112) | OH | CN | General formula (112) | OH | H | H | $C_6H_5$ | H |
| 279' | General formula (112) | OH | CN | OH | General formula (112) | H | $C_6H_5$ | H | H |
| 280' | General formula (112) | OH | CN | OH | General formula (112) | H | H | $C_6H_5$ | H |
| 281' | General formula (112) | OH | CN | OH | OH | H | $C_6H_5$ | H | H |
| 282' | General formula (112) | OH | CN | OH | OH | H | H | $C_6H_5$ | H |
| 283' | General formula (112) | General formula (112) | CN | General formula (112) | Cl | H | $C_6H_5$ | H | H |
| 284' | General formula (112) | General formula (112) | CN | General formula (112) | Cl | H | H | $C_6H_5$ | H |
| 285' | General formula (112) | General formula (112) | CN | General formula (112) | F | H | $C_6H_5$ | H | H |
| 286' | General formula (112) | General formula (112) | CN | General formula (112) | F | H | H | $C_6H_5$ | H |
| 287' | General formula (112) | General formula (112) | CN | General formula (112) | $CH_3O$ | H | $C_6H_5$ | H | H |
| 288' | General formula (112) | General formula (112) | CN | General formula (112) | $CH_3O$ | H | H | $C_6H_5$ | H |
| 289' | General formula (112) | General formula (112) | CN | General formula (112) | $C_2H_5O$ | H | $C_6H_5$ | H | H |
| 290' | General formula (112) | General formula (112) | CN | General formula (112) | $C_2H_5O$ | H | H | $C_6H_5$ | H |
| 291' | General formula (112) | General formula (112) | CN | General formula (112) | $C_6H_5O$ | H | $C_6H_5$ | H | H |
| 292' | General formula (112) | General formula (112) | CN | General formula (112) | $C_6H_5O$ | H | H | $C_6H_5$ | H |
| 293' | General formula (112) | General formula (112) | CN | General formula (112) | Formula (121) | H | $C_6H_5$ | H | H |
| 294' | General formula (112) | General formula (112) | CN | General formula (112) | Formula (121) | H | H | $C_6H_5$ | H |
| 295' | General formula (112) | General formula (112) | CN | General formula (112) | Formula (122) | H | $C_6H_5$ | H | H |
| 296' | General formula (112) | General formula (112) | CN | General formula (112) | Formula (122) | H | H | $C_6H_5$ | H |
| 297' | General formula (112) | General formula (112) | CN | General formula (112) | Formula (123) | H | $C_6H_5$ | H | H |
| 298' | General formula (112) | General formula (112) | CN | General formula (112) | Formula (123) | H | H | $C_6H_5$ | H |
| 299' | General formula (112) | General formula (112) | CN | General formula (112) | Formula (124) | H | $C_6H_5$ | H | H |
| 300' | General formula (112) | General formula (112) | CN | General formula (112) | Formula (124) | H | H | $C_6H_5$ | H |

TABLE 2

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 301 | General formula (112) | CN | General formula (112) | General formula (112) | General formula (112) | H | H | H | H |
| 302 | General formula (112) | CN | General formula (112) | General formula (112) | General formula (112) | H | $CH_3$ | H | H |
| 303 | General formula (112) | CN | General formula (112) | General formula (112) | General formula (112) | H | $CH_3O$ | H | H |
| 304 | General formula (112) | CN | General formula (112) | General formula (112) | General formula (112) | H | H | $CH_3$ | H |
| 305 | General formula (112) | CN | General formula (112) | General formula (112) | General formula (112) | H | H | $CH_3O$ | H |
| 306 | General formula (112) | CN | General formula (112) | General formula (112) | General formula (112) | H | H | $t-C_4H_9$ | H |
| 307 | General formula (112) | CN | General formula (112) | General formula (112) | General formula (112) | H | H | Cl | H |
| 308 | General formula (112) | CN | General formula (112) | General formula (112) | General formula (112) | H | H | F | H |

TABLE 2-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}$, $R^{38}$ | $R^{32}$, $R^{37}$ | $R^{33}$, $R^{36}$ | $R^{34}$, $R^{35}$ |
| 309 | General formula (112) | CN | General formula (112) | General formula (112) | General formula (112) | H | H | H | CH$_3$ |
| 310 | General formula (112) | CN | General formula (112) | General formula (112) | General formula (112) | H | H | H | CH$_3$O |
| 311 | General formula (112) | CN | General formula (112) | General formula (112) | H | H | H | H | H |
| 312 | General formula (112) | CN | General formula (112) | General formula (112) | H | H | H | CH$_3$ | H |
| 313 | General formula (112) | CN | General formula (112) | General formula (112) | H | H | H | CH$_3$O | H |
| 314 | General formula (112) | CN | General formula (112) | H | General formula (112) | H | H | H | H |
| 315 | General formula (112) | CN | General formula (112) | H | General formula (112) | H | H | CH$_3$ | H |
| 316 | General formula (112) | CN | General formula (112) | H | General formula (112) | H | H | CH$_3$O | H |
| 317 | General formula (112) | CN | H | General formula (112) | General formula (112) | H | H | H | H |
| 318 | General formula (112) | CN | H | General formula (112) | General formula (112) | H | H | CH$_3$ | H |
| 319 | General formula (112) | CN | H | General formula (112) | General formula (112) | H | H | CH$_3$O | H |
| 320 | H | CN | General formula (112) | General formula (112) | General formula (112) | H | H | H | H |
| 321 | H | CN | General formula (112) | General formula (112) | General formula (112) | H | H | CH$_3$ | H |
| 322 | H | CN | General formula (112) | General formula (112) | General formula (112) | H | H | CH$_3$O | H |
| 323 | General formula (112) | CN | General formula (112) | H | H | H | H | H | H |
| 324 | General formula (112) | CN | General formula (112) | H | H | H | H | CH$_3$ | H |
| 325 | General formula (112) | CN | General formula (112) | H | H | H | H | CH$_3$O | H |
| 326 | General formula (112) | CN | H | General formula (112) | H | H | H | H | H |
| 327 | General formula (112) | CN | H | General formula (112) | H | H | H | CH$_3$ | H |
| 328 | General formula (112) | CN | H | General formula (112) | H | H | H | CH$_3$O | H |
| 329 | H | CN | General formula (112) | General formula (112) | H | H | H | H | H |
| 330 | H | CN | General formula (112) | General formula (112) | H | H | H | CH$_3$ | H |
| 331 | H | CN | General formula (112) | General formula (112) | H | H | H | CH$_3$O | H |
| 332 | General formula (112) | CN | H | H | General formula (112) | H | H | H | H |
| 333 | General formula (112) | CN | H | H | General formula (112) | H | H | CH$_3$ | H |
| 334 | General formula (112) | CN | H | H | General formula (112) | H | H | CH$_3$O | H |
| 335 | H | CN | General formula (112) | H | General formula (112) | H | H | H | H |
| 336 | H | CN | General formula (112) | H | General formula (112) | H | H | CH$_3$ | H |
| 337 | H | CN | General formula (112) | H | General formula (112) | H | H | CH$_3$O | H |
| 338 | H | CN | H | General formula (112) | General formula (112) | H | H | H | H |
| 339 | H | CN | H | General formula (112) | General formula (112) | H | H | CH$_3$ | H |
| 340 | H | CN | H | General formula (112) | General formula (112) | H | H | CH$_3$O | H |
| 341 | General formula (112) | CN | H | H | H | H | H | H | H |
| 342 | General formula (112) | CN | H | H | H | H | H | CH$_3$ | H |
| 343 | General formula (112) | CN | H | H | H | H | H | CH$_3$O | H |
| 344 | H | CN | General formula (112) | H | H | H | H | H | H |
| 345 | H | CN | General formula (112) | H | H | H | H | CH$_3$ | H |
| 346 | H | CN | General formula (112) | H | H | H | H | CH$_3$O | H |

TABLE 2-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 347 | H | CN | H | General formula (112) | H | H | H | H | H |
| 348 | H | CN | H | General formula (112) | H | H | H | $CH_3$ | H |
| 349 | H | CN | H | General formula (112) | H | H | H | $CH_3O$ | H |
| 350 | General formula (112) | CN | General formula (112) | General formula (112) | F | H | H | H | H |
| 351 | General formula (112) | CN | General formula (112) | General formula (112) | F | H | H | $CH_3$ | H |
| 352 | General formula (112) | CN | General formula (112) | General formula (112) | F | H | H | $CH_3O$ | H |
| 353 | General formula (112) | CN | General formula (112) | F | General formula (112) | H | H | H | H |
| 354 | General formula (112) | CN | General formula (112) | F | General formula (112) | H | H | $CH_3$ | H |
| 355 | General formula (112) | CN | General formula (112) | F | General formula (112) | H | H | $CH_3O$ | H |
| 356 | General formula (112) | CN | F | General formula (112) | General formula (112) | H | H | H | H |
| 357 | General formula (112) | CN | F | General formula (112) | General formula (112) | H | H | $CH_3$ | H |
| 358 | General formula (112) | CN | F | General formula (112) | General formula (112) | H | H | $CH_3O$ | H |
| 359 | F | CN | General formula (112) | General formula (112) | General formula (112) | H | H | H | H |
| 360 | F | CN | General formula (112) | General formula (112) | General formula (112) | H | H | $CH_3$ | H |
| 361 | F | CN | General formula (112) | General formula (112) | General formula (112) | H | H | $CH_3O$ | H |
| 362 | General formula (112) | CN | General formula (112) | F | F | H | H | H | H |
| 363 | General formula (112) | CN | General formula (112) | F | F | H | H | $CH_3$ | H |
| 364 | General formula (112) | CN | General formula (112) | F | F | H | H | $CH_3O$ | H |
| 365 | General formula (112) | CN | F | General formula (112) | F | H | H | H | H |
| 366 | General formula (112) | CN | F | General formula (112) | F | H | H | $CH_3$ | H |
| 367 | General formula (112) | CN | F | General formula (112) | F | H | H | $CH_3O$ | H |
| 368 | F | CN | General formula (112) | General formula (112) | F | H | H | H | H |
| 369 | F | CN | General formula (112) | General formula (112) | F | H | H | $CH_3$ | H |
| 370 | F | CN | General formula (112) | General formula (112) | F | H | H | $CH_3O$ | H |
| 371 | General formula (112) | CN | F | F | General formula (112) | H | H | H | H |
| 372 | General formula (112) | CN | F | F | General formula (112) | H | H | $CH_3$ | H |
| 373 | General formula (112) | CN | F | F | General formula (112) | H | H | $CH_3O$ | H |
| 374 | F | CN | General formula (112) | F | General formula (112) | H | H | H | H |
| 375 | F | CN | General formula (112) | F | General formula (112) | H | H | $CH_3$ | H |
| 376 | F | CN | General formula (112) | F | General formula (112) | H | H | $CH_3O$ | H |
| 377 | F | CN | F | General formula (112) | General formula (112) | H | H | H | H |
| 378 | F | CN | F | General formula (112) | General formula (112) | H | H | $CH_3$ | H |
| 379 | F | CN | F | General formula (112) | General formula (112) | H | H | $CH_3O$ | H |
| 380 | General formula (112) | CN | F | F | F | H | H | H | H |
| 381 | General formula (112) | CN | F | F | F | H | H | $CH_3$ | H |
| 382 | General formula (112) | CN | F | F | F | H | H | $CH_3O$ | H |
| 383 | F | CN | General formula (112) | F | F | H | H | H | H |
| 384 | F | CN | General formula (112) | F | F | H | H | $CH_3$ | H |

TABLE 2-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}$, $R^{38}$ | $R^{32}$, $R^{37}$ | $R^{33}$, $R^{36}$ | $R^{34}$, $R^{35}$ |
| 385 | F | CN | General formula (112) | F | F | H | H | $CH_3O$ | H |
| 386 | F | CN | F | General formula (112) | F | H | H | H | H |
| 387 | F | CN | F | General formula (112) | F | H | H | $CH_3$ | H |
| 388 | F | CN | F | General formula (112) | F | H | H | $CH_3O$ | H |
| 389 | General formula (112) | CN | General formula (112) | General formula (112) | OH | H | H | H | H |
| 390 | General formula (112) | CN | General formula (112) | General formula (112) | OH | H | H | $CH_3$ | H |
| 391 | General formula (112) | CN | General formula (112) | General formula (112) | OH | H | H | $CH_3O$ | H |
| 392 | General formula (112) | CN | General formula (112) | OH | General formula (112) | H | H | H | H |
| 393 | General formula (112) | CN | General formula (112) | OH | General formula (112) | H | H | CH | H |
| 394 | General formula (112) | CN | General formula (112) | OH | General formula (112) | H | H | $CH_3O$ | H |
| 395 | General formula (112) | CN | General formula (112) | OH | General formula (112) | H | H | $t$-$C_4H_9$ | H |
| 396 | General formula (112) | CN | General formula (112) | OH | General formula (112) | H | H | Cl | H |
| 397 | General formula (112) | CN | General formula (112) | OH | General formula (112) | H | H | F | H |
| 398 | General formula (112) | CN | OH | General formula (112) | General formula (112) | H | H | H | H |
| 399 | General formula (112) | CN | OH | General formula (112) | General formula (112) | H | H | $CH_3$ | H |
| 400 | General formula (112) | CN | OH | General formula (112) | General formula (112) | H | H | $CH_3O$ | H |
| 401 | OH | CN | General formula (112) | General formula (112) | General formula (112) | H | H | H | H |
| 402 | OH | CN | General formula (112) | General formula (112) | General formula (112) | H | H | $CH_3$ | H |
| 403 | OH | CN | General formula (112) | General formula (112) | General formula (112) | H | H | $CH_3O$ | H |
| 404 | General formula (112) | CN | General formula (112) | OH | OH | H | H | H | H |
| 405 | General formula (112) | CN | General formula (112) | OH | OH | H | H | $CH_3$ | H |
| 406 | General formula (112) | CN | General formula (112) | OH | OH | H | H | $CH_3O$ | H |
| 407 | General formula (112) | CN | OH | General formula (112) | OH | H | H | H | H |
| 408 | General formula (112) | CN | OH | General formula (112) | OH | H | H | $CH_3$ | H |
| 409 | General formula (112) | CN | OH | General formula (112) | OH | H | H | $CH_3O$ | H |
| 410 | OH | CN | General formula (112) | General formula (112) | OH | H | H | H | H |
| 411 | OH | CN | General formula (112) | General formula (112) | OH | H | H | $CH_3$ | H |
| 412 | OH | CN | General formula (112) | General formula (112) | OH | H | H | $CH_3O$ | H |
| 413 | General formula (112) | CN | OH | OH | General formula (112) | H | H | H | H |
| 414 | General formula (112) | CN | OH | OH | General formula (112) | H | H | $CH_3$ | H |
| 415 | General formula (112) | CN | OH | OH | General formula (112) | H | H | $CH_3O$ | H |
| 416 | OH | CN | General formula (112) | OH | General formula (112) | H | H | H | H |
| 417 | OH | CN | General formula (112) | OH | General formula (112) | H | H | $CH_3$ | H |
| 418 | OH | CN | General formula (112) | OH | General formula (112) | H | H | $CH_3O$ | H |
| 419 | OH | CN | OH | General formula (112) | General formula (112) | H | H | H | H |
| 420 | OH | CN | OH | General formula (112) | General formula (112) | H | H | $CH_3$ | H |
| 421 | OH | CN | OH | General formula (112) | General formula (112) | H | H | $CH_3O$ | H |
| 422 | General formula (112) | CN | OH | OH | OH | H | H | H | H |

TABLE 2-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 423 | General formula (112) | CN | OH | OH | OH | H | H | $CH_3$ | H |
| 424 | General formula (112) | CN | OH | OH | OH | H | H | $CH_3O$ | H |
| 425 | OH | CN | General formula (112) | OH | OH | H | H | H | H |
| 426 | OH | CN | General formula (112) | OH | OH | H | H | $CH_3$ | H |
| 427 | OH | CN | General formula (112) | OH | OH | H | H | $CH_3O$ | H |
| 428 | OH | CN | OH | General formula (112) | OH | H | H | H | H |
| 429 | OH | CN | OH | General formula (112) | OH | H | H | $CH_3$ | H |
| 430 | OH | CN | OH | General formula (112) | OH | H | H | $CH_3O$ | H |
| 431 | OH | CN | OH | OH | General formula (112) | H | H | H | H |
| 432 | OH | CN | OH | OH | General formula (112) | H | H | $CH_3$ | H |
| 433 | OH | CN | OH | OH | General formula (112) | H | H | $CH_3O$ | H |
| 434 | General formula (112) | CN | General formula (112) | Cl | General formula (112) | H | H | H | H |
| 435 | General formula (112) | CN | General formula (112) | Cl | General formula (112) | H | H | $CH_3$ | H |
| 436 | General formula (112) | CN | General formula (112) | Cl | General formula (112) | H | H | $CH_3O$ | H |
| 437 | General formula (112) | CN | General formula (112) | Cl | General formula (112) | H | H | $t-C_4H_9$ | H |
| 438 | General formula (112) | CN | General formula (112) | Cl | General formula (112) | H | H | Cl | H |
| 439 | General formula (112) | CN | General formula (112) | Cl | General formula (112) | H | H | F | H |
| 440 | General formula (112) | CN | General formula (112) | F | General formula (112) | H | H | H | H |
| 441 | General formula (112) | CN | General formula (112) | F | General formula (112) | H | H | $CH_3$ | H |
| 442 | General formula (112) | CN | General formula (112) | F | General formula (112) | H | H | $CH_3O$ | H |
| 443 | General formula (112) | CN | General formula (112) | F | General formula (112) | H | H | $t-C_4H_9$ | H |
| 444 | General formula (112) | CN | General formula (112) | F | General formula (112) | H | H | Cl | H |
| 445 | General formula (112) | CN | General formula (112) | F | General formula (112) | H | H | F | H |
| 446 | General formula (112) | CN | General formula (112) | $CH_3O$ | General formula (112) | H | H | H | H |
| 447 | General formula (112) | CN | General formula (112) | $CH_3O$ | General formula (112) | H | H | $CH_3$ | H |
| 448 | General formula (112) | CN | General formula (112) | $CH_3O$ | General formula (112) | H | H | $CH_3O$ | H |
| 449 | General formula (112) | CN | General formula (112) | $CH_3O$ | General formula (112) | H | H | $t-C_4H_9$ | H |
| 450 | General formula (112) | CN | General formula (112) | $CH_3O$ | General formula (112) | H | H | Cl | H |
| 451 | General formula (112) | CN | General formula (112) | $CH_3O$ | General formula (112) | H | H | F | H |
| 452 | General formula (112) | CN | General formula (112) | $C_2H_5O$ | General formula (112) | H | H | H | H |
| 453 | General formula (112) | CN | General formula (112) | $C_2H_5O$ | General formula (112) | H | H | $CH_3$ | H |
| 454 | General formula (112) | CN | General formula (112) | $C_2H_5O$ | General formula (112) | H | H | $CH_3O$ | H |
| 455 | General formula (112) | CN | General formula (112) | $C_2H_5O$ | General formula (112) | H | H | $t-C_4H_9$ | H |
| 456 | General formula (112) | CN | General formula (112) | $C_2H_5O$ | General formula (112) | H | H | Cl | H |
| 457 | General formula (112) | CN | General formula (112) | $C_2H_5O$ | General formula (112) | H | H | F | H |
| 458 | General formula (112) | CN | General formula (112) | $C_6H_5O$ | General formula (112) | H | H | H | H |
| 459 | General formula (112) | CN | General formula (112) | $C_6H_5O$ | General formula (112) | H | H | $CH_3$ | H |
| 460 | General formula (112) | CN | General formula (112) | $C_6H_5O$ | General formula (112) | H | H | $CH_3O$ | H |

TABLE 2-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 461 | General formula (112) | CN | General formula (112) | $C_6H_5O$ | General formula (112) | H | H | t-$C_4H_9$ | H |
| 462 | General formula (112) | CN | General formula (112) | $C_6H_5O$ | General formula (112) | H | H | Cl | H |
| 463 | General formula (112) | CN | General formula (112) | $C_6H_5O$ | General formula (112) | H | H | F | H |
| 464 | General formula (112) | CN | General formula (112) | Formula (121) | General formula (112) | H | H | H | H |
| 465 | General formula (112) | CN | General formula (112) | Formula (121) | General formula (112) | H | H | $CH_3$ | H |
| 466 | General formula (112) | CN | General formula (112) | Formula (121) | General formula (112) | H | H | $CH_3O$ | H |
| 467 | General formula (112) | CN | General formula (112) | Formula (121) | General formula (112) | H | H | t-$C_4H_9$ | H |
| 468 | General formula (112) | CN | General formula (112) | Formula (121) | General formula (112) | H | H | Cl | H |
| 469 | General formula (112) | CN | General formula (112) | Formula (121) | General formula (112) | H | H | F | H |
| 470 | General formula (112) | CN | General formula (112) | Formula (122) | General formula (112) | H | H | H | H |
| 471 | General formula (112) | CN | General formula (112) | Formula (122) | General formula (112) | H | H | $CH_3$ | H |
| 472 | General formula (112) | CN | General formula (112) | Formula (122) | General formula (112) | H | H | $CH_3O$ | H |
| 473 | General formula (112) | CN | General formula (112) | Formula (122) | General formula (112) | H | H | t-$C_4H_9$ | H |
| 474 | General formula (112) | CN | General formula (112) | Formula (122) | General formula (112) | H | H | Cl | H |
| 475 | General formula (112) | CN | General formula (112) | Formula (122) | General formula (112) | H | H | F | H |
| 476 | General formula (112) | CN | General formula (112) | Formula (123) | General formula (112) | H | H | H | H |
| 477 | General formula (112) | CN | General formula (112) | Formula (123) | General formula (112) | H | H | $CH_3$ | H |
| 478 | General formula (112) | CN | General formula (112) | Formula (123) | General formula (112) | H | H | $CH_3O$ | H |
| 479 | General formula (112) | CN | General formula (112) | Formula (123) | General formula (112) | H | H | t-$C_4H_9$ | H |
| 480 | General formula (112) | CN | General formula (112) | Formula (123) | General formula (112) | H | H | Cl | H |
| 481 | General formula (112) | CN | General formula (112) | Formula (123) | General formula (112) | H | H | F | H |
| 482 | General formula (112) | CN | General formula (112) | Formula (124) | General formula (112) | H | H | H | H |
| 483 | General formula (112) | CN | General formula (112) | Formula (124) | General formula (112) | H | H | $CH_3$ | H |
| 484 | General formula (112) | CN | General formula (112) | Formula (124) | General formula (112) | H | H | $CH_3O$ | H |
| 485 | General formula (112) | CN | General formula (112) | Formula (124) | General formula (112) | H | H | t-$C_4H_9$ | H |
| 486 | General formula (112) | CN | General formula (112) | Formula (124) | General formula (112) | H | H | Cl | H |
| 487 | General formula (112) | CN | General formula (112) | Formula (124) | General formula (112) | H | H | F | H |
| 488 | General formula (112) | CN | General formula (112) | General formula (112) | General formula (112) | H | $C_6H_5$ | H | H |
| 489 | General formula (112) | CN | General formula (112) | General formula (112) | General formula (112) | H | H | $C_6H_5$ | H |
| 490 | General formula (112) | CN | General formula (112) | General formula (112) | H | H | $C_6H_5$ | H | H |
| 491 | General formula (112) | CN | General formula (112) | General formula (112) | H | H | H | $C_6H_5$ | H |
| 492 | General formula (112) | CN | General formula (112) | H | General formula (112) | H | $C_6H_5$ | H | H |
| 493 | General formula (112) | CN | General formula (112) | H | General formula (112) | H | H | $C_6H_5$ | H |
| 494 | General formula (112) | CN | H | General formula (112) | General formula (112) | H | $C_6H_5$ | H | H |
| 495 | General formula (112) | CN | H | General formula (112) | General formula (112) | H | H | $C_6H_5$ | H |
| 496 | H | CN | General formula (112) | General formula (112) | General formula (112) | H | $C_6H_5$ | H | H |
| 497 | H | CN | General formula (112) | General formula (112) | General formula (112) | H | H | $C_6H_5$ | H |
| 498 | General formula (112) | CN | General formula (112) | H | H | H | $C_6H_5$ | H | H |

TABLE 2-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 499 | General formula (112) | CN | General formula (112) | H | H | H | H | $C_6H_5$ | H |
| 500-1 | General formula (112) | CN | H | General formula (112) | H | H | $C_6H_5$ | H | H |
| 500-2 | General formula (112) | CN | H | General formula (112) | H | H | H | $C_6H_5$ | H |
| 500-3 | H | CN | General formula (112) | General formula (112) | H | H | $C_6H_5$ | H | H |
| 500-4 | H | CN | General formula (112) | General formula (112) | H | H | H | $C_6H_5$ | H |
| 500-5 | General formula (112) | CN | H | H | General formula (112) | H | $C_6H_5$ | H | H |
| 500-6 | General formula (112) | CN | H | H | General formula (112) | H | H | $C_6H_5$ | H |
| 500-7 | H | CN | General formula (112) | H | General formula (112) | H | $C_6H_5$ | H | H |
| 500-8 | H | CN | General formula (112) | H | General formula (112) | H | H | $C_6H_5$ | H |
| 500-9 | H | CN | H | General formula (112) | General formula (112) | H | $C_6H_5$ | H | H |
| 500-10 | H | CN | H | General formula (112) | General formula (112) | H | H | $C_6H_5$ | H |
| 500-11 | General formula (112) | CN | H | H | H | H | $C_6H_5$ | H | H |
| 500-12 | General formula (112) | CN | H | H | H | H | H | $C_6H_5$ | H |
| 500-13 | H | CN | General formula (112) | H | H | H | $C_6H_5$ | H | H |
| 500-14 | H | CN | General formula (112) | H | H | H | H | $C_6H_5$ | H |
| 500-15 | H | CN | H | General formula (112) | H | H | $C_6H_5$ | H | H |
| 500-16 | H | CN | H | General formula (112) | H | H | H | $C_6H_5$ | H |
| 500-17 | General formula (112) | CN | General formula (112) | General formula (112) | F | H | H | $C_6H_5$ | H |
| 500-18 | General formula (112) | CN | General formula (112) | F | General formula (112) | H | H | $C_6H_5$ | H |
| 500-19 | General formula (112) | CN | F | General formula (112) | General formula (112) | H | H | $C_6H_5$ | H |
| 500-20 | F | CN | General formula (112) | General formula (112) | General formula (112) | H | H | $C_6H_5$ | H |
| 500-21 | General formula (112) | CN | General formula (112) | F | F | H | H | $C_6H_5$ | H |
| 500-22 | General formula (112) | CN | F | General formula (112) | F | H | H | $C_6H_5$ | H |
| 500-23 | F | CN | General formula (112) | General formula (112) | F | H | H | $C_6H_5$ | H |
| 500-24 | General formula (112) | CN | F | F | General formula (112) | H | H | $C_6H_5$ | H |
| 500-25 | F | CN | General formula (112) | F | General formula (112) | H | H | $C_6H_5$ | H |
| 500-26 | F | CN | F | General formula (112) | General formula (112) | H | H | $C_6H_5$ | H |
| 500-27 | General formula (112) | CN | F | F | F | H | H | $C_6H_5$ | H |
| 500-28 | F | CN | General formula (112) | F | F | H | H | $C_6H_5$ | H |
| 500-29 | F | CN | F | General formula (112) | F | H | H | $C_6H_5$ | H |
| 500-30 | General formula (112) | CN | General formula (112) | General formula (112) | OH | H | H | $C_6H_5$ | H |
| 500-31 | General formula (112) | CN | General formula (112) | OH | General formula (112) | H | H | $C_6H_5$ | H |
| 500-32 | General formula (112) | CN | OH | General formula (112) | General formula (112) | H | H | $C_6H_5$ | H |
| 500-33 | OH | CN | General formula (112) | General formula (112) | General formula (112) | H | H | $C_6H_5$ | H |
| 500-34 | General formula (112) | CN | General formula (112) | OH | OH | H | H | $C_6H_5$ | H |
| 500-35 | General formula (112) | CN | OH | General formula (112) | OH | H | H | $C_6H_5$ | H |
| 500-36 | OH | CN | General formula (112) | General formula (112) | OH | H | H | $C_6H_5$ | H |
| 500-37 | General formula (112) | CN | OH | OH | General formula (112) | H | H | $C_6H_5$ | H |

TABLE 2-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 500-38 | OH | CN | General formula (112) | OH | General formula (112) | H | H | $C_6H_5$ | H |
| 500-39 | OH | CN | OH | General formula (112) | General formula (112) | H | H | $C_6H_5$ | H |
| 500-40 | General formula (112) | CN | OH | OH | OH | H | H | $C_6H_5$ | H |
| 500-41 | OH | CN | General formula (112) | OH | OH | H | H | $C_6H_5$ | H |
| 500-42 | OH | CN | OH | General formula (112) | OH | H | H | $C_6H_5$ | H |
| 500-43 | OH | CN | OH | OH | General formula (112) | H | H | $C_6H_5$ | H |
| 500-44 | General formula (112) | CN | General formula (112) | Cl | General formula (112) | H | H | $C_6H_5$ | H |
| 500-45 | General formula (112) | CN | General formula (112) | F | General formula (112) | H | H | $C_6H_5$ | H |
| 500-46 | General formula (112) | CN | General formula (112) | $CH_3O$ | General formula (112) | H | H | $C_6H_5$ | H |
| 500-47 | General formula (112) | CN | General formula (112) | $C_2H_5O$ | General formula (112) | H | H | $C_6H_5$ | H |
| 500-48 | General formula (112) | CN | General formula (112) | $C_6H_5O$ | General formula (112) | H | H | $C_6H_5$ | H |
| 500-49 | General formula (112) | CN | General formula (112) | Formula (121) | General formula (112) | H | H | $C_6H_5$ | H |
| 500-50 | General formula (112) | CN | General formula (112) | Formula (122) | General formula (112) | H | H | $C_6H_5$ | H |
| 500-51 | General formula (112) | CN | General formula (112) | Formula (123) | General formula (112) | H | H | $C_6H_5$ | H |
| 500-52 | General formula (112) | CN | General formula (112) | Formula (124) | General formula (112) | H | H | $C_6H_5$ | H |

TABLE 3

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 501 | CN | General formula (112) | General formula (112) | General formula (112) | General formula (112) | H | H | H | H |
| 502 | CN | General formula (112) | General formula (112) | General formula (112) | General formula (112) | H | $CH_3$ | H | H |
| 503 | CN | General formula (112) | General formula (112) | General formula (112) | General formula (112) | H | $CH_3O$ | H | H |
| 504 | CN | General formula (112) | General formula (112) | General formula (112) | General formula (112) | H | H | $CH_3$ | H |
| 505 | CN | General formula (112) | General formula (112) | General formula (112) | General formula (112) | H | H | $CH_3O$ | H |
| 506 | CN | General formula (112) | General formula (112) | General formula (112) | General formula (112) | H | H | $t-C_4H_9$ | H |
| 507 | CN | General formula (112) | General formula (112) | General formula (112) | General formula (112) | H | H | Cl | H |
| 508 | CN | General formula (112) | General formula (112) | General formula (112) | General formula (112) | H | H | F | H |
| 509 | CN | General formula (112) | General formula (112) | General formula (112) | General formula (112) | H | H | H | $CH_3$ |
| 510 | CN | General formula (112) | General formula (112) | General formula (112) | General formula (112) | H | H | H | $CH_3O$ |
| 511 | CN | General formula (112) | General formula (112) | H | H | H | H | H | H |
| 512 | CN | General formula (112) | General formula (112) | H | H | H | H | $CH_3$ | H |
| 513 | CN | General formula (112) | General formula (112) | H | H | H | H | $CH_3O$ | H |
| 514 | CN | General formula (112) | General formula (112) | H | General formula (112) | H | H | H | H |
| 515 | CN | General formula (112) | General formula (112) | H | General formula (112) | H | H | $CH_3$ | H |
| 516 | CN | General formula (112) | General formula (112) | H | General formula (112) | H | H | $CH_3O$ | H |
| 517 | CN | General formula (112) | General formula (112) | H | H | H | H | H | H |
| 518 | CN | General formula (112) | General formula (112) | H | H | H | H | $CH_3$ | H |

TABLE 3-continued

| Compound No. | \multicolumn{5}{c|}{General formula (101)} | \multicolumn{4}{c}{General formula (112)} |
| | $R^1$ | $R^2$ | $R^3$ | $R^4$ | $R^5$ | $R^{31}$, $R^{38}$ | $R^{32}$, $R^{37}$ | $R^{33}$, $R^{36}$ | $R^{34}$, $R^{35}$ |
|---|---|---|---|---|---|---|---|---|---|
| 519 | CN | General formula (112) | General formula (112) | H | H | H | H | CH$_3$O | H |
| 520 | CN | General formula (112) | H | General formula (112) | H | H | H | H | H |
| 521 | CN | General formula (112) | H | General formula (112) | H | H | H | CH$_3$ | H |
| 522 | CN | General formula (112) | H | General formula (112) | H | H | H | CH$_3$O | H |
| 523 | CN | H | General formula (112) | General formula (112) | H | H | H | H | H |
| 524 | CN | H | General formula (112) | General formula (112) | H | H | H | CH$_3$ | H |
| 525 | CN | H | General formula (112) | General formula (112) | H | H | H | CH$_3$O | H |
| 526 | CN | General formula (112) | H | H | General formula (112) | H | H | H | H |
| 527 | CN | General formula (112) | H | H | General formula (112) | H | H | CH$_3$ | H |
| 528 | CN | General formula (112) | H | H | General formula (112) | H | H | CH$_3$O | H |
| 529 | CN | General formula (112) | H | H | H | H | H | H | H |
| 530 | CN | General formula (112) | H | H | H | H | H | CH$_3$ | H |
| 531 | CN | General formula (112) | H | H | H | H | H | CH$_3$O | H |
| 532 | CN | H | General formula (112) | H | H | H | H | H | H |
| 533 | CN | H | General formula (112) | H | H | H | H | CH$_3$ | H |
| 534 | CN | H | General formula (112) | H | H | H | H | CH$_3$O | H |
| 535 | CN | General formula (112) | General formula (112) | General formula (112) | F | H | H | H | H |
| 536 | CN | General formula (112) | General formula (112) | General formula (112) | F | H | H | CH$_3$ | H |
| 537 | CN | General formula (112) | General formula (112) | General formula (112) | F | H | H | CH$_3$O | H |
| 538 | CN | General formula (112) | General formula (112) | F | General formula (112) | H | H | H | H |
| 539 | CN | General formula (112) | General formula (112) | F | General formula (112) | H | H | CH$_3$ | H |
| 540 | CN | General formula (112) | General formula (112) | F | General formula (112) | H | H | CH$_3$O | H |
| 541 | CN | General formula (112) | General formula (112) | F | F | H | H | H | H |
| 542 | CN | General formula (112) | General formula (112) | F | F | H | H | CH$_3$ | H |
| 543 | CN | General formula (112) | General formula (112) | F | F | H | H | CH$_3$O | H |
| 544 | CN | General formula (112) | F | General formula (112) | F | H | H | H | H |
| 545 | CN | General formula (112) | F | General formula (112) | F | H | H | CH$_3$ | H |
| 546 | CN | General formula (112) | F | General formula (112) | F | H | H | CH$_3$O | H |
| 547 | CN | F | General formula (112) | General formula (112) | F | H | H | H | H |
| 548 | CN | F | General formula (112) | General formula (112) | F | H | H | CH$_3$ | H |
| 549 | CN | F | General formula (112) | General formula (112) | F | H | H | CH$_3$O | H |
| 550 | CN | General formula (112) | F | F | General formula (112) | H | H | H | H |
| 551 | CN | General formula (112) | F | F | General formula (112) | H | H | CH$_3$ | H |
| 552 | CN | General formula (112) | F | F | General formula (112) | H | H | CH$_3$O | H |
| 553 | CN | General formula (112) | F | F | F | H | H | H | H |
| 554 | CN | General formula (112) | F | F | F | H | H | CH$_3$ | H |
| 555 | CN | General formula (112) | F | F | F | H | H | CH$_3$O | H |
| 556 | CN | F | General formula (112) | F | F | H | H | H | H |

TABLE 3-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 557 | CN | F | General formula (112) | F | F | H | H | $CH_3$ | H |
| 558 | CN | F | General formula (112) | F | F | H | H | $CH_3O$ | H |
| 559 | CN | General formula (112) | General formula (112) | General formula (112) | OH | H | H | H | H |
| 560 | CN | General formula (112) | General formula (112) | General formula (112) | OH | H | H | $CH_3$ | H |
| 561 | CN | General formula (112) | General formula (112) | General formula (112) | OH | H | H | $CH_3O$ | H |
| 562 | CN | General formula (112) | General formula (112) | OH | General formula (112) | H | H | H | H |
| 563 | CN | General formula (112) | General formula (112) | OH | General formula (112) | H | H | $CH_3$ | H |
| 654 | CN | General formula (112) | General formula (112) | OH | General formula (112) | H | H | $CH_3O$ | H |
| 565 | CN | General formula (112) | General formula (112) | OH | General formula (112) | H | H | Cl | H |
| 566 | CN | General formula (112) | General formula (112) | OH | General formula (112) | H | H | F | H |
| 567 | CN | General formula (112) | General formula (112) | OH | OH | H | H | H | H |
| 568 | CN | General formula (112) | General formula (112) | OH | OH | H | H | $CH_3$ | H |
| 569 | CN | General formula (112) | General formula (112) | OH | OH | H | H | $CH_3O$ | H |
| 570 | CN | General formula (112) | OH | General formula (112) | OH | H | H | H | H |
| 571 | CN | General formula (112) | OH | General formula (112) | OH | H | H | $CH_3$ | H |
| 572 | CN | General formula (112) | OH | General formula (112) | OH | H | H | $CH_3O$ | H |
| 573 | CN | OH | General formula (112) | General formula (112) | OH | H | H | H | H |
| 574 | CN | OH | General formula (112) | General formula (112) | OH | H | H | $CH_3$ | H |
| 575 | CN | OH | General formula (112) | General formula (112) | OH | H | H | $CH_3O$ | H |
| 576 | CN | General formula (112) | OH | OH | General formula (112) | H | H | H | H |
| 577 | CN | General formula (112) | OH | OH | General formula (112) | H | H | $CH_3$ | H |
| 578 | CN | General formula (112) | OH | OH | General formula (112) | H | H | $CH_3O$ | H |
| 579 | CN | General formula (112) | OH | OH | OH | H | H | H | H |
| 580 | CN | General formula (112) | OH | OH | OH | H | H | $CH_3$ | H |
| 581 | CN | General formula (112) | OH | OH | OH | H | H | $CH_3O$ | H |
| 582 | CN | OH | General formula (112) | OH | OH | H | H | H | H |
| 583 | CN | OH | General formula (112) | OH | OH | H | H | $CH_3$ | H |
| 584 | CN | OH | General formula (112) | OH | OH | H | H | $CH_3O$ | H |
| 585 | CN | General formula (112) | General formula (112) | Cl | General formula (112) | H | H | H | H |
| 586 | CN | General formula (112) | General formula (112) | Cl | General formula (112) | H | H | $CH_3$ | H |
| 587 | CN | General formula (112) | General formula (112) | Cl | General formula (112) | H | H | $CH_3O$ | H |
| 588 | CN | General formula (112) | General formula (112) | Cl | General formula (112) | H | H | $t\text{-}C_4H_9$ | H |
| 589 | CN | General formula (112) | General formula (112) | Cl | General formula (112) | H | H | Cl | H |
| 590 | CN | General formula (112) | General formula (112) | Cl | General formula (112) | H | H | F | H |
| 591 | CN | General formula (112) | General formula (112) | F | General formula (112) | H | H | H | H |
| 592 | CN | General formula (112) | General formula (112) | F | General formula (112) | H | H | $CH_3$ | H |
| 593 | CN | General formula (112) | General formula (112) | F | General formula (112) | H | H | $CH_3O$ | H |
| 594 | CN | General formula (112) | General formula (112) | F | General formula (112) | H | H | $t\text{-}C_4H_9$ | H |

TABLE 3-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 595 | CN | General formula (112) | General formula (112) | F | General formula (112) | H | H | Cl | H |
| 596 | CN | General formula (112) | General formula (112) | F | General formula (112) | H | H | F | H |
| 597 | CN | General formula (112) | General formula (112) | $CH_3O$ | General formula (112) | H | H | H | H |
| 598 | CN | General formula (112) | General formula (112) | $CH_3O$ | General formula (112) | H | H | $CH_3$ | H |
| 599 | CN | General formula (112) | General formula (112) | $CH_3O$ | General formula (112) | H | H | $CH_3O$ | H |
| 600 | CN | General formula (112) | General formula (112) | $CH_3O$ | General formula (112) | H | H | $t-C_4H_9$ | H |
| 601 | CN | General formula (112) | General formula (112) | $CH_3O$ | General formula (112) | H | H | Cl | H |
| 602 | CN | General formula (112) | General formula (112) | $CH_3O$ | General formula (112) | H | H | F | H |
| 603 | CN | General formula (112) | General formula (112) | $C_2H_5O$ | General formula (112) | H | H | H | H |
| 604 | CN | General formula (112) | General formula (112) | $C_2H_5O$ | General formula (112) | H | H | $CH_3$ | H |
| 605 | CN | General formula (112) | General formula (112) | $C_2H_5O$ | General formula (112) | H | H | $CH_3O$ | H |
| 606 | CN | General formula (112) | General formula (112) | $C_2H_5O$ | General formula (112) | H | H | $t-C_4H_9$ | H |
| 607 | CN | General formula (112) | General formula (112) | $C_2H_5O$ | General formula (112) | H | H | Cl | H |
| 608 | CN | General formula (112) | General formula (112) | $C_2H_5O$ | General formula (112) | H | H | F | H |
| 609 | CN | General formula (112) | General formula (112) | $C_6H_5O$ | General formula (112) | H | H | H | H |
| 610 | CN | General formula (112) | General formula (112) | $C_6H_5O$ | General formula (112) | H | H | $CH_3$ | H |
| 611 | CN | General formula (112) | General formula (112) | $C_6H_5O$ | General formula (112) | H | H | $CH_3O$ | H |
| 612 | CN | General formula (112) | General formula (112) | $C_6H_5O$ | General formula (112) | H | H | $t-C_4H_9$ | H |
| 613 | CN | General formula (112) | General formula (112) | $C_6H_5O$ | General formula (112) | H | H | Cl | H |
| 614 | CN | General formula (112) | General formula (112) | $C_6H_5O$ | General formula (112) | H | H | F | H |
| 615 | CN | General formula (112) | General formula (112) | Formula (121) | General formula (112) | H | H | H | H |
| 616 | CN | General formula (112) | General formula (112) | Formula (121) | General formula (112) | H | H | $CH_3$ | H |
| 617 | CN | General formula (112) | General formula (112) | Formula (121) | General formula (112) | H | H | $CH_3O$ | H |
| 618 | CN | General formula (112) | General formula (112) | Formula (121) | General formula (112) | H | H | $t-C_4H_9$ | H |
| 619 | CN | General formula (112) | General formula (112) | Formula (121) | General formula (112) | H | H | Cl | H |
| 620 | CN | General formula (112) | General formula (112) | Formula (121) | General formula (112) | H | H | F | H |
| 621 | CN | General formula (112) | General formula (112) | Formula (122) | General formula (112) | H | H | H | H |
| 622 | CN | General formula (112) | General formula (112) | Formula (122) | General formula (112) | H | H | $CH_3$ | H |
| 623 | CN | General formula (112) | General formula (112) | Formula (122) | General formula (112) | H | H | $CH_3O$ | H |
| 624 | CN | General formula (112) | General formula (112) | Formula (122) | General formula (112) | H | H | $t-C_4H_9$ | H |
| 625 | CN | General formula (112) | General formula (112) | Formula (122) | General formula (112) | H | H | Cl | H |
| 626 | CN | General formula (112) | General formula (112) | Formula (122) | General formula (112) | H | H | F | H |
| 627 | CN | General formula (112) | General formula (112) | Formula (123) | General formula (112) | H | H | H | H |
| 628 | CN | General formula (112) | General formula (112) | Formula (123) | General formula (112) | H | H | $CH_3$ | H |
| 629 | CN | General formula (112) | General formula (112) | Formula (123) | General formula (112) | H | H | $CH_3O$ | H |
| 630 | CN | General formula (112) | General formula (112) | Formula (123) | General formula (112) | H | H | $t-C_4H_9$ | H |
| 631 | CN | General formula (112) | General formula (112) | Formula (123) | General formula (112) | H | H | Cl | H |
| 632 | CN | General formula (112) | General formula (112) | Formula (123) | General formula (112) | H | H | F | H |

TABLE 3-continued

| Compound No. | \multicolumn{5}{c}{General formula (101)} | \multicolumn{4}{c}{General formula (112)} |
| --- | --- | --- | --- | --- | --- | --- | --- | --- | --- |
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 633 | CN | General formula (112) | General formula (112) | Formula (124) | General formula (112) | H | H | H | H |
| 634 | CN | General formula (112) | General formula (112) | Formula (124) | General formula (112) | H | H | CH$_3$ | H |
| 635 | CN | General formula (112) | General formula (112) | Formula (124) | General formula (112) | H | H | CH$_3$O | H |
| 636 | CN | General formula (112) | General formula (112) | Formula (124) | General formula (112) | H | H | t-C$_4$H$_9$ | H |
| 637 | CN | General formula (112) | General formula (112) | Formula (124) | General formula (112) | H | H | Cl | H |
| 638 | CN | General formula (112) | General formula (112) | Formula (124) | General formula (112) | H | H | F | H |
| 639 | CN | General formula (112) | General formula (112) | General formula (112) | General formula (112) | H | C$_6$H$_5$ | H | H |
| 640 | CN | General formula (112) | General formula (112) | General formula (112) | General formula (112) | H | H | C$_6$H$_5$ | H |
| 641 | CN | General formula (112) | General formula (112) | General formula (112) | H | H | C$_6$H$_5$ | H | H |
| 642 | CN | General formula (112) | General formula (112) | General formula (112) | H | H | H | C$_6$H$_5$ | H |
| 643 | CN | General formula (112) | General formula (112) | H | General formula (112) | H | C$_6$H$_5$ | H | H |
| 644 | CN | General formula (112) | General formula (112) | H | General formula (112) | H | H | C$_6$H$_5$ | H |
| 645 | CN | General formula (112) | General formula (112) | H | H | H | C$_6$H$_5$ | H | H |
| 646 | CN | General formula (112) | General formula (112) | H | H | H | H | C$_6$H$_5$ | H |
| 647 | CN | General formula (112) | H | General formula (112) | H | H | C$_6$H$_5$ | H | H |
| 648 | CN | General formula (112) | H | General formula (112) | H | H | H | C$_6$H$_5$ | H |
| 649 | CN | H | General formula (112) | General formula (112) | H | H | C$_6$H$_5$ | H | H |
| 650 | CN | H | General formula (112) | General formula (112) | H | H | H | C$_6$H$_5$ | H |
| 651 | CN | H | H | General formula (112) | General formula (112) | H | C$_6$H$_5$ | H | H |
| 652 | CN | H | H | General formula (112) | General formula (112) | H | H | C$_6$H$_5$ | H |
| 653 | CN | General formula (112) | H | H | H | H | C$_6$H$_5$ | H | H |
| 654 | CN | General formula (112) | H | H | H | H | H | C$_6$H$_5$ | H |
| 655 | CN | H | General formula (112) | H | H | H | C$_6$H$_5$ | H | H |
| 656 | CN | H | General formula (112) | H | H | H | H | C$_6$H$_5$ | H |
| 657 | CN | General formula (112) | General formula (112) | General formula (112) | F | H | H | C$_6$H$_5$ | H |
| 658 | CN | General formula (112) | General formula (112) | F | General formula (112) | H | H | C$_6$H$_5$ | H |
| 659 | CN | General formula (112) | General formula (112) | F | F | H | H | C$_6$H$_5$ | H |
| 660 | CN | General formula (112) | F | General formula (112) | F | H | H | C$_6$H$_5$ | H |
| 661 | CN | F | General formula (112) | General formula (112) | F | H | H | C$_6$H$_5$ | H |
| 662 | CN | F | F | General formula (112) | General formula (112) | H | H | C$_6$H$_5$ | H |
| 663 | CN | General formula (112) | F | F | F | H | H | C$_6$H$_5$ | H |
| 664 | CN | F | General formula (112) | F | F | H | H | C$_6$H$_5$ | H |
| 665 | CN | General formula (112) | General formula (112) | General formula (112) | OH | H | H | C$_6$H$_5$ | H |
| 666 | CN | General formula (112) | General formula (112) | OH | General formula (112) | H | H | C$_6$H$_5$ | H |
| 667 | CN | General formula (112) | General formula (112) | OH | OH | H | H | C$_6$H$_5$ | H |
| 668 | CN | General formula (112) | OH | General formula (112) | OH | H | H | C$_6$H$_5$ | H |
| 669 | CN | OH | General formula (112) | General formula (112) | OH | H | H | C$_6$H$_5$ | H |
| 670 | CN | OH | OH | General formula (112) | General formula (112) | H | H | C$_6$H$_5$ | H |

TABLE 3-continued

| Compound No. | General formula (101) | | | | | General formula (112) | | | |
|---|---|---|---|---|---|---|---|---|---|
| | $R^1$ | $R^2$ | $R^3$ | $R^4$ | $R^5$ | $R^{31}$, $R^{38}$ | $R^{32}$, $R^{37}$ | $R^{33}$, $R^{36}$ | $R^{34}$, $R^{35}$ |
| 671 | CN | General formula (112) | OH | OH | OH | H | H | $C_6H_5$ | H |
| 672 | CN | OH | General formula (112) | OH | OH | H | H | $C_6H_5$ | H |
| 673 | CN | General formula (112) | General formula (112) | Cl | General formula (112) | H | H | $C_6H_5$ | H |
| 674 | CN | General formula (112) | General formula (112) | F | General formula (112) | H | H | $C_6H_5$ | H |
| 675 | CN | General formula (112) | General formula (112) | $CH_3O$ | General formula (112) | H | H | $C_6H_5$ | H |
| 676 | CN | General formula (112) | General formula (112) | $C_2H_5O$ | General formula (112) | H | H | $C_6H_5$ | H |
| 677 | CN | General formula (112) | General formula (112) | $C_6H_5O$ | General formula (112) | H | H | $C_6H_5$ | H |
| 678 | CN | General formula (112) | General formula (112) | Formula (121) | General formula (112) | H | H | $C_6H_5$ | H |
| 679 | CN | General formula (112) | General formula (112) | Formula (122) | General formula (112) | H | H | $C_6H_5$ | H |
| 680 | CN | General formula (112) | General formula (112) | Formula (123) | General formula (112) | H | H | $C_6H_5$ | H |
| 681 | CN | General formula (112) | General formula (112) | Formula (124) | General formula (112) | H | H | $C_6H_5$ | H |

TABLE 4

| Compound No. | General formula (101) | | | | |
|---|---|---|---|---|---|
| | $R^1$ | $R^2$ | $R^3$ | $R^4$ | $R^5$ |
| 701 | General formula (113) | General formula (113) | CN | General formula (113) | General formula (113) |
| 702 | General formula (113) | General formula (113) | CN | General formula (113) | General formula (113) |
| 703 | General formula (113) | General formula (113) | CN | General formula (113) | General formula (113) |
| 704 | General formula (113) | General formula (113) | CN | General formula (113) | General formula (113) |
| 705 | General formula (113) | General formula (113) | CN | General formula (113) | General formula (113) |
| 706 | General formula (113) | General formula (113) | CN | General formula (113) | General formula (113) |
| 707 | General formula (113) | General formula (113) | CN | General formula (113) | General formula (113) |
| 708 | General formula (113) | General formula (113) | CN | General formula (113) | General formula (113) |
| 709 | General formula (113) | General formula (113) | CN | General formula (113) | General formula (113) |
| 710 | General formula (113) | General formula (113) | CN | General formula (113) | General formula (113) |
| 711 | General formula (113) | General formula (113) | CN | General formula (113) | General formula (113) |
| 712 | General formula (113) | General formula (113) | CN | General formula (113) | General formula (113) |
| 713 | General formula (113) | General formula (113) | CN | General formula (113) | General formula (113) |
| 714 | General formula (113) | General formula (113) | CN | General formula (113) | General formula (113) |
| 715 | General formula (113) | General formula (113) | CN | General formula (113) | General formula (113) |
| 716 | General formula (113) | General formula (113) | CN | General formula (113) | General formula (113) |
| 717 | General formula (113) | General formula (113) | CN | General formula (113) | General formula (113) |
| 718 | General formula (113) | General formula (113) | CN | General formula (113) | General formula (113) |
| 719 | General formula (113) | General formula (113) | CN | General formula (113) | General formula (113) |
| 720 | General formula (113) | General formula (113) | CN | General formula (113) | General formula (113) |
| 721 | General formula (113) | General formula (113) | CN | General formula (113) | General formula (113) |
| 722 | General formula (113) | General formula (113) | CN | General formula (113) | General formula (113) |
| 723 | General formula (113) | General formula (113) | CN | General formula (113) | General formula (113) |
| 724 | General formula (113) | General formula (113) | CN | General formula (113) | General formula (113) |
| 725 | General formula (113) | General formula (113) | CN | General formula (113) | General formula (113) |
| 726 | General formula (113) | General formula (113) | CN | General formula (113) | General formula (113) |
| 727 | General formula (113) | General formula (113) | CN | General formula (113) | General formula (113) |
| 728 | General formula (113) | General formula (113) | CN | General formula (113) | General formula (113) |
| 729 | General formula (113) | General formula (113) | CN | General formula (113) | General formula (113) |
| 730 | General formula (113) | General formula (113) | CN | General formula (113) | General formula (113) |
| 731 | General formula (113) | General formula (113) | CN | General formula (113) | General formula (113) |
| 732 | General formula (113) | General formula (113) | CN | General formula (113) | General formula (113) |
| 733 | General formula (113) | General formula (113) | CN | General formula (113) | General formula (113) |
| 734 | General formula (113) | General formula (113) | CN | General formula (113) | General formula (113) |
| 735 | General formula (113) | General formula (113) | CN | General formula (113) | H |
| 736 | General formula (113) | General formula (113) | CN | H | General formula (113) |
| 737 | General formula (113) | General formula (113) | CN | H | H |
| 738 | General formula (113) | H | CN | General formula (113) | H |
| 739 | H | General formula (113) | CN | General formula (113) | H |
| 740 | General formula (113) | H | CN | H | H |
| 741 | General formula (113) | General formula (113) | CN | General formula (113) | F |
| 742 | General formula (113) | General formula (113) | CN | F | General formula (113) |
| 743 | General formula (113) | General formula (113) | CN | F | F |
| 744 | General formula (113) | F | CN | General formula (113) | F |

TABLE 4-continued

| | | | | | |
|---|---|---|---|---|---|
| 745 | F | General formula (113) | CN | General formula (113) | F |
| 746 | General formula (113) | F | CN | F | F |
| 747 | General formula (113) | General formula (113) | CN | General formula (113) | OH |
| 748 | General formula (113) | General formula (113) | CN | OH | General formula (113) |
| 749 | General formula (113) | General formula (113) | CN | OH | OH |
| 750 | General formula (113) | OH | CN | General formula (113) | OH |
| 751 | OH | General formula (113) | CN | General formula (113) | OH |
| 752 | General formula (113) | OH | CN | OH | OH |
| 753 | General formula (113) | General formula (113) | CN | Cl | General formula (113) |
| 754 | General formula (113) | General formula (113) | CN | Cl | General formula (113) |
| 755 | General formula (113) | General formula (113) | CN | Cl | General formula (113) |
| 756 | General formula (113) | General formula (113) | CN | Cl | General formula (113) |
| 757 | General formula (113) | General formula (113) | CN | Cl | General formula (113) |
| 758 | General formula (113) | General formula (113) | CN | Cl | General formula (113) |
| 759 | General formula (113) | General formula (113) | CN | F | General formula (113) |
| 760 | General formula (113) | General formula (113) | CN | F | General formula (113) |
| 761 | General formula (113) | General formula (113) | CN | F | General formula (113) |
| 762 | General formula (113) | General formula (113) | CN | F | General formula (113) |
| 763 | General formula (113) | General formula (113) | CN | F | General formula (113) |
| 764 | General formula (113) | General formula (113) | CN | F | General formula (113) |
| 765 | General formula (113) | General formula (113) | CN | CH$_3$O | General formula (113) |
| 766 | General formula (113) | General formula (113) | CN | CH$_3$O | General formula (113) |
| 767 | General formula (113) | General formula (113) | CN | CH$_3$O | General formula (113) |
| 768 | General formula (113) | General formula (113) | CN | CH$_3$O | General formula (113) |
| 769 | General formula (113) | General formula (113) | CN | CH$_3$O | General formula (113) |
| 770 | General formula (113) | General formula (113) | CN | CH$_3$O | General formula (113) |
| 771 | General formula (113) | General formula (113) | CN | C$_2$H$_5$O | General formula (113) |
| 772 | General formula (113) | General formula (113) | CN | C$_2$H$_5$O | General formula (113) |
| 773 | General formula (113) | General formula (113) | CN | C$_2$H$_5$O | General formula (113) |
| 774 | General formula (113) | General formula (113) | CN | C$_2$H$_5$O | General formula (113) |
| 775 | General formula (113) | General formula (113) | CN | C$_2$H$_5$O | General formula (113) |
| 776 | General formula (113) | General formula (113) | CN | C$_2$H$_5$O | General formula (113) |
| 777 | General formula (113) | General formula (113) | CN | C$_6$H$_5$O | General formula (113) |
| 778 | General formula (113) | General formula (113) | CN | C$_6$H$_5$O | General formula (113) |
| 779 | General formula (113) | General formula (113) | CN | C$_6$H$_5$O | General formula (113) |
| 780 | General formula (113) | General formula (113) | CN | C$_6$H$_5$O | General formula (113) |
| 781 | General formula (113) | General formula (113) | CN | C$_6$H$_5$O | General formula (113) |
| 782 | General formula (113) | General formula (113) | CN | C$_6$H$_5$O | General formula (113) |
| 783 | General formula (113) | General formula (113) | CN | Formula (121) | General formula (113) |
| 784 | General formula (113) | General formula (113) | CN | Formula (121) | General formula (113) |
| 785 | General formula (113) | General formula (113) | CN | Formula (121) | General formula (113) |
| 786 | General formula (113) | General formula (113) | CN | Formula (121) | General formula (113) |
| 787 | General formula (113) | General formula (113) | CN | Formula (121) | General formula (113) |
| 788 | General formula (113) | General formula (113) | CN | Formula (121) | General formula (113) |
| 789 | General formula (113) | General formula (113) | CN | Formula (122) | General formula (113) |
| 790 | General formula (113) | General formula (113) | CN | Formula (122) | General formula (113) |
| 791 | General formula (113) | General formula (113) | CN | Formula (122) | General formula (113) |
| 792 | General formula (113) | General formula (113) | CN | Formula (122) | General formula (113) |
| 793 | General formula (113) | General formula (113) | CN | Formula (122) | General formula (113) |
| 794 | General formula (113) | General formula (113) | CN | Formula (122) | General formula (113) |
| 795 | General formula (113) | General formula (113) | CN | Formula (123) | General formula (113) |
| 796 | General formula (113) | General formula (113) | CN | Formula (123) | General formula (113) |
| 797 | General formula (113) | General formula (113) | CN | Formula (123) | General formula (113) |
| 798 | General formula (113) | General formula (113) | CN | Formula (123) | General formula (113) |
| 799 | General formula (113) | General formula (113) | CN | Formula (123) | General formula (113) |
| 800 | General formula (113) | General formula (113) | CN | Formula (123) | General formula (113) |
| 801 | General formula (113) | General formula (113) | CN | Formula (124) | General formula (113) |
| 802 | General formula (113) | General formula (113) | CN | Formula (124) | General formula (113) |
| 803 | General formula (113) | General formula (113) | CN | Formula (124) | General formula (113) |
| 804 | General formula (113) | General formula (113) | CN | Formula (124) | General formula (113) |
| 805 | General formula (113) | General formula (113) | CN | Formula (124) | General formula (113) |
| 806 | General formula (113) | General formula (113) | CN | Formula (124) | General formula (113) |

| Compound No. | General formula (113) | | | | | |
|---|---|---|---|---|---|---|
| | $R^{41}$ | $R^{42}$ | $R^{43}$ | $R^{44}$ | $R^{45}$ | $R^{46}$ |
| 701 | H | H | H | H | H | H |
| 702 | H | CH$_3$ | H | H | H | H |
| 703 | H | CH$_3$O | H | H | H | H |
| 704 | H | H | CH$_3$ | H | H | H |
| 705 | H | H | CH$_3$O | H | H | H |
| 706 | H | H | t-C$_4$H$_9$ | H | H | H |
| 707 | H | H | Cl | H | H | H |
| 708 | H | H | F | H | H | H |
| 709 | H | H | H | CH$_3$ | H | H |
| 710 | H | H | H | CH$_3$O | H | H |
| 711 | H | H | H | H | CH$_3$ | H |
| 712 | H | H | H | H | CH$_3$O | H |
| 713 | H | H | H | H | t-C$_4$H$_9$ | H |

TABLE 4-continued

| | | | | | | |
|---|---|---|---|---|---|---|
| 714 | H | H | H | H | Cl | H |
| 715 | H | H | H | H | F | H |
| 716 | H | H | H | H | C₆H₅ | H |
| 717 | H | H | H | H | p-CH₃C₆H₄ | H |
| 718 | H | H | H | H | 2,4,6-(CH₃)₃C₆H₂ | H |
| 719 | H | H | H | H | p-CH₃OC₆H₄ | H |
| 720 | H | H | H | H | p-(CH₃)₂NC₆H₄ | H |
| 721 | H | H | H | H | p-FC₆H₄ | H |
| 722 | H | H | H | H | p-CNC₆H₄ | H |
| 723 | H | H | H | H | H | CH₃ |
| 724 | H | H | H | H | H | CH₃O |
| 725 | H | H | H | H | H | t-C₄H₉ |
| 726 | H | H | H | H | H | Cl |
| 727 | H | H | H | H | H | F |
| 728 | H | H | H | H | H | C₆H₅ |
| 729 | H | H | H | H | H | p-CH₃C₆H₄ |
| 730 | H | H | H | H | H | 2,4,6-(CH₃)₃C₆H₂ |
| 731 | H | H | H | H | H | p-CH₃OC₆H₄ |
| 732 | H | H | H | H | H | p-(CH₃)₂NC₆H₄ |
| 733 | H | H | H | H | H | p-FC₆H₄ |
| 734 | H | H | H | H | H | p-CNC₆H₄ |
| 735 | H | H | H | H | H | H |
| 736 | H | H | H | H | H | H |
| 737 | H | H | H | H | H | H |
| 738 | H | H | H | H | H | H |
| 739 | H | H | H | H | H | H |
| 740 | H | H | H | H | H | H |
| 741 | H | H | H | H | H | H |
| 742 | H | H | H | H | H | H |
| 743 | H | H | H | H | H | H |
| 744 | H | H | H | H | H | H |
| 745 | H | H | H | H | H | H |
| 746 | H | H | H | H | H | H |
| 747 | H | H | H | H | H | H |
| 748 | H | H | H | H | H | H |
| 749 | H | H | H | H | H | H |
| 750 | H | H | H | H | H | H |
| 751 | H | H | H | H | H | H |
| 752 | H | H | H | H | H | H |
| 753 | H | H | H | H | H | H |
| 754 | H | H | CH₃ | H | H | H |
| 755 | H | H | CH₃O | H | H | H |
| 756 | H | H | t-C₄H₉ | H | H | H |
| 757 | H | H | Cl | H | H | H |
| 758 | H | H | F | H | H | H |
| 759 | H | H | H | H | H | H |
| 760 | H | H | CH₃ | H | H | H |
| 761 | H | H | CH₃O | H | H | H |
| 762 | H | H | t-C₄H₉ | H | H | H |
| 763 | H | H | Cl | H | H | H |
| 764 | H | H | F | H | H | H |
| 765 | H | H | H | H | H | H |
| 766 | H | H | CH₃ | H | H | H |
| 767 | H | H | CH₃O | H | H | H |
| 768 | H | H | t-C₄H₉ | H | H | H |
| 769 | H | H | Cl | H | H | H |
| 770 | H | H | F | H | H | H |
| 771 | H | H | H | H | H | H |
| 772 | H | H | CH₃ | H | H | H |
| 773 | H | H | CH₃O | H | H | H |
| 774 | H | H | t-C₄H₉ | H | H | H |
| 775 | H | H | Cl | H | H | H |
| 776 | H | H | F | H | H | H |
| 777 | H | H | H | H | H | H |
| 778 | H | H | CH₃ | H | H | H |
| 779 | H | H | CH₃O | H | H | H |
| 780 | H | H | t-C₄H₉ | H | H | H |
| 781 | H | H | Cl | H | H | H |
| 782 | H | H | F | H | H | H |
| 783 | H | H | H | H | H | H |
| 784 | H | H | CH₃ | H | H | H |
| 785 | H | H | CH₃O | H | H | H |
| 786 | H | H | t-C₄H₉ | H | H | H |
| 787 | H | H | Cl | H | H | H |
| 788 | H | H | F | H | H | H |
| 789 | H | H | H | H | H | H |
| 790 | H | H | CH₃ | H | H | H |
| 791 | H | H | CH₃O | H | H | H |
| 792 | H | H | t-C₄H₉ | H | H | H |
| 793 | H | H | Cl | H | H | H |

TABLE 4-continued

| | | | | | | |
|---|---|---|---|---|---|---|
| 794 | H | H | F | H | H | H |
| 795 | H | H | H | H | H | H |
| 796 | H | H | CH$_3$ | H | H | H |
| 797 | H | H | CH$_3$O | H | H | H |
| 798 | H | H | t-C$_4$H$_9$ | H | H | H |
| 799 | H | H | Cl | H | H | H |
| 800 | H | H | F | H | H | H |
| 801 | H | H | H | H | H | H |
| 802 | H | H | CH$_3$ | H | H | H |
| 803 | H | H | CH$_3$O | H | H | H |
| 804 | H | H | t-C$_4$H$_9$ | H | H | H |
| 805 | H | H | Cl | H | H | H |
| 806 | H | H | F | H | H | H |

TABLE 5

| Compound No. | General formula (101) | | | | |
|---|---|---|---|---|---|
| | R$^1$ | R$^2$ | R$^3$ | R$^4$ | R$^5$ |
| 901 | General formula (114) | General formula (114) | CN | General formula (114) | General formula (114) |
| 902 | General formula (114) | General formula (114) | CN | General formula (114) | General formula (114) |
| 903 | General formula (114) | General formula (114) | CN | General formula (114) | General formula (114) |
| 904 | General formula (114) | General formula (114) | CN | General formula (114) | General formula (114) |
| 905 | General formula (114) | General formula (114) | CN | General formula (114) | General formula (114) |
| 906 | General formula (114) | General formula (114) | CN | General formula (114) | General formula (114) |
| 907 | General formula (114) | General formula (114) | CN | General formula (114) | General formula (114) |
| 908 | General formula (114) | General formula (114) | CN | General formula (114) | General formula (114) |
| 909 | General formula (114) | General formula (114) | CN | General formula (114) | General formula (114) |
| 910 | General formula (114) | General formula (114) | CN | General formula (114) | General formula (114) |
| 911 | General formula (114) | General formula (114) | CN | General formula (114) | General formula (114) |
| 912 | General formula (114) | General formula (114) | CN | General formula (114) | General formula (114) |
| 913 | General formula (114) | General formula (114) | CN | General formula (114) | General formula (114) |
| 914 | General formula (114) | General formula (114) | CN | General formula (114) | General formula (114) |
| 915 | General formula (114) | General formula (114) | CN | General formula (114) | General formula (114) |
| 916 | General formula (114) | General formula (114) | CN | General formula (114) | General formula (114) |
| 917 | General formula (114) | General formula (114) | CN | General formula (114) | General formula (114) |
| 918 | General formula (114) | General formula (114) | CN | General formula (114) | General formula (114) |
| 919 | General formula (114) | General formula (114) | CN | General formula (114) | H |
| 920 | General formula (114) | General formula (114) | CN | H | General formula (114) |
| 921 | General formula (114) | General formula (114) | CN | H | H |
| 922 | General formula (114) | H | CN | General formula (114) | H |
| 923 | H | General formula (114) | CN | General formula (114) | H |
| 924 | General formula (114) | H | CN | H | H |
| 925 | General formula (114) | General formula (114) | CN | General formula (114) | F |
| 926 | General formula (114) | General formula (114) | CN | F | General formula (114) |
| 927 | General formula (114) | General formula (114) | CN | F | F |
| 928 | General formula (114) | F | CN | General formula (114) | F |
| 929 | F | General formula (114) | CN | General formula (114) | F |
| 930 | General formula (114) | F | CN | F | F |
| 931 | General formula (114) | General formula (114) | CN | General formula (114) | OH |
| 932 | General formula (114) | General formula (114) | CN | OH | General formula (114) |
| 933 | General formula (114) | General formula (114) | CN | OH | OH |
| 934 | General formula (114) | OH | CN | General formula (114) | OH |
| 935 | OH | General formula (114) | CN | General formula (114) | OH |
| 936 | General formula (114) | OH | CN | OH | OH |
| 937 | General formula (114) | General formula (114) | CN | Cl | General formula (114) |
| 938 | General formula (114) | General formula (114) | CN | Cl | General formula (114) |
| 939 | General formula (114) | General formula (114) | CN | Cl | General formula (114) |
| 940 | General formula (114) | General formula (114) | CN | Cl | General formula (114) |
| 941 | General formula (114) | General formula (114) | CN | Cl | General formula (114) |
| 942 | General formula (114) | General formula (114) | CN | Cl | General formula (114) |
| 943 | General formula (114) | General formula (114) | CN | F | General formula (114) |
| 944 | General formula (114) | General formula (114) | CN | F | General formula (114) |
| 945 | General formula (114) | General formula (114) | CN | F | General formula (114) |
| 946 | General formula (114) | General formula (114) | CN | F | General formula (114) |
| 947 | General formula (114) | General formula (114) | CN | F | General formula (114) |
| 948 | General formula (114) | General formula (114) | CN | F | General formula (114) |
| 949 | General formula (114) | General formula (114) | CN | CH$_3$O | General formula (114) |
| 950 | General formula (114) | General formula (114) | CN | CH$_3$O | General formula (114) |
| 951 | General formula (114) | General formula (114) | CN | CH$_3$O | General formula (114) |
| 952 | General formula (114) | General formula (114) | CN | CH$_3$O | General formula (114) |
| 953 | General formula (114) | General formula (114) | CN | CH$_3$O | General formula (114) |
| 954 | General formula (114) | General formula (114) | CN | CH$_3$O | General formula (114) |
| 955 | General formula (114) | General formula (114) | CN | C$_2$H$_5$O | General formula (114) |
| 956 | General formula (114) | General formula (114) | CN | C$_2$H$_5$O | General formula (114) |
| 957 | General formula (114) | General formula (114) | CN | C$_2$H$_5$O | General formula (114) |

TABLE 5-continued

| | | | | | |
|---|---|---|---|---|---|
| 958 | General formula (114) | General formula (114) | CN | $C_2H_5O$ | General formula (114) |
| 959 | General formula (114) | General formula (114) | CN | $C_2H_5O$ | General formula (114) |
| 960 | General formula (114) | General formula (114) | CN | $C_2H_5O$ | General formula (114) |
| 961 | General formula (114) | General formula (114) | CN | $C_6H_5O$ | General formula (114) |
| 962 | General formula (114) | General formula (114) | CN | $C_6H_5O$ | General formula (114) |
| 963 | General formula (114) | General formula (114) | CN | $C_6H_5O$ | General formula (114) |
| 964 | General formula (114) | General formula (114) | CN | $C_6H_5O$ | General formula (114) |
| 965 | General formula (114) | General formula (114) | CN | $C_6H_5O$ | General formula (114) |
| 966 | General formula (114) | General formula (114) | CN | $C_6H_5O$ | General formula (114) |
| 967 | General formula (114) | General formula (114) | CN | Formula (121) | General formula (114) |
| 968 | General formula (114) | General formula (114) | CN | Formula (121) | General formula (114) |
| 969 | General formula (114) | General formula (114) | CN | Formula (121) | General formula (114) |
| 970 | General formula (114) | General formula (114) | CN | Formula (121) | General formula (114) |
| 971 | General formula (114) | General formula (114) | CN | Formula (121) | General formula (114) |
| 972 | General formula (114) | General formula (114) | CN | Formula (121) | General formula (114) |
| 973 | General formula (114) | General formula (114) | CN | Formula (122) | General formula (114) |
| 974 | General formula (114) | General formula (114) | CN | Formula (122) | General formula (114) |
| 975 | General formula (114) | General formula (114) | CN | Formula (122) | General formula (114) |
| 976 | General formula (114) | General formula (114) | CN | Formula (122) | General formula (114) |
| 977 | General formula (114) | General formula (114) | CN | Formula (122) | General formula (114) |
| 978 | General formula (114) | General formula (114) | CN | Formula (122) | General formula (114) |
| 989 | General formula (114) | General formula (114) | CN | Formula (123) | General formula (114) |
| 980 | General formula (114) | General formula (114) | CN | Formula (123) | General formula (114) |
| 981 | General formula (114) | General formula (114) | CN | Formula (123) | General formula (114) |
| 982 | General formula (114) | General formula (114) | CN | Formula (123) | General formula (114) |
| 983 | General formula (114) | General formula (114) | CN | Formula (123) | General formula (114) |
| 984 | General formula (114) | General formula (114) | CN | Formula (123) | General formula (114) |
| 985 | General formula (114) | General formula (114) | CN | Formula (124) | General formula (114) |
| 986 | General formula (114) | General formula (114) | CN | Formula (124) | General formula (114) |
| 987 | General formula (114) | General formula (114) | CN | Formula (124) | General formula (114) |
| 988 | General formula (114) | General formula (114) | CN | Formula (124) | General formula (114) |
| 989 | General formula (114) | General formula (114) | CN | Formula (124) | General formula (114) |
| 990 | General formula (114) | General formula (114) | CN | Formula (124) | General formula (114) |

| | General formula (113) | | | | | | | |
|---|---|---|---|---|---|---|---|---|
| Compound No. | $R^{52}$ | $R^{53}$ | $R^{54}$ | $R^{55}$ | $R^{57}$ | $R^{59}$ | $R^{61}$ | $R^{51}, R^{56}, R^{58}, R^{60}, R^{62}$ |
| 901 | H | H | H | H | H | H | H | H |
| 902 | $CH_3$ | H | H | H | H | H | H | H |
| 903 | $CH_3O$ | H | H | H | H | H | H | H |
| 904 | H | $CH_3$ | H | H | H | H | H | H |
| 905 | H | $CH_3O$ | H | H | H | H | H | H |
| 906 | H | $t-C_4H_9$ | H | H | H | H | H | H |
| 907 | H | Cl | H | H | H | H | H | H |
| 908 | H | F | H | H | H | H | H | H |
| 909 | H | H | $CH_3$ | H | H | H | H | H |
| 910 | H | H | $CH_3O$ | H | H | H | H | H |
| 911 | H | H | H | $CH_3$ | H | H | H | H |
| 912 | H | H | H | $CH_3O$ | H | H | H | H |
| 913 | H | H | H | H | $CH_3$ | H | H | H |
| 914 | H | H | H | H | $CH_3O$ | H | H | H |
| 915 | H | H | H | H | H | $CH_3$ | H | H |
| 916 | H | H | H | H | H | $CH_3O$ | H | H |
| 917 | H | H | H | H | H | H | $CH_3$ | H |
| 918 | H | H | H | H | H | H | $CH_3O$ | H |
| 919 | H | H | H | H | H | H | H | H |
| 920 | H | H | H | H | H | H | H | H |
| 921 | H | H | H | H | H | H | H | H |
| 922 | H | H | H | H | H | H | H | H |
| 923 | H | H | H | H | H | H | H | H |
| 924 | H | H | H | H | H | H | H | H |
| 925 | H | H | H | H | H | H | H | H |
| 926 | H | H | H | H | H | H | H | H |
| 927 | H | H | H | H | H | H | H | H |
| 928 | H | H | H | H | H | H | H | H |
| 929 | H | H | H | H | H | H | H | H |
| 930 | H | H | H | H | H | H | H | H |
| 931 | H | H | H | H | H | H | H | H |
| 932 | H | H | H | H | H | H | H | H |
| 933 | H | H | H | H | H | H | H | H |
| 934 | H | H | H | H | H | H | H | H |
| 935 | H | H | H | H | H | H | H | H |
| 936 | H | H | H | H | H | H | H | H |
| 937 | H | H | H | H | H | H | H | H |
| 938 | H | $CH_3$ | H | H | H | H | H | H |
| 939 | H | $CH_3O$ | H | H | H | H | H | H |
| 940 | H | $t-C_4H_9$ | H | H | H | H | H | H |
| 941 | H | Cl | H | H | H | H | H | H |

TABLE 5-continued

| | | | | | | | | |
|---|---|---|---|---|---|---|---|---|
| 942 | H | F | H | H | H | H | H | H |
| 943 | H | H | H | H | H | H | H | H |
| 944 | H | CH$_3$ | H | H | H | H | H | H |
| 945 | H | CH$_3$O | H | H | H | H | H | H |
| 946 | H | t-C$_4$H$_9$ | H | H | H | H | H | H |
| 947 | H | Cl | H | H | H | H | H | H |
| 948 | H | F | H | H | H | H | H | H |
| 949 | H | H | H | H | H | H | H | H |
| 950 | H | CH$_3$ | H | H | H | H | H | H |
| 951 | H | CH$_3$O | H | H | H | H | H | H |
| 952 | H | t-C$_4$H$_9$ | H | H | H | H | H | H |
| 953 | H | Cl | H | H | H | H | H | H |
| 954 | H | F | H | H | H | H | H | H |
| 955 | H | H | H | H | H | H | H | H |
| 956 | H | CH$_3$ | H | H | H | H | H | H |
| 957 | H | CH$_3$O | H | H | H | H | H | H |
| 958 | H | t-C$_4$H$_9$ | H | H | H | H | H | H |
| 959 | H | Cl | H | H | H | H | H | H |
| 960 | H | F | H | H | H | H | H | H |
| 961 | H | H | H | H | H | H | H | H |
| 962 | H | CH$_3$ | H | H | H | H | H | H |
| 963 | H | CH$_3$O | H | H | H | H | H | H |
| 964 | H | t-C$_4$H$_9$ | H | H | H | H | H | H |
| 965 | H | Cl | H | H | H | H | H | H |
| 966 | H | F | H | H | H | H | H | H |
| 967 | H | H | H | H | H | H | H | H |
| 968 | H | CH$_3$ | H | H | H | H | H | H |
| 969 | H | CH$_3$O | H | H | H | H | H | H |
| 970 | H | t-C$_4$H$_9$ | H | H | H | H | H | H |
| 971 | H | Cl | H | H | H | H | H | H |
| 972 | H | F | H | H | H | H | H | H |
| 973 | H | H | H | H | H | H | H | H |
| 974 | H | CH$_3$ | H | H | H | H | H | H |
| 975 | H | CH$_3$O | H | H | H | H | H | H |
| 976 | H | t-C$_4$H$_9$ | H | H | H | H | H | H |
| 977 | H | Cl | H | H | H | H | H | H |
| 978 | H | F | H | H | H | H | H | H |
| 989 | H | H | H | H | H | H | H | H |
| 980 | H | CH$_3$ | H | H | H | H | H | H |
| 981 | H | CH$_3$O | H | H | H | H | H | H |
| 982 | H | t-C$_4$H$_9$ | H | H | H | H | H | H |
| 983 | H | Cl | H | H | H | H | H | H |
| 984 | H | F | H | H | H | H | H | H |
| 985 | H | H | H | H | H | H | H | H |
| 986 | H | CH$_3$ | H | H | H | H | H | H |
| 987 | H | CH$_3$O | H | H | H | H | H | H |
| 988 | H | t-C$_4$H$_9$ | H | H | H | H | H | H |
| 989 | H | Cl | H | H | H | H | H | H |
| 990 | H | F | H | H | H | H | H | H |

TABLE 6

| Compound No. | General formula (101) | | | | |
|---|---|---|---|---|---|
| | $R^1$ | $R^2$ | $R^3$ | $R^4$ | $R^5$ |
| 1001 | General formula (115) | General formula (115) | CN | General formula (115) | General formula (115) |
| 1002 | General formula (115) | General formula (115) | CN | General formula (115) | General formula (115) |
| 1003 | General formula (115) | General formula (115) | CN | General formula (115) | General formula (115) |
| 1004 | General formula (115) | General formula (115) | CN | General formula (115) | General formula (115) |
| 1005 | General formula (115) | General formula (115) | CN | General formula (115) | General formula (115) |
| 1006 | General formula (115) | General formula (115) | CN | General formula (115) | General formula (115) |
| 1007 | General formula (115) | General formula (115) | CN | General formula (115) | General formula (115) |
| 1008 | General formula (115) | General formula (115) | CN | General formula (115) | General formula (115) |
| 1009 | General formula (115) | General formula (115) | CN | General formula (115) | General formula (115) |
| 1010 | General formula (115) | General formula (115) | CN | General formula (115) | General formula (115) |
| 1011 | General formula (115) | General formula (115) | CN | General formula (115) | General formula (115) |
| 1012 | General formula (115) | General formula (115) | CN | General formula (115) | General formula (115) |
| 1013 | General formula (115) | General formula (115) | CN | General formula (115) | General formula (115) |
| 1014 | General formula (115) | General formula (115) | CN | General formula (115) | General formula (115) |
| 1015 | General formula (115) | General formula (115) | CN | General formula (115) | H |
| 1016 | General formula (115) | General formula (115) | CN | H | General formula (115) |
| 1017 | General formula (115) | General formula (115) | CN | H | H |
| 1018 | General formula (115) | H | CN | General formula (115) | H |
| 1019 | H | General formula (115) | CN | General formula (115) | H |
| 1020 | General formula (115) | H | CN | H | H |
| 1021 | General formula (115) | General formula (115) | CN | General formula (115) | F |

TABLE 6-continued

| | | | | | |
|---|---|---|---|---|---|
| 1022 | General formula (115) | General formula (115) | CN | F | General formula (115) |
| 1023 | General formula (115) | General formula (115) | CN | F | F |
| 1024 | General formula (115) | F | CN | General formula (115) | F |
| 1025 | F | General formula (115) | CN | General formula (115) | F |
| 1026 | General formula (115) | F | CN | F | F |
| 1027 | General formula (115) | General formula (115) | CN | General formula (115) | OH |
| 1028 | General formula (115) | General formula (115) | CN | OH | General formula (115) |
| 1029 | General formula (115) | General formula (115) | CN | OH | OH |
| 1030 | General formula (115) | OH | CN | General formula (115) | OH |
| 1031 | OH | General formula (115) | CN | General formula (115) | OH |
| 1032 | General formula (115) | OH | CN | OH | OH |
| 1033 | General formula (115) | General formula (115) | CN | Cl | General formula (115) |
| 1034 | General formula (115) | General formula (115) | CN | Cl | General formula (115) |
| 1035 | General formula (115) | General formula (115) | CN | Cl | General formula (115) |
| 1036 | General formula (115) | General formula (115) | CN | Cl | General formula (115) |
| 1037 | General formula (115) | General formula (115) | CN | Cl | General formula (115) |
| 1038 | General formula (115) | General formula (115) | CN | Cl | General formula (115) |
| 1039 | General formula (115) | General formula (115) | CN | F | General formula (115) |
| 1040 | General formula (115) | General formula (115) | CN | F | General formula (115) |
| 1041 | General formula (115) | General formula (115) | CN | F | General formula (115) |
| 1042 | General formula (115) | General formula (115) | CN | F | General formula (115) |
| 1043 | General formula (115) | General formula (115) | CN | F | General formula (115) |
| 1044 | General formula (115) | General formula (115) | CN | F | General formula (115) |
| 1045 | General formula (115) | General formula (115) | CN | $CH_3O$ | General formula (115) |
| 1046 | General formula (115) | General formula (115) | CN | $CH_3O$ | General formula (115) |
| 1047 | General formula (115) | General formula (115) | CN | $CH_3O$ | General formula (115) |
| 1048 | General formula (115) | General formula (115) | CN | $CH_3O$ | General formula (115) |
| 1049 | General formula (115) | General formula (115) | CN | $CH_3O$ | General formula (115) |
| 1050 | General formula (115) | General formula (115) | CN | $CH_3O$ | General formula (115) |
| 1051 | General formula (115) | General formula (115) | CN | $C_2H_5O$ | General formula (115) |
| 1052 | General formula (115) | General formula (115) | CN | $C_2H_5O$ | General formula (115) |
| 1053 | General formula (115) | General formula (115) | CN | $C_2H_5O$ | General formula (115) |
| 1054 | General formula (115) | General formula (115) | CN | $C_2H_5O$ | General formula (115) |
| 1055 | General formula (115) | General formula (115) | CN | $C_2H_5O$ | General formula (115) |
| 1056 | General formula (115) | General formula (115) | CN | $C_2H_5O$ | General formula (115) |
| 1057 | General formula (115) | General formula (115) | CN | $C_6H_5O$ | General formula (115) |
| 1058 | General formula (115) | General formula (115) | CN | $C_6H_5O$ | General formula (115) |
| 1059 | General formula (115) | General formula (115) | CN | $C_6H_5O$ | General formula (115) |
| 1060 | General formula (115) | General formula (115) | CN | $C_6H_5O$ | General formula (115) |
| 1061 | General formula (115) | General formula (115) | CN | $C_6H_5O$ | General formula (115) |
| 1062 | General formula (115) | General formula (115) | CN | $C_6H_5O$ | General formula (115) |
| 1063 | General formula (115) | General formula (115) | CN | Formula (121) | General formula (115) |
| 1064 | General formula (115) | General formula (115) | CN | Formula (121) | General formula (115) |
| 1065 | General formula (115) | General formula (115) | CN | Formula (121) | General formula (115) |
| 1066 | General formula (115) | General formula (115) | CN | Formula (121) | General formula (115) |
| 1067 | General formula (115) | General formula (115) | CN | Formula (121) | General formula (115) |
| 1068 | General formula (115) | General formula (115) | CN | Formula (121) | General formula (115) |
| 1069 | General formula (115) | General formula (115) | CN | Formula (122) | General formula (115) |
| 1070 | General formula (115) | General formula (115) | CN | Formula (122) | General formula (115) |
| 1071 | General formula (115) | General formula (115) | CN | Formula (122) | General formula (115) |
| 1072 | General formula (115) | General formula (115) | CN | Formula (122) | General formula (115) |
| 1073 | General formula (115) | General formula (115) | CN | Formula (122) | General formula (115) |
| 1074 | General formula (115) | General formula (115) | CN | Formula (122) | General formula (115) |
| 1075 | General formula (115) | General formula (115) | CN | Formula (123) | General formula (115) |
| 1076 | General formula (115) | General formula (115) | CN | Formula (123) | General formula (115) |
| 1077 | General formula (115) | General formula (115) | CN | Formula (123) | General formula (115) |
| 1078 | General formula (115) | General formula (115) | CN | Formula (123) | General formula (115) |
| 1079 | General formula (115) | General formula (115) | CN | Formula (123) | General formula (115) |
| 1080 | General formula (115) | General formula (115) | CN | Formula (123) | General formula (115) |
| 1081 | General formula (115) | General formula (115) | CN | Formula (124) | General formula (115) |
| 1082 | General formula (115) | General formula (115) | CN | Formula (124) | General formula (115) |
| 1083 | General formula (115) | General formula (115) | CN | Formula (124) | General formula (115) |
| 1084 | General formula (115) | General formula (115) | CN | Formula (124) | General formula (115) |
| 1085 | General formula (115) | General formula (115) | CN | Formula (124) | General formula (115) |
| 1086 | General formula (115) | General formula (115) | CN | Formula (124) | General formula (115) |

| Compound No. | General formula (115) | | | | |
|---|---|---|---|---|---|
| | $R^{71}, R^{80}$ | $R^{72}, R^{79}$ | $R^{73}, R^{78}$ | $R^{74}, R^{77}$ | $R^{75}, R^{76}$ |
| 1001 | H | H | H | H | H |
| 1002 | H | $CH_3$ | H | H | H |
| 1003 | H | $CH_3O$ | H | H | H |
| 1004 | H | $C_6H_5$ | H | H | H |
| 1005 | H | $CH_3$ | H | $CH_3$ | H |
| 1006 | H | $CH_3O$ | H | $CH_3O$ | H |
| 1007 | H | $C_6H_5$ | H | $C_6H_5$ | H |
| 1008 | H | H | $CH_3$ | H | H |
| 1009 | H | H | $CH_3O$ | H | H |
| 1010 | H | H | $t-C_4H_9$ | H | H |

TABLE 6-continued

| | | | | | |
|---|---|---|---|---|---|
| 1011 | H | H | Cl | H | H |
| 1012 | H | H | F | H | H |
| 1013 | H | H | C$_6$H$_5$ | H | H |
| 1014 | H | H | p-C$_6$H$_5$—C$_6$H$_4$ | H | H |
| 1015 | H | H | H | H | H |
| 1016 | H | H | H | H | H |
| 1017 | H | H | H | H | H |
| 1018 | H | H | H | H | H |
| 1019 | H | H | H | H | H |
| 1020 | H | H | H | H | H |
| 1021 | H | H | H | H | H |
| 1022 | H | H | H | H | H |
| 1023 | H | H | H | H | H |
| 1024 | H | H | H | H | H |
| 1025 | H | H | H | H | H |
| 1026 | H | H | H | H | H |
| 1027 | H | H | H | H | H |
| 1028 | H | H | H | H | H |
| 1029 | H | H | H | H | H |
| 1030 | H | H | H | H | H |
| 1031 | H | H | H | H | H |
| 1032 | H | H | H | H | H |
| 1033 | H | H | H | H | H |
| 1034 | H | H | CH$_3$ | H | H |
| 1035 | H | H | CH$_3$O | H | H |
| 1036 | H | H | t-C$_4$H$_9$ | H | H |
| 1037 | H | H | Cl | H | H |
| 1038 | H | H | F | H | H |
| 1039 | H | H | H | H | H |
| 1040 | H | H | CH$_3$ | H | H |
| 1041 | H | H | CH$_3$O | H | H |
| 1042 | H | H | t-C$_4$H$_9$ | H | H |
| 1043 | H | H | Cl | H | H |
| 1044 | H | H | F | H | H |
| 1045 | H | H | H | H | H |
| 1046 | H | H | CH$_3$ | H | H |
| 1047 | H | H | CH$_3$O | H | H |
| 1048 | H | H | t-C$_4$H$_9$ | H | H |
| 1049 | H | H | Cl | H | H |
| 1050 | H | H | F | H | H |
| 1051 | H | H | H | H | H |
| 1052 | H | H | CH$_3$ | H | H |
| 1053 | H | H | CH$_3$O | H | H |
| 1054 | H | H | t-C$_4$H$_9$ | H | H |
| 1055 | H | H | Cl | H | H |
| 1056 | H | H | F | H | H |
| 1057 | H | H | H | H | H |
| 1058 | H | H | CH$_3$ | H | H |
| 1059 | H | H | CH$_3$O | H | H |
| 1060 | H | H | t-C$_4$H$_9$ | H | H |
| 1061 | H | H | Cl | H | H |
| 1062 | H | H | F | H | H |
| 1063 | H | H | H | H | H |
| 1064 | H | H | CH$_3$ | H | H |
| 1065 | H | H | CH$_3$O | H | H |
| 1066 | H | H | t-C$_4$H$_9$ | H | H |
| 1067 | H | H | Cl | H | H |
| 1068 | H | H | F | H | H |
| 1069 | H | H | H | H | H |
| 1070 | H | H | CH$_3$ | H | H |
| 1071 | H | H | CH$_3$O | H | H |
| 1072 | H | H | t-C$_4$H$_9$ | H | H |
| 1073 | H | H | Cl | H | H |
| 1074 | H | H | F | H | H |
| 1075 | H | H | H | H | H |
| 1076 | H | H | CH$_3$ | H | H |
| 1077 | H | H | CH$_3$O | H | H |
| 1078 | H | H | t-C$_4$H$_9$ | H | H |
| 1079 | H | H | Cl | H | H |
| 1080 | H | H | F | H | H |
| 1081 | H | H | H | H | H |
| 1082 | H | H | CH$_3$ | H | H |
| 1083 | H | H | CH$_3$O | H | H |
| 1084 | H | H | t-C$_4$H$_9$ | H | H |
| 1085 | H | H | Cl | H | H |
| 1086 | H | H | F | H | H |

Preferred delayed fluorescent materials include the following compounds.

[1] A compound represented by the following general formula (131):

[Chem. 16]

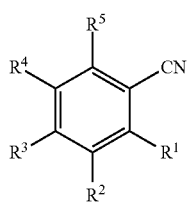

General Formula (131)

[In the general formula (131), from 0 to 1 of $R^1$ to $R^5$ represents a cyano group, from 1 to 5 of $R^1$ to $R^5$ each represent a group represented by the following general formula (132), and the balance of $R^1$ to $R^5$ each represent a hydrogen atom or a substituent other than the above.]

[Chem. 17]

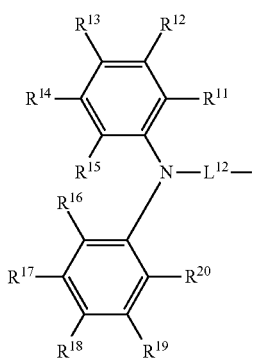

General Formula (132)

[In the general formula (132), $R^{11}$ to $R^{20}$ each independently represent a hydrogen atom or a substituent. $R^{11}$ and $R^{12}$, $R^{12}$ and $R^{13}$, $R^{13}$ and $R^{14}$, $R^{14}$ and $R^{15}$, $R^{15}$ and $R^{16}$, $R^{16}$ and $R^{17}$, $R^{17}$ and $R^{18}$, $R^{18}$ and $R^{19}$, and $R^{19}$ and $R^{20}$ each may be bonded to each other to form a cyclic structure. $L^{12}$ represents a substituted or unsubstituted arylene group or a substituted or unsubstituted heteroarylene group.]

[2] The compound according to [1], wherein the group represented by the general formula (132) is a group represented by any one of the following general formulae (133) to (138):

[Chem. 18]

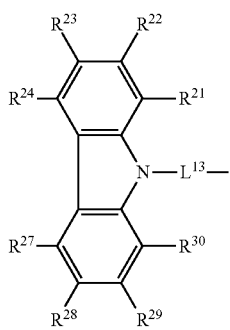

General Formula (133)

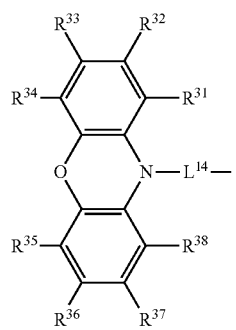

General Formula (134)

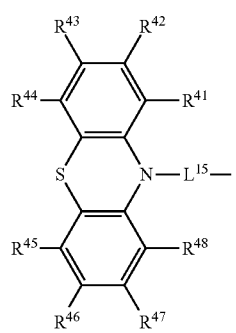

General Formula (135)

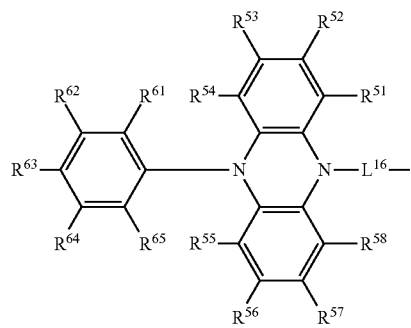

General Formula (136)

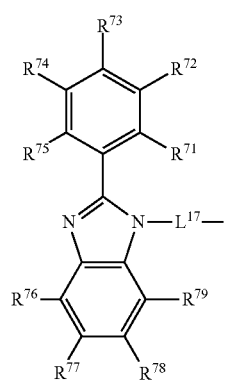

General Formula (137)

General Formula (138)

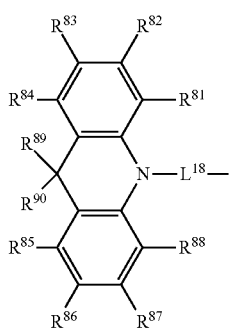

[In the general formulae (133) to (138), $R^{21}$ to $R^{24}$, $R^{27}$ to $R^{38}$, $R^{41}$ to $R^{48}$, $R^{51}$ to $R^{58}$, $R^{61}$ to $R^{65}$, $R^{71}$ to $R^{79}$, $R^{81}$ to $R^{90}$ each independently represent a hydrogen atom or a substituent. $R^{21}$ and $R^{22}$, $R^{22}$ and $R^{23}$, $R^{23}$ and $R^{24}$, $R^{27}$ and $R^{28}$, $R^8$ and $R^9$, $R^{29}$ and $R^{30}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{64}$ and $R^{65}$, $R^{54}$ and $R^{61}$, $R^{55}$ and $R^{65}$, $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$, $R^{81}$ and $R^{82}$, $R^{82}$ and $R^{83}$, $R^{83}$ and $R^{84}$, $R^{85}$ and $R^{86}$, $R^{86}$ and $R^{87}$, $R^{87}$ and $R^{88}$, and $R^{89}$ and $R^{90}$ each may be bonded to each other to form a cyclic structure. $L^{13}$ to $L^{18}$ each independently represent a substituted or unsubstituted arylene group or a substituted or unsubstituted heteroarylene group.]

[3] The compound according to [1] or [2], wherein in the general formula (131), $R^3$ represents a cyano group.

[4] The compound according to any one of [1] to [3], wherein in the general formula (131), $R^1$ and $R^4$ each represent a group represented by the general formula (132).

[5] The compound according to any one of [1] to [4], wherein in the general formula (132), $L^{12}$ represents a phenylene group.

[6] The compound according to any one of [1] to [5], wherein the group represented by the general formula (132) is a group represented by the general formula (133).

[7] The compound according to [6], wherein in the general formula (133), $L^{13}$ represents a 1,3-phenylene group.

[8] The compound according to any one of [1] to [5], wherein the group represented by the general formula (132) is a group represented by the general formula (134).

[9] The compound according to [8], wherein in the general formula (134), $L^{14}$ represents a 1,4-phenylene group.

[10] The compound according to any one of [1] to [5], wherein the group represented by the general formula (132) is a group represented by the general formula (138).

[11] The compound according to [10], wherein in the general formula (132), $L^{18}$ represents a 1,4-phenylene group.

Examples of the compound include the following compounds.

[Chem. 19]

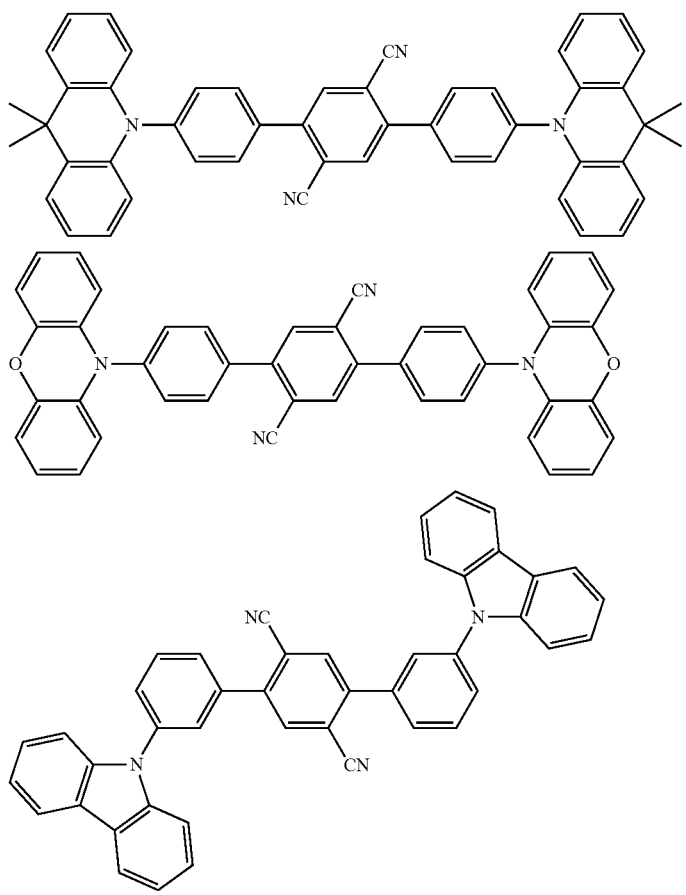

-continued
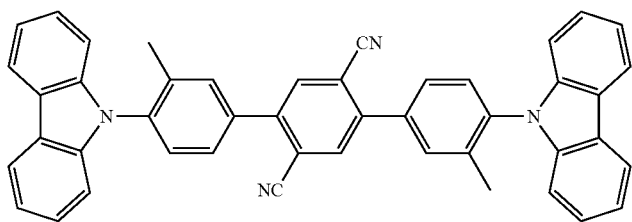
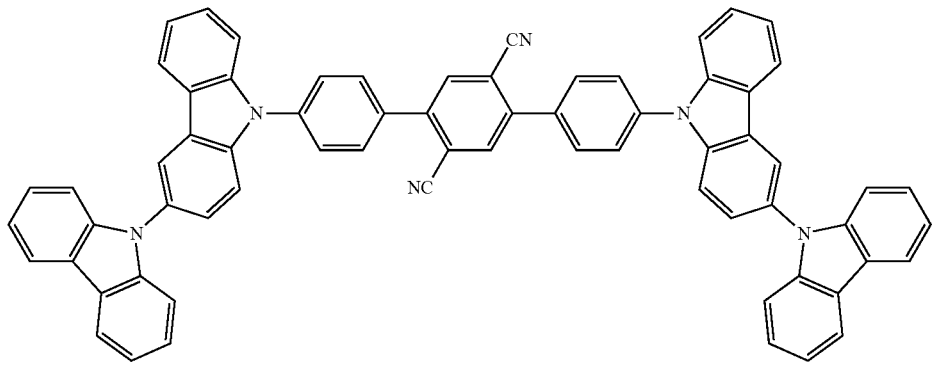
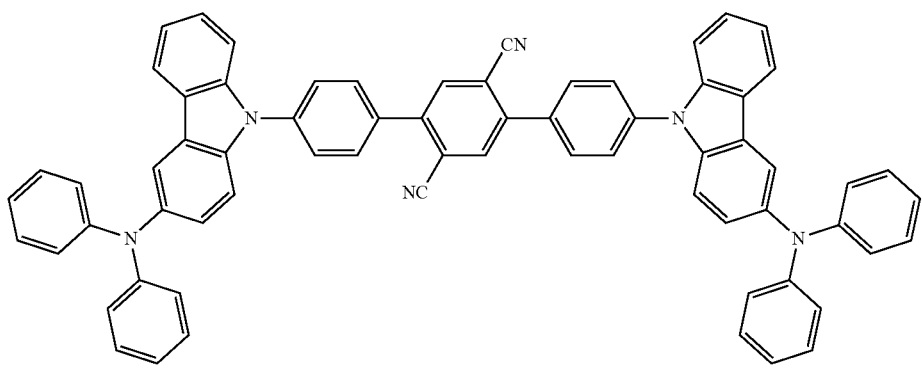
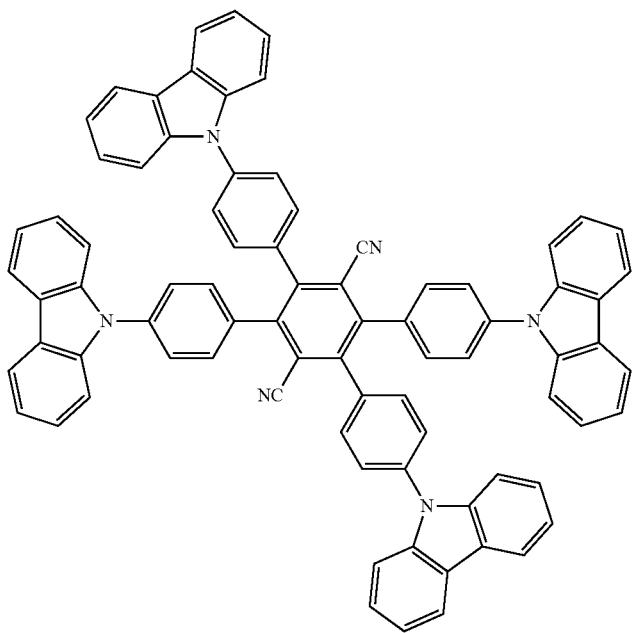

-continued
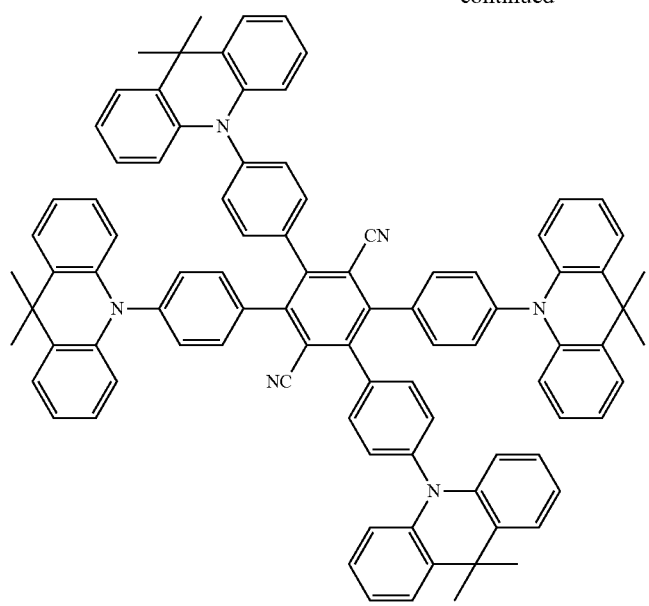
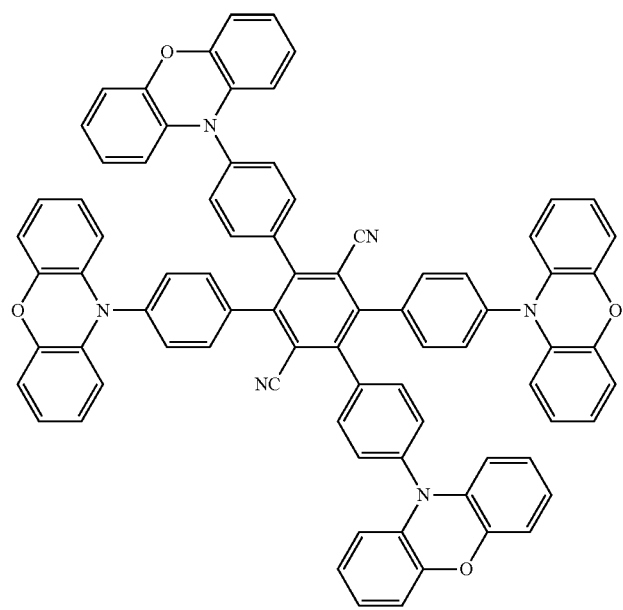

-continued
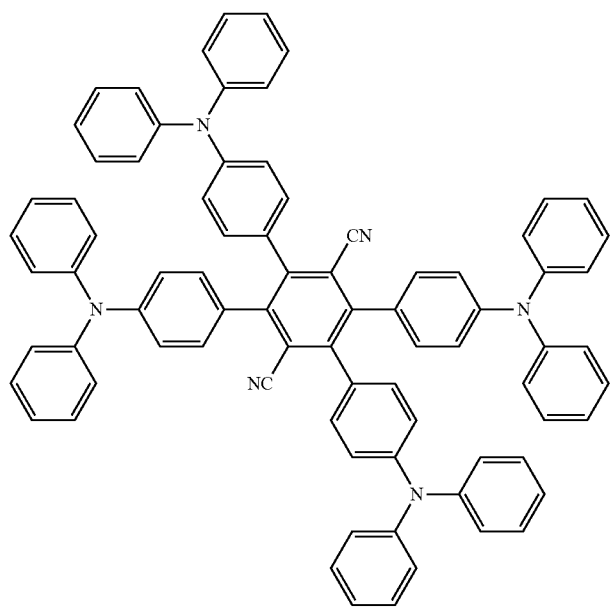
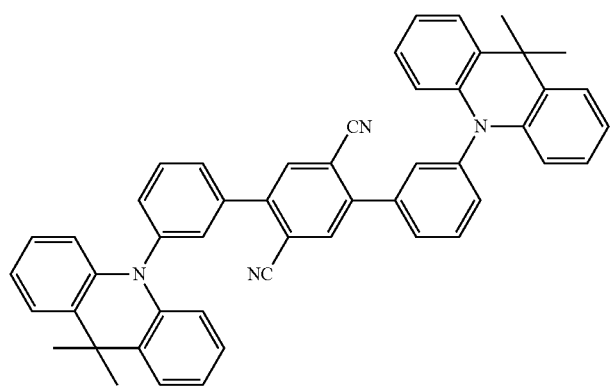
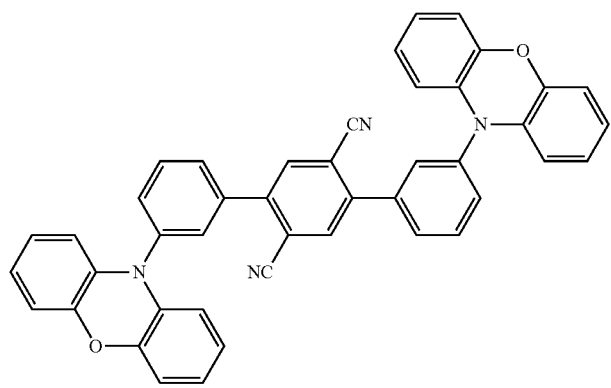

-continued
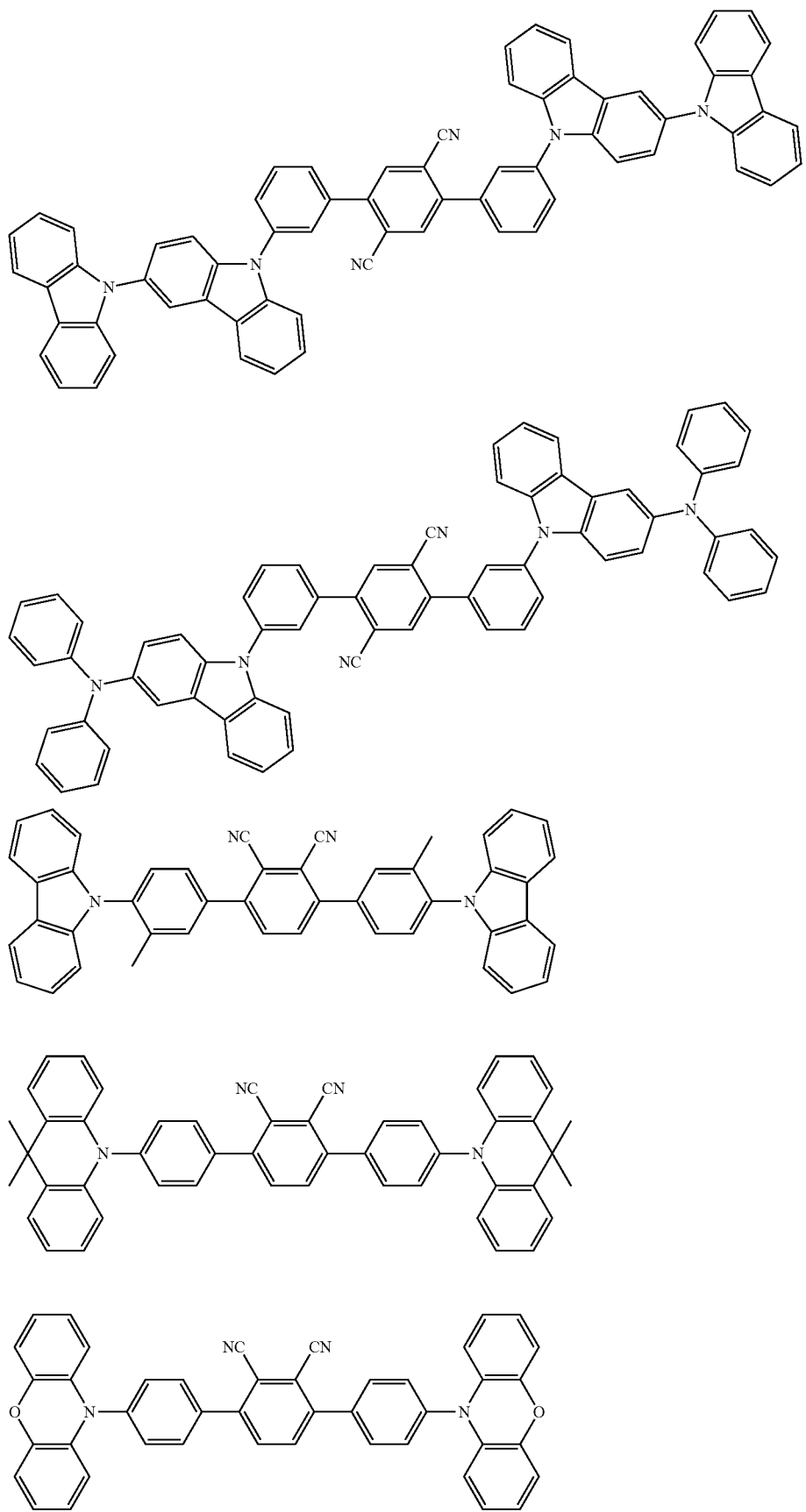

-continued
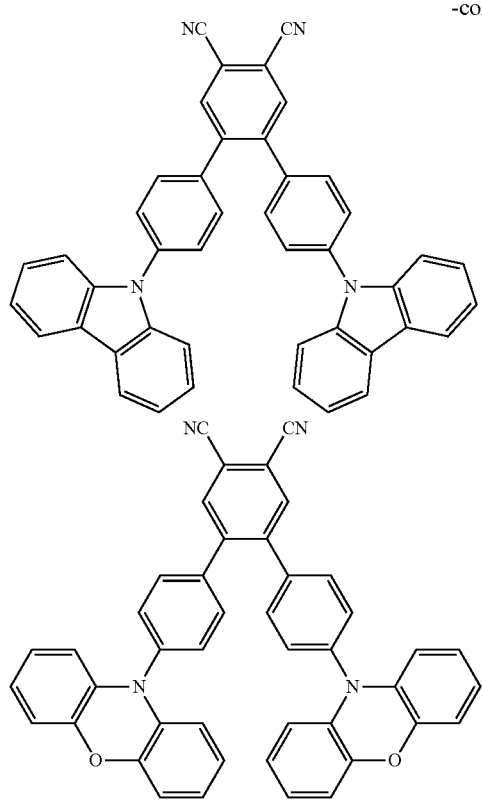
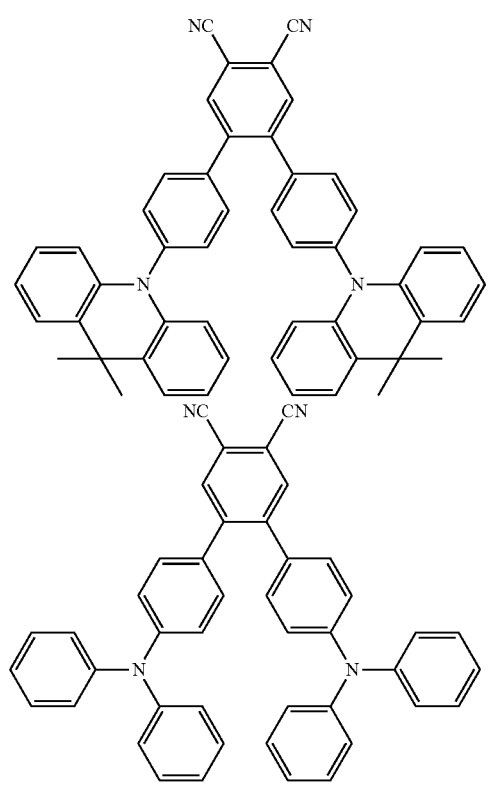
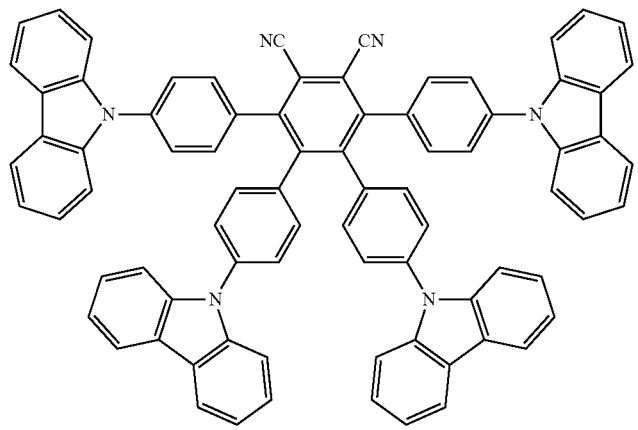
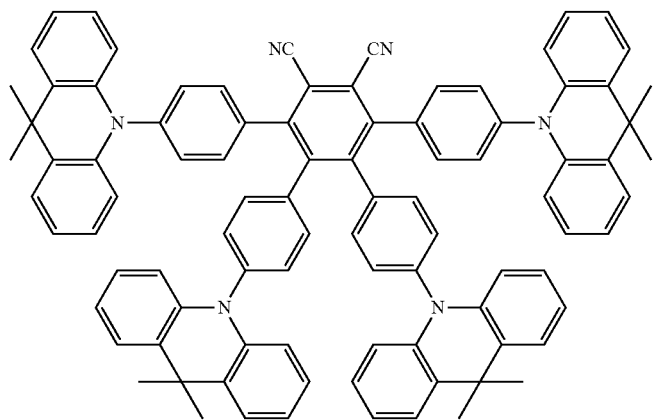

-continued
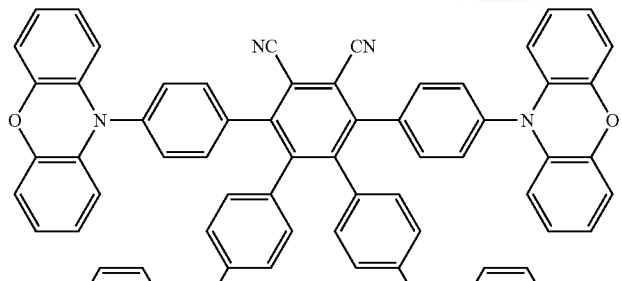
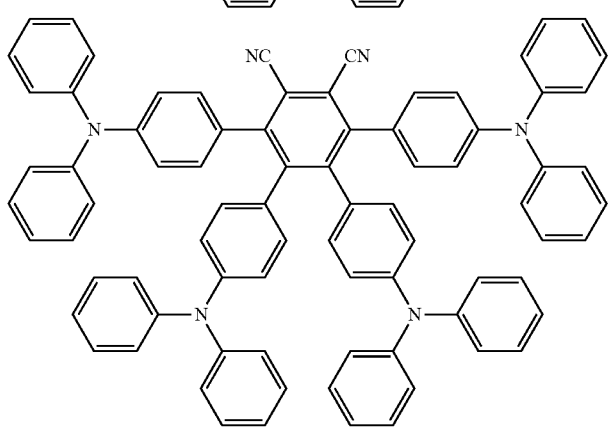
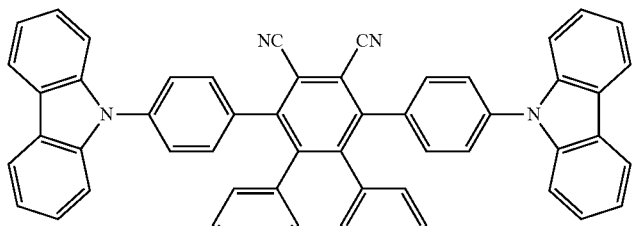
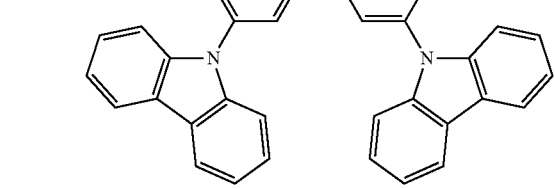
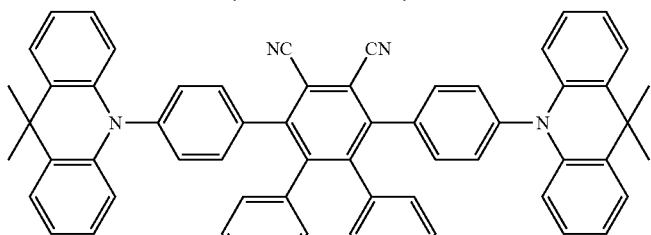
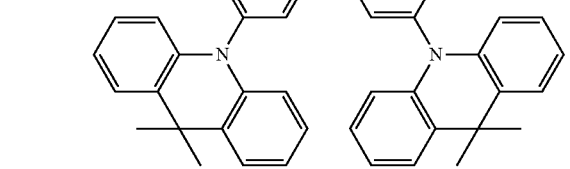

-continued
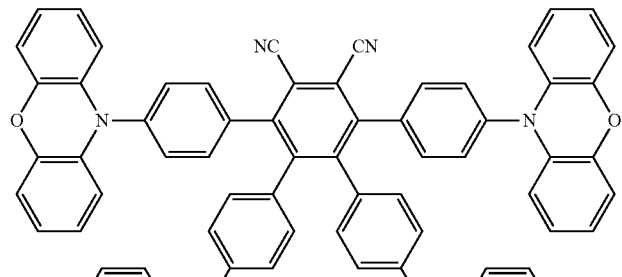
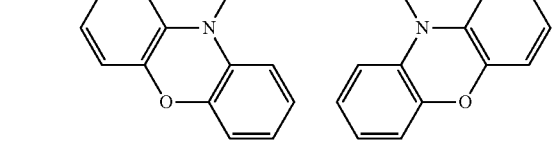
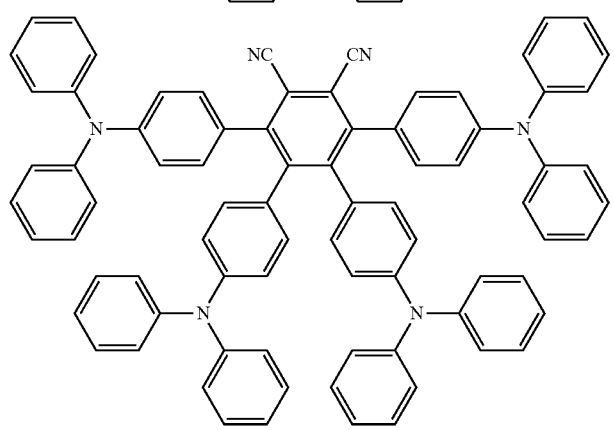
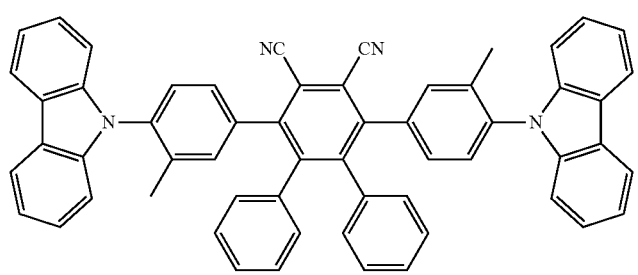
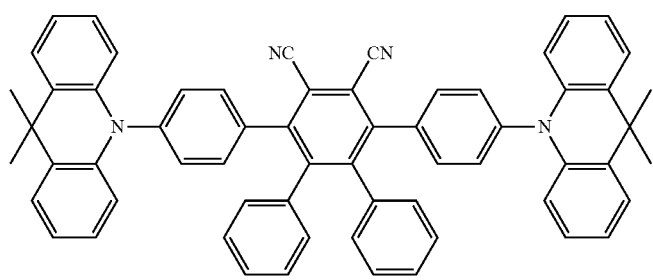
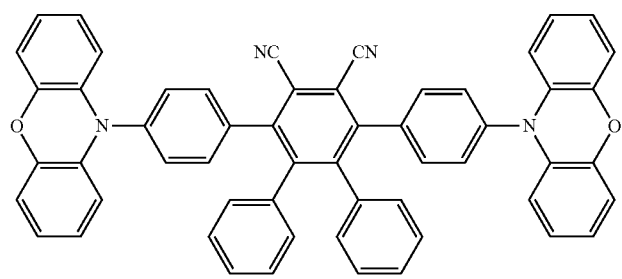

-continued

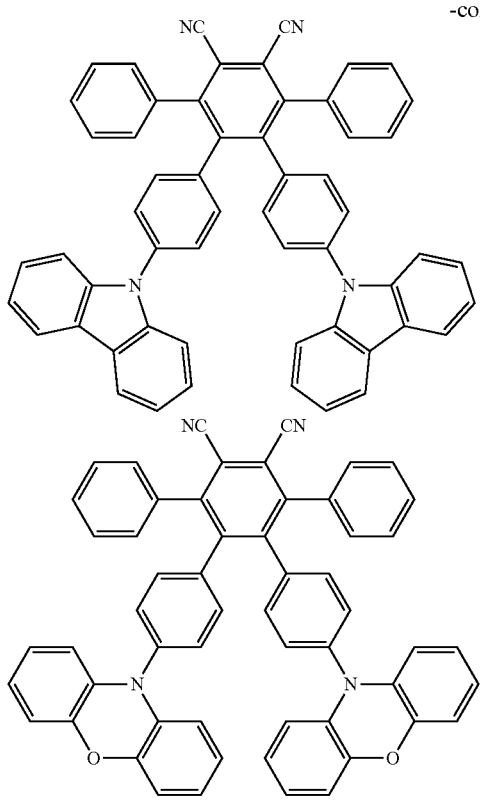

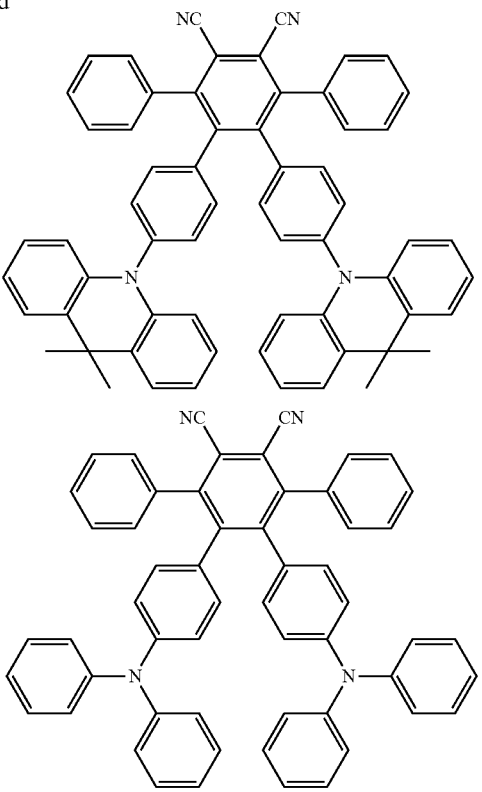

Examples of the preferred delayed fluorescent material include compounds represented by the following general formula. The entire description of WO 2013/011954 including the paragraphs 0007 to 0047 and 0073 to 0085 is incorporated herein by reference as a part of the description of the present application.

[Chem. 20]

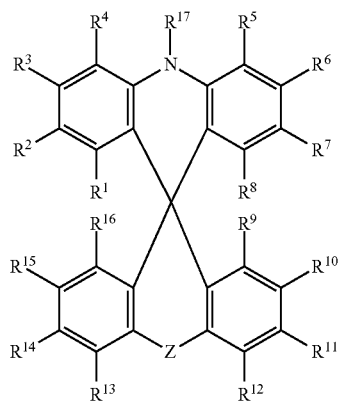

General Formula (141)

[In the general formula (141), $R^1$, $R^2$, $R^3$, $R^4$, $R^5$, $R^6$, $R^7$, $R^8$ and $R^{17}$ each independently represent a hydrogen atom or an electron donating group, provided that at least one thereof represents an electron donating group. $R^9$, $R^{10}$, $R^{11}$, $R^{12}$, $R^{13}$, $R^{14}$, $R^{15}$ and $R^{16}$ each independently represent a hydro-gen atom or an electron withdrawing group having no unshared electron pair at the α-position. Z represents a single bond or >C=Y, wherein Y represents O, S, $C(CN)_2$ or $C(COOH)_2$, provided that when Z represents a single bond, at least one of $R^9$, $R^{10}$, $R^{11}$, $R^{12}$, $R^{13}$, $R^{14}$, $R^{15}$ and $R^{16}$ represents an electron withdrawing group having no unshared electron pair at the α-position.

Specific examples of the compounds include the compounds shown in the following Table 7 to Table 16. In the Tables, D1 to D3 represent the following aryl groups substituted by an electron donating group, respectively; A1 to A5 represent the following electron withdrawing groups, respectively; H represents a hydrogen atom; and Ph represents a phenyl group.

[Chem. 21]

D1

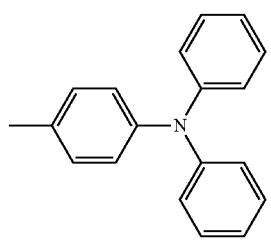

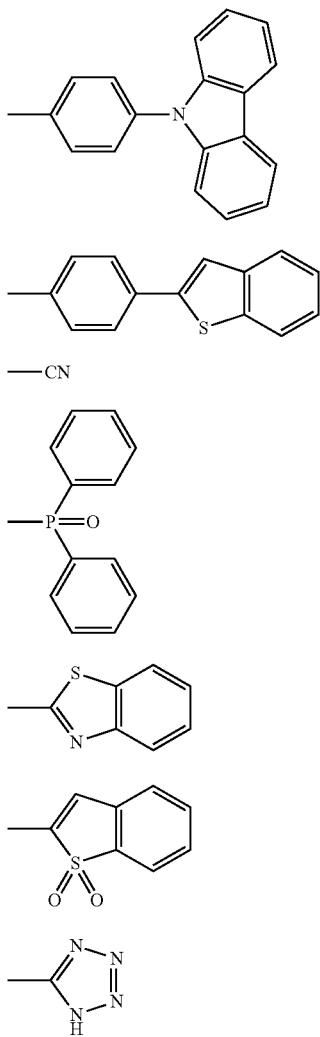

| Label | |
|---|---|
| D2 | (N-(p-tolyl)carbazole) |
| D3 | (2-(p-tolyl)benzothiophene) |
| A1 | —CN |
| A2 | —P(=O)Ph₂ |
| A3 | (2-methylbenzothiazole) |
| A4 | (2-methylbenzothiophene S,S-dioxide) |
| A5 | (5-methyl-1H-tetrazole) |

TABLE 7

| Compound No. | R² | R⁷ | R¹⁰ | R¹⁵ | R¹⁷ | Z | Other Rs |
|---|---|---|---|---|---|---|---|
| 2001 | H | H | A1 | A1 | Ph | single bond | H |
| 2002 | H | D1 | A1 | A1 | Ph | single bond | H |
| 2003 | H | D2 | A1 | A1 | Ph | single bond | H |
| 2004 | H | D3 | A1 | A1 | Ph | single bond | H |
| 2005 | H | H | A2 | A2 | Ph | single bond | H |
| 2006 | H | D1 | A2 | A2 | Ph | single bond | H |
| 2007 | H | D2 | A2 | A2 | Ph | single bond | H |
| 2008 | H | D3 | A2 | A2 | Ph | single bond | H |
| 2009 | H | H | A3 | A3 | Ph | single bond | H |
| 2010 | H | D1 | A3 | A3 | Ph | single bond | H |
| 2011 | H | D2 | A3 | A3 | Ph | single bond | H |
| 2012 | H | D3 | A3 | A3 | Ph | single bond | H |
| 2013 | H | H | A4 | A4 | Ph | single bond | H |
| 2014 | H | D1 | A4 | A4 | Ph | single bond | H |
| 2015 | H | D2 | A4 | A4 | Ph | single bond | H |
| 2016 | H | D3 | A4 | A4 | Ph | single bond | H |
| 2017 | H | H | A5 | A5 | Ph | single bond | H |
| 2018 | H | D1 | A5 | A5 | Ph | single bond | H |
| 2019 | H | D2 | A5 | A5 | Ph | single bond | H |
| 2020 | H | D3 | A5 | A5 | Ph | single bond | H |
| 2021 | D1 | D1 | A1 | A1 | Ph | single bond | H |
| 2022 | D2 | D2 | A1 | A1 | Ph | single bond | H |
| 2023 | D3 | D3 | A1 | A1 | Ph | single bond | H |
| 2024 | D1 | D1 | A2 | A2 | Ph | single bond | H |
| 2025 | D2 | D2 | A2 | A2 | Ph | single bond | H |
| 2026 | D3 | D3 | A2 | A2 | Ph | single bond | H |
| 2027 | D1 | D1 | A3 | A3 | Ph | single bond | H |
| 2028 | D2 | D2 | A3 | A3 | Ph | single bond | H |
| 2029 | D3 | D3 | A3 | A3 | Ph | single bond | H |
| 2030 | D1 | D1 | A4 | A4 | Ph | single bond | H |
| 2031 | D2 | D2 | A4 | A4 | Ph | single bond | H |
| 2032 | D3 | D3 | A4 | A4 | Ph | single bond | H |
| 2033 | D1 | D1 | A5 | A5 | Ph | single bond | H |
| 2034 | D2 | D2 | A5 | A5 | Ph | single bond | H |
| 2035 | D3 | D3 | A5 | A5 | Ph | single bond | H |

TABLE 8

| Compound No. | R³ | R⁶ | R¹¹ | R¹⁴ | R¹⁷ | Z | Other Rs |
|---|---|---|---|---|---|---|---|
| 2036 | H | H | H | A1 | Ph | single bond | H |
| 2037 | H | D1 | H | A1 | Ph | single bond | H |
| 2038 | H | D2 | H | A1 | Ph | single bond | H |
| 2039 | H | D3 | H | A1 | Ph | single bond | H |
| 2040 | H | H | H | A2 | Ph | single bond | H |
| 2041 | H | D1 | H | A2 | Ph | single bond | H |
| 2042 | H | D2 | H | A2 | Ph | single bond | H |
| 2043 | H | D3 | H | A2 | Ph | single bond | H |
| 2044 | H | H | H | A3 | Ph | single bond | H |
| 2045 | H | D1 | H | A3 | Ph | single bond | H |
| 2046 | H | D2 | H | A3 | Ph | single bond | H |
| 2047 | H | D3 | H | A3 | Ph | single bond | H |
| 2048 | H | H | H | A4 | Ph | single bond | H |
| 2049 | H | D1 | H | A4 | Ph | single bond | H |
| 2050 | H | D2 | H | A4 | Ph | single bond | H |
| 2051 | H | D3 | H | A4 | Ph | single bond | H |
| 2052 | H | H | H | A5 | Ph | single bond | H |
| 2053 | H | D1 | H | A5 | Ph | single bond | H |
| 2054 | H | D2 | H | A5 | Ph | single bond | H |
| 2055 | H | D3 | H | A5 | Ph | single bond | H |
| 2056 | D1 | D1 | H | A1 | Ph | single bond | H |
| 2057 | D2 | D2 | H | A1 | Ph | single bond | H |
| 2058 | D3 | D3 | H | A1 | Ph | single bond | H |
| 2059 | D1 | D1 | H | A2 | Ph | single bond | H |
| 2060 | D2 | D2 | H | A2 | Ph | single bond | H |
| 2061 | D3 | D3 | H | A2 | Ph | single bond | H |
| 2062 | D1 | D1 | H | A3 | Ph | single bond | H |
| 2063 | D2 | D2 | H | A3 | Ph | single bond | H |
| 2064 | D3 | D3 | H | A3 | Ph | single bond | H |
| 2065 | D1 | D1 | H | A4 | Ph | single bond | H |
| 2066 | D2 | D2 | H | A4 | Ph | single bond | H |
| 2067 | D3 | D3 | H | A4 | Ph | single bond | H |
| 2068 | D1 | D1 | H | A5 | Ph | single bond | H |
| 2069 | D2 | D2 | H | A5 | Ph | single bond | H |
| 2070 | D3 | D3 | H | A5 | Ph | single bond | H |

TABLE 9

| Compound No. | R² | R⁷ | R¹⁰ | R¹⁵ | R¹⁷ | Z | Other Rs |
|---|---|---|---|---|---|---|---|
| 2071 | H | H | A1 | A1 | Ph | C=O | H |
| 2072 | H | D1 | A1 | A1 | Ph | C=O | H |
| 2073 | H | D2 | A1 | A1 | Ph | C=O | H |
| 2074 | H | D3 | A1 | A1 | Ph | C=O | H |
| 2075 | H | H | A2 | A2 | Ph | C=O | H |
| 2076 | H | D1 | A2 | A2 | Ph | C=O | H |
| 2077 | H | D2 | A2 | A2 | Ph | C=O | H |
| 2078 | H | D3 | A2 | A2 | Ph | C=O | H |
| 2079 | H | H | A3 | A3 | Ph | C=O | H |
| 2080 | H | D1 | A3 | A3 | Ph | C=O | H |
| 2081 | H | D2 | A3 | A3 | Ph | C=O | H |
| 2082 | H | D3 | A3 | A3 | Ph | C=O | H |
| 2083 | H | H | A4 | A4 | Ph | C=O | H |
| 2084 | H | D1 | A4 | A4 | Ph | C=O | H |
| 2085 | H | D2 | A4 | A4 | Ph | C=O | H |
| 2086 | H | D3 | A4 | A4 | Ph | C=O | H |
| 2087 | H | H | A5 | A5 | Ph | C=O | H |

TABLE 9-continued

| Compound No. | R² | R⁷ | R¹⁰ | R¹⁵ | R¹⁷ | Z | Other Rs |
|---|---|---|---|---|---|---|---|
| 2088 | H | D1 | A5 | A5 | Ph | C=O | H |
| 2089 | H | D2 | A5 | A5 | Ph | C=O | H |
| 2090 | H | D3 | A5 | A5 | Ph | C=O | H |
| 2091 | D1 | D1 | A1 | A1 | Ph | C=O | H |
| 2092 | D2 | D2 | A1 | A1 | Ph | C=O | H |
| 2093 | D3 | D3 | A1 | A1 | Ph | C=O | H |
| 2094 | D1 | D1 | A2 | A2 | Ph | C=O | H |
| 2095 | D2 | D2 | A2 | A2 | Ph | C=O | H |
| 2096 | D3 | D3 | A2 | A2 | Ph | C=O | H |
| 2097 | D1 | D1 | A3 | A3 | Ph | C=O | H |
| 2098 | D2 | D2 | A3 | A3 | Ph | C=O | H |
| 2099 | D3 | D3 | A3 | A3 | Ph | C=O | H |
| 2100 | D1 | D1 | A4 | A4 | Ph | C=O | H |
| 2101 | D2 | D2 | A4 | A4 | Ph | C=O | H |
| 2102 | D3 | D3 | A4 | A4 | Ph | C=O | H |
| 2103 | D1 | D1 | A5 | A5 | Ph | C=O | H |
| 2104 | D2 | D2 | A5 | A5 | Ph | C=O | H |
| 2105 | D3 | D3 | A5 | A5 | Ph | C=O | H |

TABLE 10

| Compound No. | R³ | R⁶ | R¹¹ | R¹⁴ | R¹⁷ | Z | Other Rs |
|---|---|---|---|---|---|---|---|
| 2106 | H | H | H | A1 | Ph | C=O | H |
| 2107 | H | D1 | H | A1 | Ph | C=O | H |
| 2108 | H | D2 | H | A1 | Ph | C=O | H |
| 2109 | H | D3 | H | A1 | Ph | C=O | H |
| 2110 | H | H | H | A2 | Ph | C=O | H |
| 2111 | H | D1 | H | A2 | Ph | C=O | H |
| 2112 | H | D2 | H | A2 | Ph | C=O | H |
| 2113 | H | D3 | H | A2 | Ph | C=O | H |
| 2114 | H | H | H | A3 | Ph | C=O | H |
| 2115 | H | D1 | H | A3 | Ph | C=O | H |
| 2116 | H | D2 | H | A3 | Ph | C=O | H |
| 2117 | H | D3 | H | A3 | Ph | C=O | H |
| 2118 | H | H | H | A4 | Ph | C=O | H |
| 2119 | H | D1 | H | A4 | Ph | C=O | H |
| 2120 | H | D2 | H | A4 | Ph | C=O | H |
| 2121 | H | D3 | H | A4 | Ph | C=O | H |
| 2122 | H | H | H | A5 | Ph | C=O | H |
| 2123 | H | D1 | H | A5 | Ph | C=O | H |
| 2124 | H | D2 | H | A5 | Ph | C=O | H |
| 2125 | H | D3 | H | A5 | Ph | C=O | H |
| 2126 | D1 | D1 | H | A1 | Ph | C=O | H |
| 2127 | D2 | D2 | H | A1 | Ph | C=O | H |
| 2128 | D3 | D3 | H | A1 | Ph | C=O | H |
| 2129 | D1 | D1 | H | A2 | Ph | C=O | H |
| 2130 | D2 | D2 | H | A2 | Ph | C=O | H |
| 2131 | D3 | D3 | H | A2 | Ph | C=O | H |
| 2132 | D1 | D1 | H | A3 | Ph | C=O | H |
| 2133 | D2 | D2 | H | A3 | Ph | C=O | H |
| 2134 | D3 | D3 | H | A3 | Ph | C=O | H |
| 2135 | D1 | D1 | H | A4 | Ph | C=O | H |
| 2136 | D2 | D2 | H | A4 | Ph | C=O | H |
| 2137 | D3 | D3 | H | A4 | Ph | C=O | H |
| 2138 | D1 | D1 | H | A5 | Ph | C=O | H |
| 2139 | D2 | D2 | H | A5 | Ph | C=O | H |
| 2140 | D3 | D3 | H | A5 | Ph | C=O | H |
| 2141 | H | H | H | H | Ph | C=O | H |

TABLE 11

| Compound No. | R² | R⁷ | R¹⁰ | R¹⁵ | R¹⁷ | Z | Other Rs |
|---|---|---|---|---|---|---|---|
| 2142 | H | H | A1 | A1 | Ph | C=S | H |
| 2143 | H | D1 | A1 | A1 | Ph | C=S | H |
| 2144 | H | D2 | A1 | A1 | Ph | C=S | H |
| 2145 | H | D3 | A1 | A1 | Ph | C=S | H |
| 2146 | H | H | A2 | A2 | Ph | C=S | H |
| 2147 | H | D1 | A2 | A2 | Ph | C=S | H |
| 2148 | H | D2 | A2 | A2 | Ph | C=S | H |
| 2149 | H | D3 | A2 | A2 | Ph | C=S | H |
| 2150 | H | H | A3 | A3 | Ph | C=S | H |
| 2151 | H | D1 | A3 | A3 | Ph | C=S | H |
| 2152 | H | D2 | A3 | A3 | Ph | C=S | H |
| 2153 | H | D3 | A3 | A3 | Ph | C=S | H |
| 2154 | H | H | A4 | A4 | Ph | C=S | H |
| 2155 | H | D1 | A4 | A4 | Ph | C=S | H |
| 2156 | H | D2 | A4 | A4 | Ph | C=S | H |
| 2157 | H | D3 | A4 | A4 | Ph | C=S | H |
| 2158 | H | H | A5 | A5 | Ph | C=S | H |
| 2159 | H | D1 | A5 | A5 | Ph | C=S | H |
| 2160 | H | D2 | A5 | A5 | Ph | C=S | H |
| 2161 | H | D3 | A5 | A5 | Ph | C=S | H |
| 2162 | D1 | D1 | A1 | A1 | Ph | C=S | H |
| 2163 | D2 | D2 | A1 | A1 | Ph | C=S | H |
| 2164 | D3 | D3 | A1 | A1 | Ph | C=S | H |
| 2165 | D1 | D1 | A2 | A2 | Ph | C=S | H |
| 2166 | D2 | D2 | A2 | A2 | Ph | C=S | H |
| 2167 | D3 | D3 | A2 | A2 | Ph | C=S | H |
| 2168 | D1 | D1 | A3 | A3 | Ph | C=S | H |
| 2169 | D2 | D2 | A3 | A3 | Ph | C=S | H |
| 2170 | D3 | D3 | A3 | A3 | Ph | C=S | H |
| 2171 | D1 | D1 | A4 | A4 | Ph | C=S | H |
| 2172 | D2 | D2 | A4 | A4 | Ph | C=S | H |
| 2173 | D3 | D3 | A4 | A4 | Ph | C=S | H |
| 2174 | D1 | D1 | A5 | A5 | Ph | C=S | H |
| 2175 | D2 | D2 | A5 | A5 | Ph | C=S | H |
| 2176 | D3 | D3 | A5 | A5 | Ph | C=S | H |

TABLE 12

| Compound No. | R³ | R⁶ | R¹¹ | R¹⁴ | R¹⁷ | Z | Other Rs |
|---|---|---|---|---|---|---|---|
| 2177 | H | H | H | A1 | Ph | C=S | H |
| 2178 | H | D1 | H | A1 | Ph | C=S | H |
| 2179 | H | D2 | H | A1 | Ph | C=S | H |
| 2180 | H | D3 | H | A1 | Ph | C=S | H |
| 2181 | H | H | H | A2 | Ph | C=S | H |
| 2182 | H | D1 | H | A2 | Ph | C=S | H |
| 2183 | H | D2 | H | A2 | Ph | C=S | H |
| 2184 | H | D3 | H | A2 | Ph | C=S | H |
| 2185 | H | H | H | A3 | Ph | C=S | H |
| 2186 | H | D1 | H | A3 | Ph | C=S | H |
| 2187 | H | D2 | H | A3 | Ph | C=S | H |
| 2188 | H | D3 | H | A3 | Ph | C=S | H |
| 2189 | H | H | H | A4 | Ph | C=S | H |
| 2190 | H | D1 | H | A4 | Ph | C=S | H |
| 2191 | H | D2 | H | A4 | Ph | C=S | H |
| 2192 | H | D3 | H | A4 | Ph | C=S | H |
| 2193 | H | H | H | A5 | Ph | C=S | H |
| 2194 | H | D1 | H | A5 | Ph | C=S | H |
| 2195 | H | D2 | H | A5 | Ph | C=S | H |
| 2196 | H | D3 | H | A5 | Ph | C=S | H |
| 2197 | D1 | D1 | H | A1 | Ph | C=S | H |
| 2198 | D2 | D2 | H | A1 | Ph | C=S | H |
| 2199 | D3 | D3 | H | A1 | Ph | C=S | H |
| 2200 | D1 | D1 | H | A2 | Ph | C=S | H |
| 2201 | D2 | D2 | H | A2 | Ph | C=S | H |
| 2202 | D3 | D3 | H | A2 | Ph | C=S | H |
| 2203 | D1 | D1 | H | A3 | Ph | C=S | H |
| 2204 | D2 | D2 | H | A3 | Ph | C=S | H |
| 2205 | D3 | D3 | H | A3 | Ph | C=S | H |
| 2206 | D1 | D1 | H | A4 | Ph | C=S | H |
| 2207 | D2 | D2 | H | A4 | Ph | C=S | H |
| 2208 | D3 | D3 | H | A4 | Ph | C=S | H |
| 2209 | D1 | D1 | H | A5 | Ph | C=S | H |
| 2210 | D2 | D2 | H | A5 | Ph | C=S | H |
| 2211 | D3 | D3 | H | A5 | Ph | C=S | H |
| 2212 | H | H | H | H | Ph | C=S | H |

TABLE 13

| Compound No. | R² | R⁷ | R¹⁰ | R¹⁵ | R¹⁷ | Z | Other Rs |
|---|---|---|---|---|---|---|---|
| 2213 | H | H | A1 | A1 | Ph | C=C(CN)₂ | H |
| 2214 | H | D1 | A1 | A1 | Ph | C=C(CN)₂ | H |
| 2215 | H | D2 | A1 | A1 | Ph | C=C(CN)₂ | H |
| 2216 | H | D3 | A1 | A1 | Ph | C=C(CN)₂ | H |
| 2217 | H | H | A2 | A2 | Ph | C=C(CN)₂ | H |
| 2218 | H | D1 | A2 | A2 | Ph | C=C(CN)₂ | H |
| 2219 | H | D2 | A2 | A2 | Ph | C=C(CN)₂ | H |
| 2220 | H | D3 | A2 | A2 | Ph | C=C(CN)₂ | H |
| 2221 | H | H | A3 | A3 | Ph | C=C(CN)₂ | H |
| 2222 | H | D1 | A3 | A3 | Ph | C=C(CN)₂ | H |
| 2223 | H | D2 | A3 | A3 | Ph | C=C(CN)₂ | H |
| 2224 | H | D3 | A3 | A3 | Ph | C=C(CN)₂ | H |
| 2225 | H | H | A4 | A4 | Ph | C=C(CN)₂ | H |
| 2226 | H | D1 | A4 | A4 | Ph | C=C(CN)₂ | H |
| 2227 | H | D2 | A4 | A4 | Ph | C=C(CN)₂ | H |
| 2228 | H | D3 | A4 | A4 | Ph | C=C(CN)₂ | H |
| 2229 | H | H | A5 | A5 | Ph | C=C(CN)₂ | H |
| 2230 | H | D1 | A5 | A5 | Ph | C=C(CN)₂ | H |
| 2231 | H | D2 | A5 | A5 | Ph | C=C(CN)₂ | H |
| 2232 | H | D3 | A5 | A5 | Ph | C=C(CN)₂ | H |
| 2233 | D1 | D1 | A1 | A1 | Ph | C=C(CN)₂ | H |
| 2234 | D2 | D2 | A1 | A1 | Ph | C=C(CN)₂ | H |
| 2235 | D3 | D3 | A1 | A1 | Ph | C=C(CN)₂ | H |
| 2236 | D1 | D1 | A2 | A2 | Ph | C=C(CN)₂ | H |
| 2237 | D2 | D2 | A2 | A2 | Ph | C=C(CN)₂ | H |
| 2238 | D3 | D3 | A2 | A2 | Ph | C=C(CN)₂ | H |
| 2239 | D1 | D1 | A3 | A3 | Ph | C=C(CN)₂ | H |
| 2240 | D2 | D2 | A3 | A3 | Ph | C=C(CN)₂ | H |
| 2241 | D3 | D3 | A3 | A3 | Ph | C=C(CN)₂ | H |
| 2242 | D1 | D1 | A4 | A4 | Ph | C=C(CN)₂ | H |
| 2243 | D2 | D2 | A4 | A4 | Ph | C=C(CN)₂ | H |
| 2244 | D3 | D3 | A4 | A4 | Ph | C=C(CN)₂ | H |
| 2245 | D1 | D1 | A5 | A5 | Ph | C=C(CN)₂ | H |
| 2246 | D2 | D2 | A5 | A5 | Ph | C=C(CN)₂ | H |
| 2247 | D3 | D3 | A5 | A5 | Ph | C=C(CN)₂ | H |

TABLE 14

| Compound No. | R³ | R⁶ | R¹¹ | R¹⁴ | R¹⁷ | Z | Other Rs |
|---|---|---|---|---|---|---|---|
| 2248 | H | H | H | A1 | Ph | C=C(CN)₂ | H |
| 2249 | H | D1 | H | A1 | Ph | C=C(CN)₂ | H |
| 2250 | H | D2 | H | A1 | Ph | C=C(CN)₂ | H |
| 2251 | H | D3 | H | A1 | Ph | C=C(CN)₂ | H |
| 2252 | H | H | H | A2 | Ph | C=C(CN)₂ | H |
| 2253 | H | D1 | H | A2 | Ph | C=C(CN)₂ | H |
| 2254 | H | D2 | H | A2 | Ph | C=C(CN)₂ | H |
| 2255 | H | D3 | H | A2 | Ph | C=C(CN)₂ | H |
| 2256 | H | H | H | A3 | Ph | C=C(CN)₂ | H |
| 2257 | H | D1 | H | A3 | Ph | C=C(CN)₂ | H |
| 2258 | H | D2 | H | A3 | Ph | C=C(CN)₂ | H |
| 2259 | H | D3 | H | A3 | Ph | C=C(CN)₂ | H |
| 2260 | H | H | H | A4 | Ph | C=C(CN)₂ | H |
| 2261 | H | D1 | H | A4 | Ph | C=C(CN)₂ | H |
| 2262 | H | D2 | H | A4 | Ph | C=C(CN)₂ | H |
| 2263 | H | D3 | H | A4 | Ph | C=C(CN)₂ | H |
| 2264 | H | H | H | A5 | Ph | C=C(CN)₂ | H |
| 2265 | H | D1 | H | A5 | Ph | C=C(CN)₂ | H |
| 2266 | H | D2 | H | A5 | Ph | C=C(CN)₂ | H |
| 2267 | H | D3 | H | A5 | Ph | C=C(CN)₂ | H |
| 2268 | D1 | D1 | H | A1 | Ph | C=C(CN)₂ | H |
| 2269 | D2 | D2 | H | A1 | Ph | C=C(CN)₂ | H |
| 2270 | D3 | D3 | H | A1 | Ph | C=C(CN)₂ | H |
| 2271 | D1 | D1 | H | A2 | Ph | C=C(CN)₂ | H |
| 2272 | D2 | D2 | H | A2 | Ph | C=C(CN)₂ | H |
| 2273 | D3 | D3 | H | A2 | Ph | C=C(CN)₂ | H |
| 2274 | D1 | D1 | H | A3 | Ph | C=C(CN)₂ | H |
| 2275 | D2 | D2 | H | A3 | Ph | C=C(CN)₂ | H |
| 2276 | D3 | D3 | H | A3 | Ph | C=C(CN)₂ | H |
| 2277 | D1 | D1 | H | A4 | Ph | C=C(CN)₂ | H |
| 2278 | D2 | D2 | H | A4 | Ph | C=C(CN)₂ | H |
| 2279 | D3 | D3 | H | A4 | Ph | C=C(CN)₂ | H |
| 2280 | D1 | D1 | H | A5 | Ph | C=C(CN)₂ | H |
| 2281 | D2 | D2 | H | A5 | Ph | C=C(CN)₂ | H |
| 2282 | D3 | D3 | H | A5 | Ph | C=C(CN)₂ | H |
| 2283 | H | H | H | H | Ph | C=C(CN)₂ | H |

TABLE 15

| Compound No. | R² | R⁷ | R¹⁰ | R¹⁵ | R¹⁷ | Z | Other Rs |
|---|---|---|---|---|---|---|---|
| 2284 | H | H | A1 | A1 | Ph | C=C(COOH)₂ | H |
| 2285 | H | D1 | A1 | A1 | Ph | C=C(COOH)₂ | H |
| 2286 | H | D2 | A1 | A1 | Ph | C=C(COOH)₂ | H |
| 2287 | H | D3 | A1 | A1 | Ph | C=C(COOH)₂ | H |
| 2288 | H | H | A2 | A2 | Ph | C=C(COOH)₂ | H |
| 2289 | H | D1 | A2 | A2 | Ph | C=C(COOH)₂ | H |
| 2290 | H | D2 | A2 | A2 | Ph | C=C(COOH)₂ | H |
| 2291 | H | D3 | A2 | A2 | Ph | C=C(COOH)₂ | H |
| 2292 | H | H | A3 | A3 | Ph | C=C(COOH)₂ | H |
| 2293 | H | D1 | A3 | A3 | Ph | C=C(COOH)₂ | H |
| 2294 | H | D2 | A3 | A3 | Ph | C=C(COOH)₂ | H |
| 2295 | H | D3 | A3 | A3 | Ph | C=C(COOH)₂ | H |
| 2296 | H | H | A4 | A4 | Ph | C=C(COOH)₂ | H |
| 2297 | H | D1 | A4 | A4 | Ph | C=C(COOH)₂ | H |
| 2298 | H | D2 | A4 | A4 | Ph | C=C(COOH)₂ | H |
| 2299 | H | D3 | A4 | A4 | Ph | C=C(COOH)₂ | H |
| 2300 | H | H | A5 | A5 | Ph | C=C(COOH)₂ | H |
| 2301 | H | D1 | A5 | A5 | Ph | C=C(COOH)₂ | H |
| 2302 | H | D2 | A5 | A5 | Ph | C=C(COOH)₂ | H |
| 2303 | H | D3 | A5 | A5 | Ph | C=C(COOH)₂ | H |
| 2304 | D1 | D1 | A1 | A1 | Ph | C=C(COOH)₂ | H |
| 2305 | D2 | D2 | A1 | A1 | Ph | C=C(COOH)₂ | H |
| 2306 | D3 | D3 | A1 | A1 | Ph | C=C(COOH)₂ | H |
| 2307 | D1 | D1 | A2 | A2 | Ph | C=C(COOH)₂ | H |
| 2308 | D2 | D2 | A2 | A2 | Ph | C=C(COOH)₂ | H |
| 2309 | D3 | D3 | A2 | A2 | Ph | C=C(COOH)₂ | H |
| 2310 | D1 | D1 | A3 | A3 | Ph | C=C(COOH)₂ | H |
| 2311 | D2 | D2 | A3 | A3 | Ph | C=C(COOH)₂ | H |
| 2312 | D3 | D3 | A3 | A3 | Ph | C=C(COOH)₂ | H |
| 2313 | D1 | D1 | A4 | A4 | Ph | C=C(COOH)₂ | H |
| 2314 | D2 | D2 | A4 | A4 | Ph | C=C(COOH)₂ | H |
| 2315 | D3 | D3 | A4 | A4 | Ph | C=C(COOH)₂ | H |
| 2316 | D1 | D1 | A5 | A5 | Ph | C=C(COOH)₂ | H |
| 2317 | D2 | D2 | A5 | A5 | Ph | C=C(COOH)₂ | H |
| 2318 | D3 | D3 | A5 | A5 | Ph | C=C(COOH)₂ | H |

TABLE 16

| Compound No. | R³ | R⁶ | R¹¹ | R¹⁴ | R¹⁷ | Z | Other Rs |
|---|---|---|---|---|---|---|---|
| 2319 | H | H | H | A1 | Ph | C=C(COOH)₂ | H |
| 2320 | H | D1 | H | A1 | Ph | C=C(COOH)₂ | H |
| 2321 | H | D2 | H | A1 | Ph | C=C(COOH)₂ | H |
| 2322 | H | D3 | H | A1 | Ph | C=C(COOH)₂ | H |
| 2323 | H | H | H | A2 | Ph | C=C(COOH)₂ | H |
| 2324 | H | D1 | H | A2 | Ph | C=C(COOH)₂ | H |
| 2325 | H | D2 | H | A2 | Ph | C=C(COOH)₂ | H |
| 2326 | H | D3 | H | A2 | Ph | C=C(COOH)₂ | H |
| 2327 | H | H | H | A3 | Ph | C=C(COOH)₂ | H |
| 2328 | H | D1 | H | A3 | Ph | C=C(COOH)₂ | H |
| 2329 | H | D2 | H | A3 | Ph | C=C(COOH)₂ | H |
| 2330 | H | D3 | H | A3 | Ph | C=C(COOH)₂ | H |
| 2331 | H | H | H | A4 | Ph | C=C(COOH)₂ | H |
| 2332 | H | D1 | H | A4 | Ph | C=C(COOH)₂ | H |
| 2333 | H | D2 | H | A4 | Ph | C=C(COOH)₂ | H |
| 2334 | H | D3 | H | A4 | Ph | C=C(COOH)₂ | H |
| 2335 | H | H | H | A5 | Ph | C=C(COOH)₂ | H |
| 2336 | H | D1 | H | A5 | Ph | C=C(COOH)₂ | H |
| 2337 | H | D2 | H | A5 | Ph | C=C(COOH)₂ | H |
| 2338 | H | D3 | H | A5 | Ph | C=C(COOH)₂ | H |
| 2339 | D1 | D1 | H | A1 | Ph | C=C(COOH)₂ | H |
| 2340 | D2 | D2 | H | A1 | Ph | C=C(COOH)₂ | H |
| 2341 | D3 | D3 | H | A1 | Ph | C=C(COOH)₂ | H |

TABLE 16-continued

| Compound No. | R³ | R⁶ | R¹¹ | R¹⁴ | R¹⁷ | Z | Other Rs |
|---|---|---|---|---|---|---|---|
| 2342 | D1 | D1 | H | A2 | Ph | C=C(COOH)₂ | H |
| 2343 | D2 | D2 | H | A2 | Ph | C=C(COOH)₂ | H |
| 2344 | D3 | D3 | H | A2 | Ph | C=C(COOH)₂ | H |
| 2345 | D1 | D1 | H | A3 | Ph | C=C(COOH)₂ | H |
| 2346 | D2 | D2 | H | A3 | Ph | C=C(COOH)₂ | H |
| 2347 | D3 | D3 | H | A3 | Ph | C=C(COOH)₂ | H |
| 2348 | D1 | D1 | H | A4 | Ph | C=C(COOH)₂ | H |
| 2349 | D2 | D2 | H | A4 | Ph | C=C(COOH)₂ | H |
| 2350 | D3 | D3 | H | A4 | Ph | C=C(COOH)₂ | H |
| 2351 | D1 | D1 | H | A5 | Ph | C=C(COOH)₂ | H |
| 2352 | D2 | D2 | H | A5 | Ph | C=C(COOH)₂ | H |
| 2353 | D3 | D3 | H | A5 | Ph | C=C(COOH)₂ | H |
| 2354 | H | H | H | H | Ph | C=C(COOH)₂ | H |

Examples of the preferred delayed fluorescent material include compounds represented by the following general formula. The entire description of WO 2013/011955 including the paragraphs 0007 to 0033 and 0059 to 0066 is incorporated herein by reference as a part of the description of the present application.

[Chem. 22]

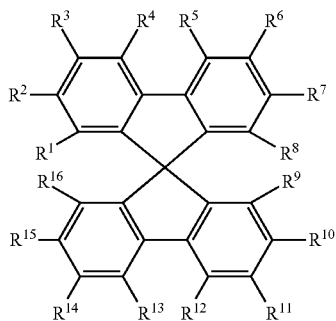

General Formula (151)

[In the general formula (151), $R^1$, $R^2$, $R^3$, $R^4$, $R^5$, $R^6$, $R^7$ and $R^8$ each independently represent a hydrogen atom or an electron donating group, provided that at least one thereof represents an electron donating group. $R^9$, $R^{10}$, $R^1$, $R^{12}$, $R^{13}$, $R^{14}$, $R^{15}$ and $R^{16}$ each independently represent a hydrogen atom or an electron withdrawing group, provided that at least one thereof represents an electron withdrawing group.]

Specific examples of the compounds include the compounds shown in the following Table 17 to Table 20. In the Tables, D11 to D20 represent the unsubstituted electron donating groups having the following structures, respectively.

[Chem. 23]

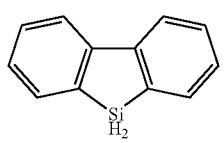
D11

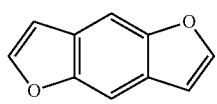
D12

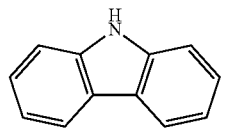
D13

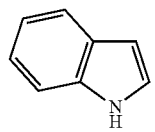
D14

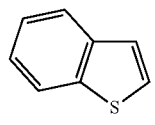
D15

D16

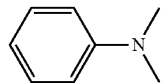
D17

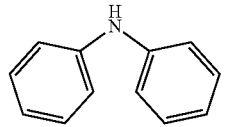
D18

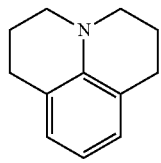
D19

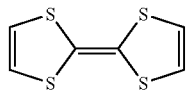
D20

[Chem. 24]

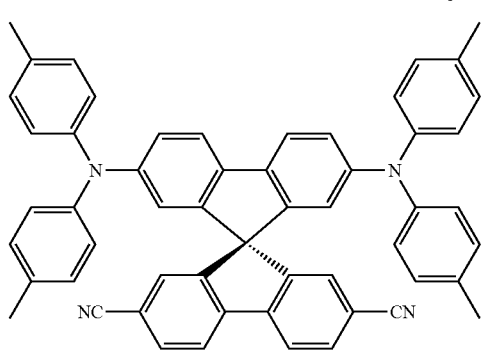

Compound 3001

TABLE 17

| Compound No. | R² | R⁷ | R¹⁰ | R¹⁵ | Other Rs |
|---|---|---|---|---|---|
| 3002 | D11 | D11 | CN | CN | H |
| 3003 | D12 | D12 | CN | CN | H |

TABLE 17-continued

| Compound No. | $R^2$ | $R^7$ | $R^{10}$ | $R^{15}$ | Other Rs |
|---|---|---|---|---|---|
| 3004 | D13 | D13 | CN | CN | H |
| 3005 | D14 | D14 | CN | CN | H |
| 3006 | D15 | D15 | CN | CN | H |
| 3007 | D16 | D16 | CN | CN | H |
| 3008 | D17 | D17 | CN | CN | H |
| 3009 | D18 | D18 | CN | CN | H |
| 3010 | D19 | D19 | CN | CN | H |
| 3011 | D20 | D20 | CN | CN | H |
| 3012 | H | D11 | H | CN | H |
| 3013 | H | D12 | H | CN | H |
| 3014 | H | D13 | H | CN | H |
| 3015 | H | D14 | H | CN | H |
| 3016 | H | D15 | H | CN | H |
| 3017 | H | D16 | H | CN | H |
| 3018 | H | D17 | H | CN | H |
| 3019 | H | D18 | H | CN | H |
| 3020 | H | D19 | H | CN | H |
| 3021 | H | D20 | H | CN | H |

TABLE 18

| Compound No. | $R^3$ | $R^6$ | $R^{11}$ | $R^{14}$ | Other Rs |
|---|---|---|---|---|---|
| 3022 | D11 | D11 | CN | CN | H |
| 3023 | D12 | D12 | CN | CN | H |
| 3024 | D13 | D13 | CN | CN | H |
| 3025 | D14 | D14 | CN | CN | H |
| 3026 | D15 | D15 | CN | CN | H |
| 3027 | D16 | D16 | CN | CN | H |
| 3028 | D17 | D17 | CN | CN | H |
| 3029 | D18 | D18 | CN | CN | H |
| 3030 | D19 | D19 | CN | CN | H |
| 3031 | D20 | D20 | CN | CN | H |
| 3032 | H | D11 | H | CN | H |
| 3033 | H | D12 | H | CN | H |
| 3034 | H | D13 | H | CN | H |
| 3035 | H | D14 | H | CN | H |
| 3036 | H | D15 | H | CN | H |
| 3037 | H | D16 | H | CN | H |
| 3038 | H | D17 | H | CN | H |
| 3039 | H | D18 | H | CN | H |
| 3040 | H | D19 | H | CN | H |
| 3041 | H | D20 | H | CN | H |

TABLE 19

| Compound No. | $R^2$, $R^7$ | $R^3$, $R^6$ | $R^{10}$, $R^{15}$ | $R^{11}$, $R^{14}$ | Other Rs |
|---|---|---|---|---|---|
| 3042 | diphenylamino group | H | CN | H | H |
| 3043 | bis(2-methylphenyl)amino group | H | CN | H | H |
| 3044 | bis(3-methylphenyl)amino group | H | CN | H | H |
| 3045 | bis(2,4-dimethylphenyl)amino group | H | CN | H | H |
| 3046 | bis(2,6-dimethylphenyl)amino group | H | CN | H | H |
| 3047 | bis(3,5-dimethylphenyl)amino group | H | CN | H | H |
| 3048 | bis(2,4,6-trimethylphenyl)amino group | H | CN | H | H |
| 3049 | bis(4-ethylphenyl)amino group | H | CN | H | H |
| 3050 | bis(4-propylphenyl)amino group | H | CN | H | H |
| 3051 | diphenylamino group | H | H | CN | H |
| 3052 | bis(2-methylphenyl)amino group | H | H | CN | H |
| 3053 | bis(3-methylphenyl)amino group | H | H | CN | H |
| 3054 | bis(4-methylphenyl)amino group | H | H | CN | H |
| 3055 | bis(2,4-dimethylphenyl)amino group | H | H | CN | H |
| 3056 | bis(2,6-dimethylphenyl)amino group | H | H | CN | H |
| 3057 | bis(3,5-dimethylphenyl)amino group | H | H | CN | H |
| 3058 | bis(2,4,6-trimethylphenyl)amino group | H | H | CN | H |
| 3059 | bis(4-ethylphenyl)amino group | H | H | CN | H |
| 3060 | bis(4-propylphenyl)amino group | H | H | CN | H |

TABLE 20

| Compound No. | $R^2$, $R^7$ | $R^3$, $R^6$ | $R^{10}$, $R^{15}$ | $R^{11}$, $R^{14}$ | Other Rs |
|---|---|---|---|---|---|
| 3061 | H | diphenylamino group | CN | H | H |
| 3062 | H | bis(2-methylphenyl)amino group | CN | H | H |
| 3063 | H | bis(3-methylphenyl)amino group | CN | H | H |
| 3064 | H | bis(4-methylphenyl)amino group | CN | H | H |
| 3065 | H | bis(2,4-dimethylphenyl)amino group | CN | H | H |
| 3066 | H | bis(2,6-dimethylphenyl)amino group | CN | H | H |
| 3067 | H | bis(3,5-dimethylphenyl)amino group | CN | H | H |
| 3068 | H | bis(2,4,6-trimethylphenyl)amino group | CN | H | H |
| 3069 | H | bis(4-ethylphenyl)amino group | CN | H | H |
| 3070 | H | bis(4-propylphenyl)amino group | CN | H | H |
| 3071 | H | diphenylamino group | H | CN | H |
| 3072 | H | bis(2-methylphenyl)amino group | H | CN | H |
| 3073 | H | bis(3-methylphenyl)amino group | H | CN | H |
| 3074 | H | bis(4-methylphenyl)amino group | H | CN | H |
| 3075 | H | bis(2,4-dimethylphenyl)amino group | H | CN | H |
| 3076 | H | bis(2,6-dimethylphenyl)amino group | H | CN | H |
| 3077 | H | bis(3,5-dimethylphenyl)amino group | H | CN | H |

TABLE 20-continued

| Compound No. | $R^2, R^7$ | $R^3, R^6$ | $R^{10}, R^{15}$ | $R^{11}, R^{14}$ | Other Rs |
|---|---|---|---|---|---|
| 3078 | H | bis(2,4,6-trimethylphenyl)amino group | H | CN | H |
| 3079 | H | bis(4-ethylphenyl)amino group | H | CN | H |
| 3080 | H | bis(4-propylphenyl)amino group | H | CN | H |

Examples of the preferred delayed fluorescent material include compounds represented by the following general formula. The entire description of WO 2013/081088 including the paragraphs 0008 to 0071 and 0118 to 0133 is incorporated herein by reference as a part of the description of the present application.

[Chem. 25]

General Formula (161)

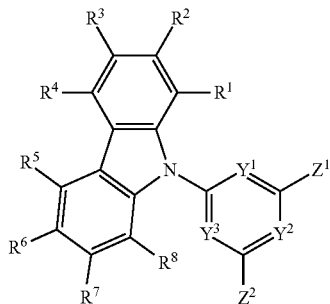

[In the general formula (161), any two of $Y^1$, $Y^2$ and $Y^3$ each represent a nitrogen atom, and the balance thereof represents a methine group, of all $Y^1$, $Y^2$ and $Y^3$ each represent a nitrogen atom. $Z^1$ and $Z^2$ each independently represent a hydrogen atom or a substituent. $R^1$ to $R^8$ each independently represent a hydrogen atom or a substituent, provided that at least one of $R^1$ to $R^8$ represents a substituted or unsubstituted diarylamino group or a substituted or unsubstituted carbazolyl group. The compound represented by the general formula (161) has at least two carbazole structures in the molecule thereof.

Examples of the compound include the following compounds.

[Chem. 26]

1

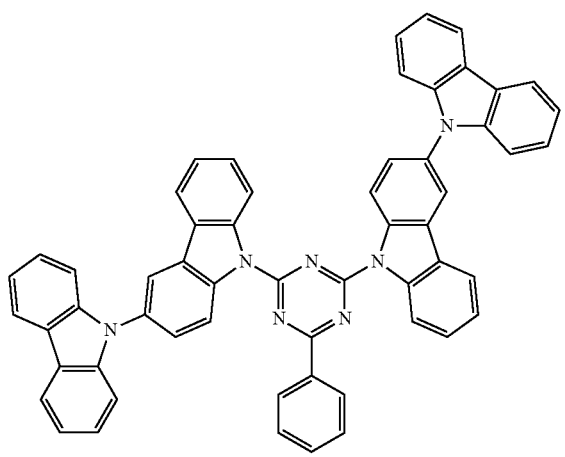

2

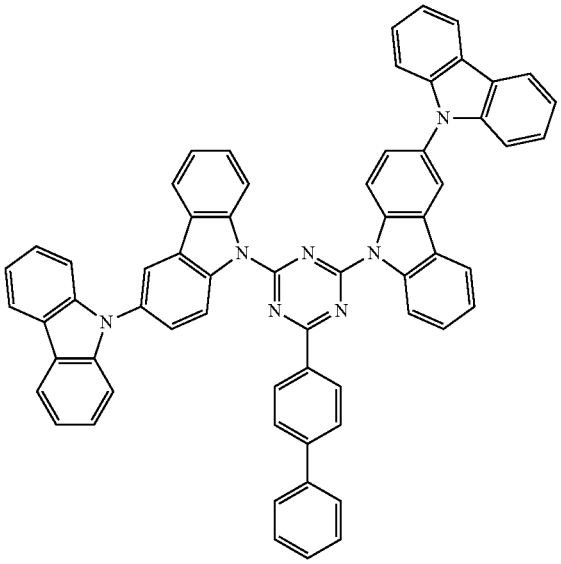

3

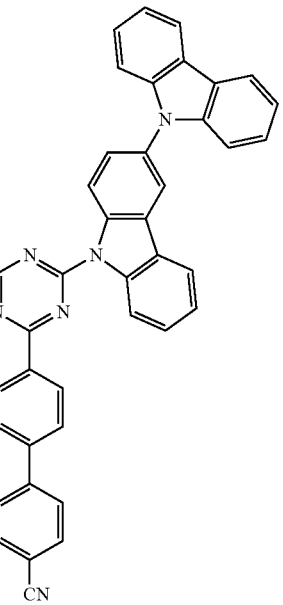

-continued
4
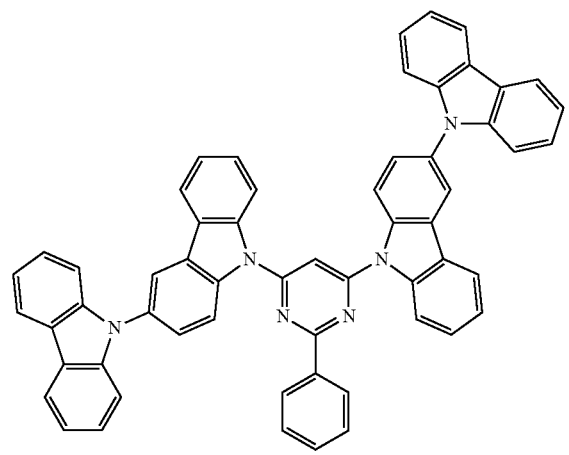
5
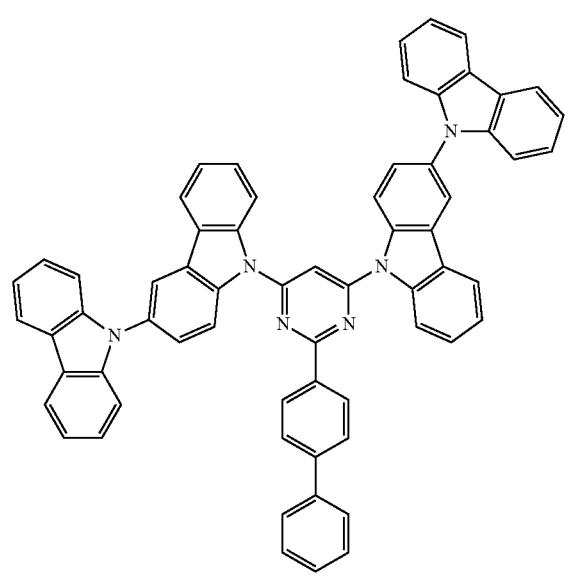
-continued
6
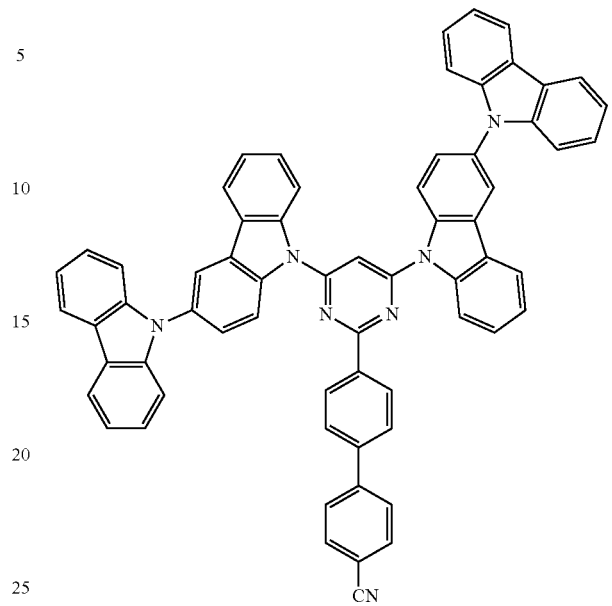
[Chem. 27]
7
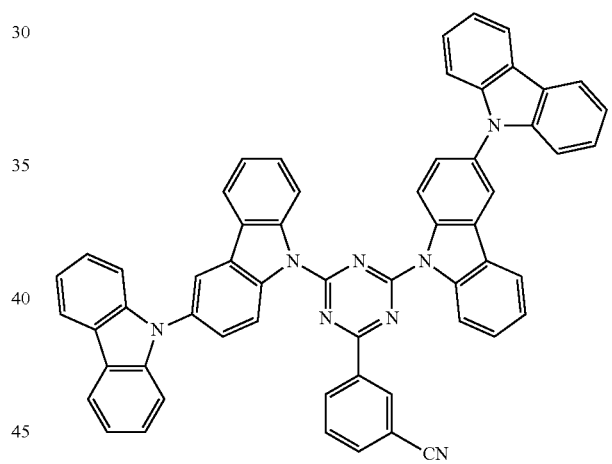
8
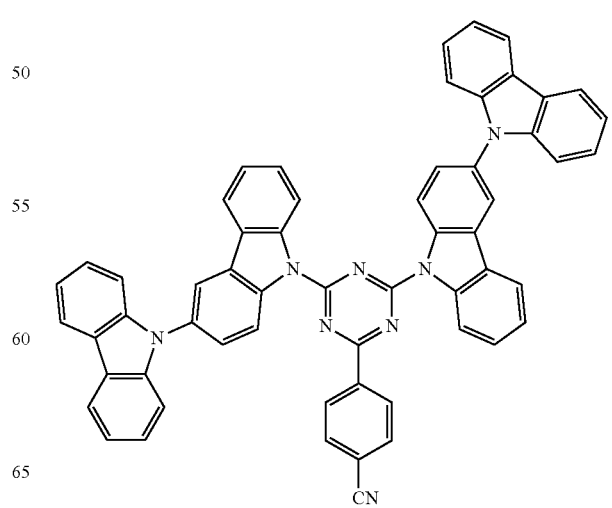

9
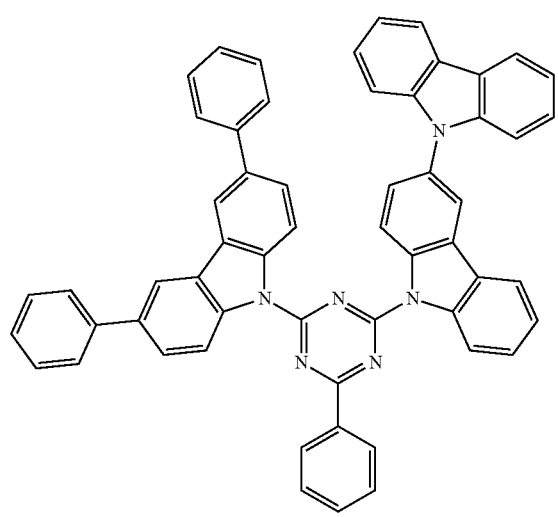
10
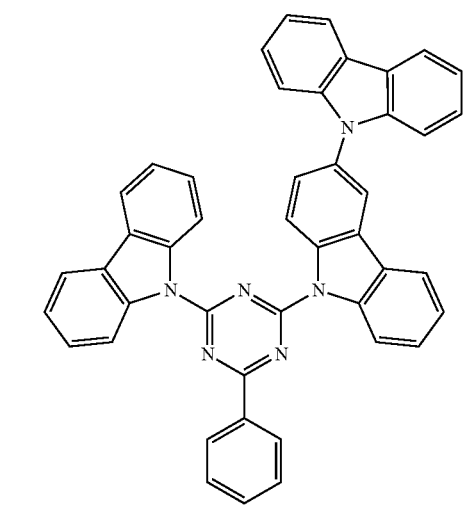
11
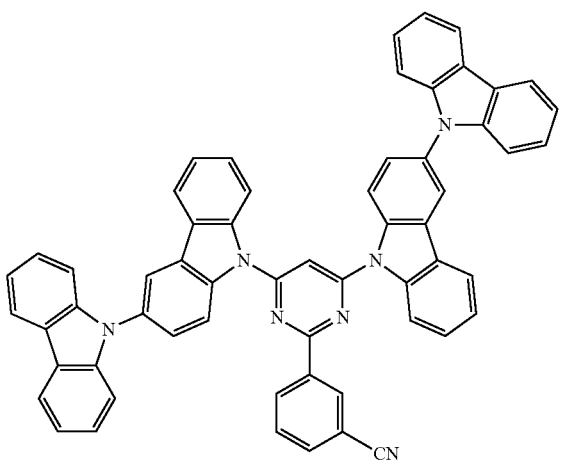
12
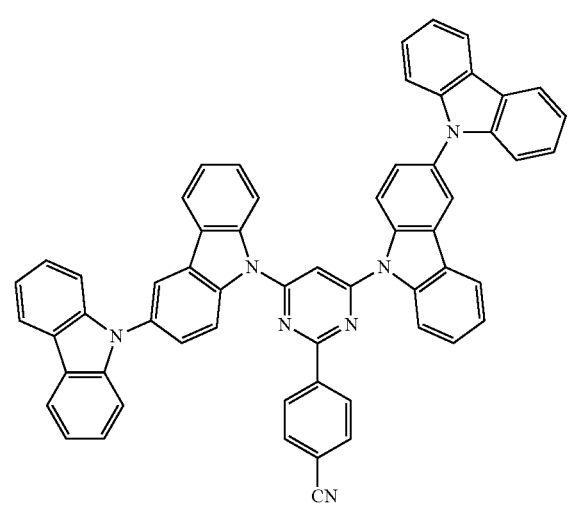
13
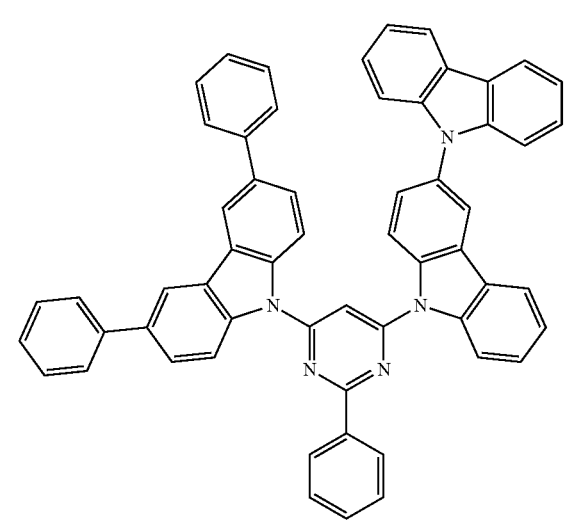
14
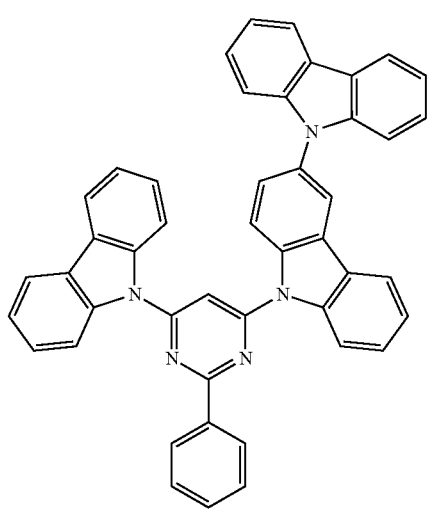

-continued
15
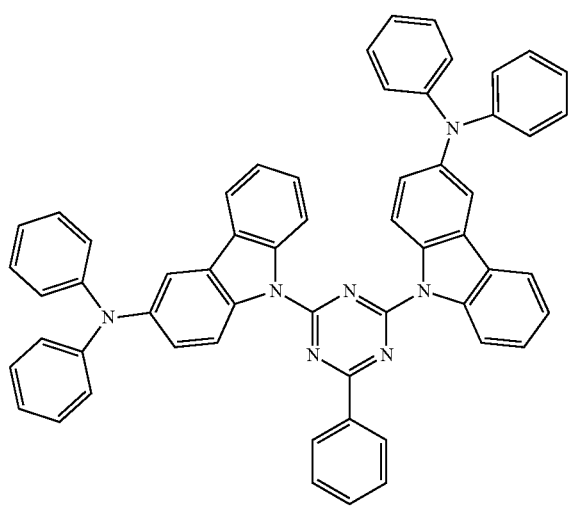
17
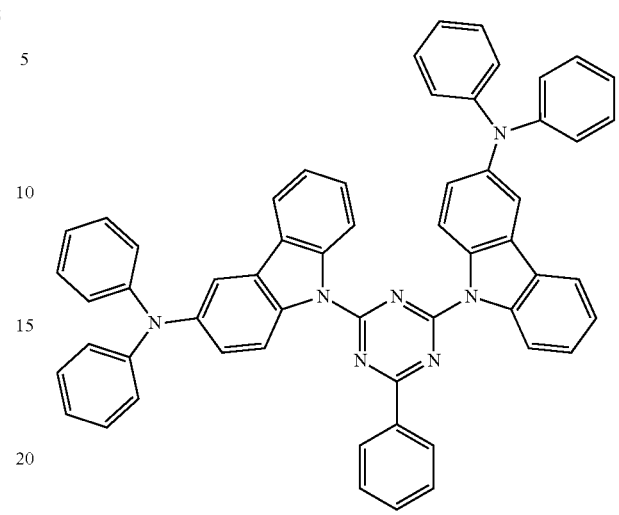
16
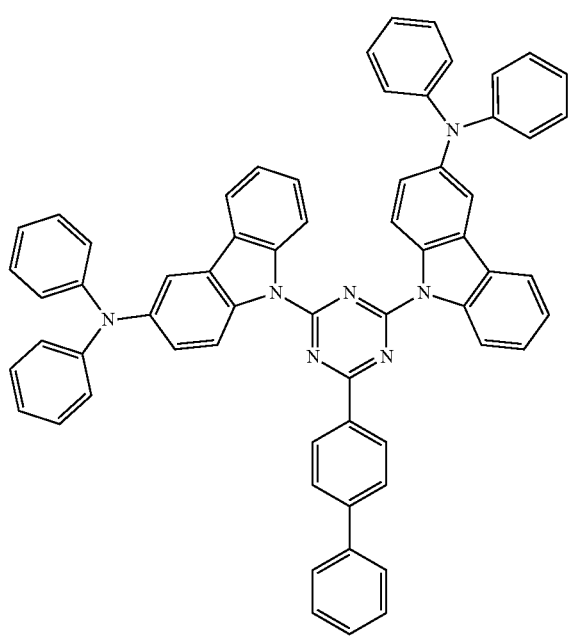
18
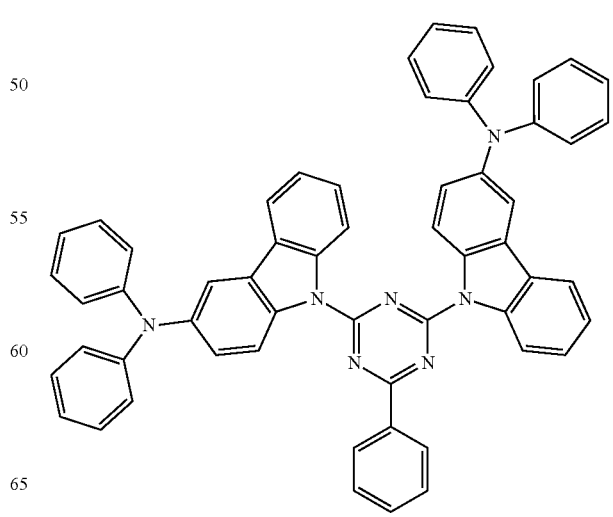

-continued
19
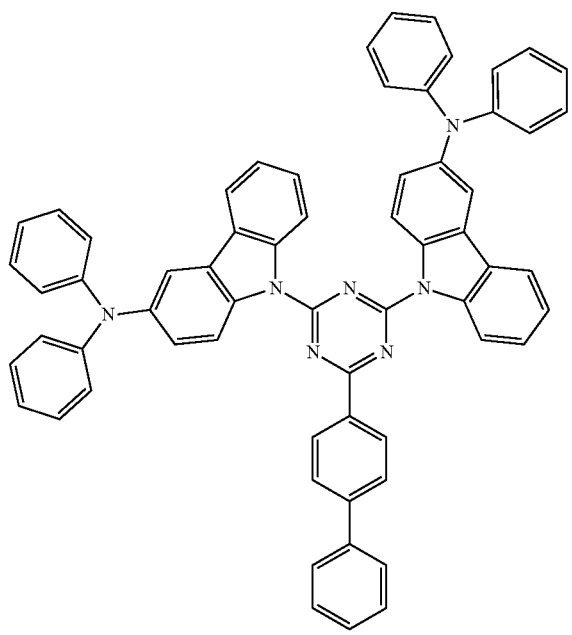
[Chem. 29]
-continued
21
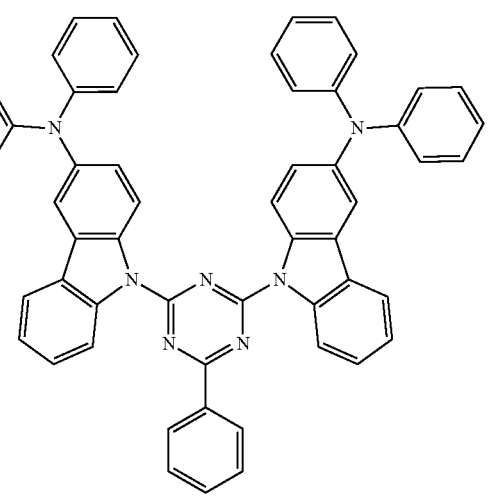
20
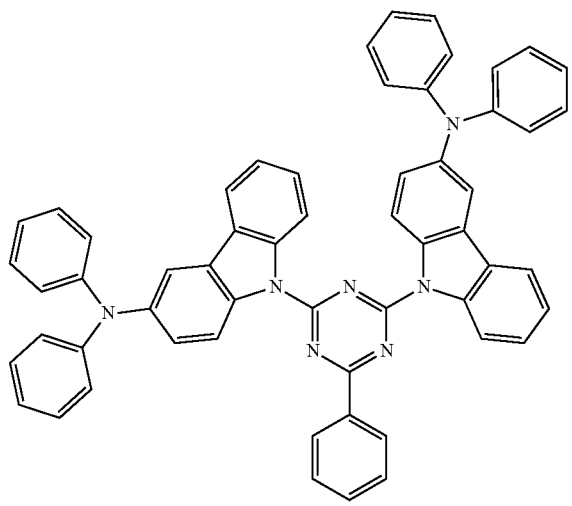
22
23
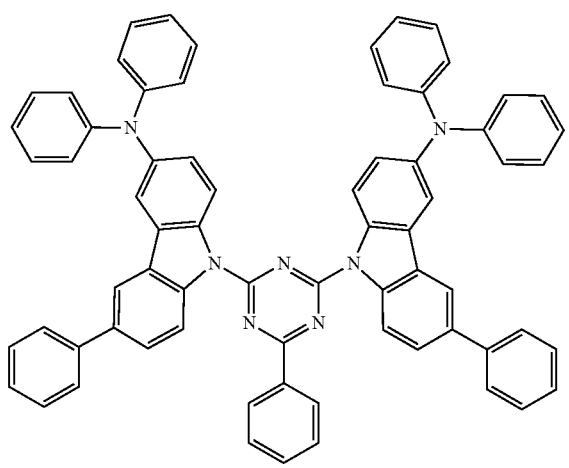

24
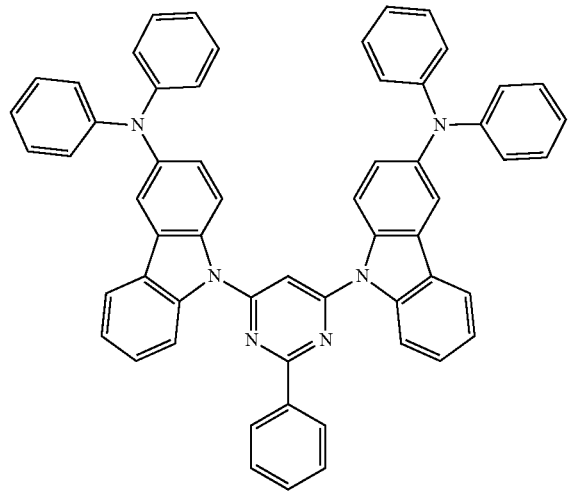
25
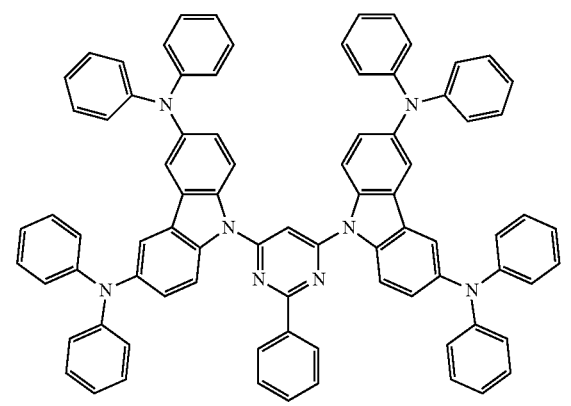
26
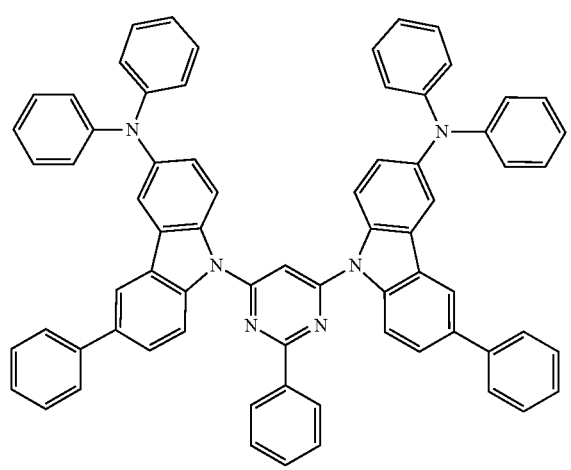
[Chem. 30]
27
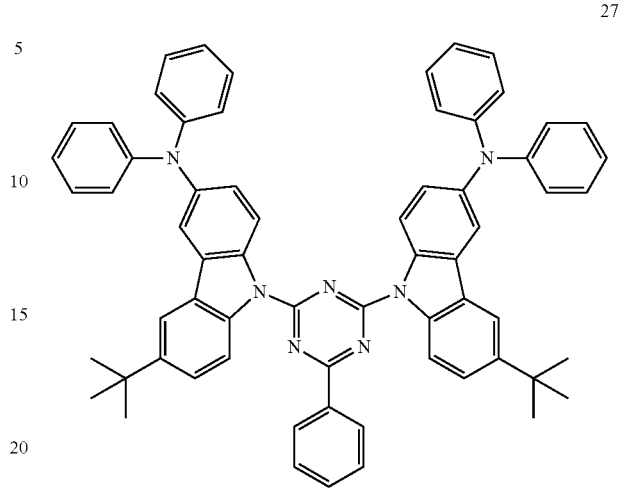
28
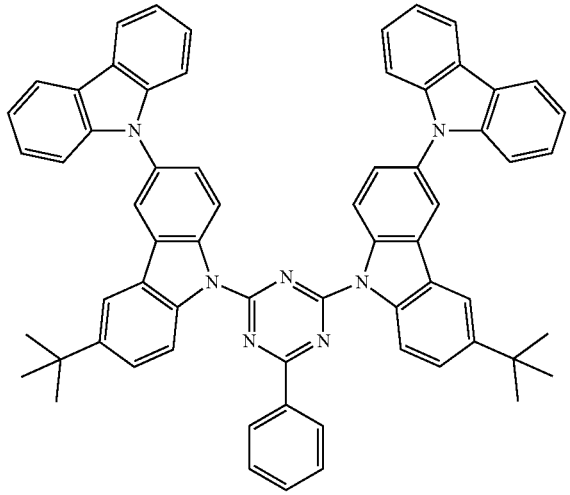
29
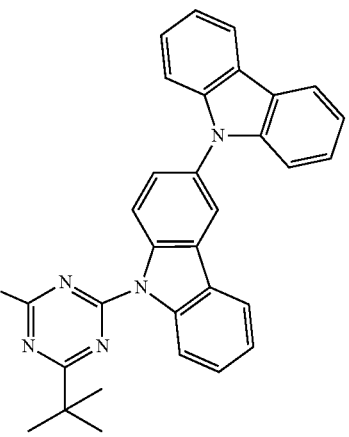

123
-continued
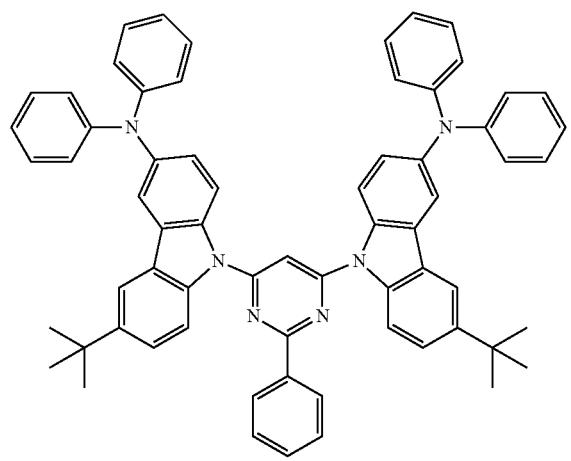
30
124
-continued
[Chem. 31]
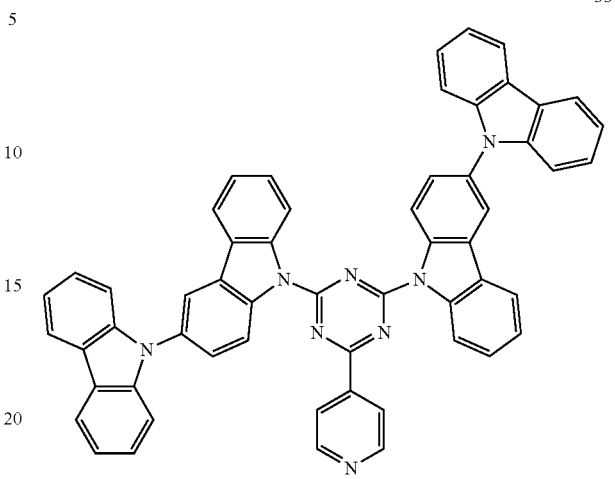
33
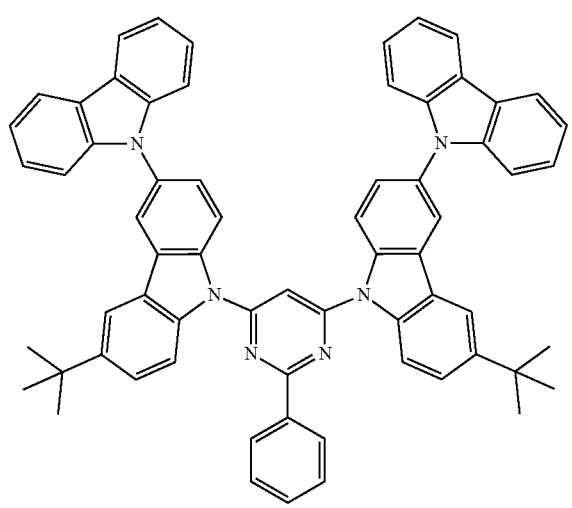
31
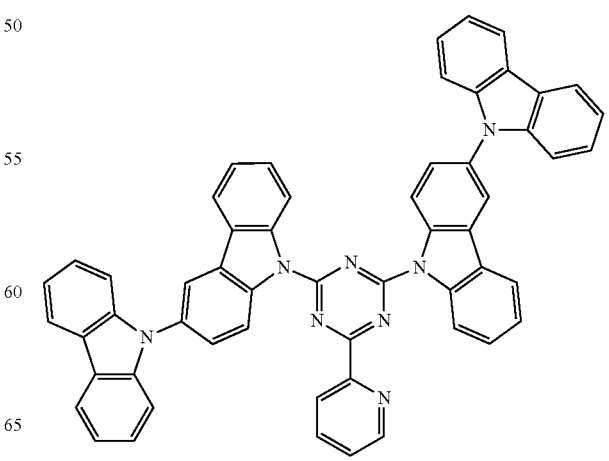
34
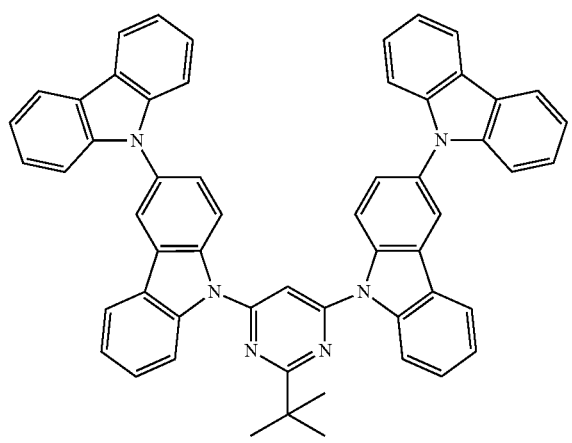
32
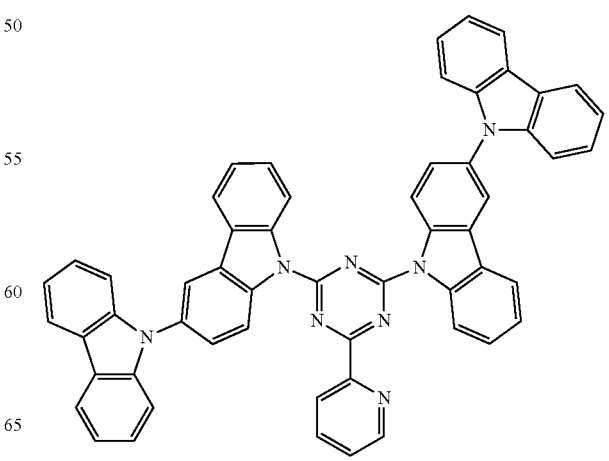
35

36
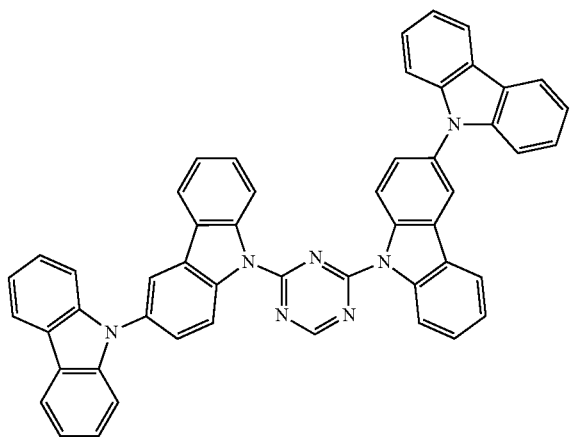
37
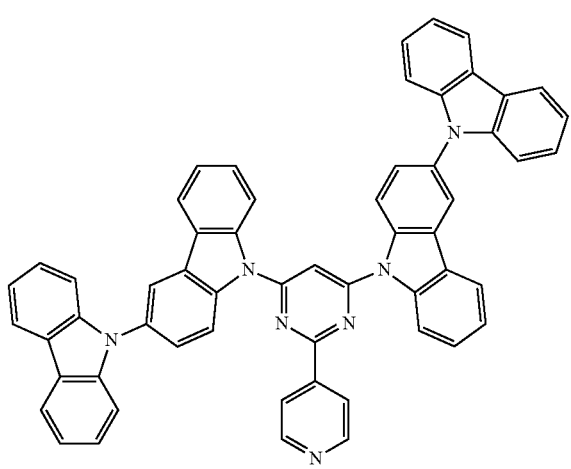
38
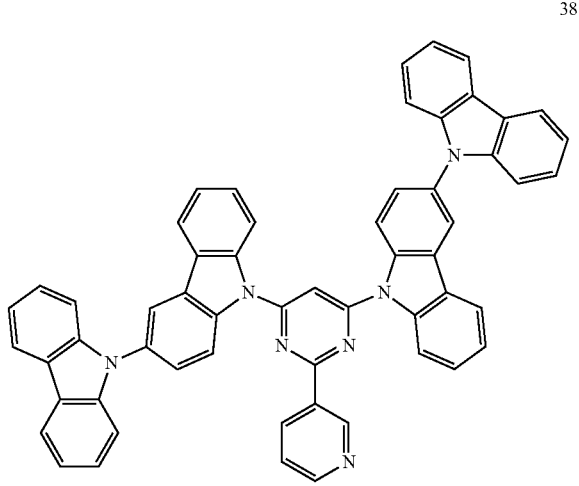
39
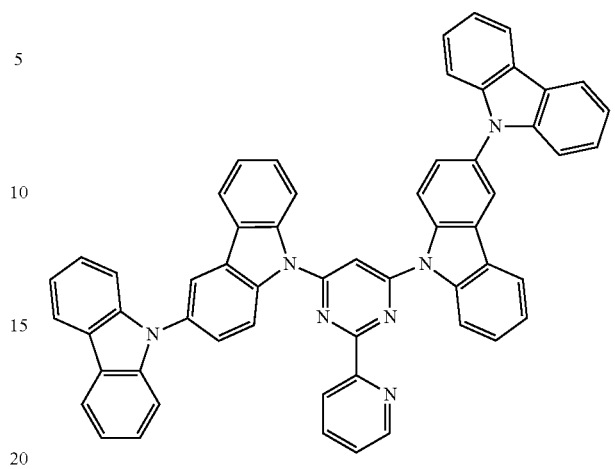
40
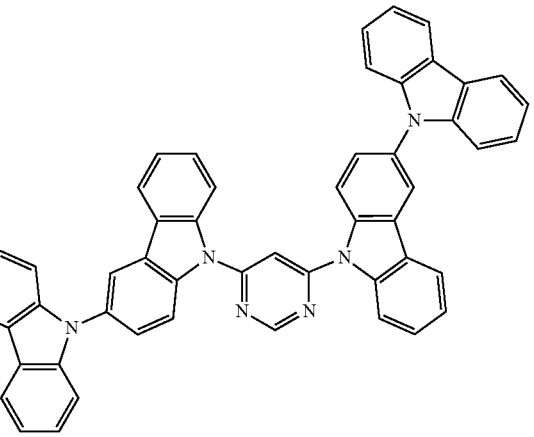
[Chem. 32]
41
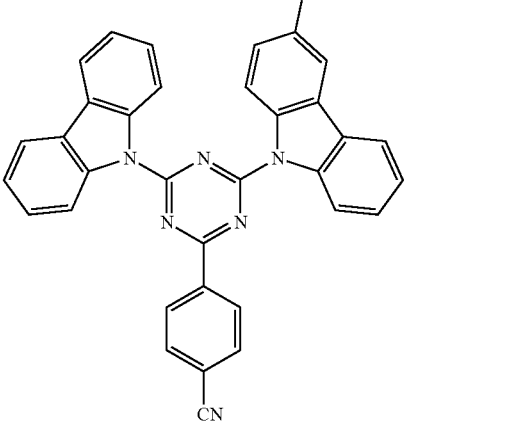

127
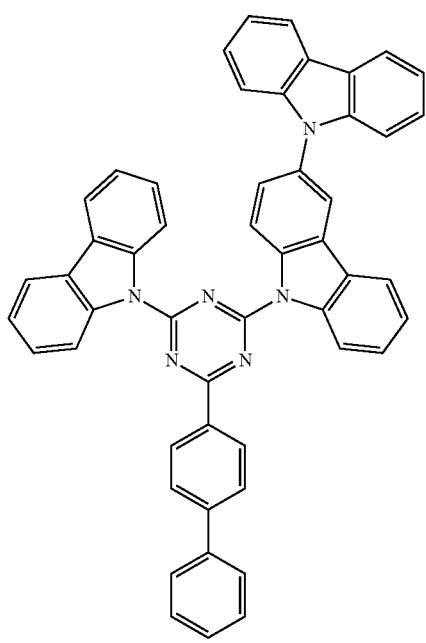
128
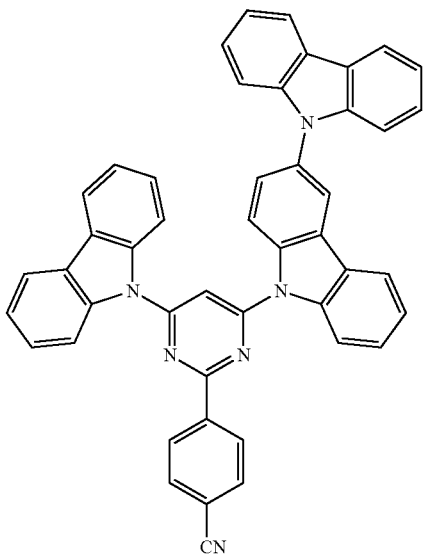
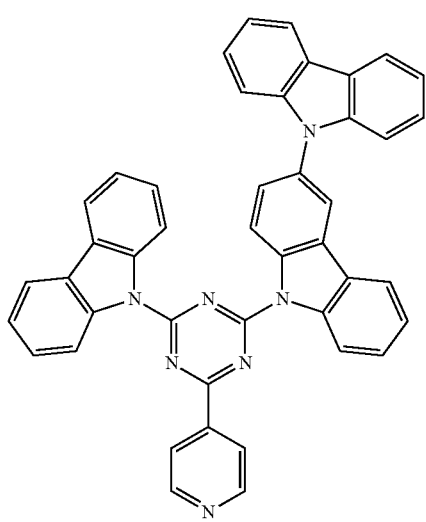
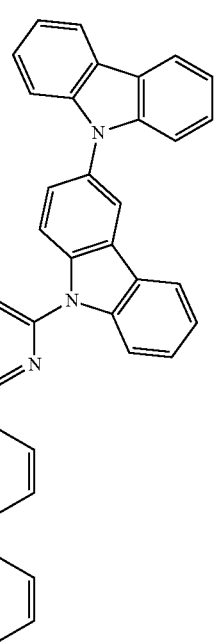

46
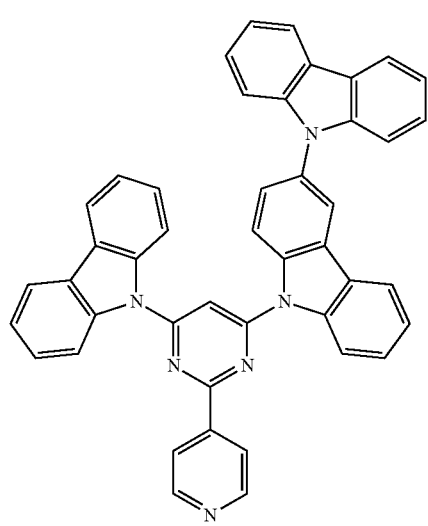
[Chem. 33]
47
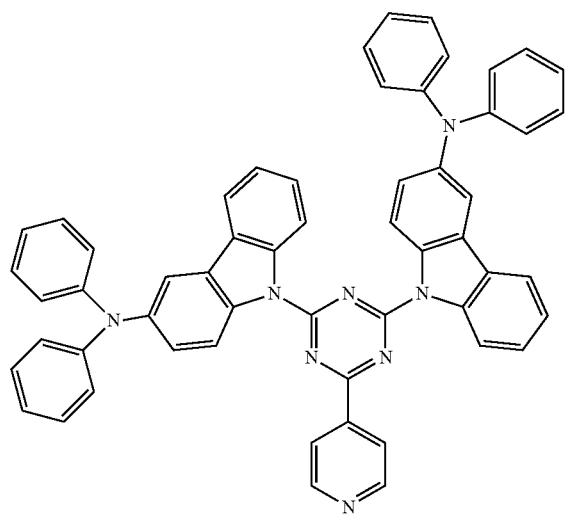
48
49
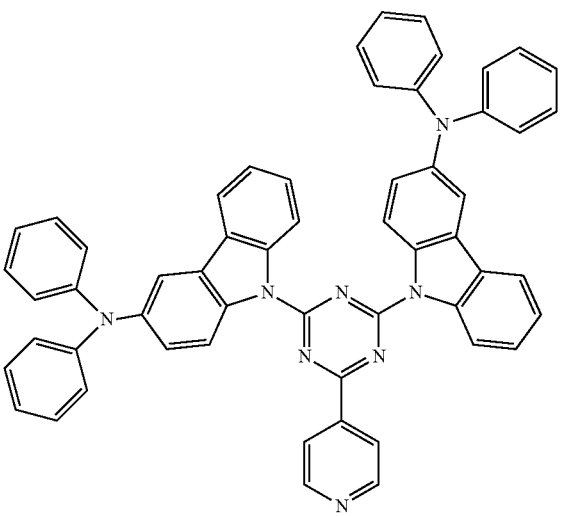
50
[Chem. 34]
51

-continued
52
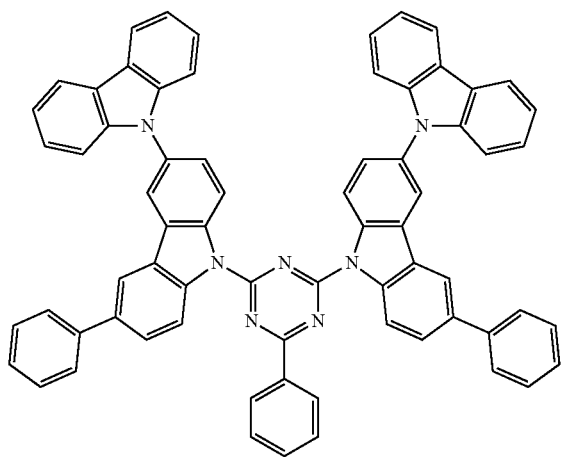
53
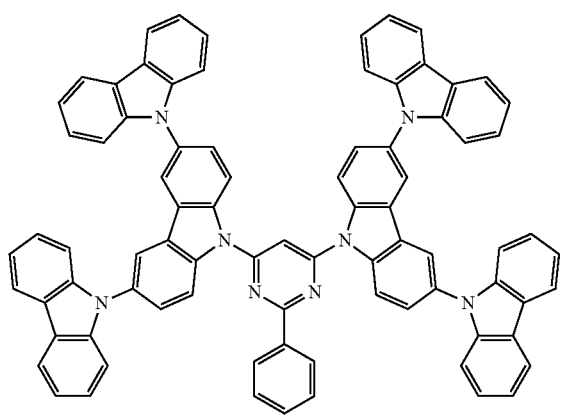
54
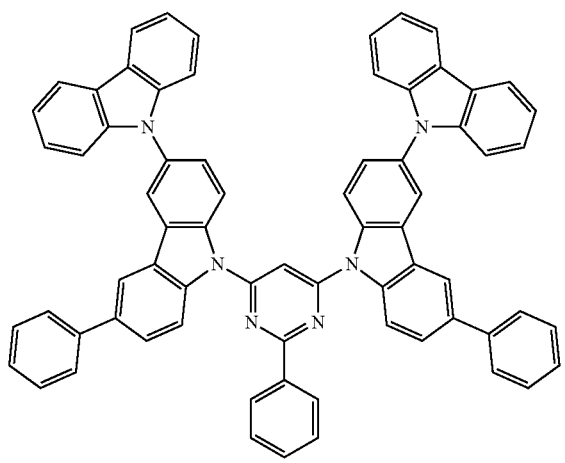
-continued
[Chem. 35]
55
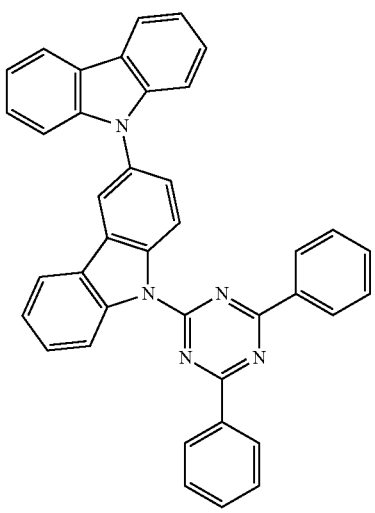
56
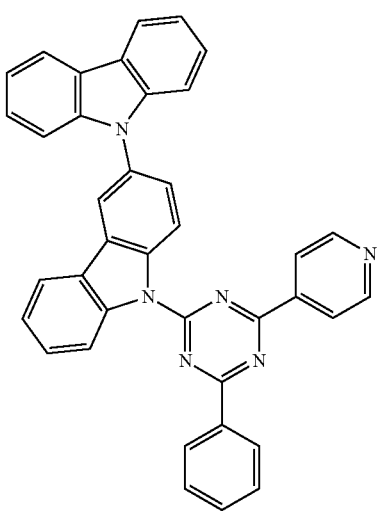
57
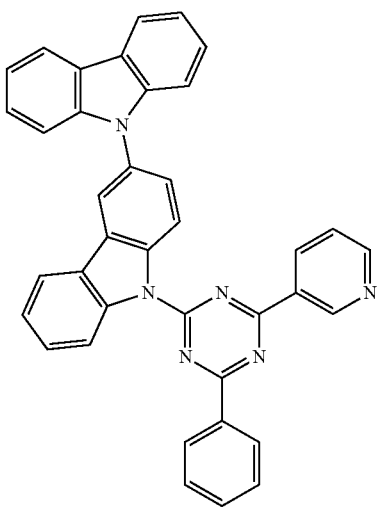

58
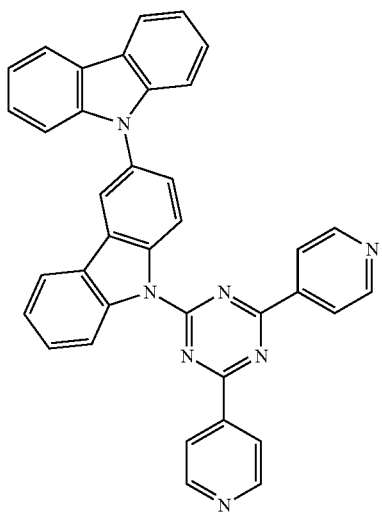
59
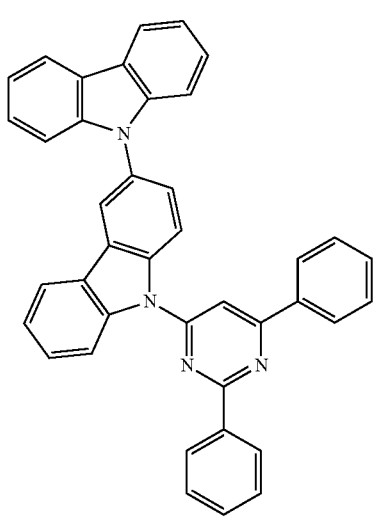
60
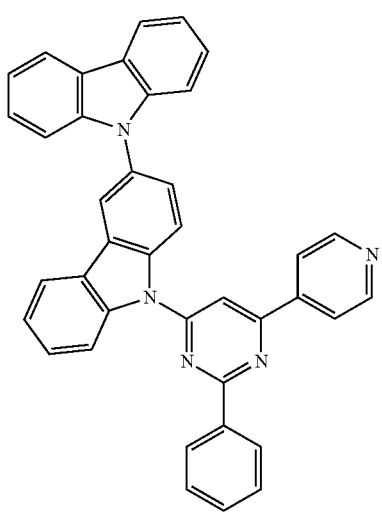
61
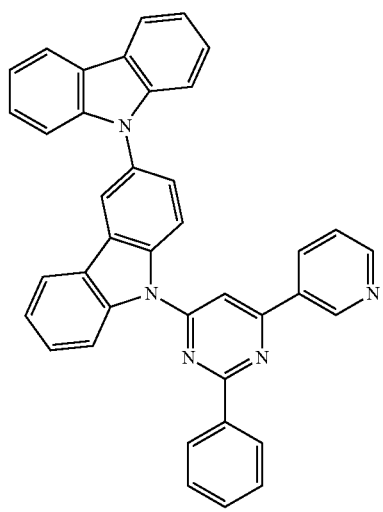
62
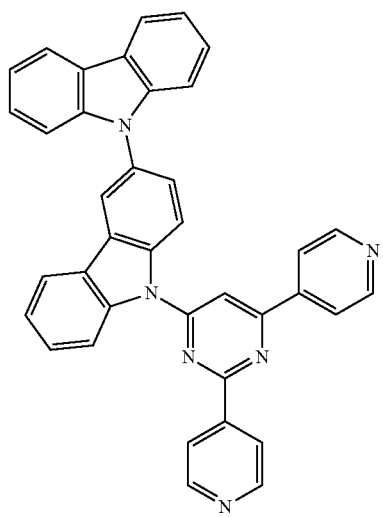
[Chem. 36]
63
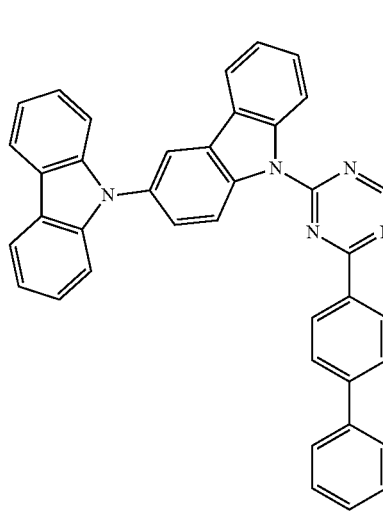

64
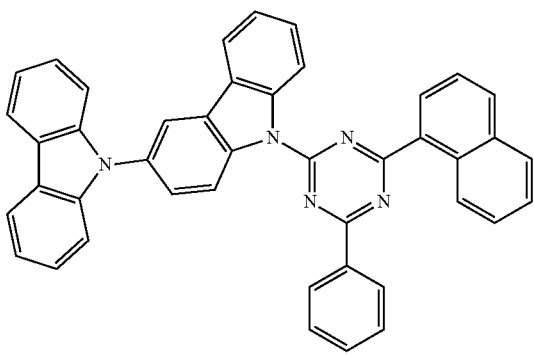
65
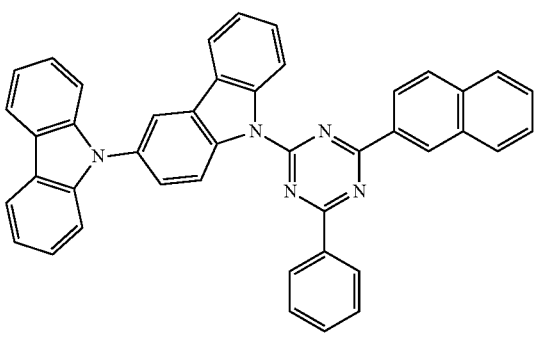
66
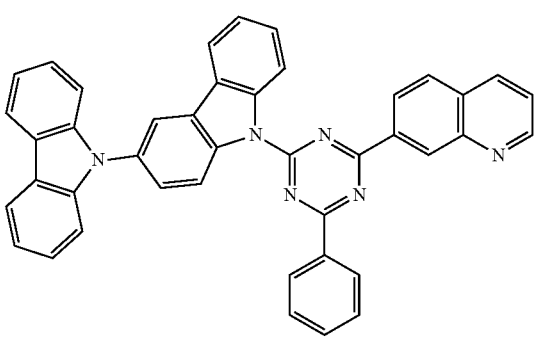
67
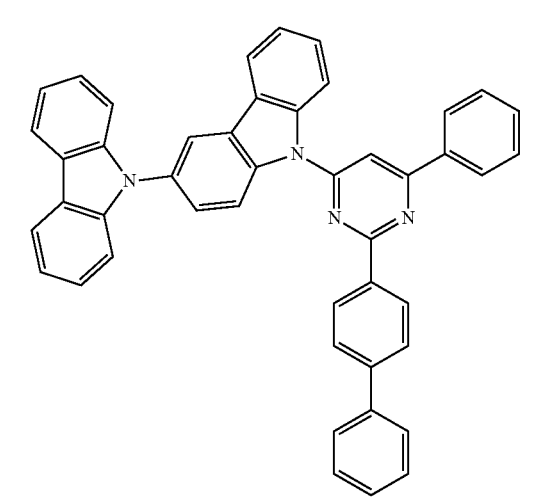
68
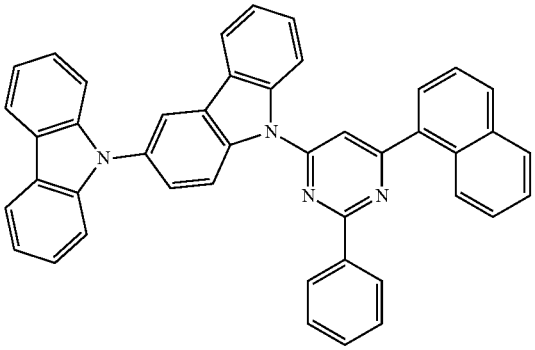
69
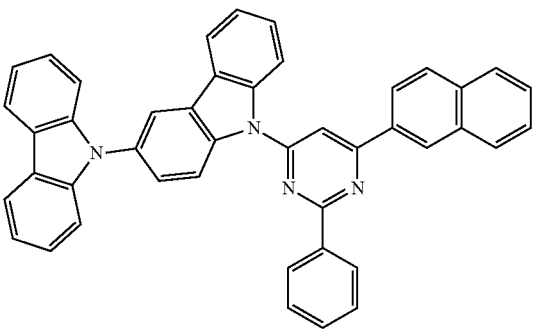
70

[Chem. 37]
71
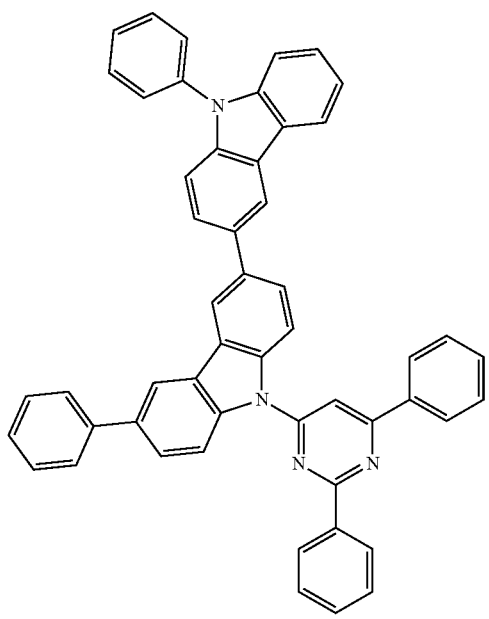
73
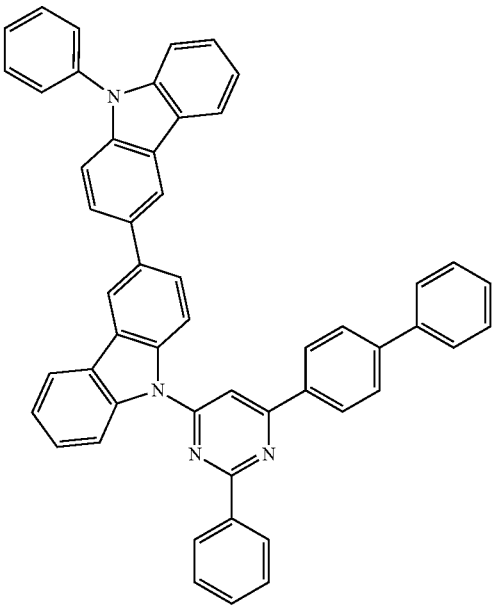
72
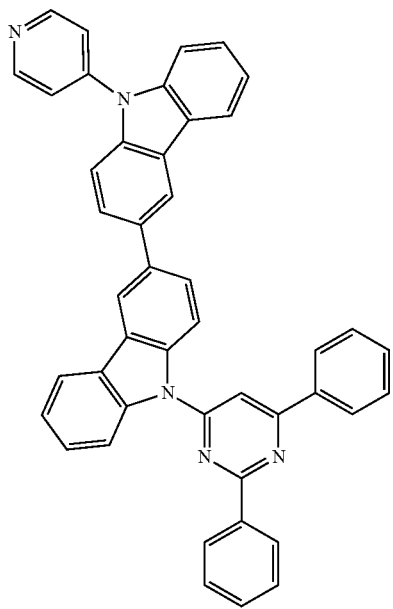
74
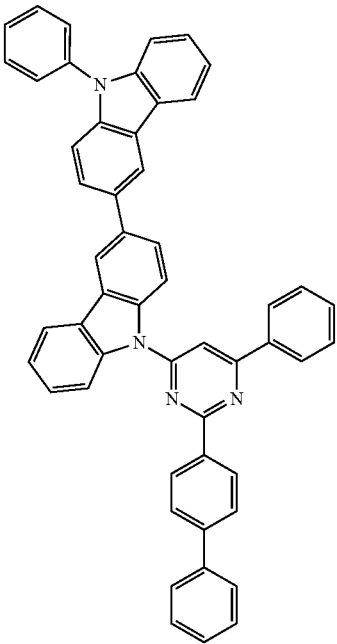

139
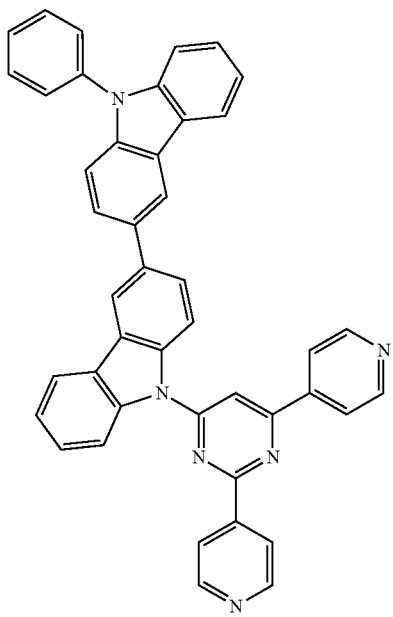
[Chem. 38]
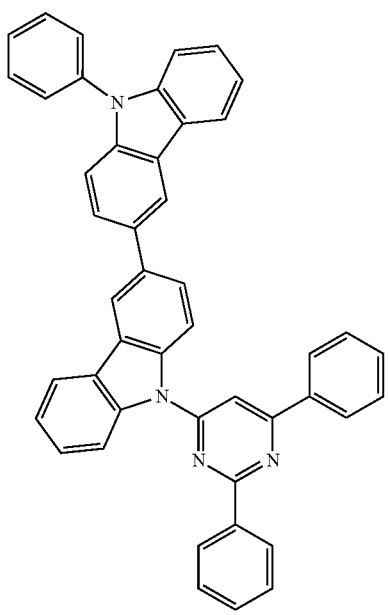
140
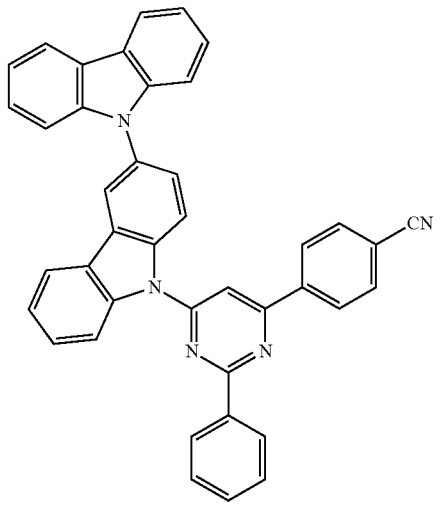
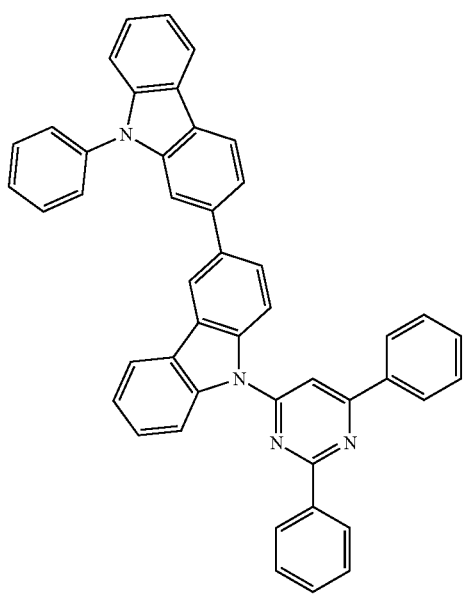

[Chem. 39]
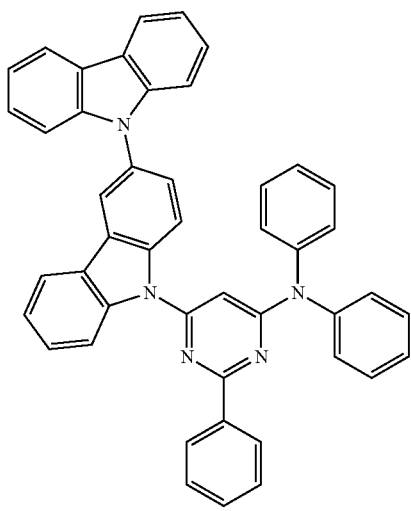
141
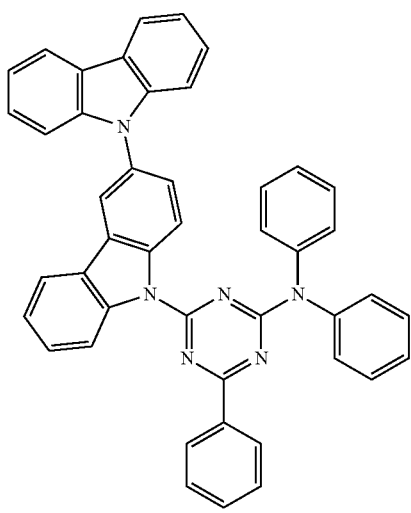
81
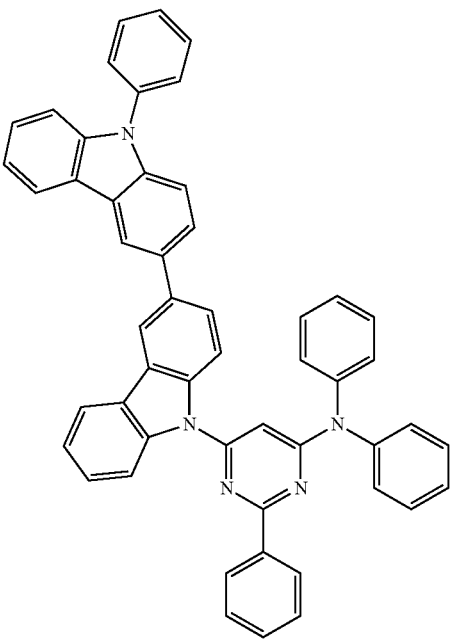
82
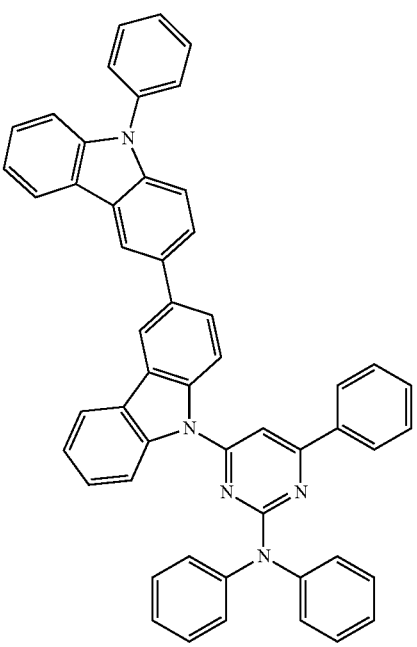
83

[Chem. 40]
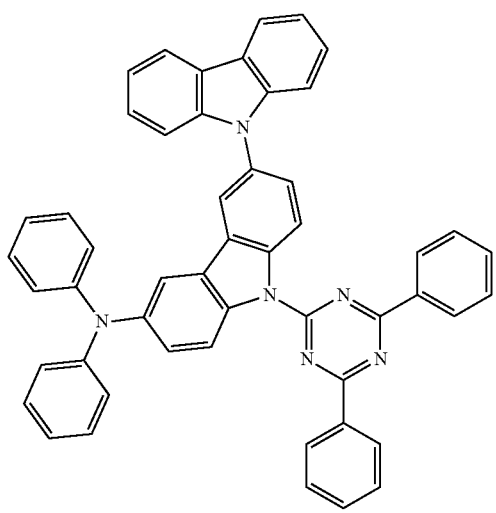
84
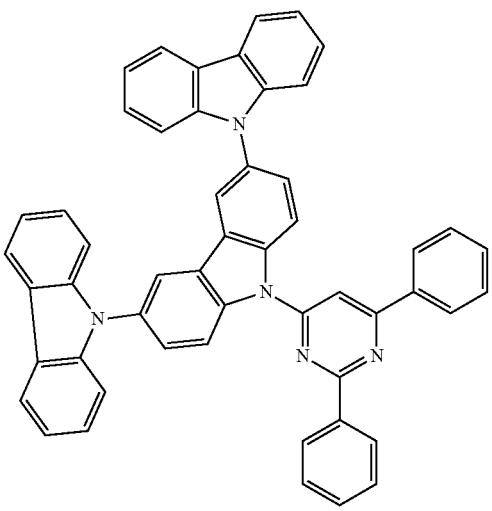
87
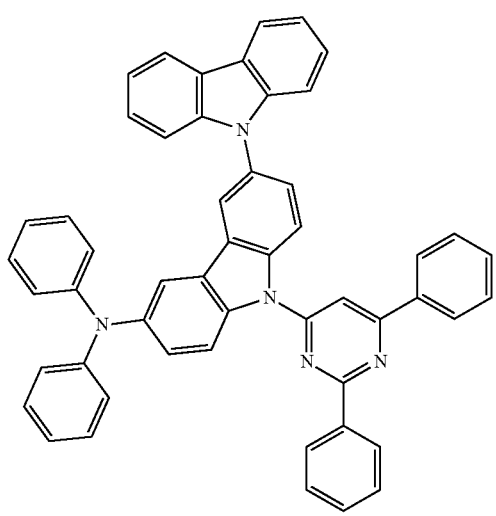
85
86
[Chem. 41]
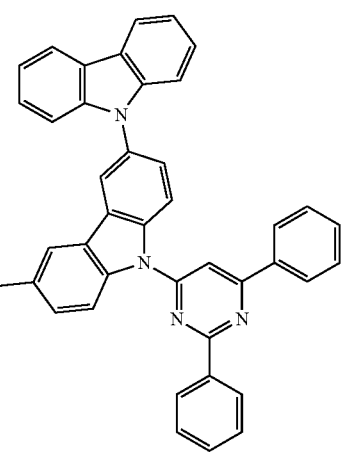
88
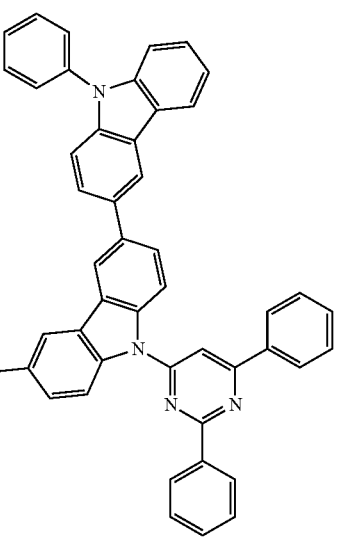
89
Examples of the preferred delayed fluorescent material include compounds represented by the following general formula. The entire description of JP-A-2013-256490 including the paragraphs 0009 to 0046 and 0093 to 0134 is incorporated herein by reference as a part of the description of the present application.

[Chem. 42]

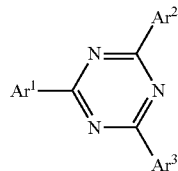

General Formula (171)

[In the general formula (171), $Ar^1$ to $Ar^3$ each independently represent a substituted or unsubstituted aryl group, and at least one of them represents a substituted aryl group represented by the following general formula (172).]

[Chem. 43]

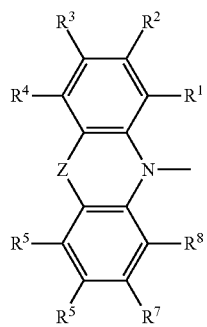

General Formula (172)

[In the general formula (172), $R^1$ to $R^8$ each independently represent a hydrogen atom or a substituent. Z represents O, S, O=C or $Ar^4$—N, $Ar^4$ represents a substituted or unsubstituted aryl group. $R^1$ and $R^2$, $R^2$ and $R^3$, $R^3$ and $R^4$, $R^5$ and $R^6$, $R^6$ and $R^7$, and $R^7$ and $R^8$ each independently may be bonded to each other to form a cyclic structure.]

Examples of the compound include the following compounds.

[Chem. 44]

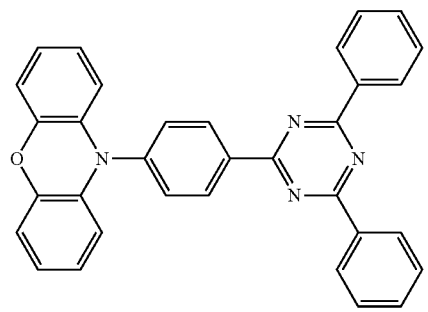

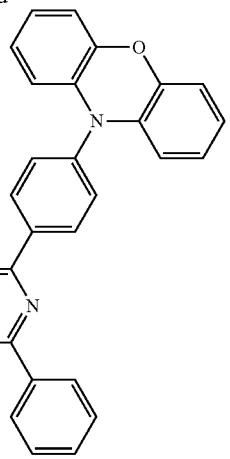

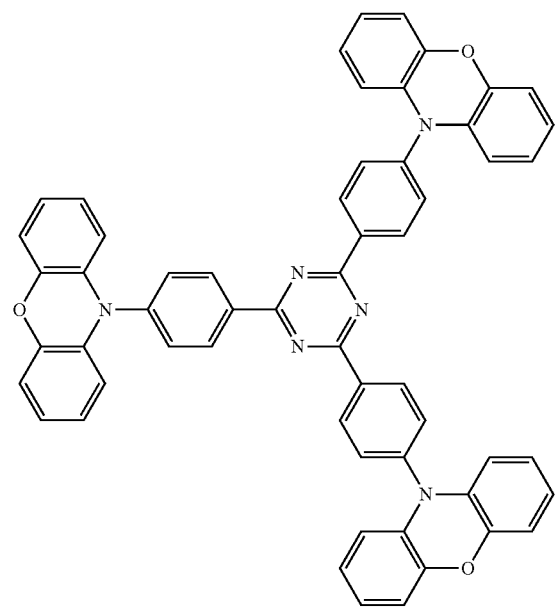

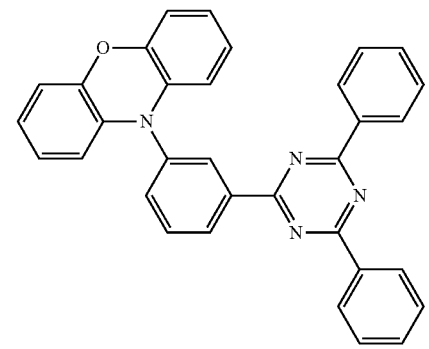

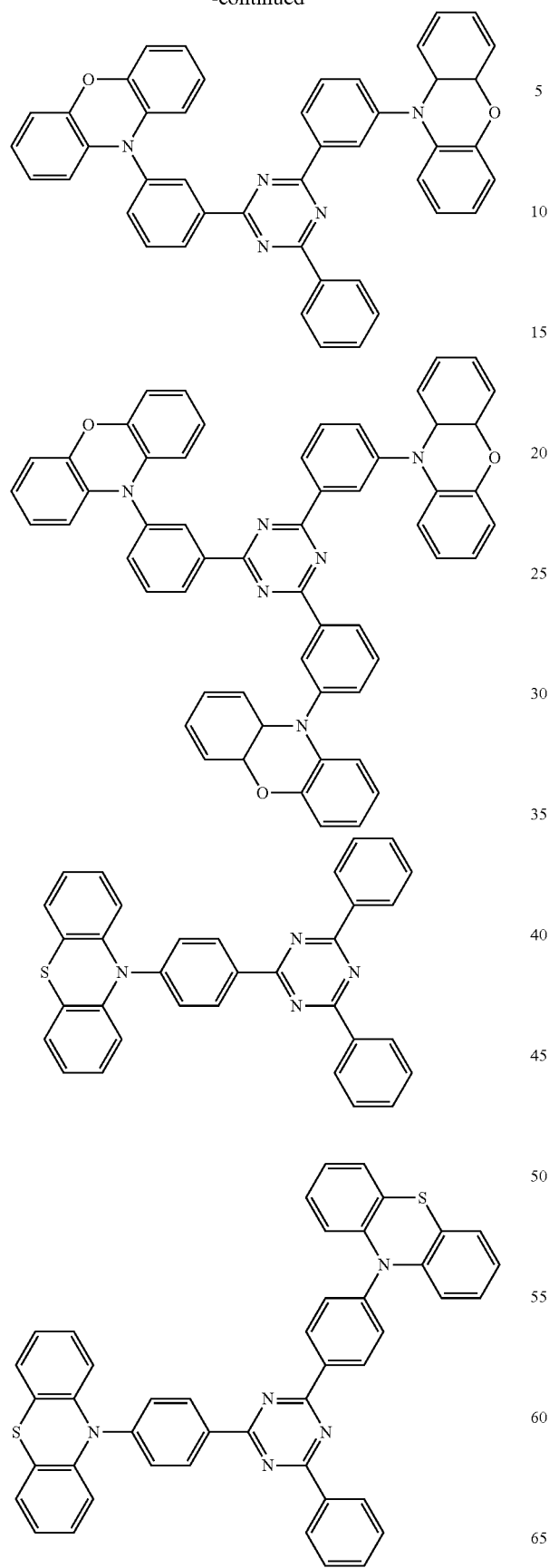
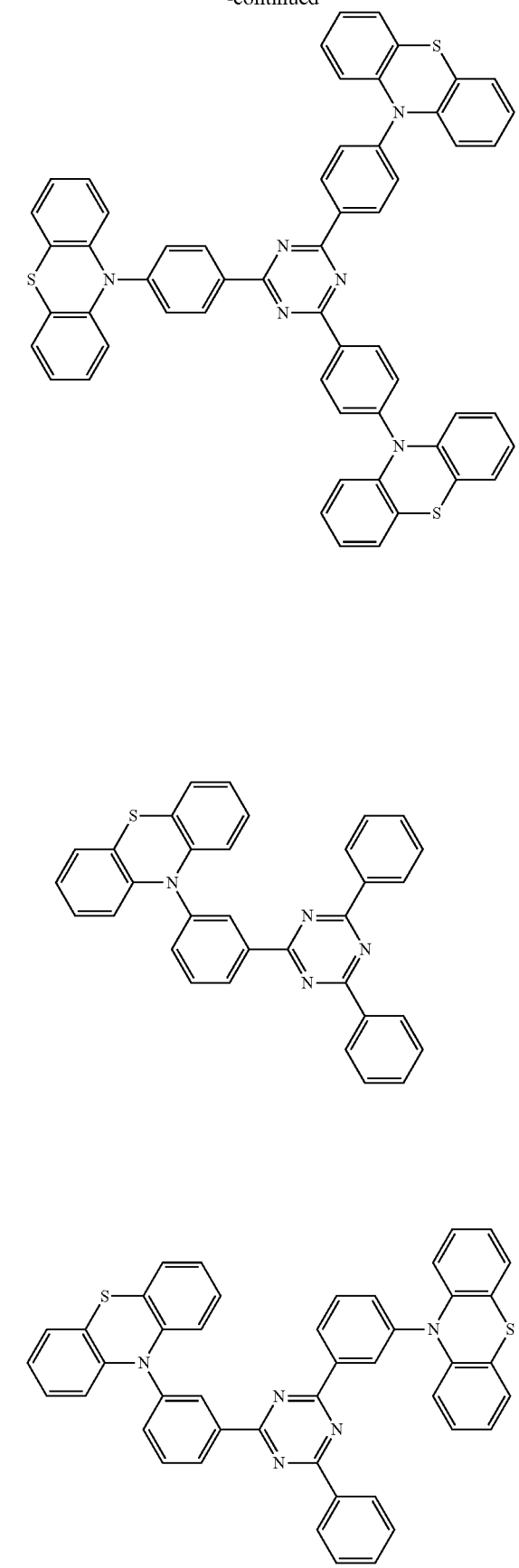

149
-continued
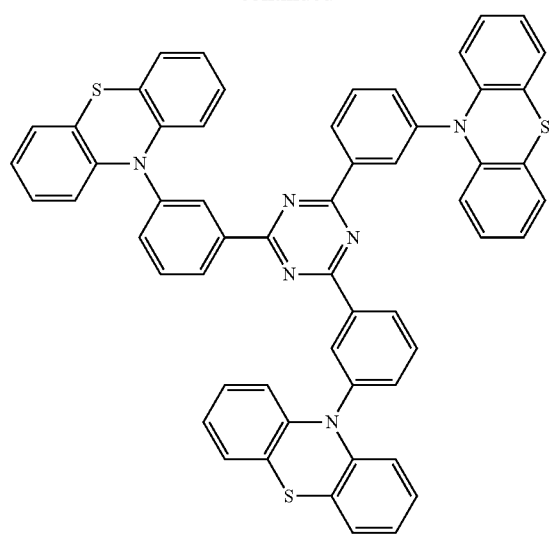
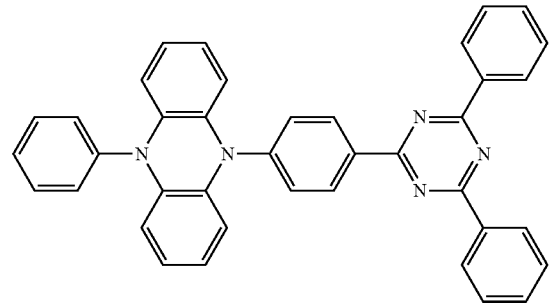
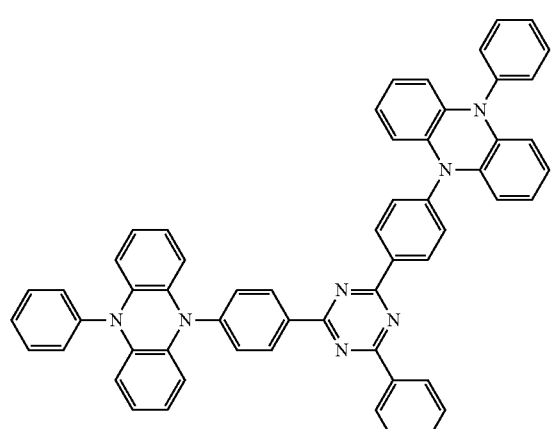
150
-continued
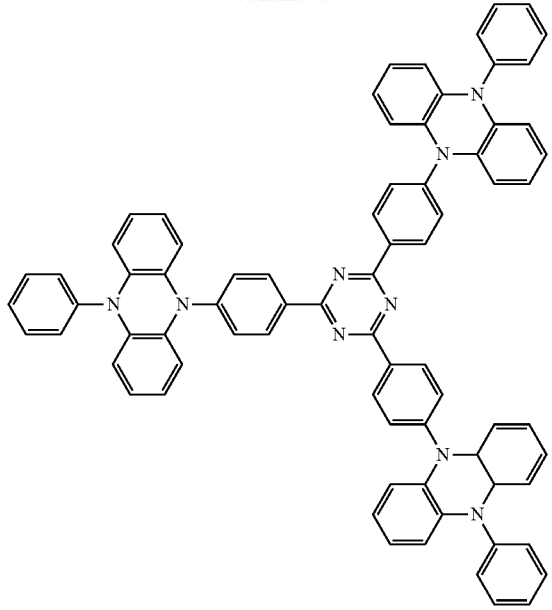
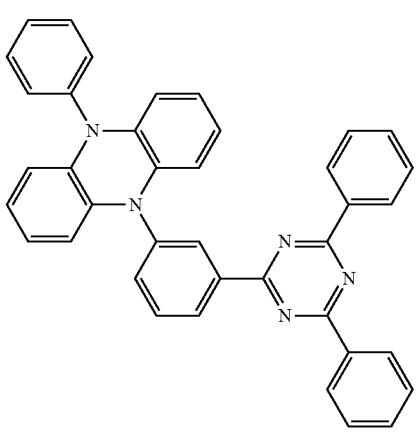
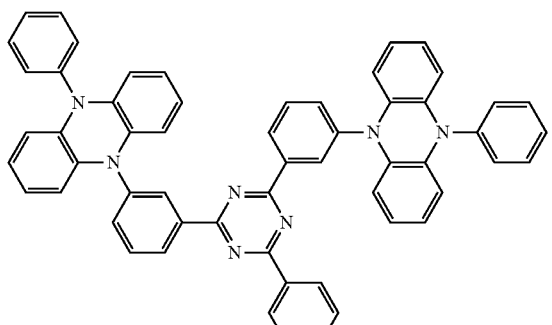

151
-continued
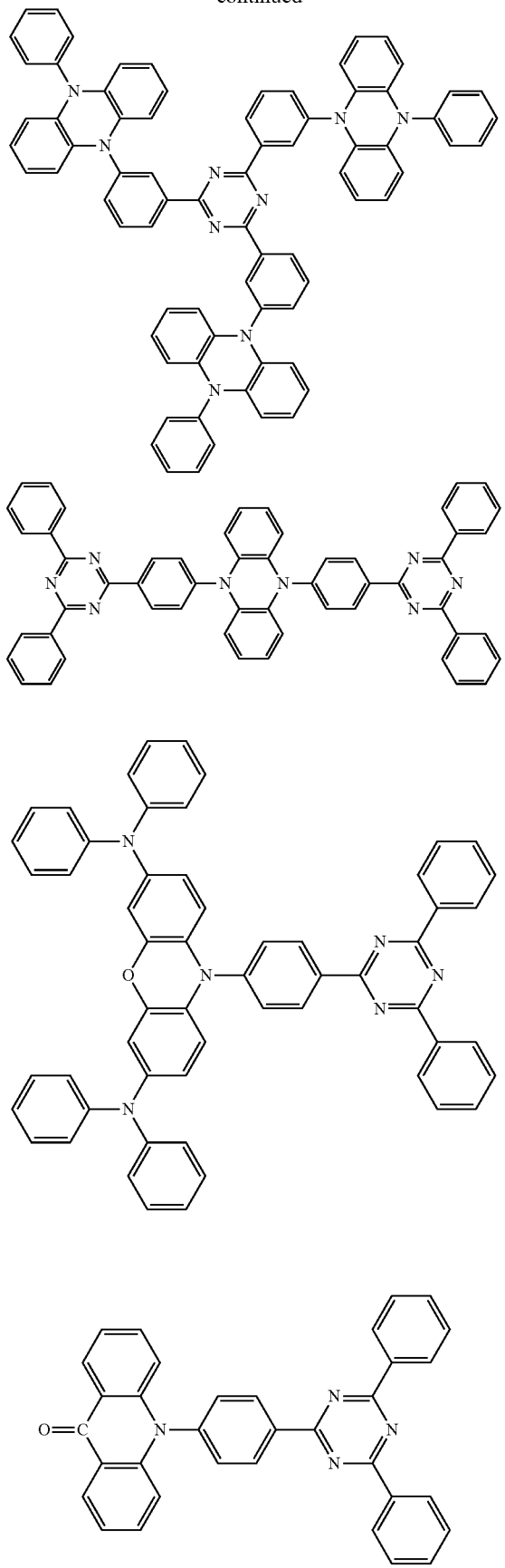
152
-continued
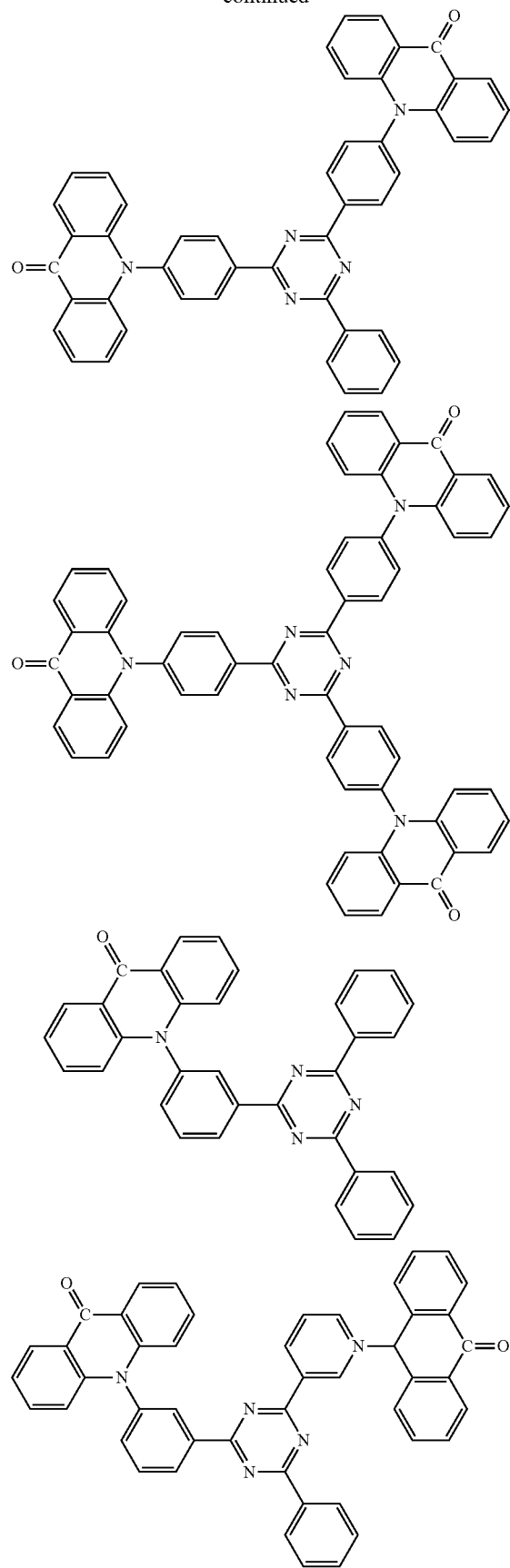

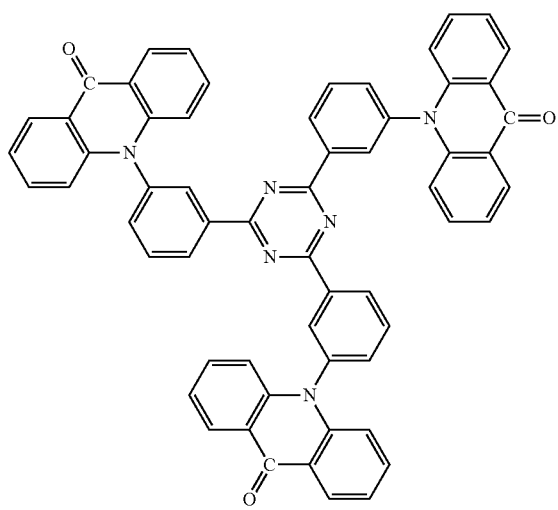 [SMILES: O=c1c2ccccc2n(-c2cccc(-c3nc(-c4cccc(-n5c6ccccc6c(=O)c6ccccc65)c4)nc(-c4cccc(-n5c6ccccc6c(=O)c6ccccc65)c4)n3)c2)c2ccccc12]

Examples of the preferred delayed fluorescent material include compounds represented by the following general formula. The entire description of JP-A-2013-116975 including the paragraphs 0008 to 0020 and 0038 to 0040 is incorporated herein by reference as a part of the description of the present application.

[Chem. 45]

General Formula (181)

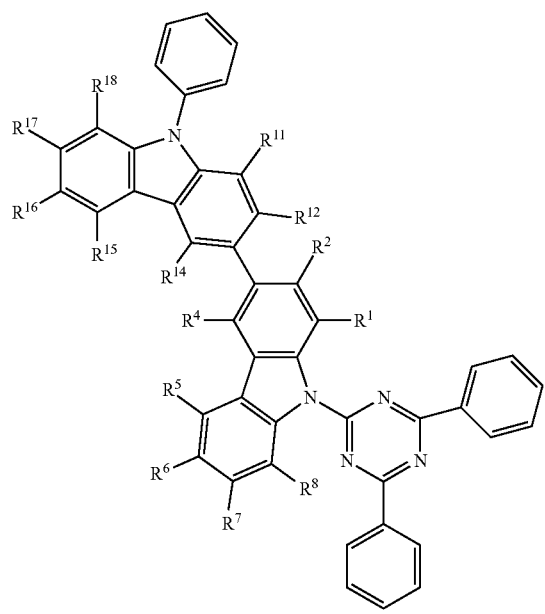

[In the general formula ($R^1$, $R^2$, $R^4$ to $R^8$, $R^{11}$, $R^{12}$ and $R^{14}$ to $R^{18}$ each independently represent a hydrogen atom or a substituent.]

[Chem. 46]

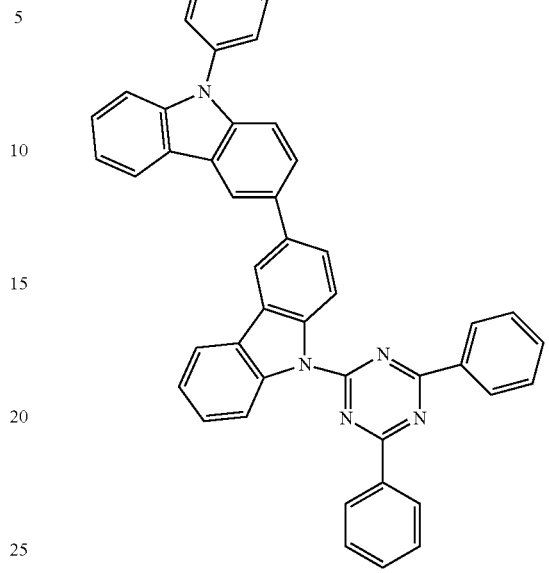

Examples of the preferred delayed fluorescent material include the following compounds.

[1] A compound represented by the following general formula (191):

[Chem. 47]

General Formula (191)

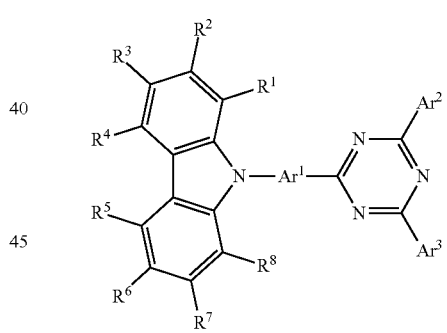

[In the general formula (191), $Ar^1$ represents a substituted or unsubstituted arylene group; $Ar^2$ and $Ar^3$ each independently represent a substituted or unsubstituted aryl group. $R^1$ to $R^8$ each independently represent a hydrogen atom or a substituent, provided that at least one of $R^1$ to $R^8$ represents a substituted or unsubstituted diarylamino group, and $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

[2] The compound according to [1], wherein in the general formula (191), at least one of $R^1$ to $R^4$ represents a substituted or unsubstituted diarylamino group, and at least one of $R^5$ to $R^8$ represents a substituted or unsubstituted diarylamino group.

[3] The compound according to [2], wherein in the general formula (191), $R^3$ and $R^6$ each represent a substituted or unsubstituted diarylamino group.

[4] The compound according to any one of [1] to [3], wherein in the general formula (191), at least one of $R^1$ to $R^8$ represents a substituted or unsubstituted diphenylamino group.

[5] The compound according to any one of [1] to [4], wherein in the general formula (191), $Ar^2$ and $Ar^3$ each independently represent a substituted or unsubstituted phenyl group.

[6] The compound according to any one of [1] to [5], wherein in the general formula (191), $Ar^1$ each independently represents a substituted or unsubstituted phenylene group, a substituted or unsubstituted naphthylene group or a substituted or unsubstituted anthracenylene group.

[7] The compound according to [1], wherein the compound has a structure represented by the following general formula (192):

[Chem. 48]

General Formula (192)

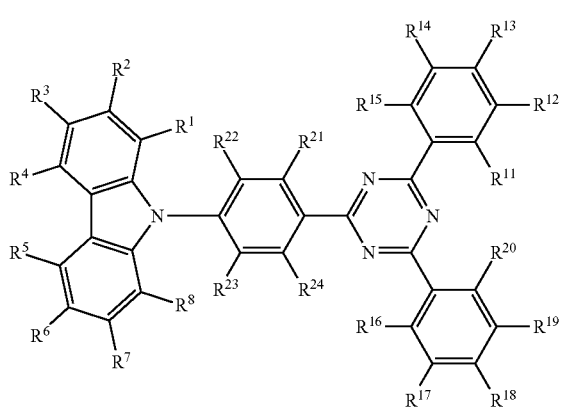

[In the general formula (192), $R^1$ to $R^8$ and $R^{11}$ to $R^{24}$ each independently represent a hydrogen atom or a substituent, provided that at least one of $R^1$ to $R^8$ represents a substituted or unsubstituted diarylamino group, and $R^1$ and $R^2$, $R^2$ and $R^3$, $R^3$ and $R^4$, $R^5$ and $R^6$, $R^6$ and $R^7$, $R^7$ and $R^8$, $R^{11}$ and $R^{12}$; $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, and $R^{23}$ and $R^{24}$ each may be bonded to each other to form a cyclic structure.]

[8] The compound according to [7], wherein in the general formula (192), at least one of $R^1$ to $R^4$ represents a substituted or unsubstituted diarylamino group, and at least one of $R^5$ to $R^8$ represents a substituted or unsubstituted diarylamino group.

[9] The compound according to [8], wherein in the general formula (192), $R^3$ and $R^6$ each represent a substituted or unsubstituted diarylamino group.

Specific examples of the compound include the following compounds. Ph represents a phenyl group.

[Chem. 49]

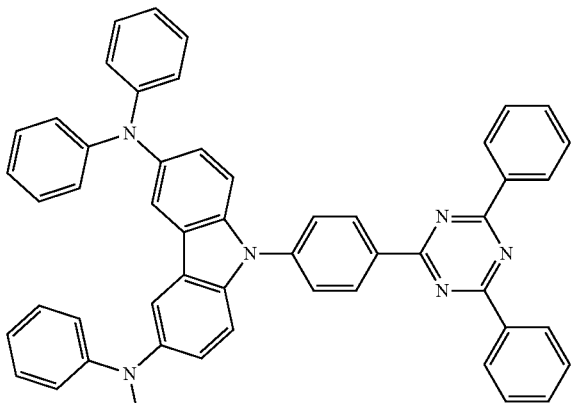

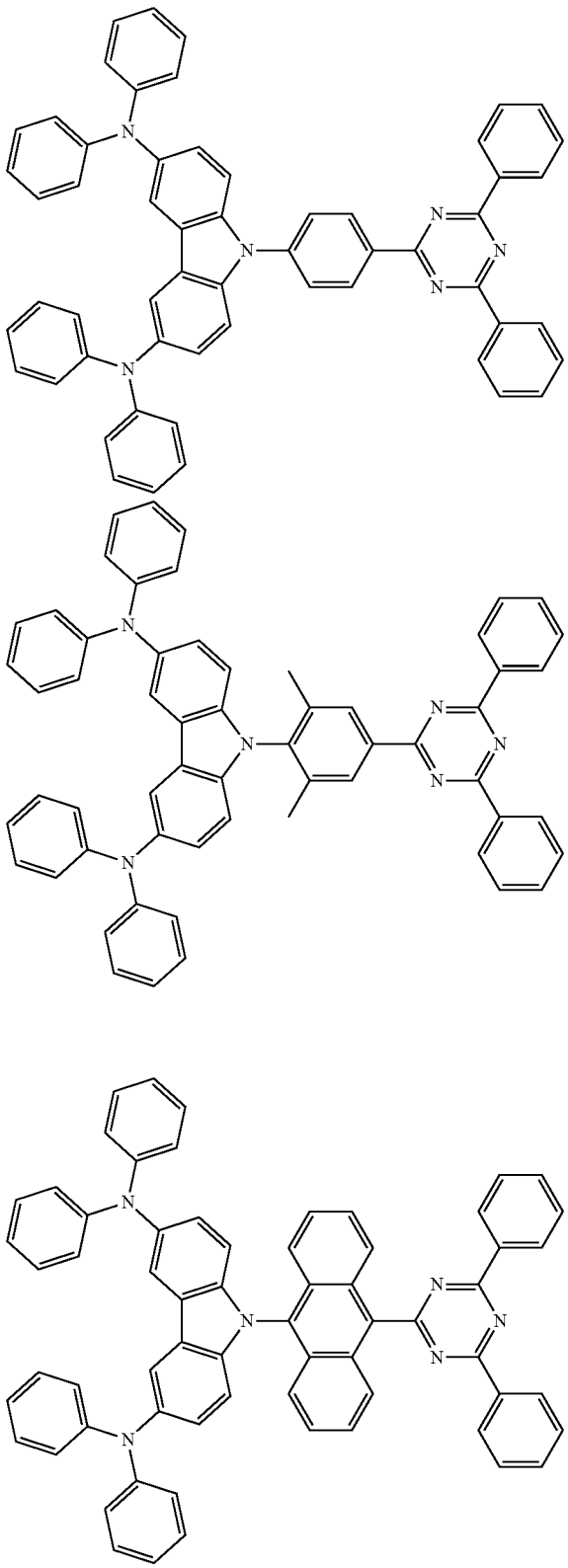

[Chem. 50]
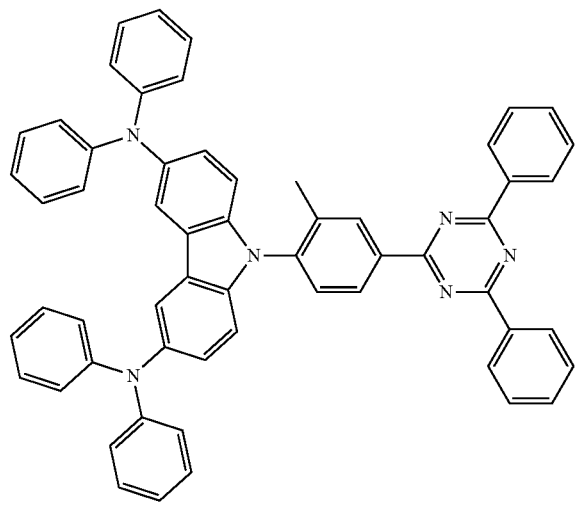
[Chem. 51]
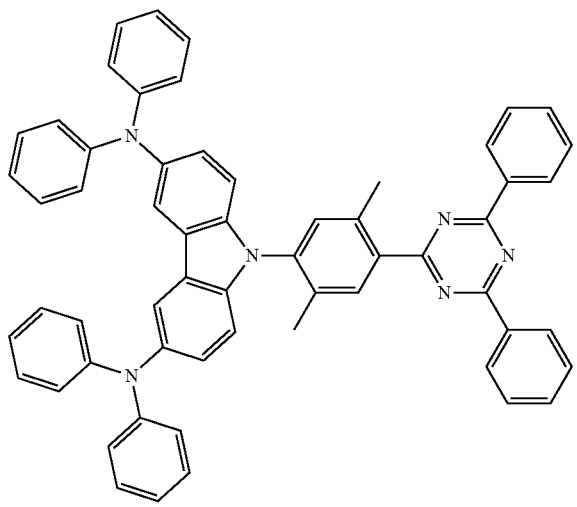
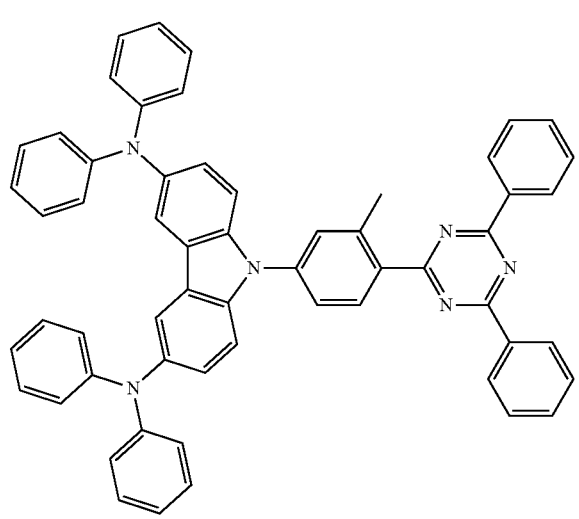
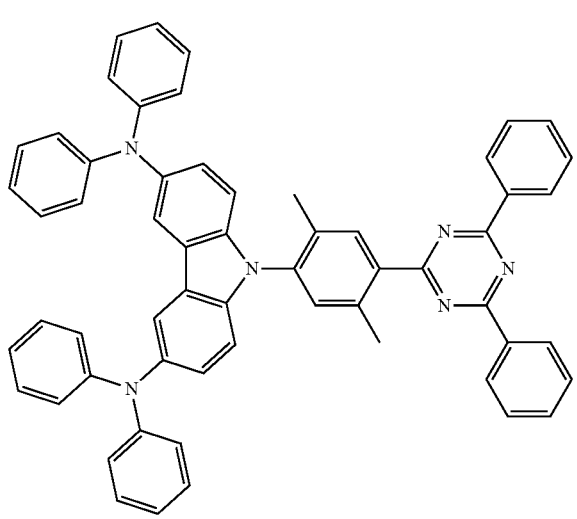
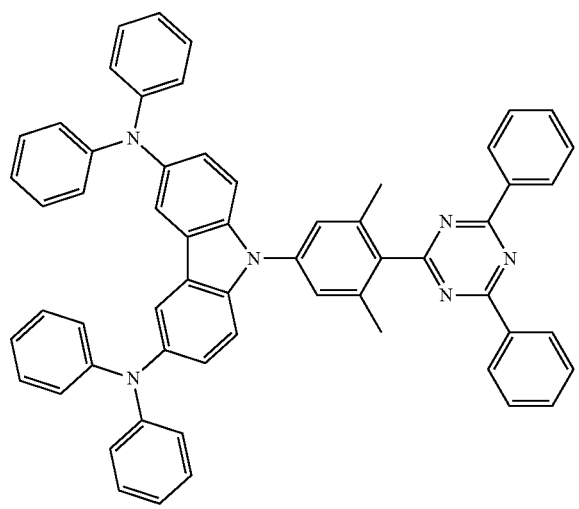
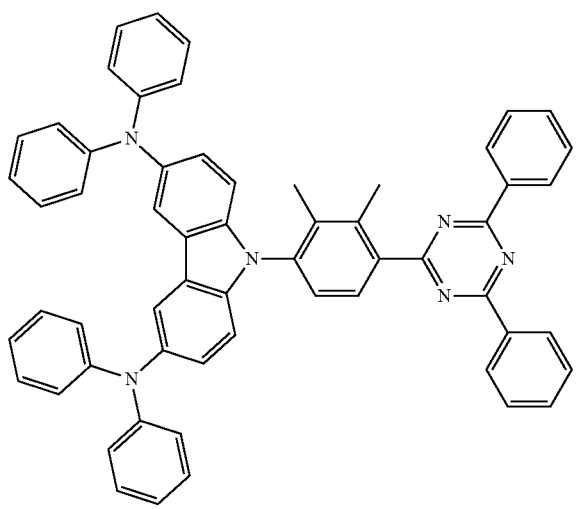

[Chem. 52]

-continued

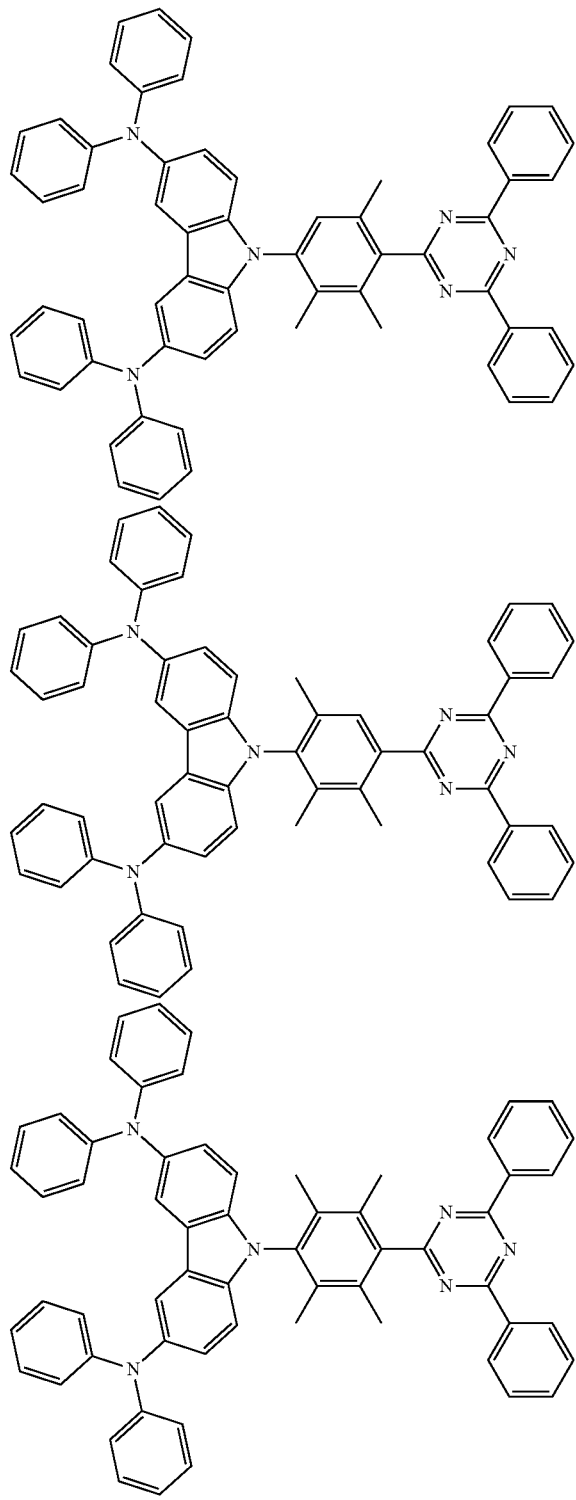

Examples of the preferred delayed fluorescent material include the following compounds.

[1] A compound represented by the following general formula (201):

[Chem. 53]

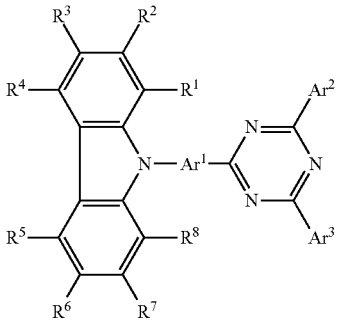

General Formula (201)

(In the above formula, $R^1$ to $R^8$ each independently represent a hydrogen atom or a substituent, provided that at least one of $R^1$ to $R^8$ represents a substituted or unsubstituted carbazolyl group. $Ar^1$ to $Ar^3$ each independently represent a substituted or unsubstituted aromatic ring or a heteroaromatic ring)

[2] The compound according to [1], wherein in the general formula (201), at least one of $R^3$ and $R^6$ represents a substituted or unsubstituted carbazolyl group.

[3] The compound according to [1] or [2], wherein the carbazolyl group is a 1-carbazolyl group, a 2-carbazolyl group, a 3-carbazolyl group or a 4-carbazolyl group.

[4] The compound according to any one of [1] to [3], wherein the carbazolyl group has a substituent on the nitrogen atom in the carbazole cyclic structure.

[5] The compound according to any one of [1] to [4], wherein in the general formula (201), at least one of $Ar^1$, $Ar^2$ and $Ar^3$ represents a benzene ring or a naphthalene ring.

[6] The compound according to any one of [1] to [5], wherein in the general formula (201), $Ar^1$, $Ar^2$ and $Ar^3$ each represent the same aromatic ring or the same heteroaromatic ring.

[7] The compound according to any one of [1] to [6], wherein in the general formula (201), $Ar^1$, $Ar^2$ and $Ar^3$ each represent a benzene ring.

Examples of the compound include the following compounds.

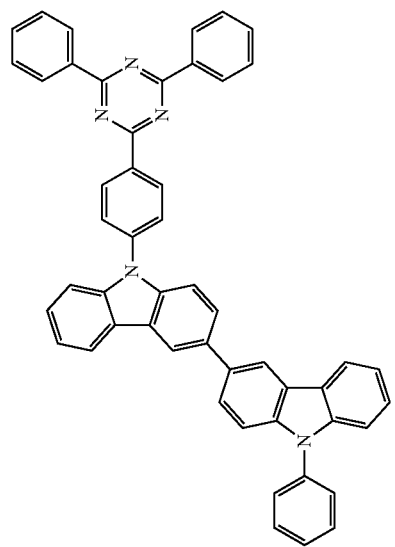
[Chem. 54]
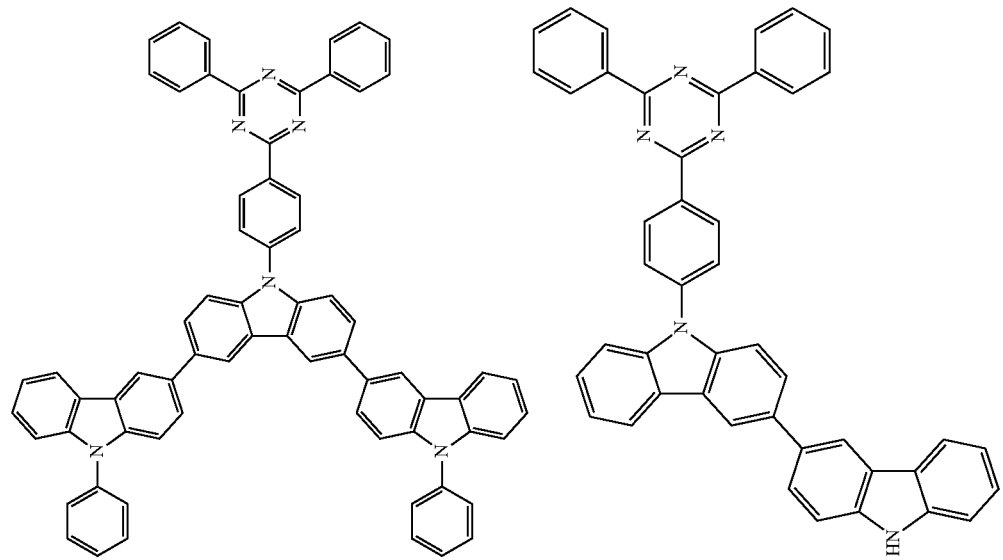

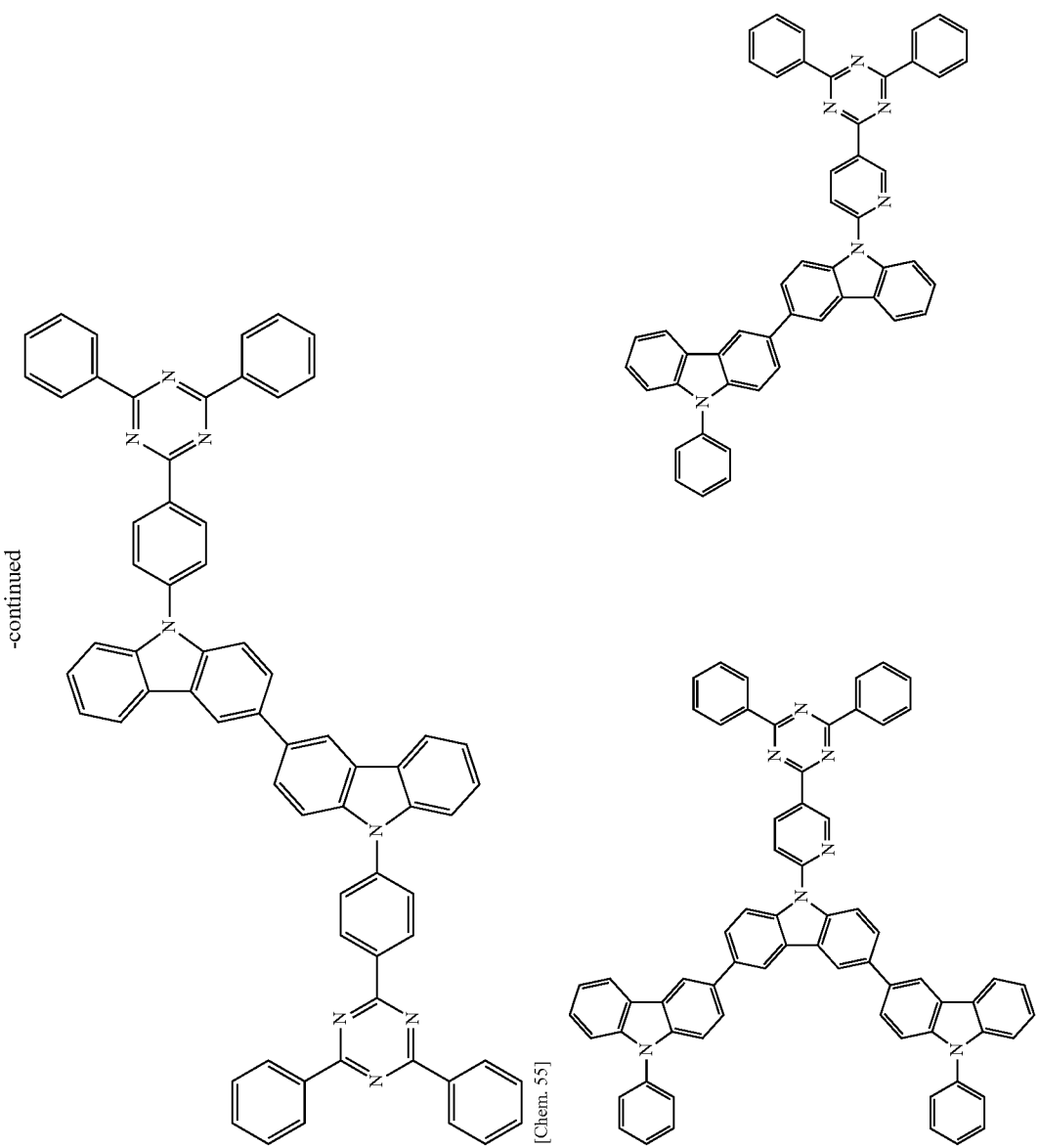
[Chem. 55]

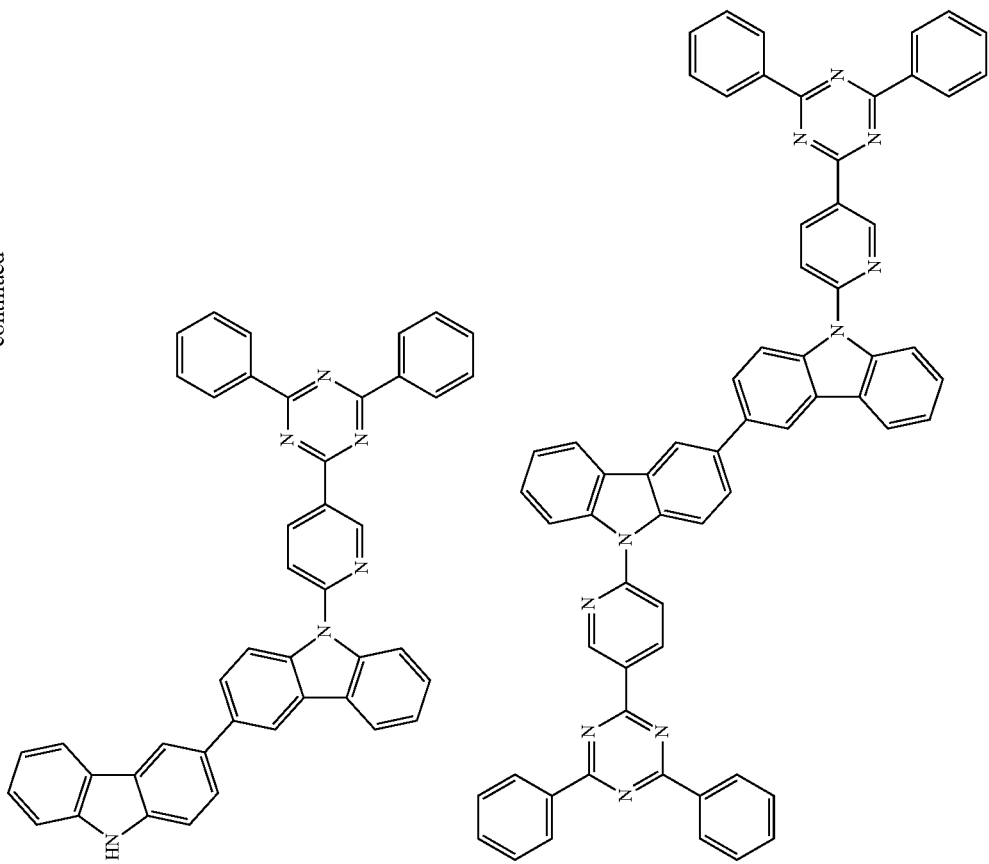

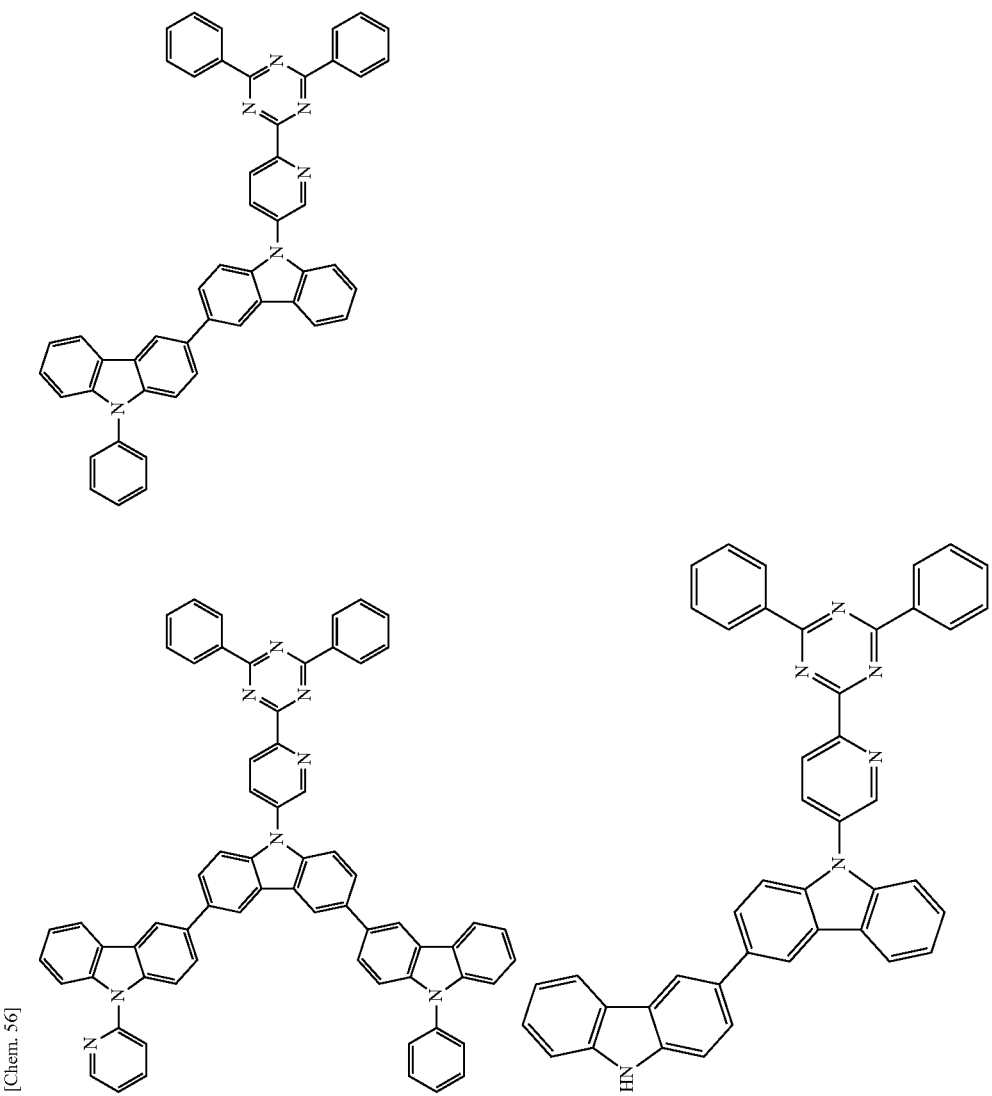
[Chem. 56]

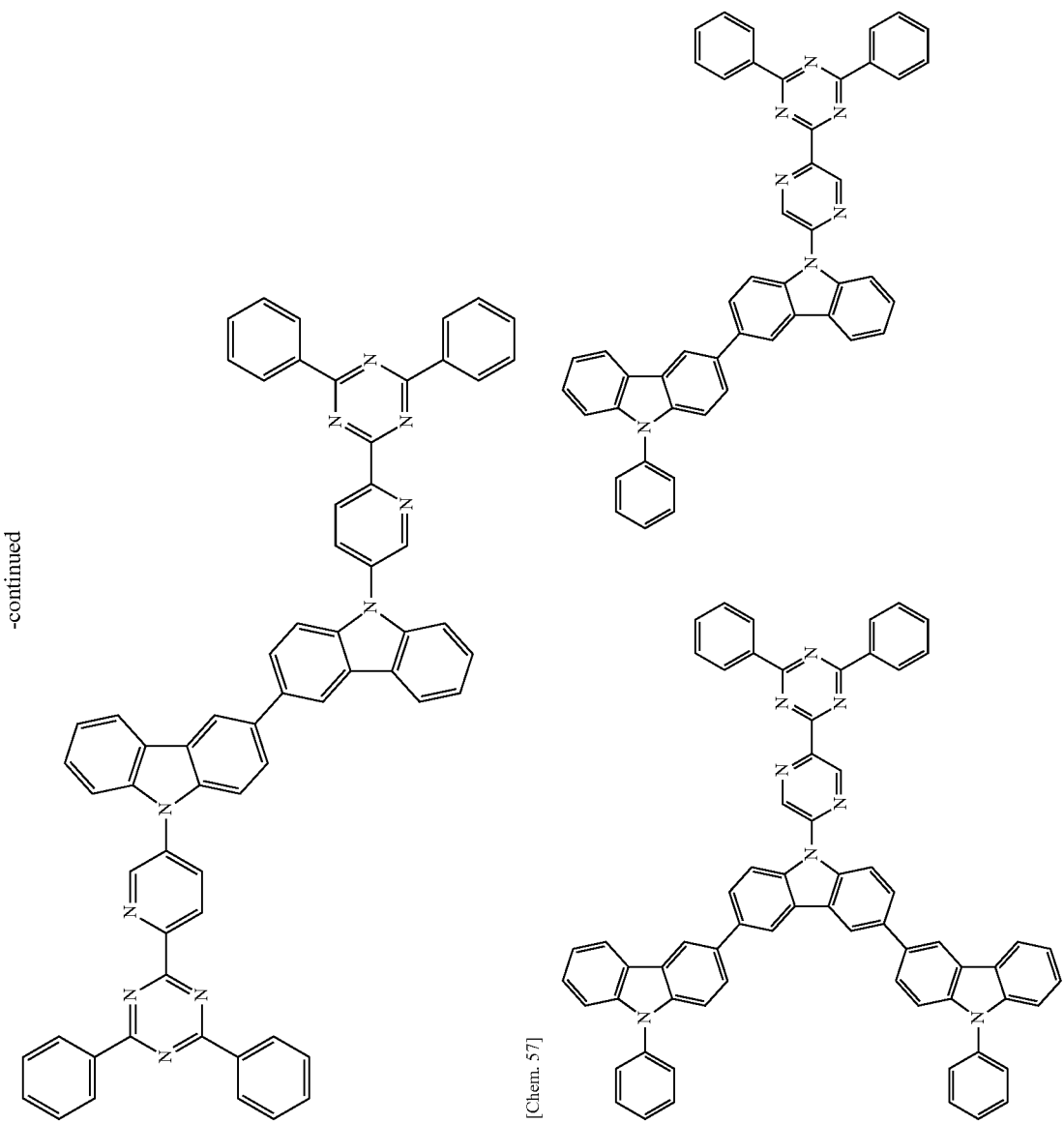
[Chem. 57]

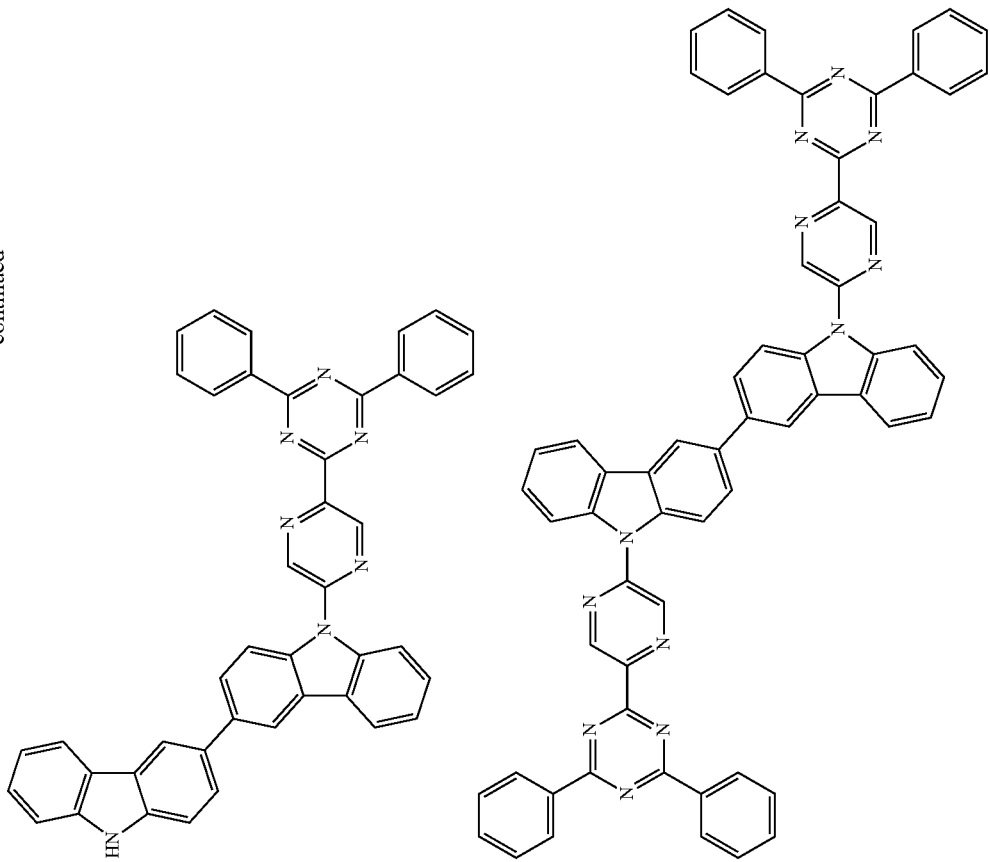

[Chem. 58]
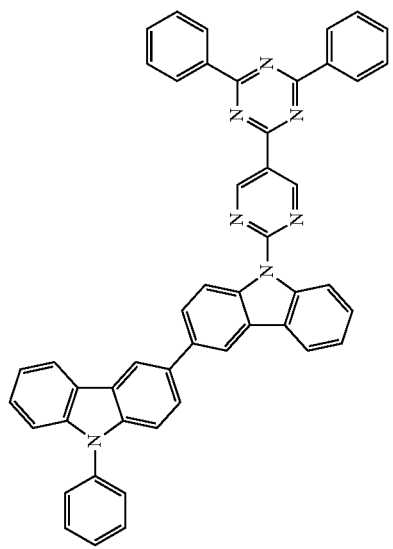
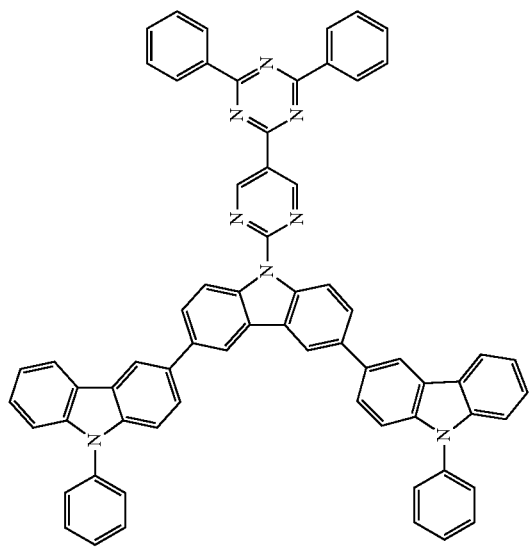
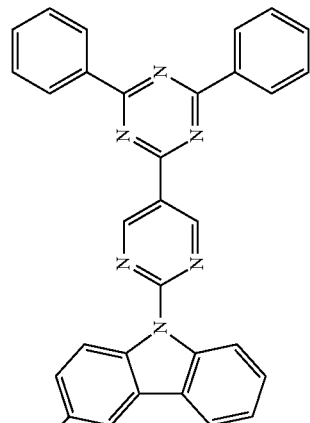

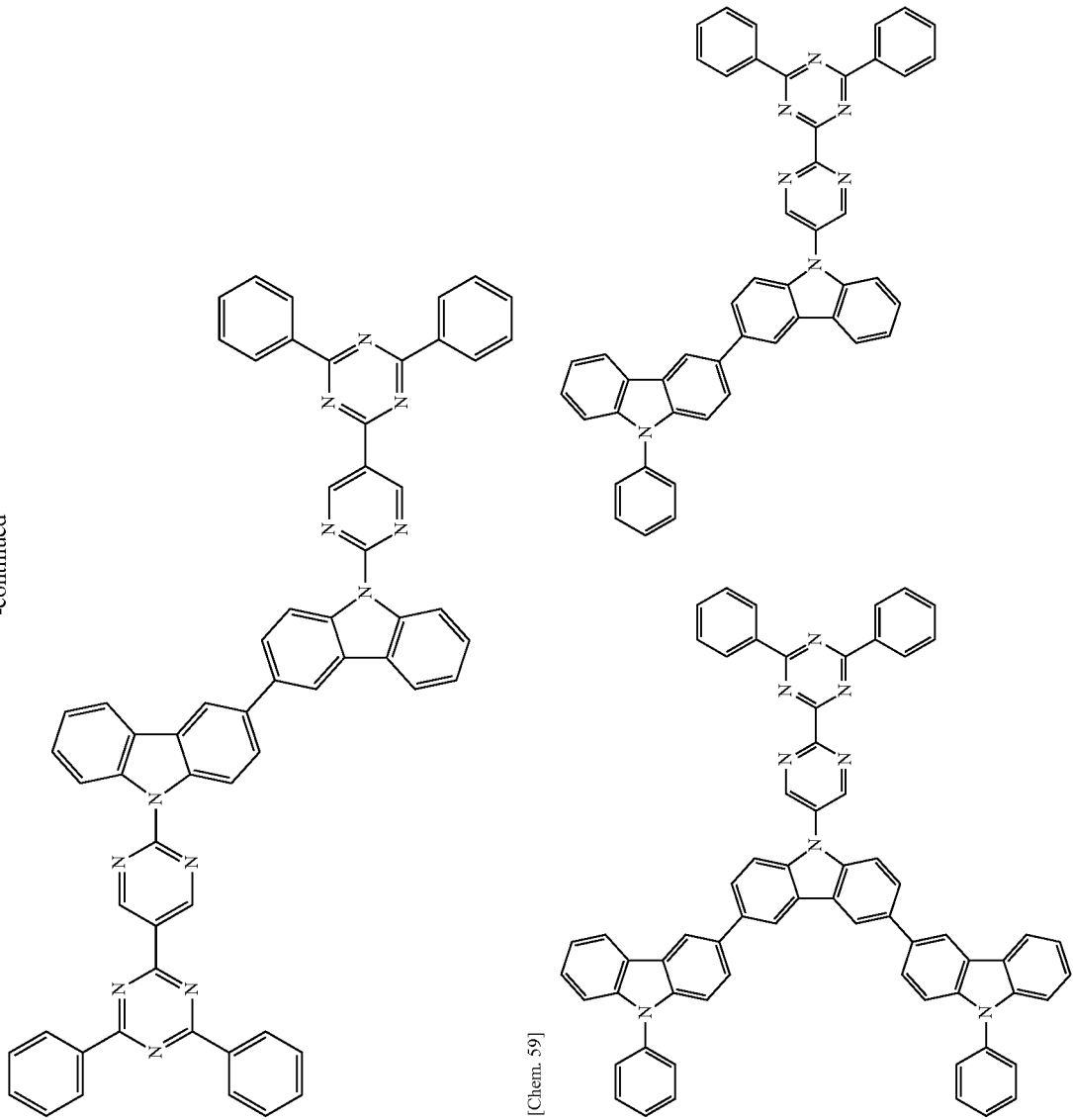
[Chem. 59]

-continued
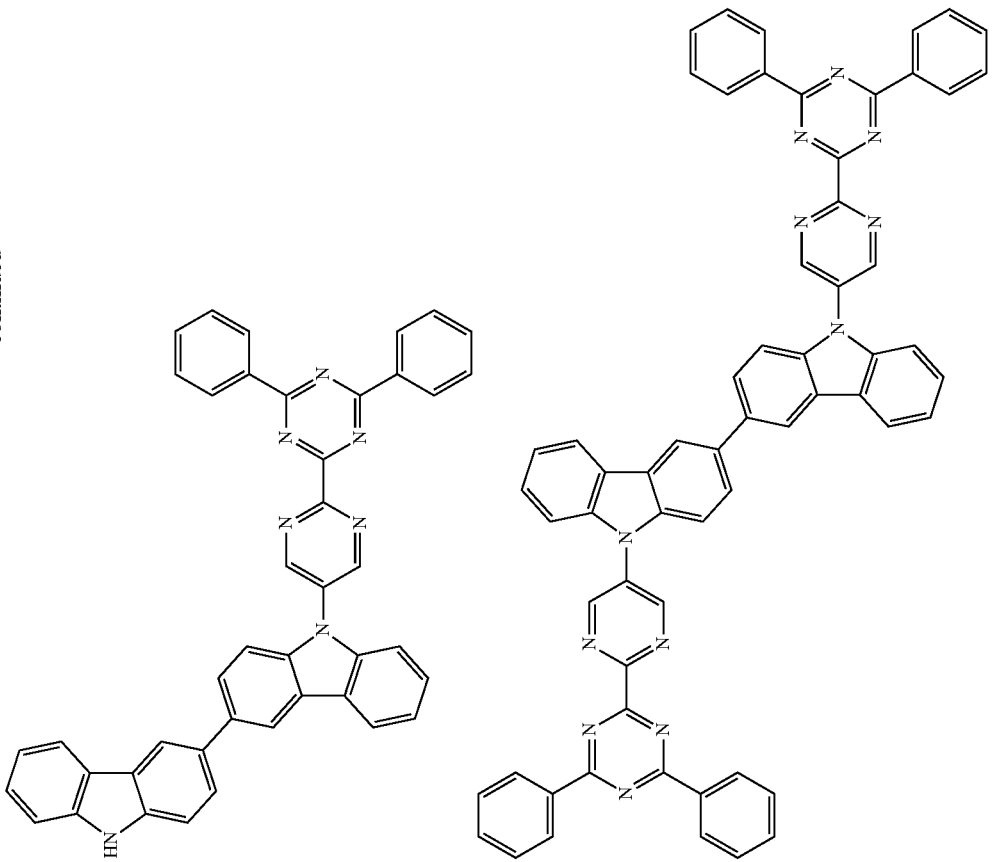

[Chem. 60]
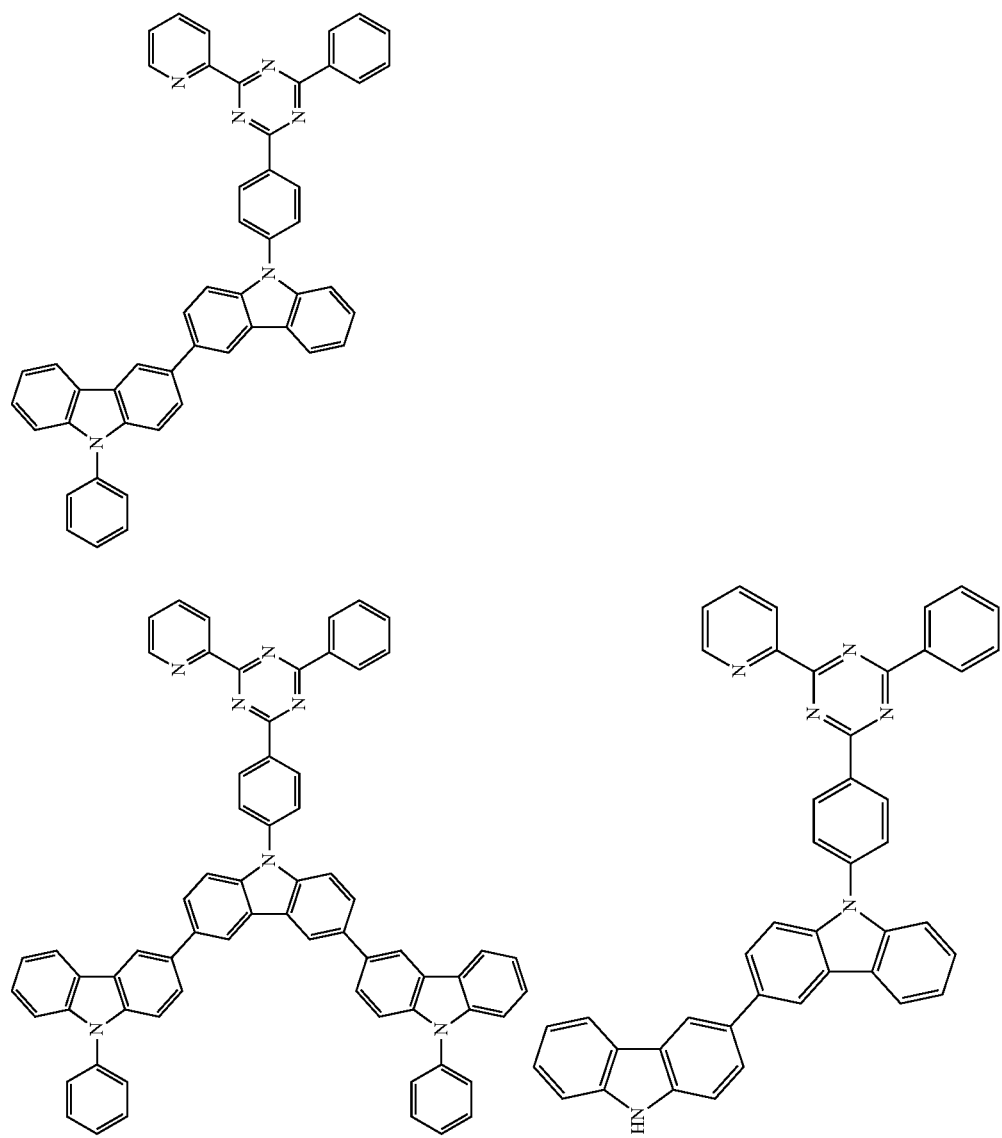

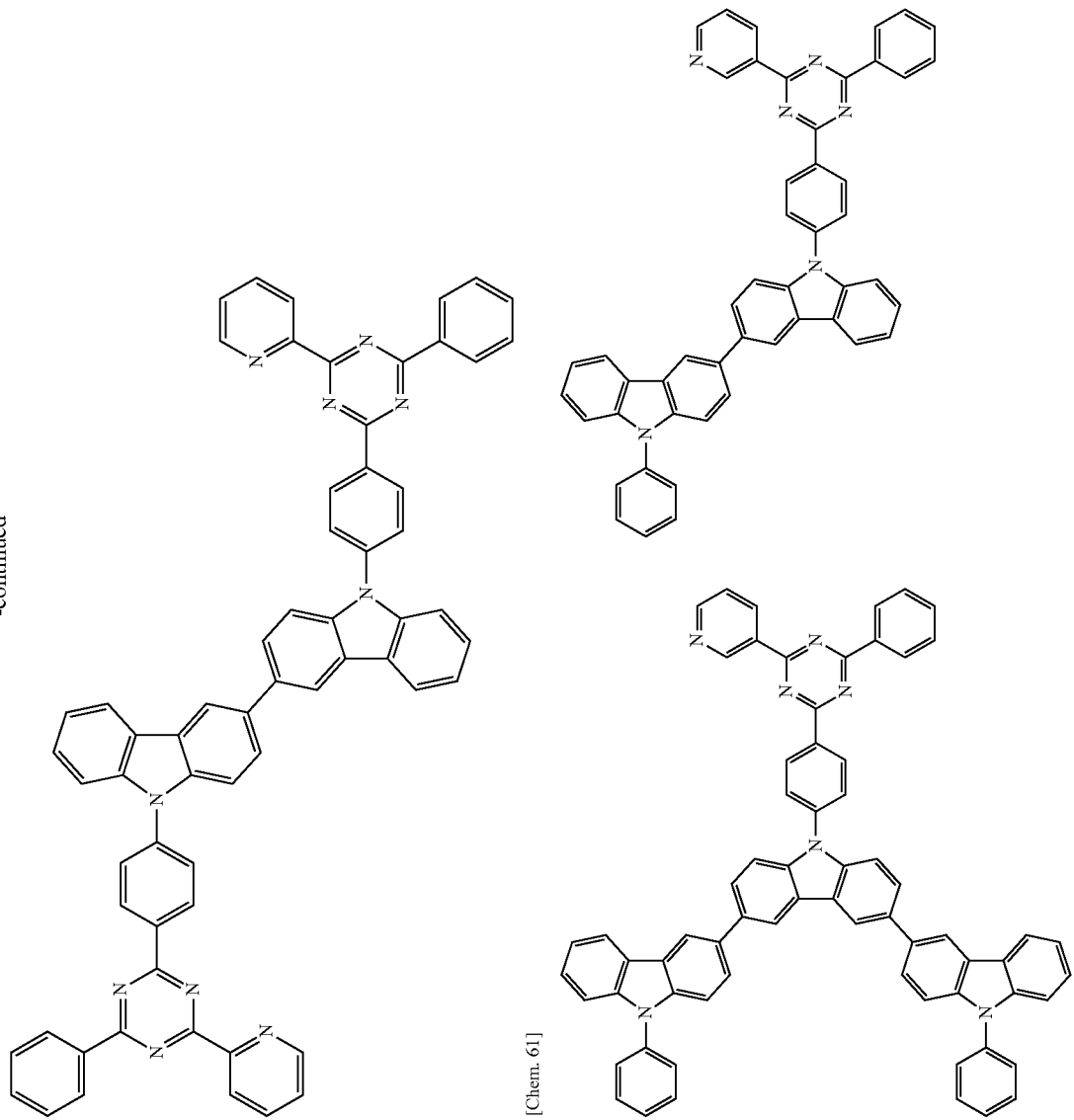
[Chem. 61]

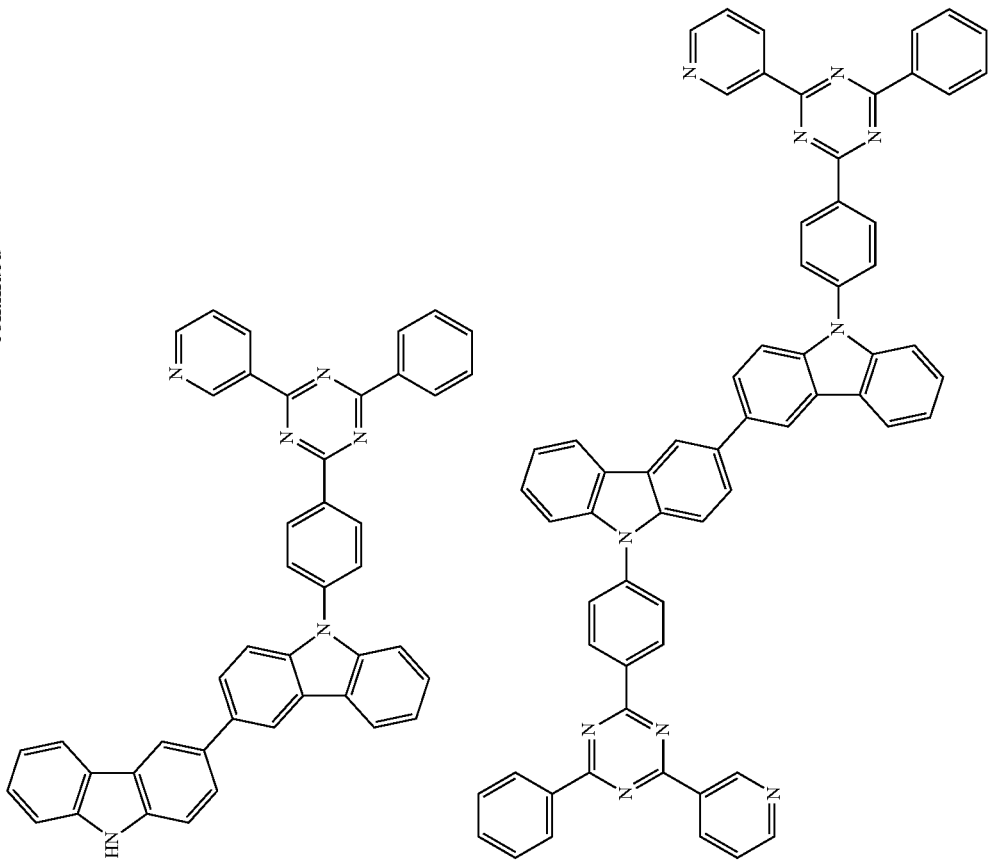

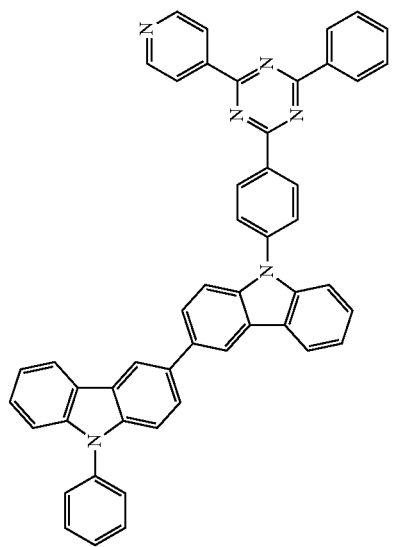
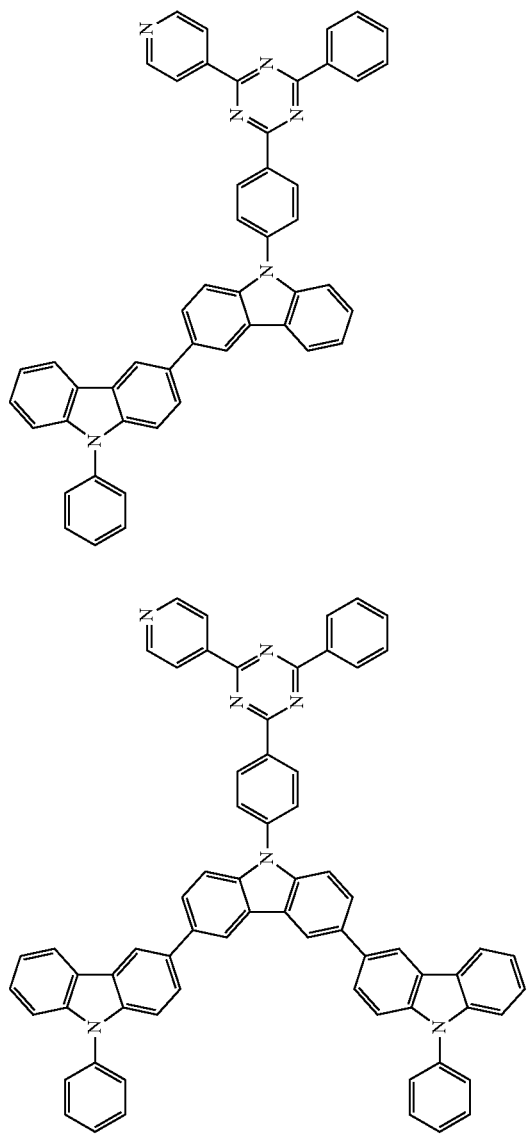
[Chem. 62]
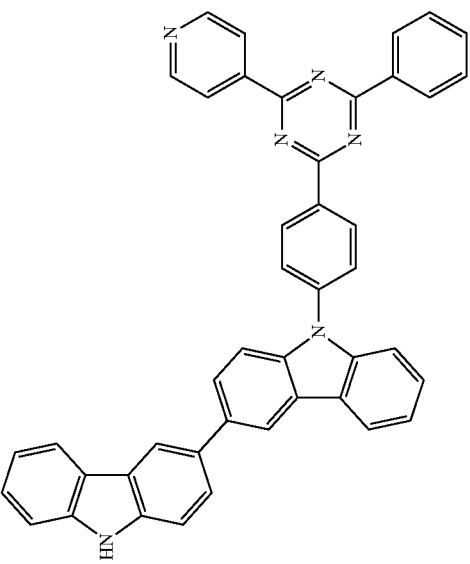

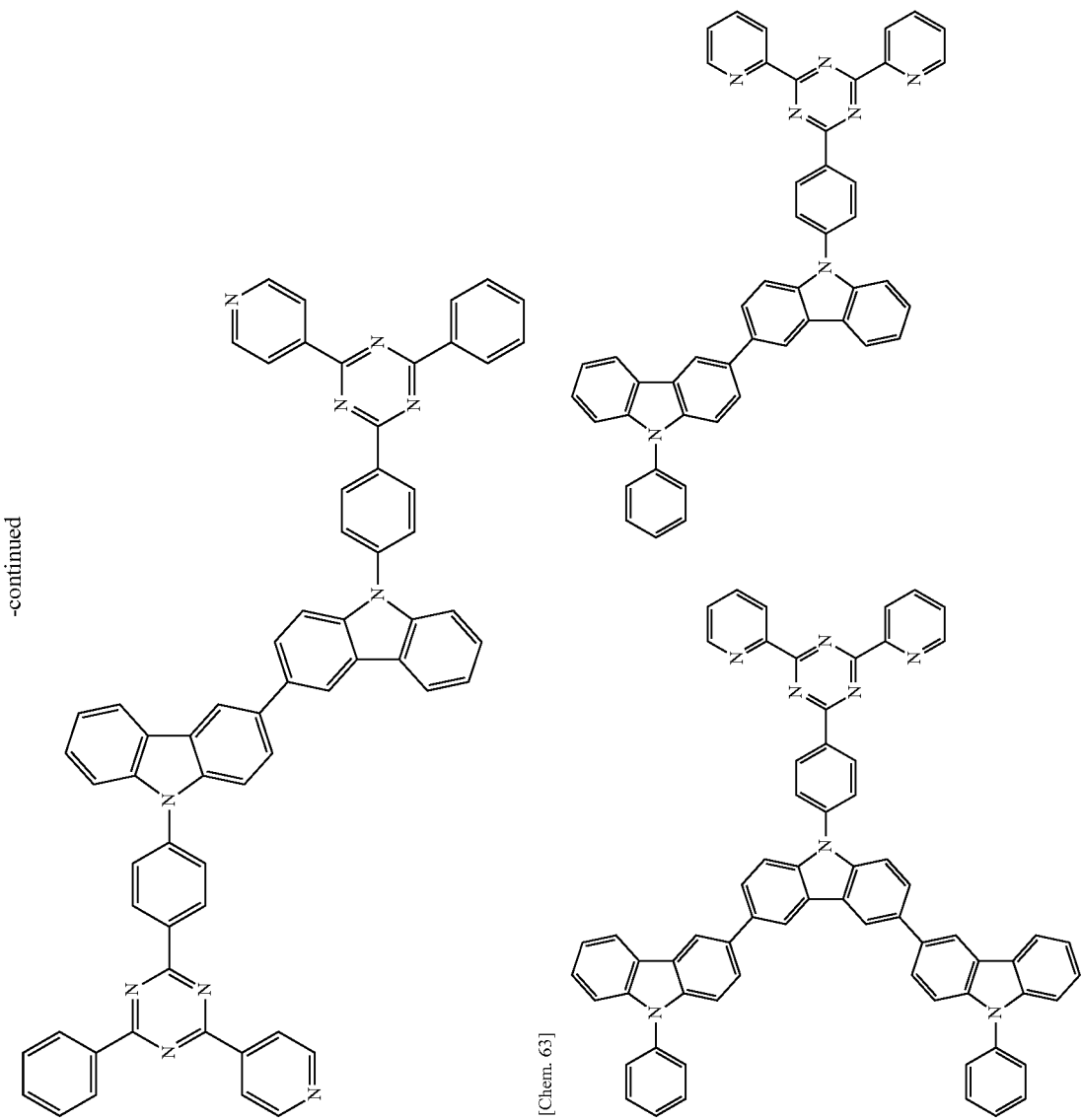
[Chem. 63]

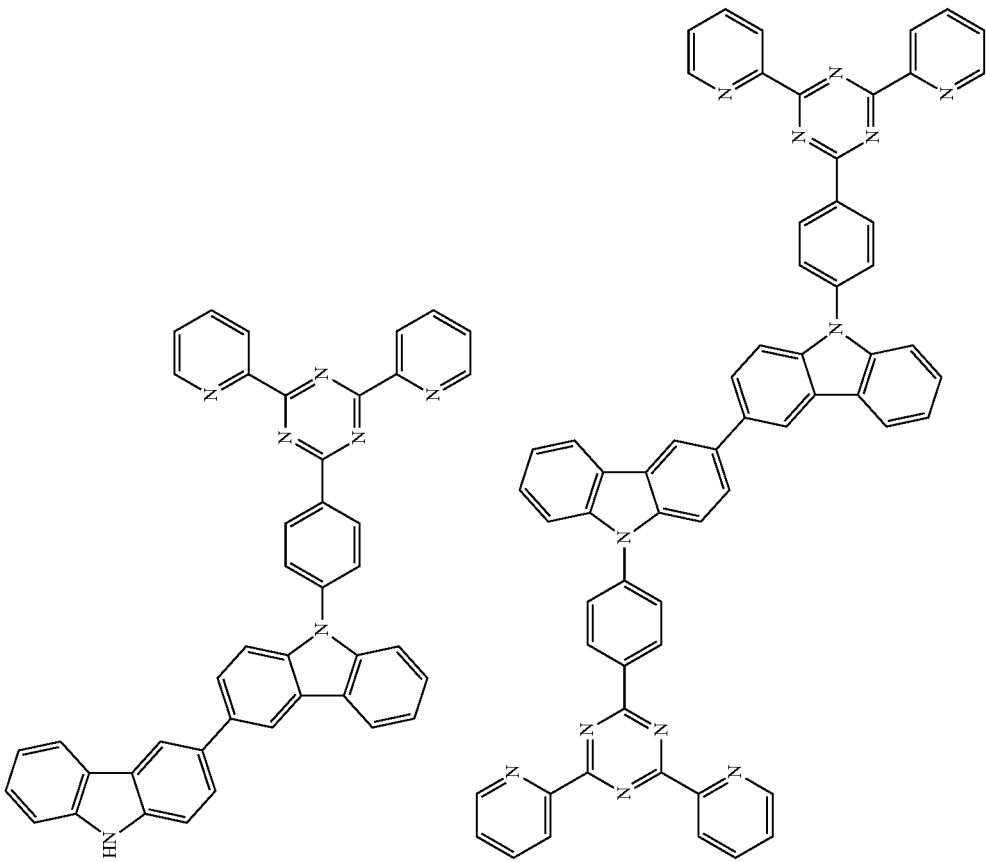

[Chem. 64]
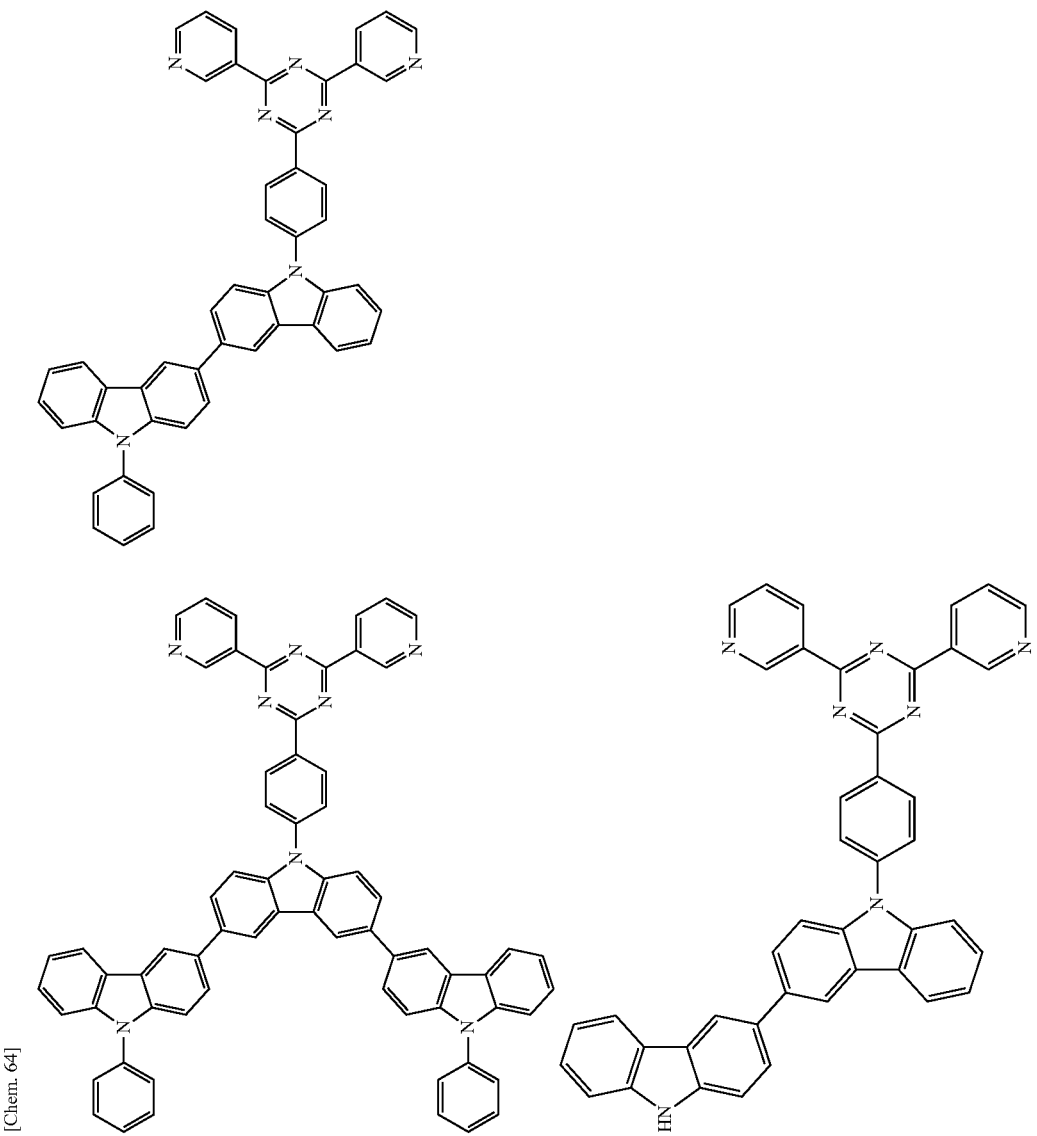

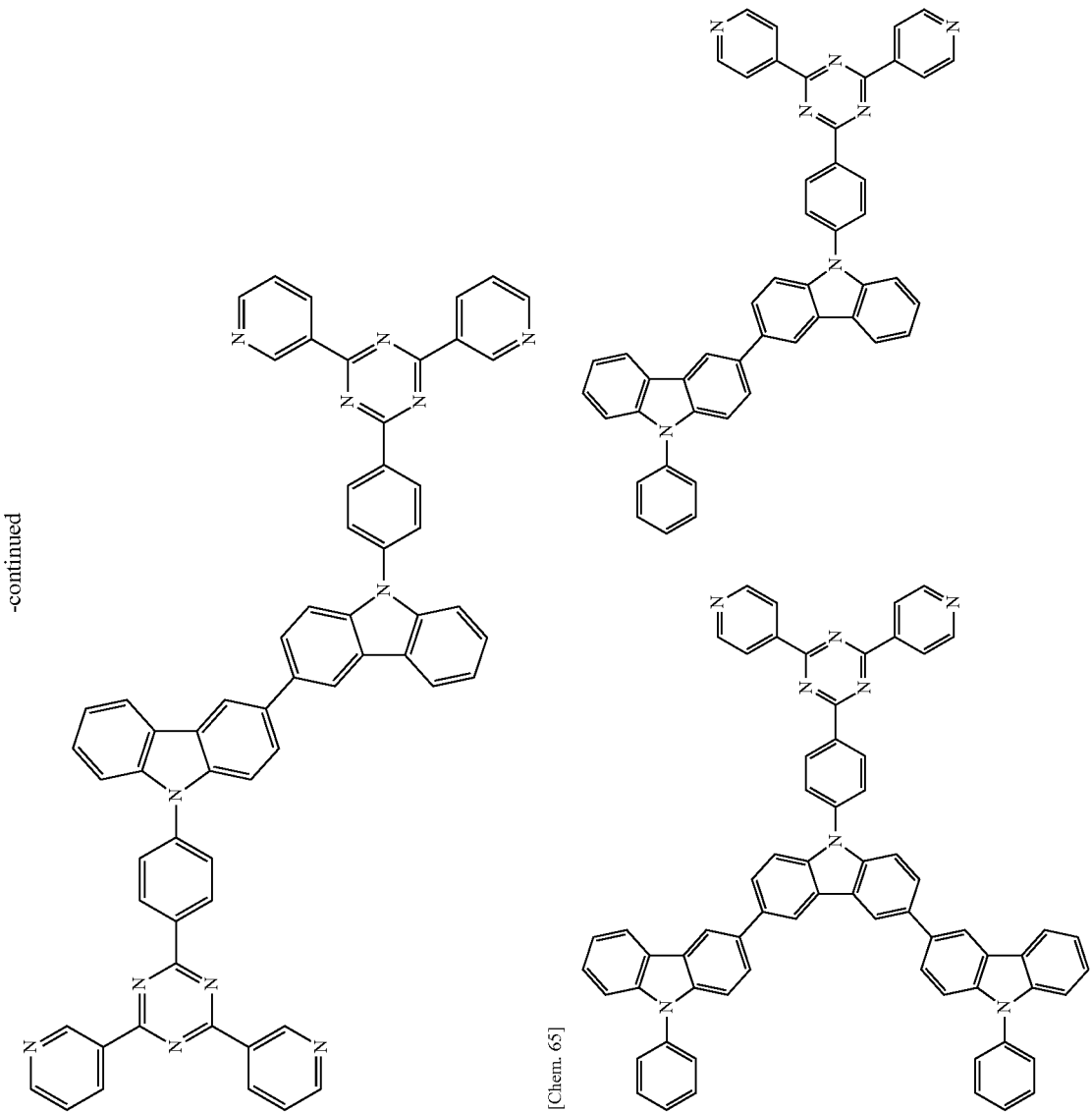

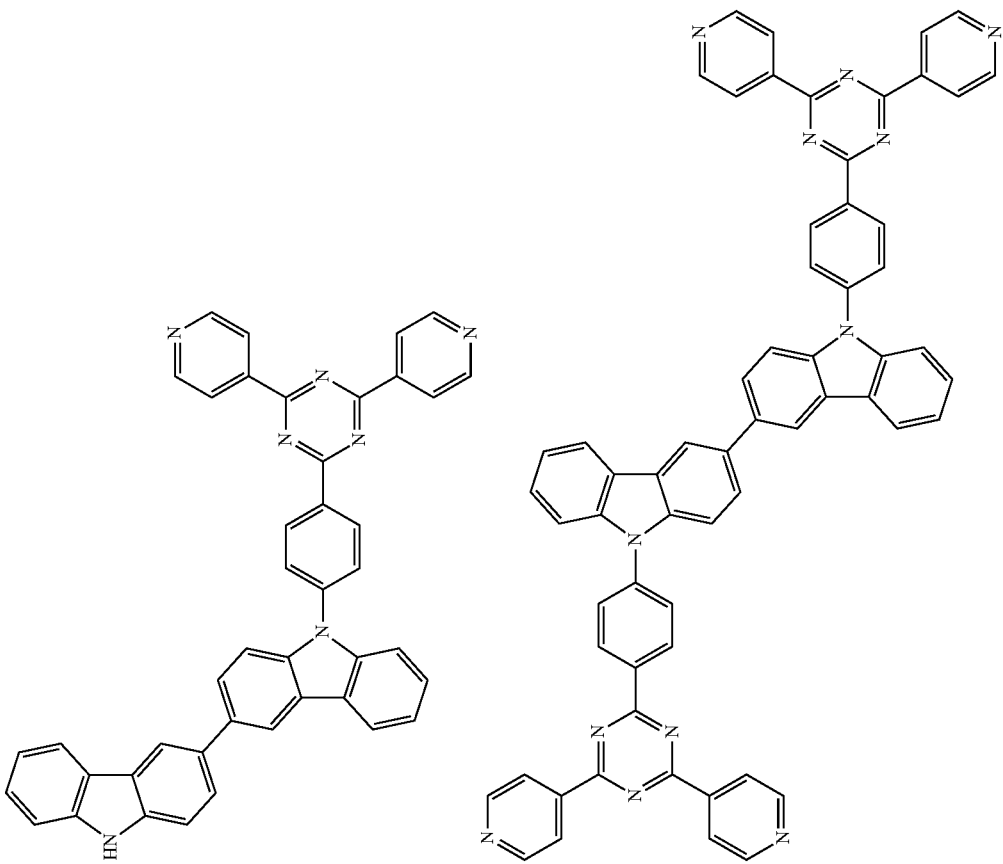

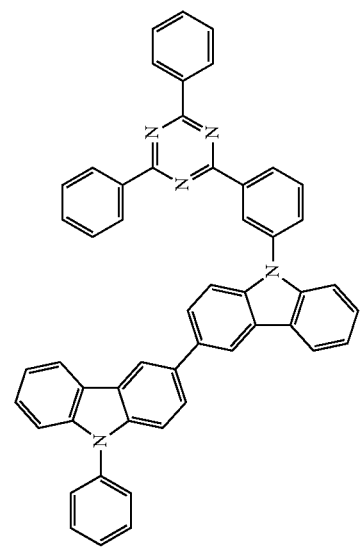
[Chem. 66]
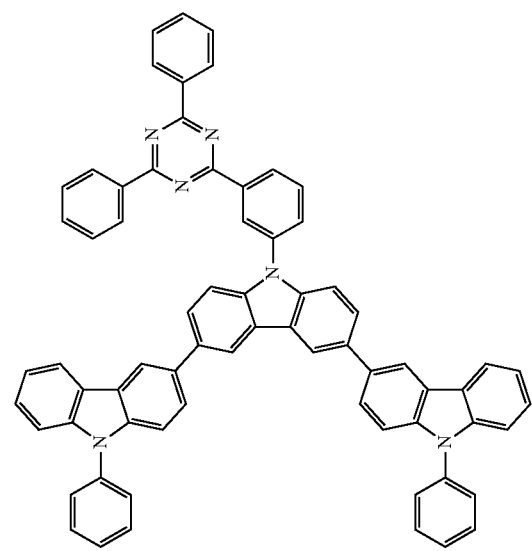 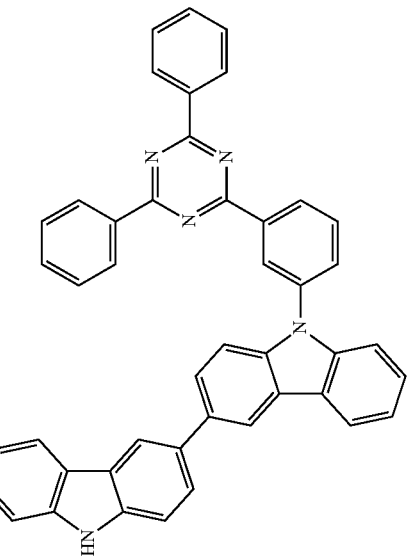

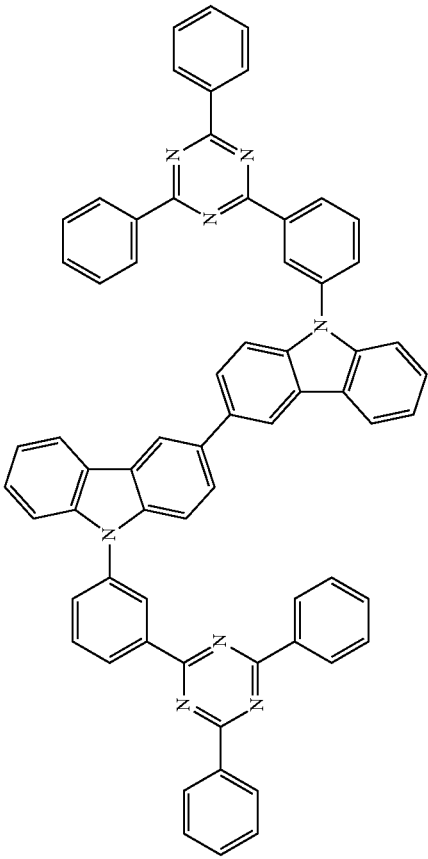
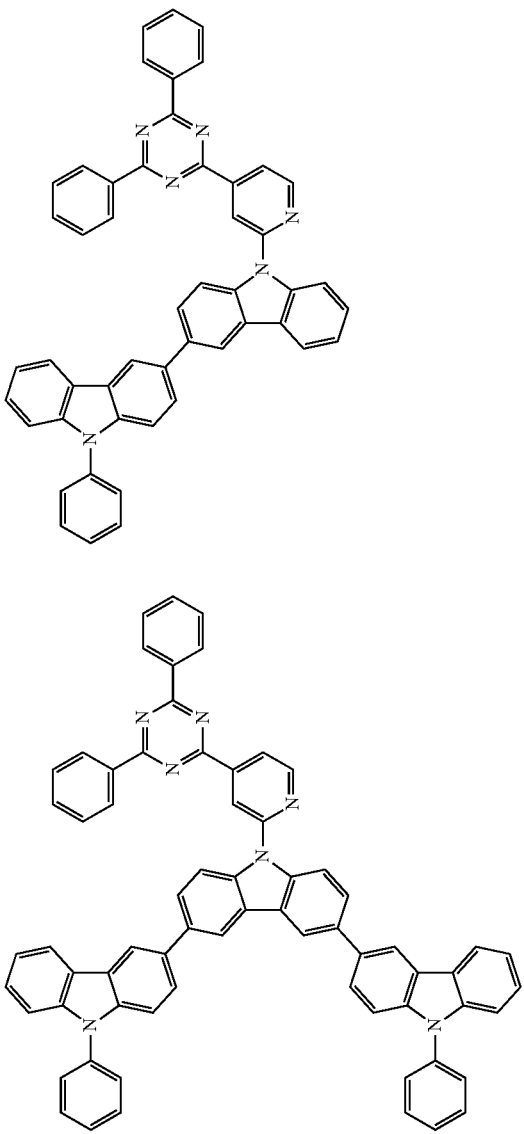
[Chem. 67]

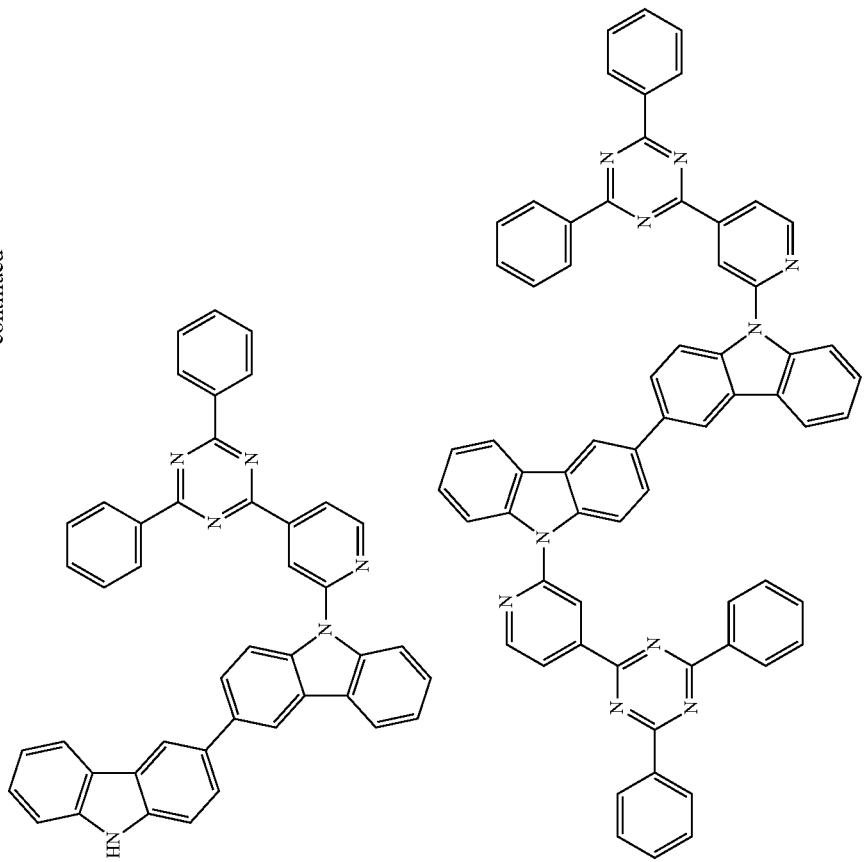

[Chem. 68]
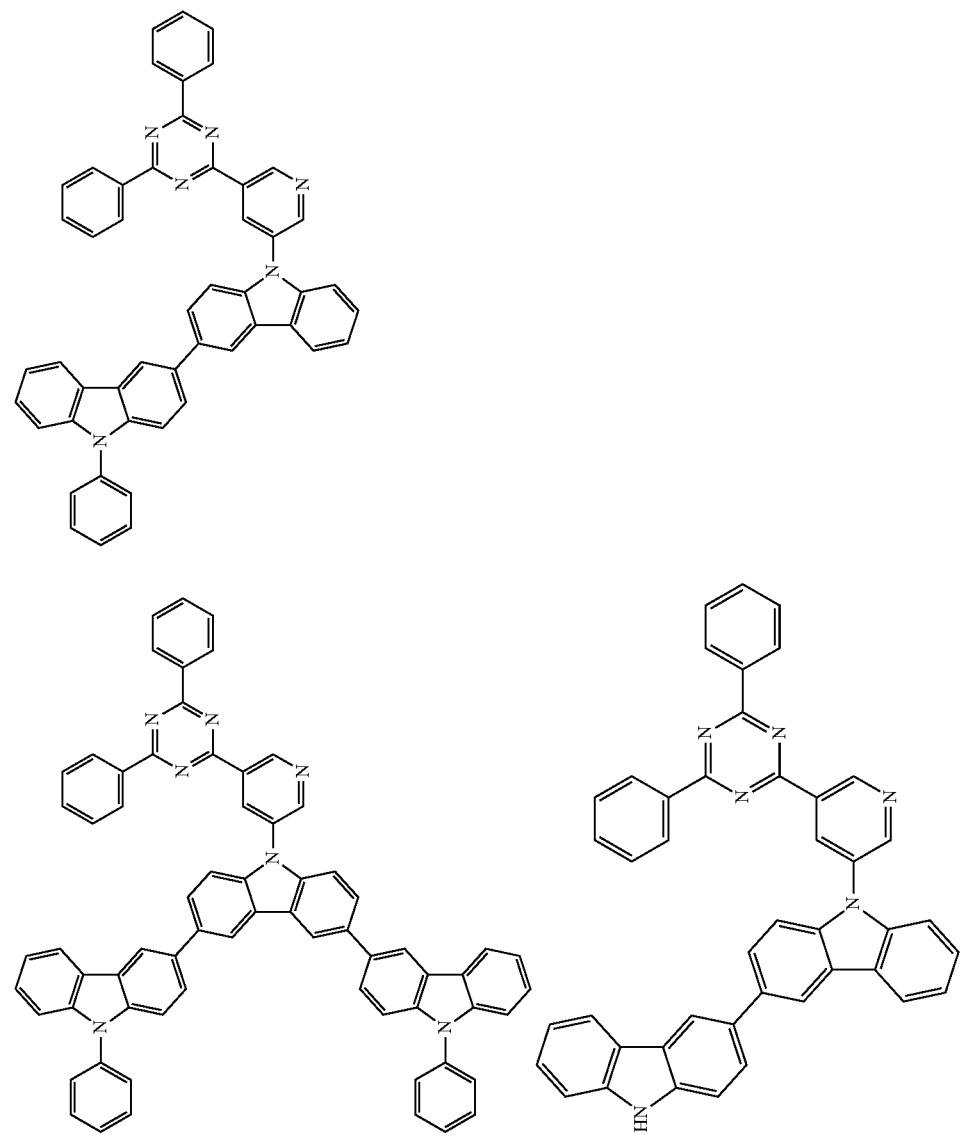

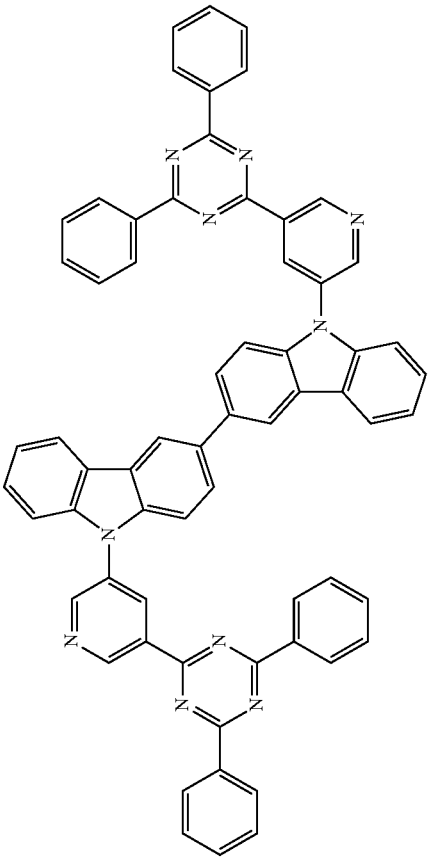
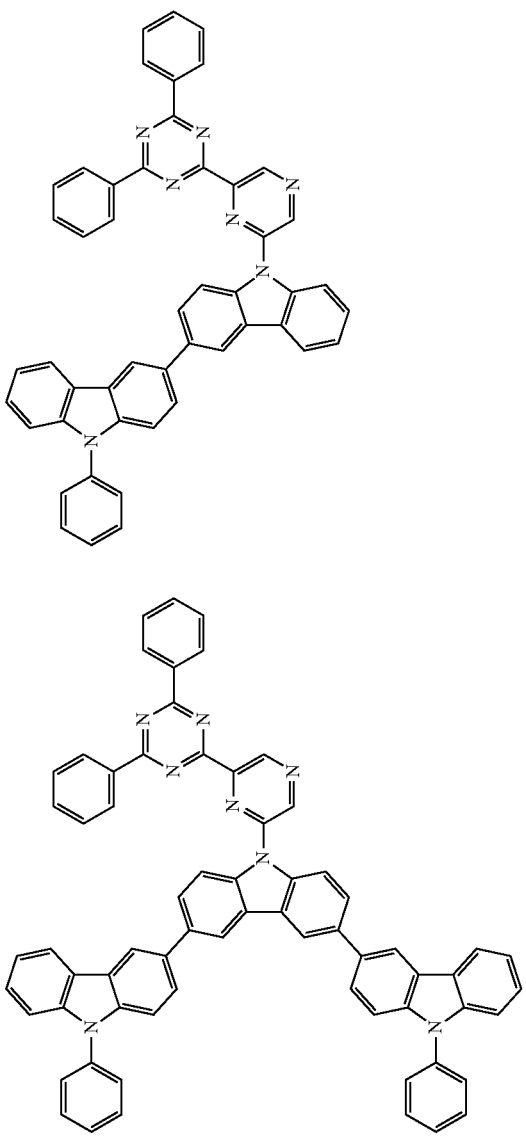
[Chem. 69]

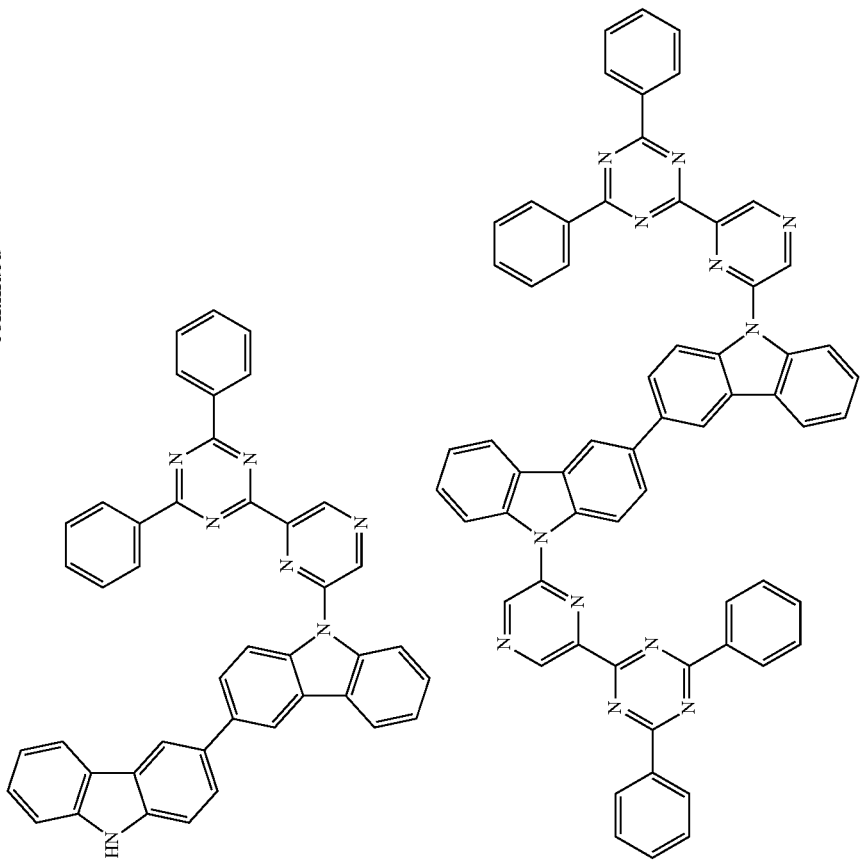

[Chem. 70]
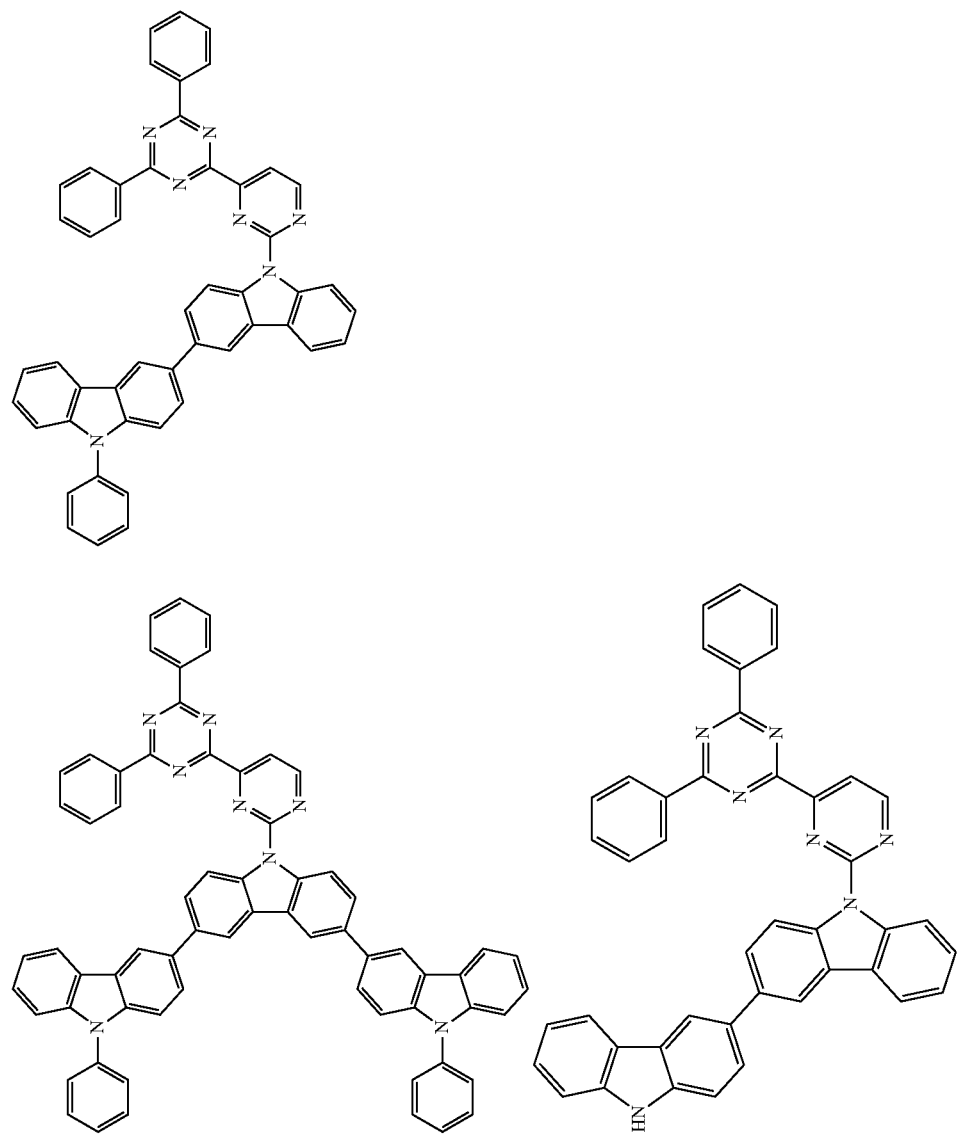

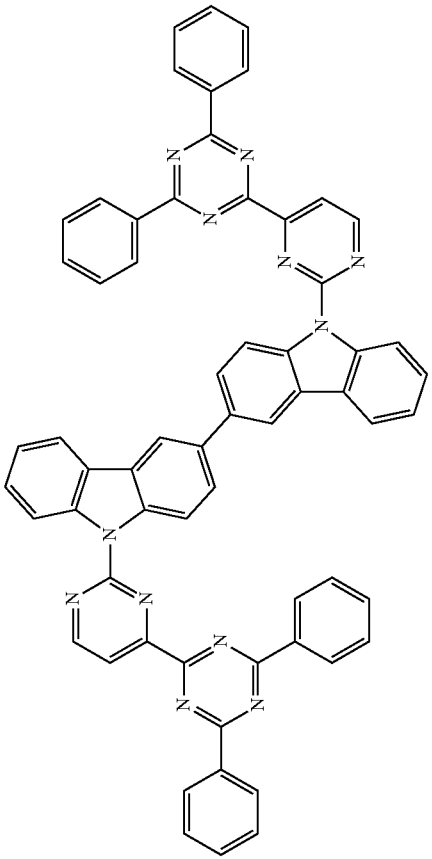
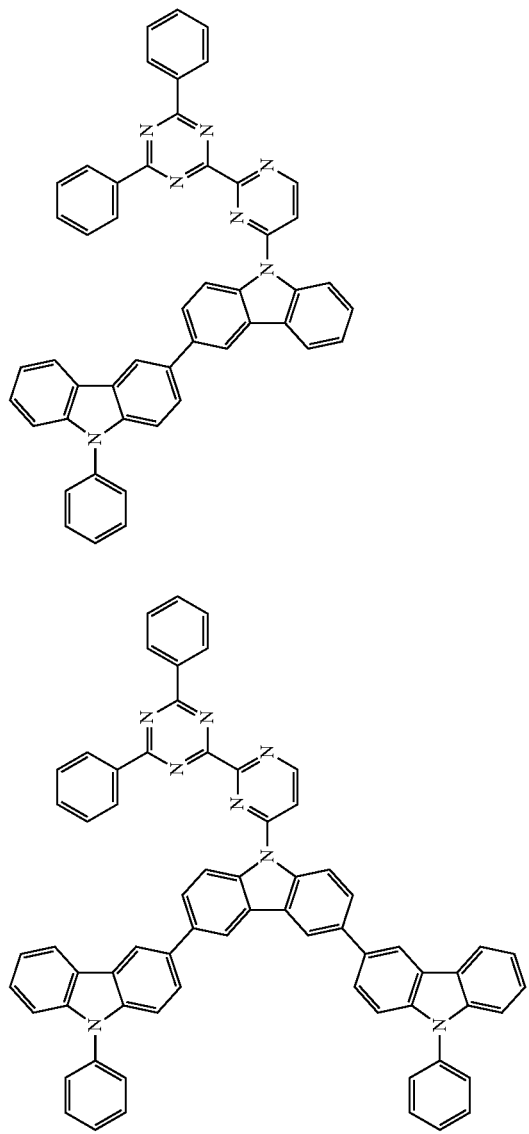
[Chem. 71]

-continued
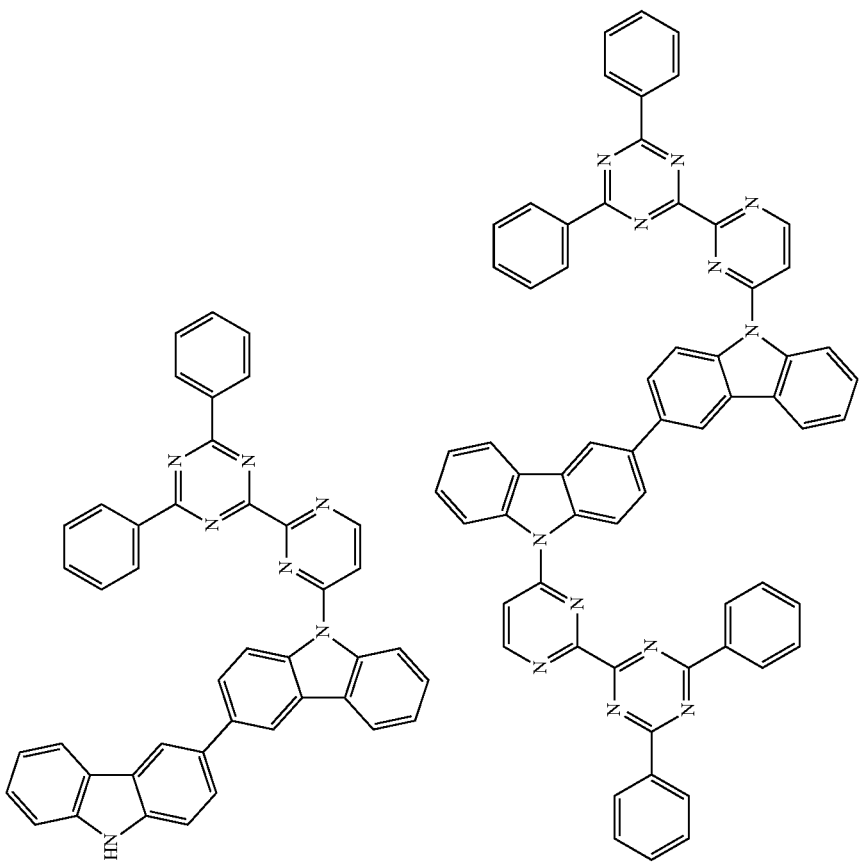

[Chem. 72]
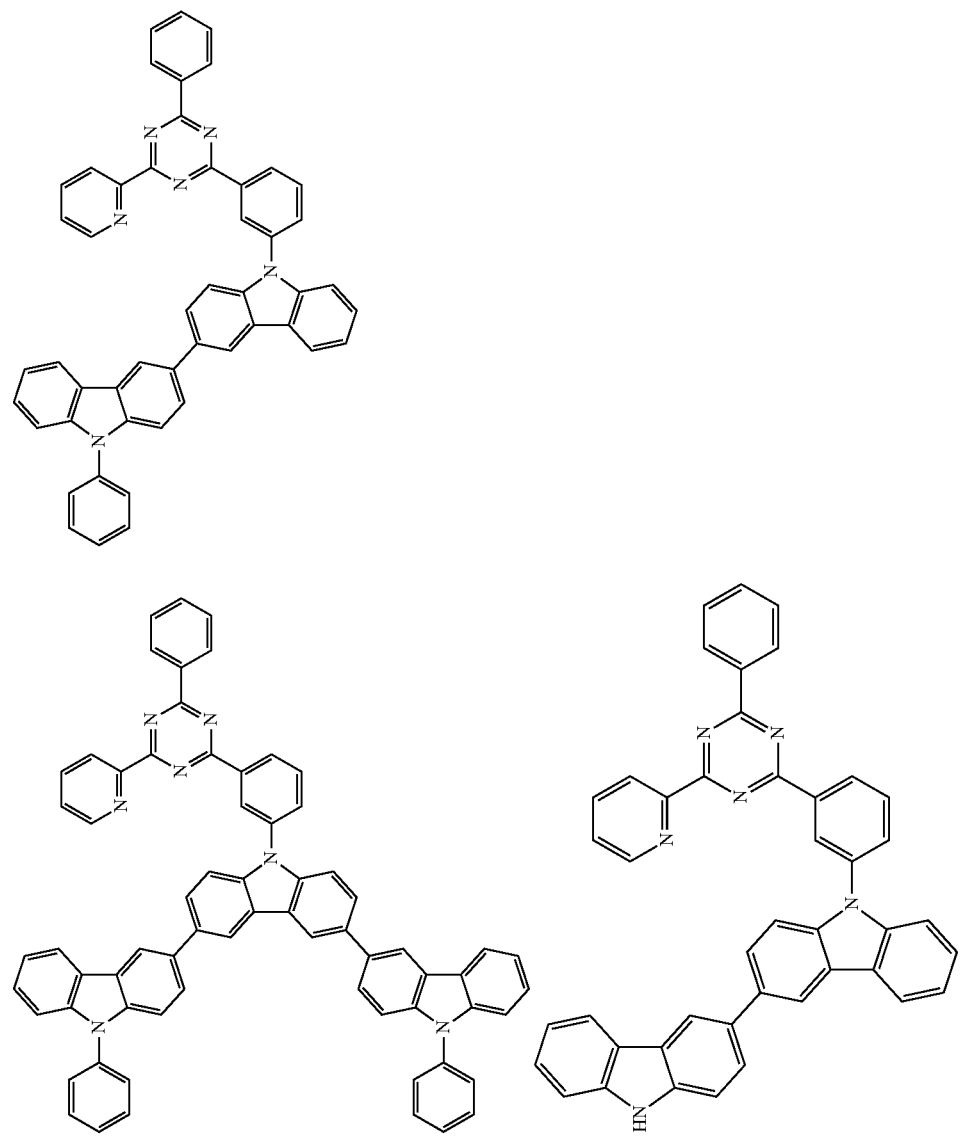

-continued
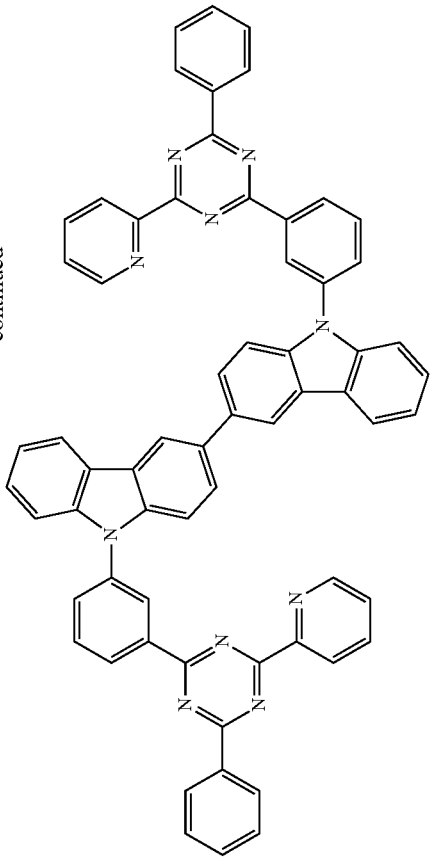
[Chem. 73]
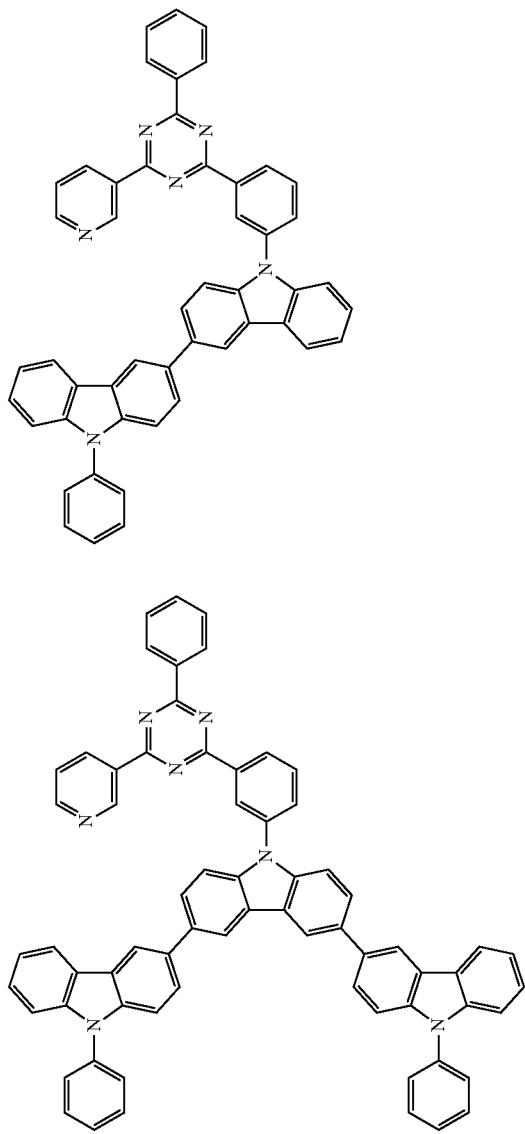

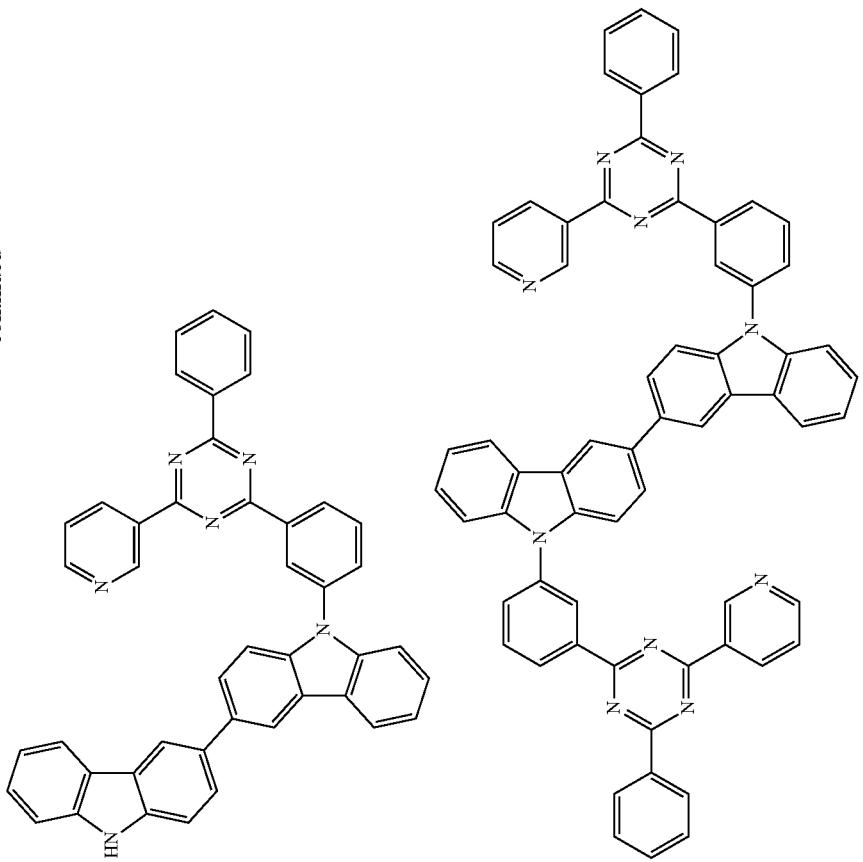

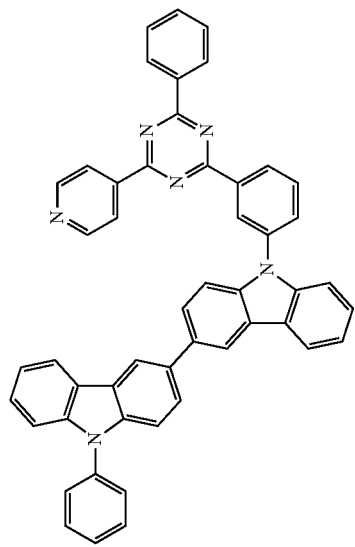
[Chem. 74]
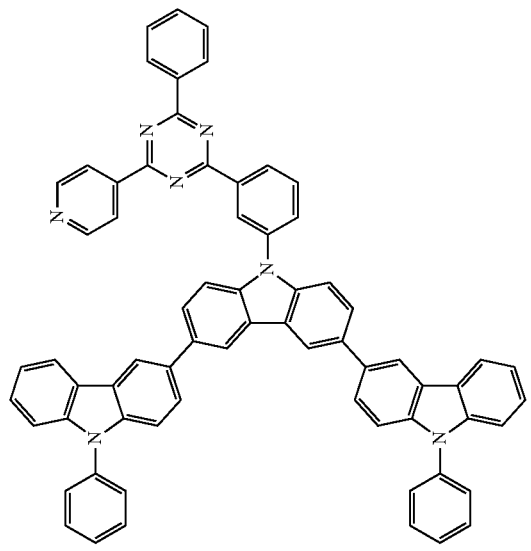 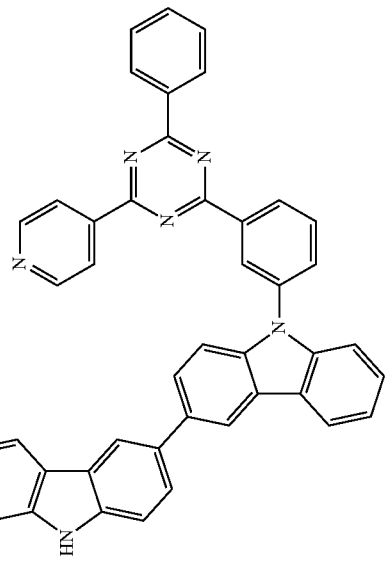

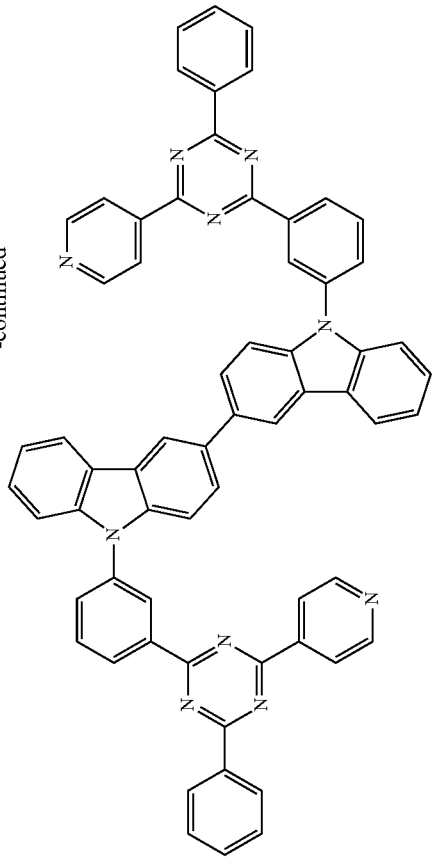
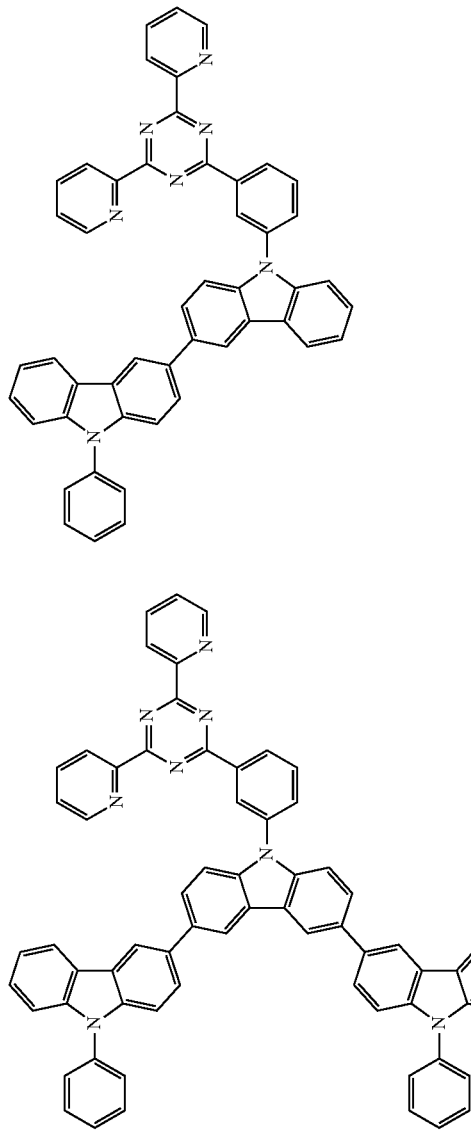
[Chem. 75]

-continued
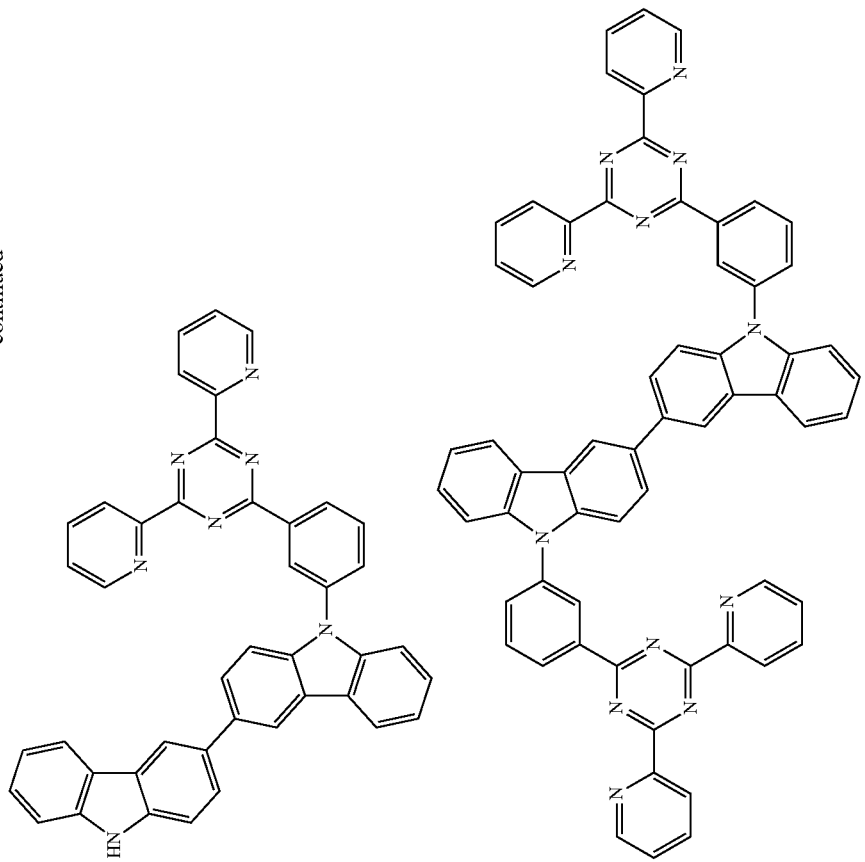

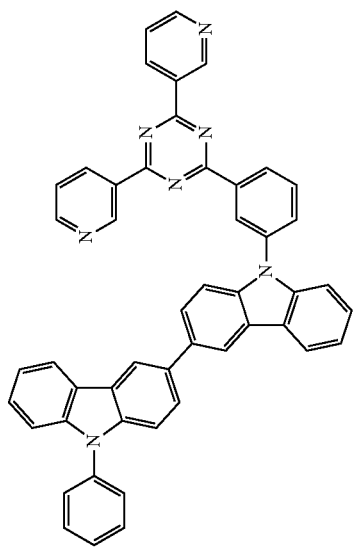
[Chem. 76]
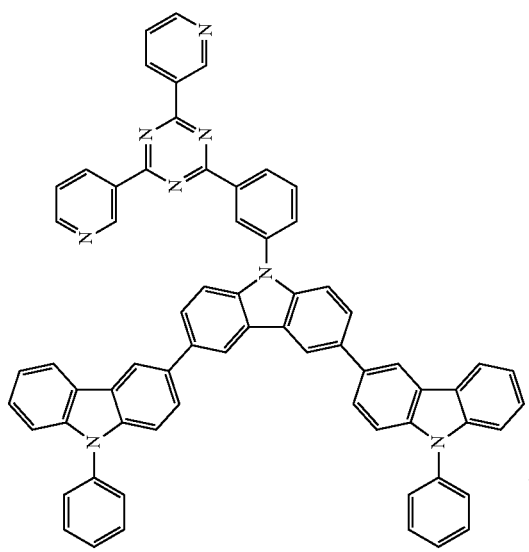
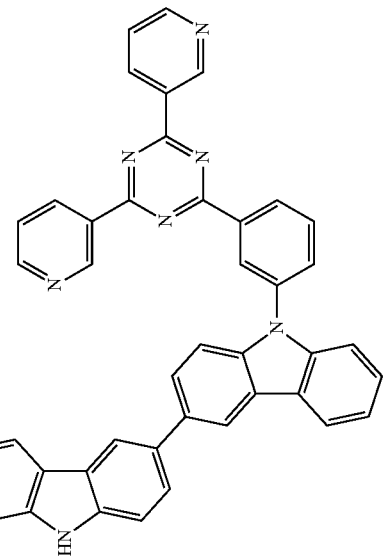

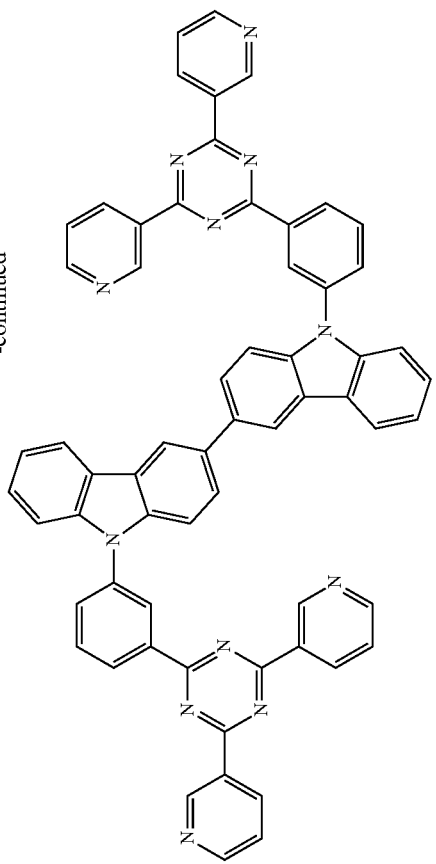
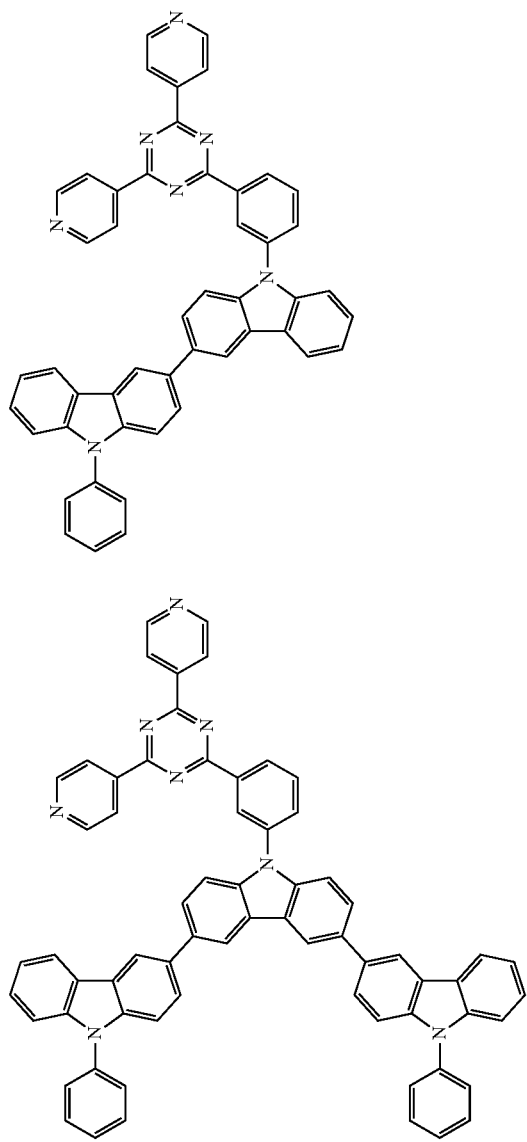
[Chem. 77]

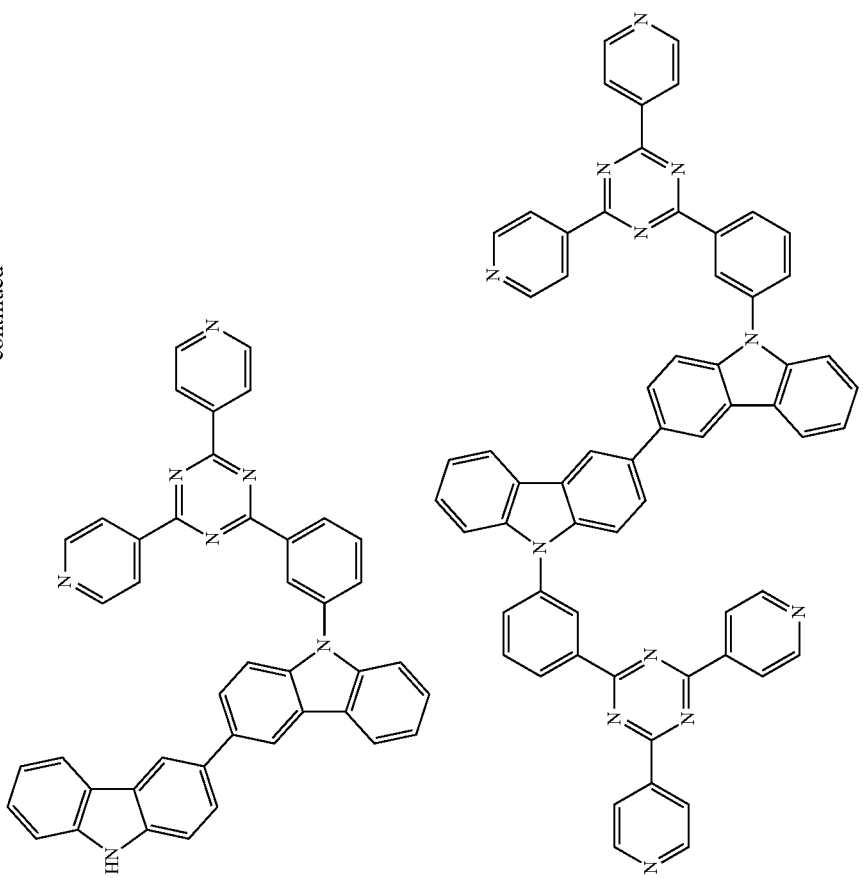

Examples of the preferred delayed fluorescent material include compounds represented by the following general formulae. The entire description of WO 2013/133359 including the paragraphs 0007 to 0032 and 0079 to 0084 is incorporated herein by reference as a part of the description of the present application.

[Chem. 78]

General Formula (211)

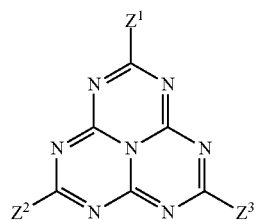

[In the general formula (211), $Z^1$, $Z^2$ and $Z^3$ each independently represent a substituent.]

[Chem. 79]

General Formula (212)

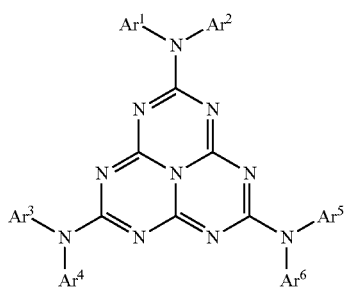

[In the general formula (212), $Ar^1$, $Ar^2$, $Ar^3$, $Ar^4$, $Ar^5$ and $Ar^6$ each independently represent a substituted or unsubstituted aryl group.]

Specific examples of the compound represented by the general formula (212) include the compound represented by the following structural formula.

[Chem. 80]

Compound 4001

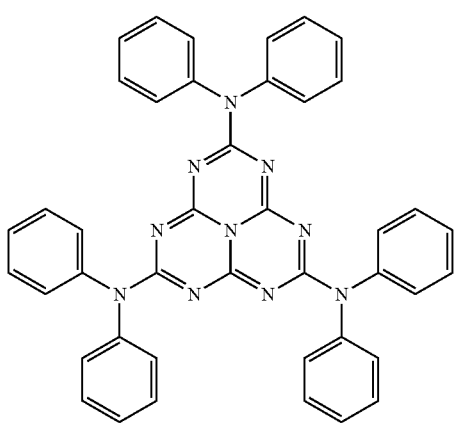

Specific examples of the compound represented by the general formula (212) include the compounds shown in the following table. Here, $Ar^1$, $Ar^2$, $Ar^3$, $Ar^4$, $Ar^5$ and $Ar^6$ are the same as each other, and are expressed by Ar.

TABLE 21

| Compound No. | Ar |
|---|---|
| 4002 | 4-fluorophenyl |
| 4003 | 3-fluorophenyl |
| 4004 | 2-fluorophenyl |
| 4005 | 3,5-difluorophenyl |
| 4006 | 2,4,6-trifluorophenyl |
| 4007 | 4-methylphenyl |
| 4008 | 3-methylphenyl |
| 4009 | 2-methylphenyl |
| 4010 | 3,5-dimethylphenyl |
| 4011 | 2,4,6-trimethylphenyl |
| 4012 | 4-ethylphenyl |
| 4013 | 3-ethylphenyl |
| 4014 | 2-ethylphenyl |
| 4015 | 3,5-diethylphenyl |
| 4016 | 4-propylphenyl |
| 4017 | 3-propylphenyl |
| 4018 | 3,5-dipropylphenyl |
| 4019 | 4-tert-butylphenyl |
| 4020 | 3-tert-butylphenyl |
| 4021 | 3,5-di-tert-butylphenyl |
| 4022 | 1-naphthyl |
| 4023 | 2-naphthyl |

Examples of the preferred delayed fluorescent material include compounds represented by the following general formula. The entire description of WO 2013/161437 including the paragraphs 0008 to 0054 and 0101 to 0121 is incorporated herein by reference as a part of the description of the present application.

[Chem. 81]

General Formula (221)

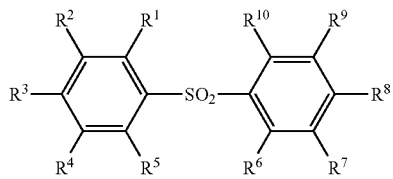

[In the general formula (221), $R^1$ to $R^{10}$ each independently represent a hydrogen atom or a substituent, provided that at least one of $R^1$ to $R^{10}$ represents a substituted or unsubstituted aryl group, a substituted or unsubstituted diarylamino group or a substituted or unsubstituted 9-carbazolyl group. $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^8$ and $R^9$, and $R^9$ and $R^{10}$ each may be bonded to each other to form a cyclic structure.]

Specific examples of the compound include the following compounds.

[Chem. 82]
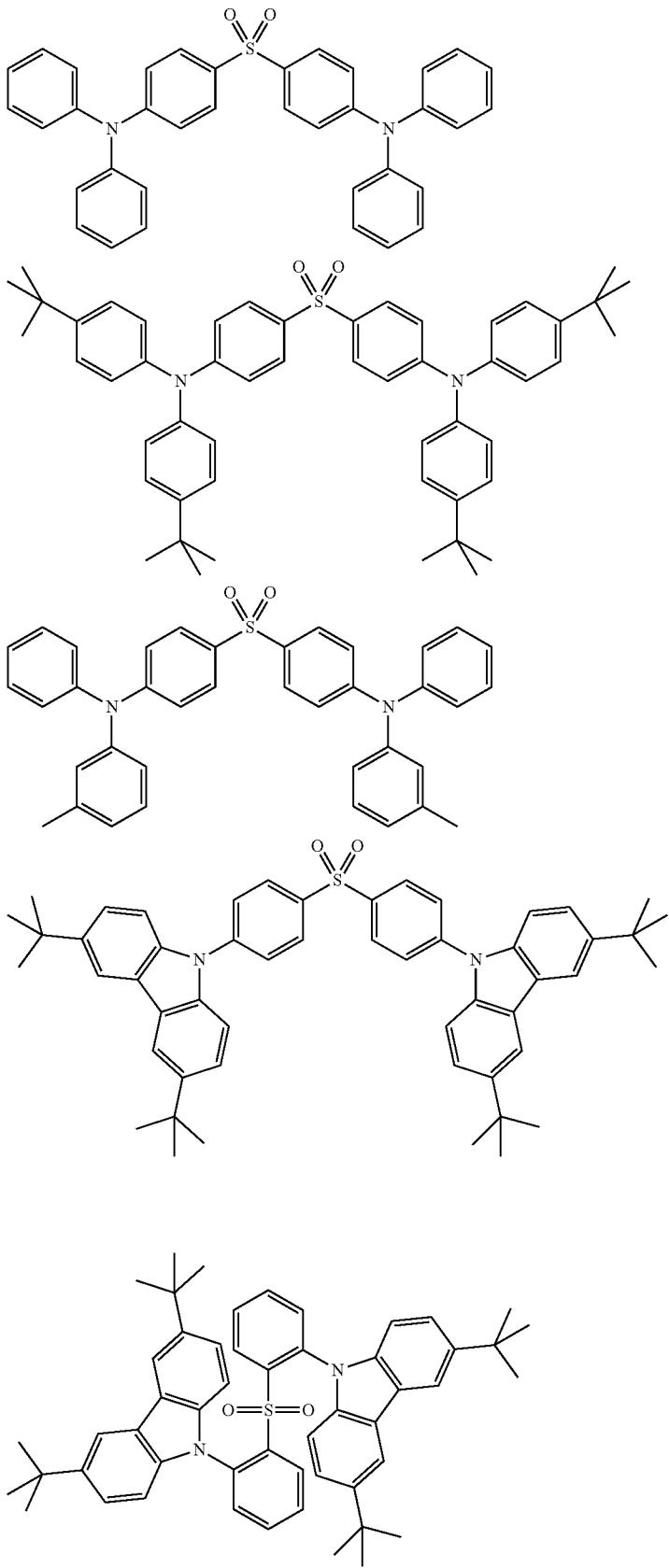

-continued
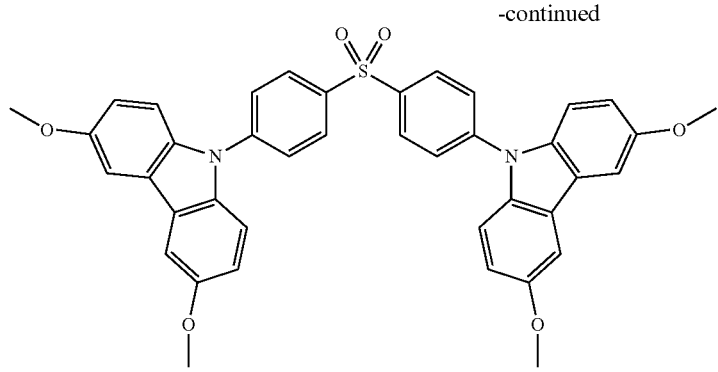
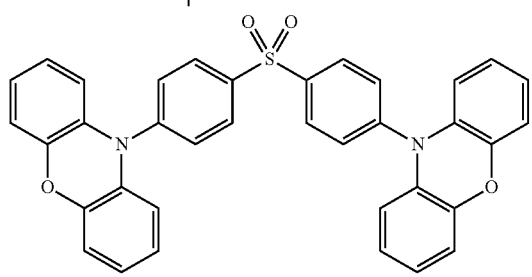
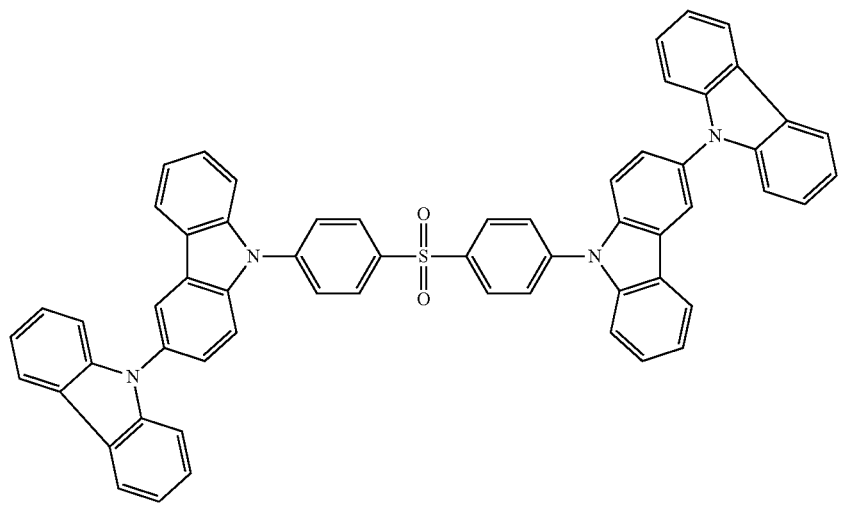
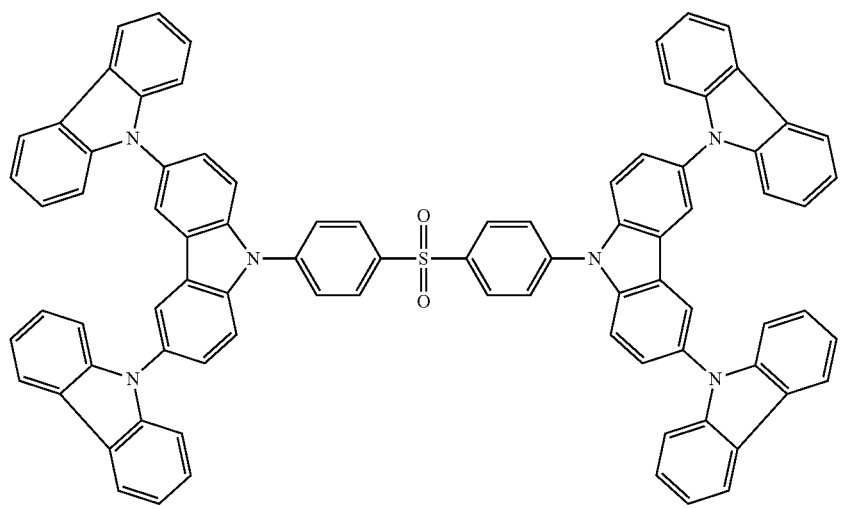

-continued
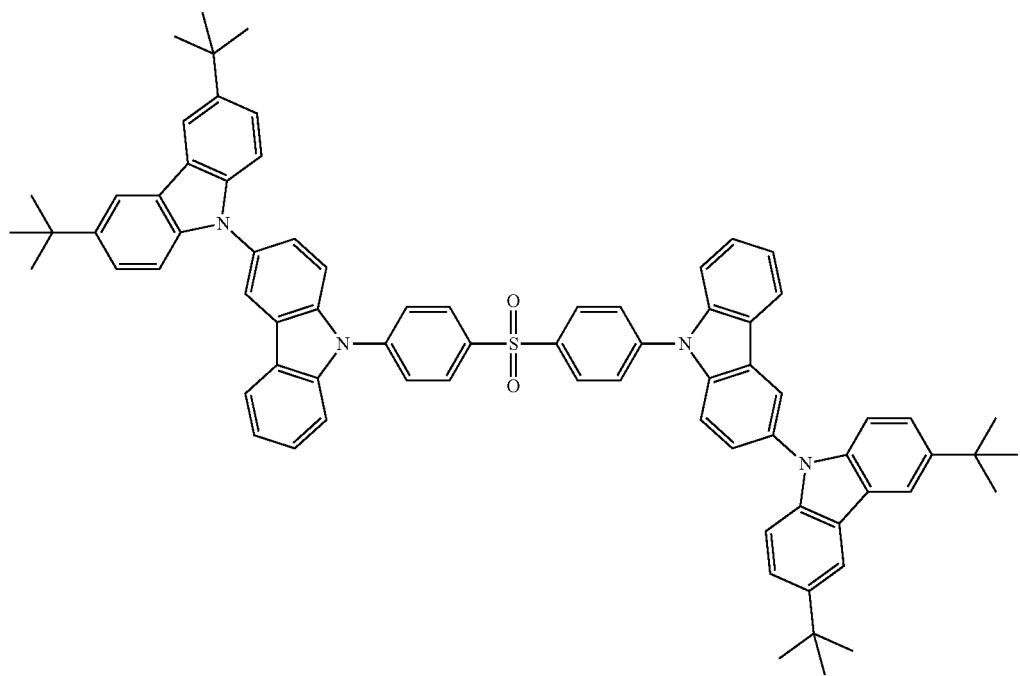
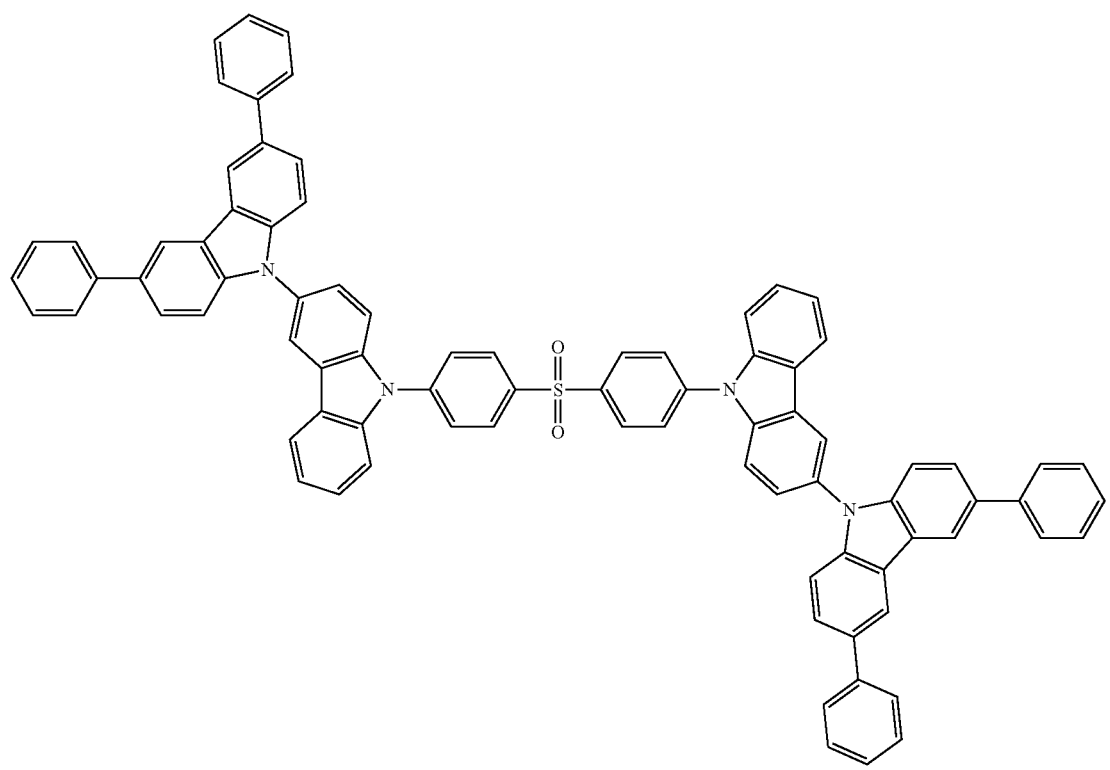

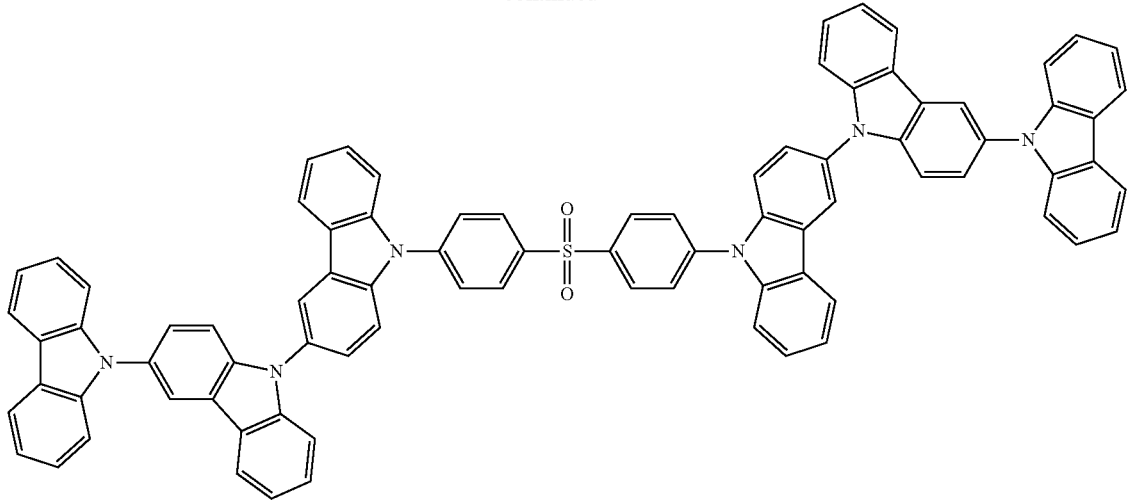

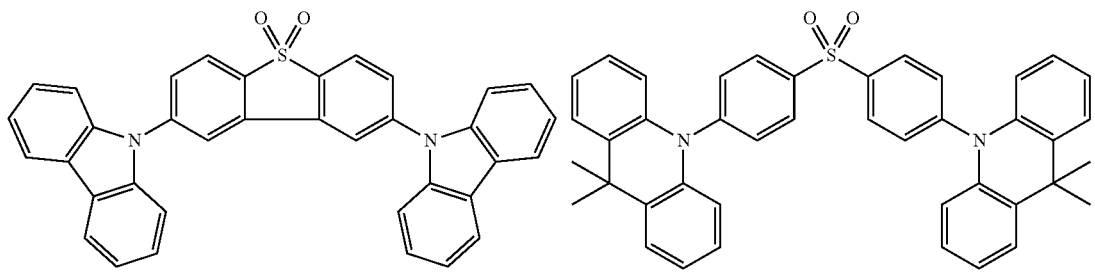

Examples of the preferred delayed fluorescent material include compounds represented by the following general formula. The entire description of JP-A-2014-9352 including the paragraphs 0007 to 0041 and 0060 to 0069 is incorporated herein by reference as a part of the description of the present application.

[Chem. 83]

General Formula (231)

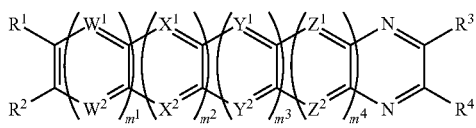

[In the general formula (231), $R^1$ to $R^4$ each independently represent a hydrogen atom or a substituted or unsubstituted (N,N-diarylamino)aryl group, provided that at least one of $R^1$ to $R^4$ represents a substituted or unsubstituted (N,N-diarylamino)aryl group. Two aryl groups constituting the diarylamino moiety of the (N,N-diarylamino)aryl group may be bonded to each other. $W^1$, $W^2$, $X^1$, $X^2$, $Y^1$, $Y^2$, $Z^1$ and $Z^2$ each independently represent a carbon atom or a nitrogen atom. $m^1$ to $m^4$ each independently represent 0, 1 or 2.]

Examples of the compound include the following compounds.

[Chem. 84]
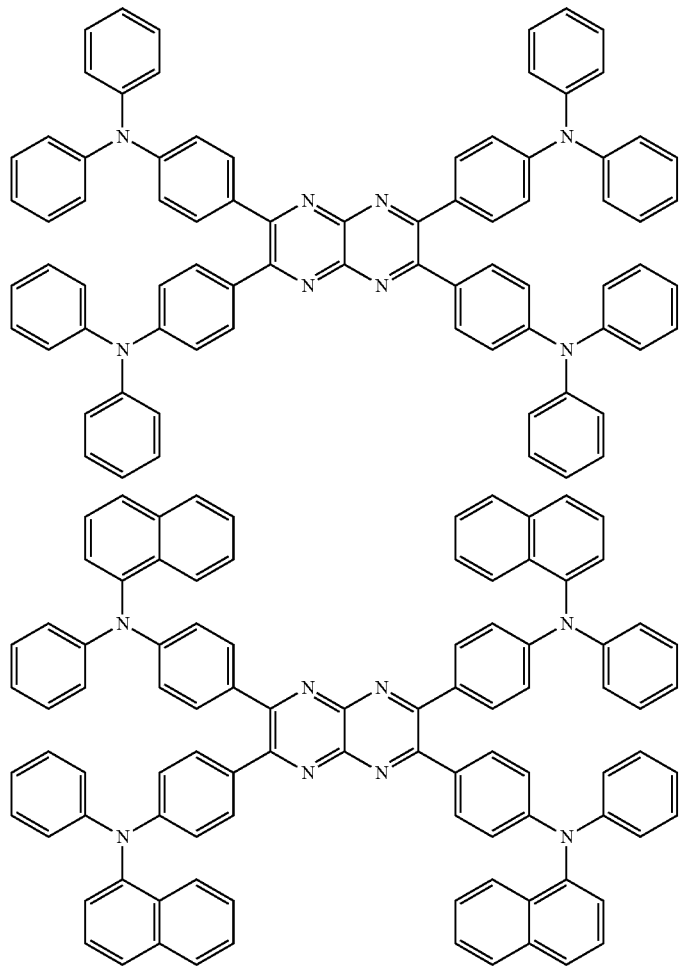
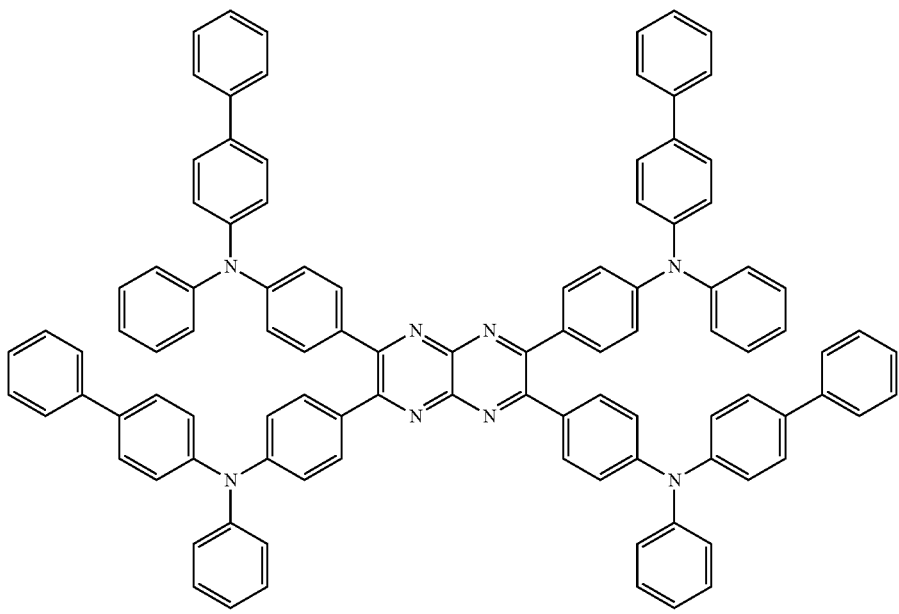

-continued
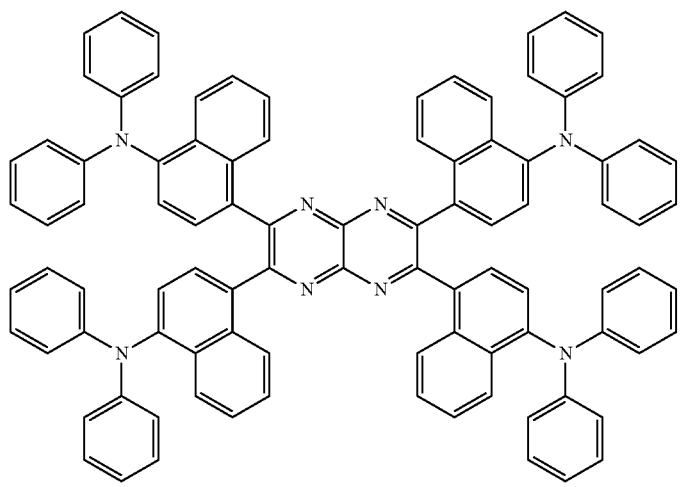
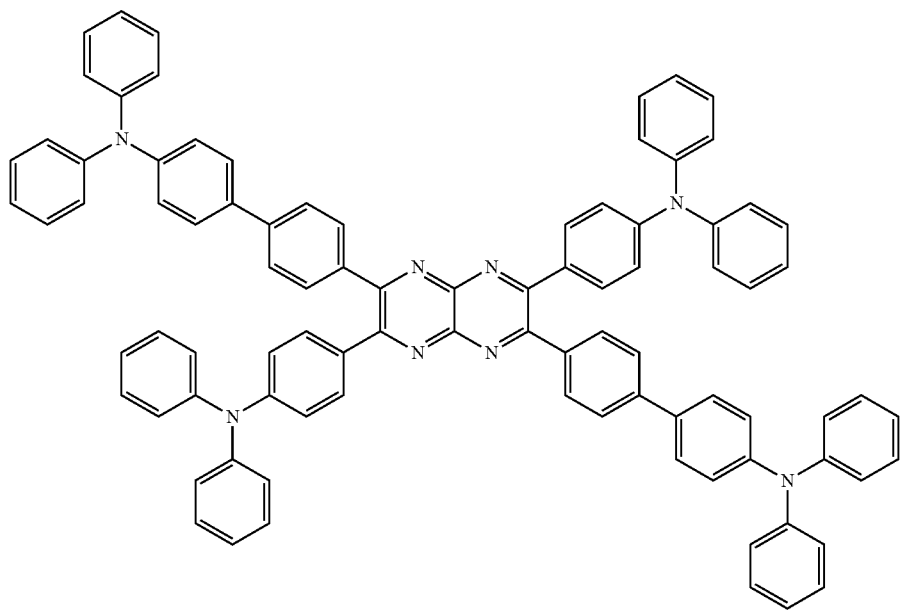
[Chem. 85]
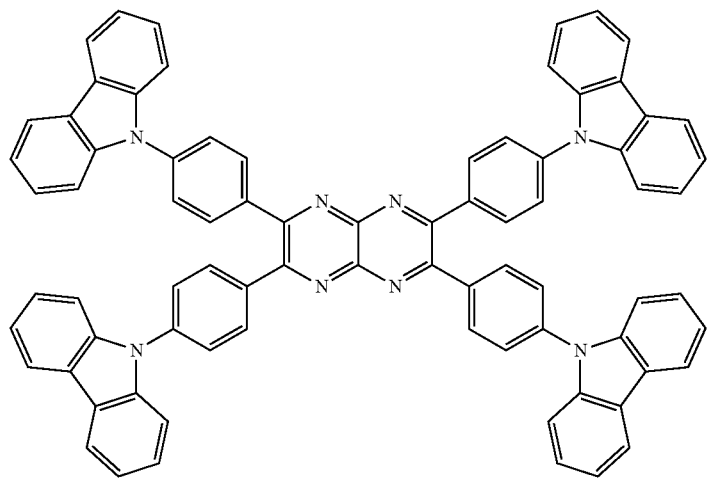

-continued
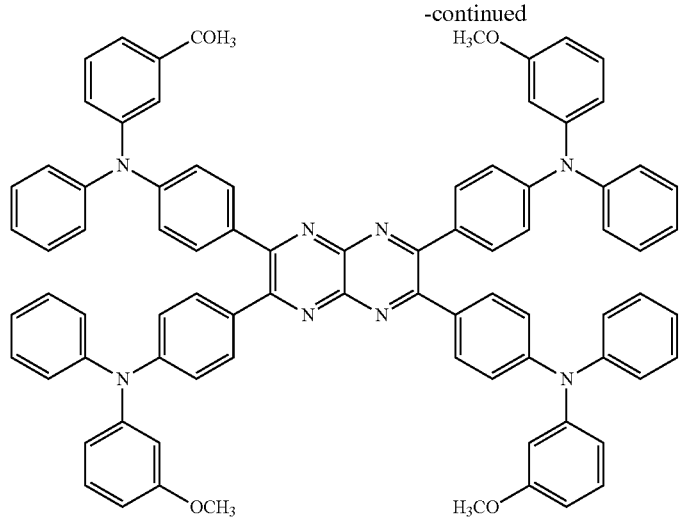
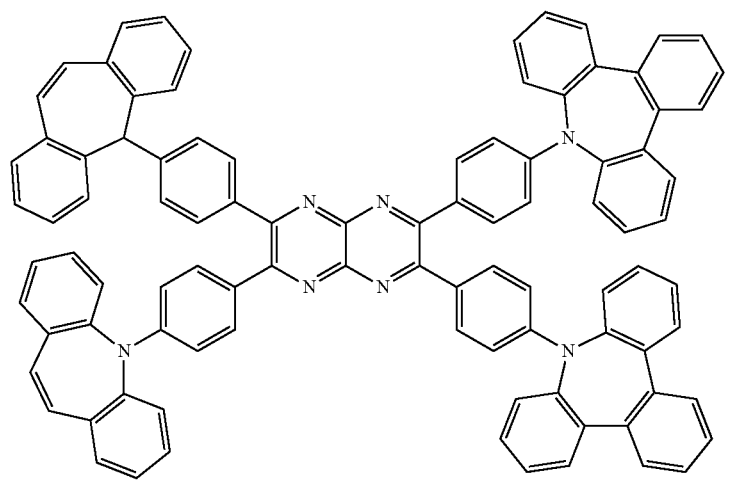
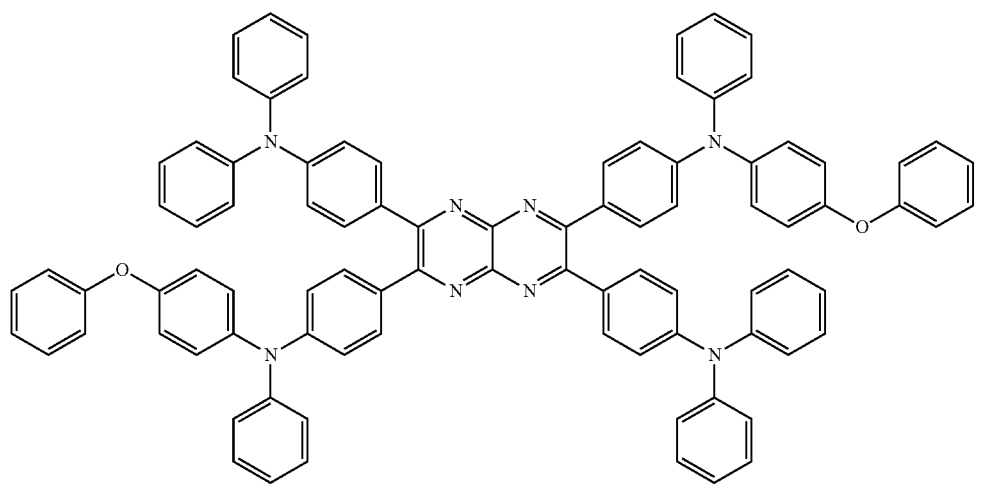

-continued
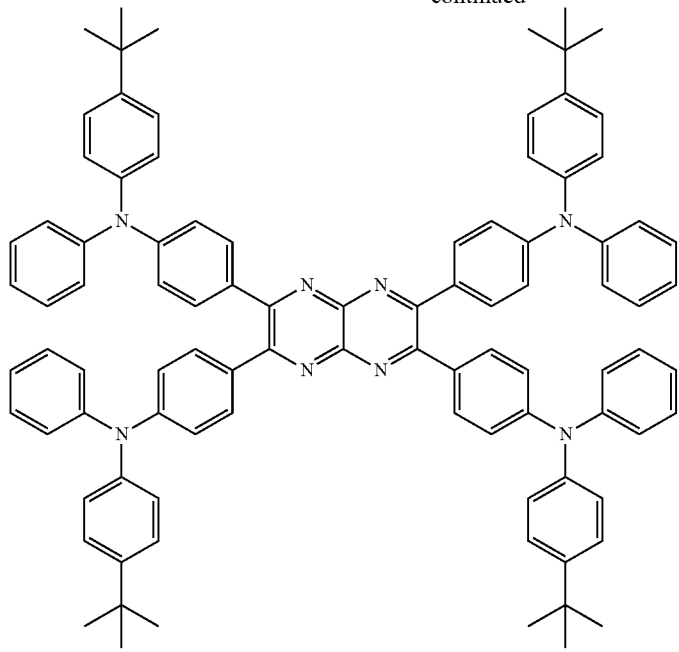 [SMILES: CC(C)(C)c1ccc(N(c2ccccc2)c2ccc(-c3nc4nc(-c5ccc(N(c6ccccc6)c6ccc(C(C)(C)C)cc6)cc5)c(-c5ccc(N(c6ccccc6)c6ccc(C(C)(C)C)cc6)cc5)nc4nc3-c3ccc(N(c4ccccc4)c4ccc(C(C)(C)C)cc4)cc3)cc2)cc1]
[Chem. 86]
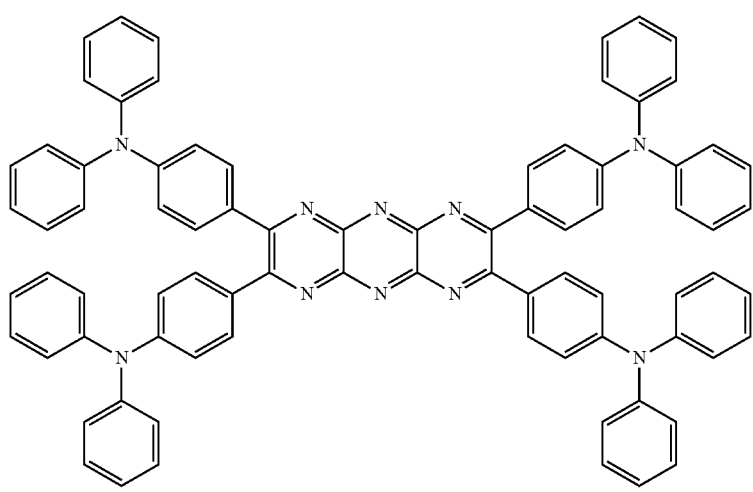
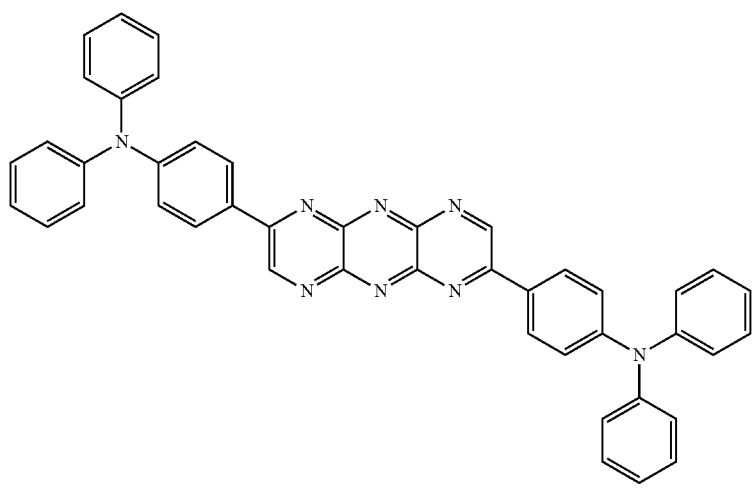

-continued
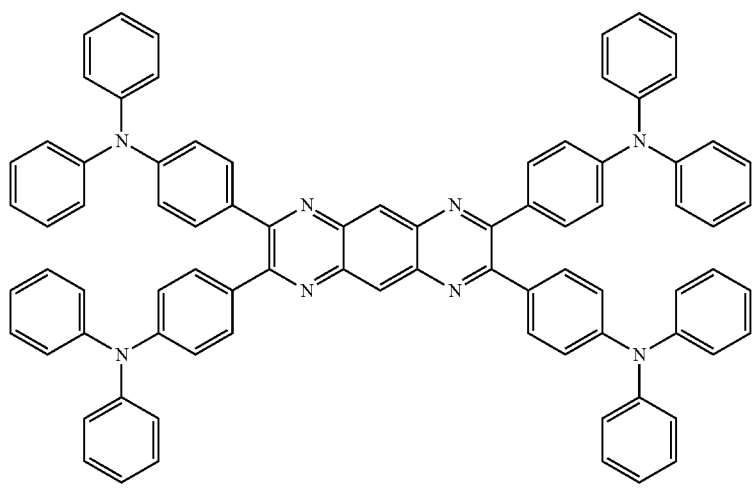
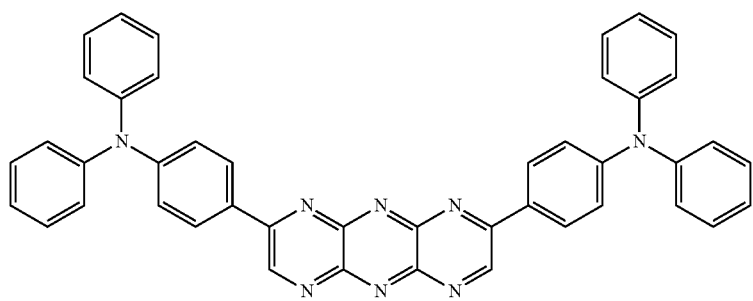
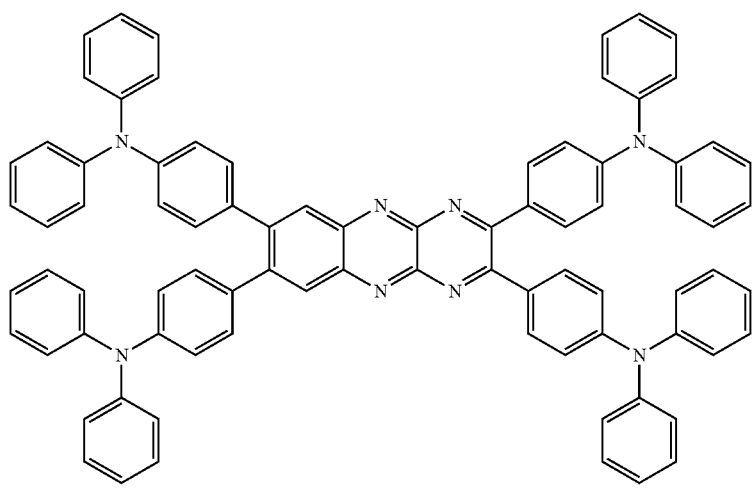

[Chem. 87]
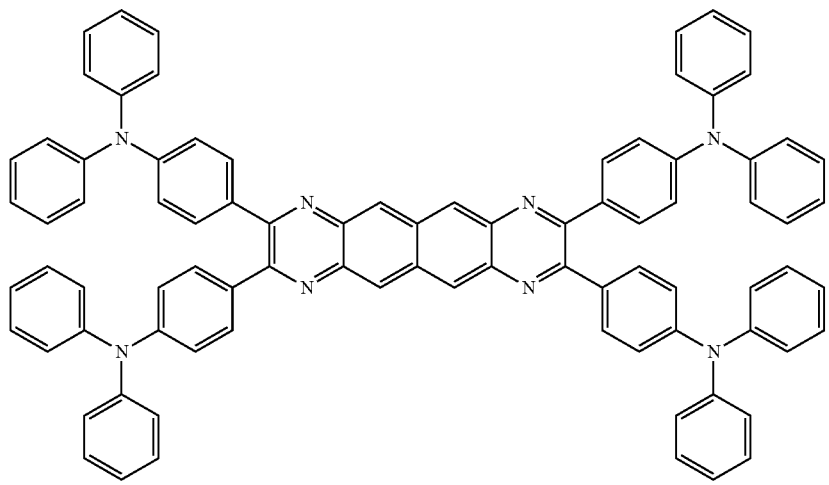
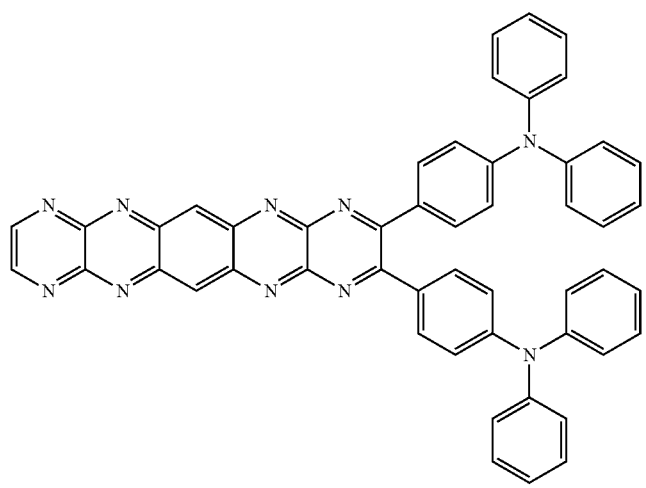
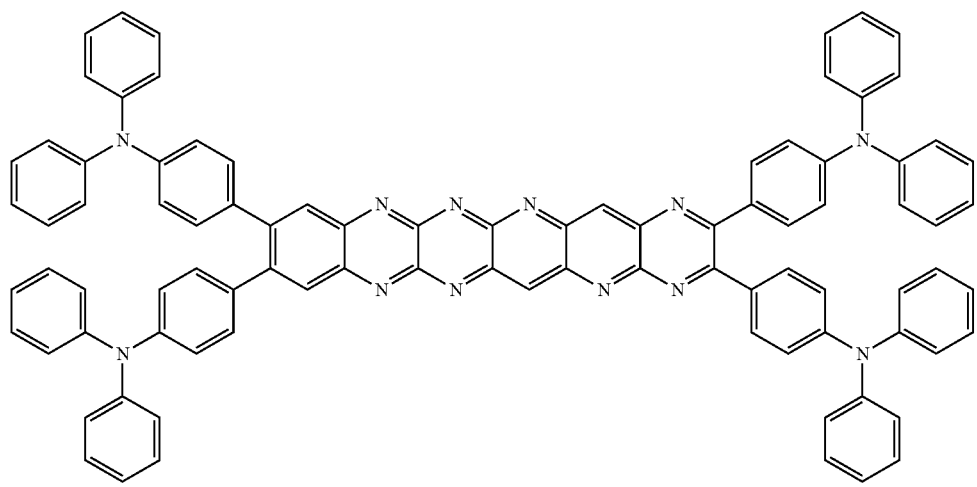

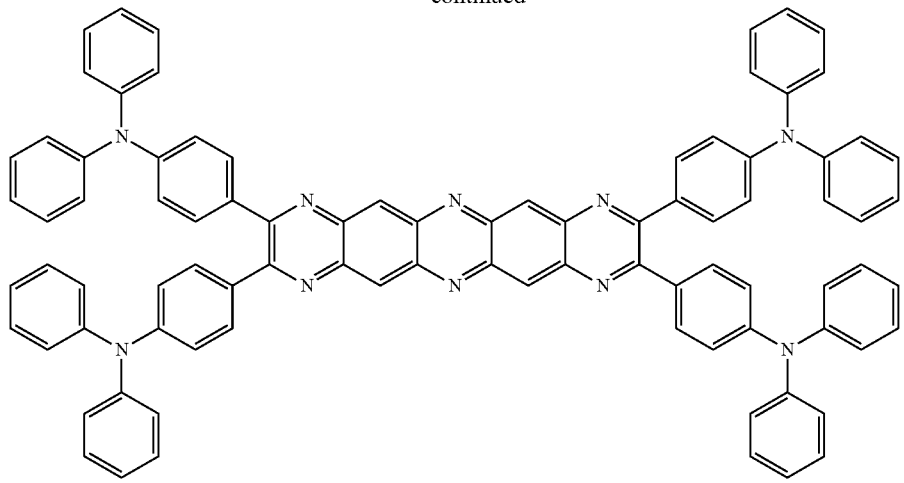
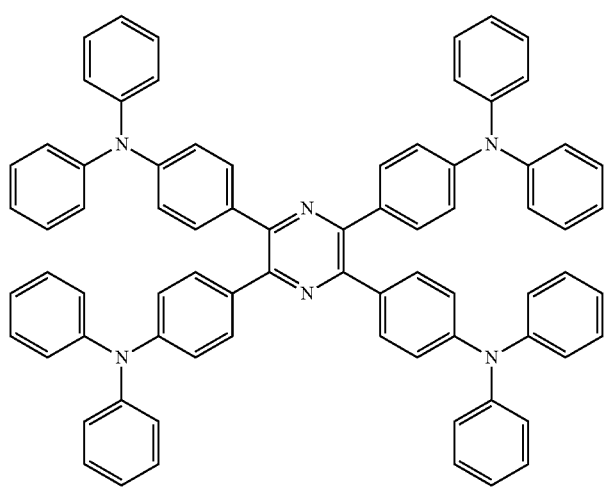 [SMILES: c1ccc(N(c2ccccc2)c2ccc(-c3nc(-c4ccc(N(c5ccccc5)c5ccccc5)cc4)c(-c4ccc(N(c5ccccc5)c5ccccc5)cc4)nc3-c3ccc(N(c4ccccc4)c4ccccc4)cc3)cc2)cc1]

Examples of the preferred delayed fluorescent material include compounds represented by the following general formula. The entire description of JP-A-2014-9224 including the paragraphs 0008 to 0048 and 0067 to 0076 is incorporated herein by reference as a part of the description of the present application.

[Chem. 88]

General Formula (241)

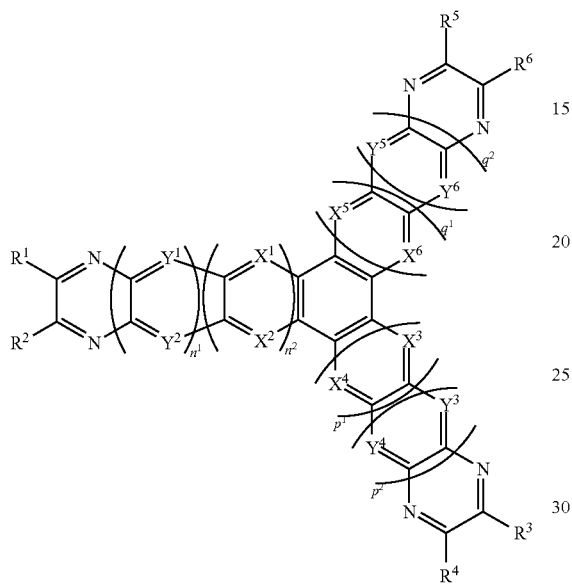

[In the general formula (241), $R^1$ to $R^6$ each independently represent a hydrogen atom or a substituent, provided that at least one of $R^1$ to $R^6$ represents a substituted or unsubstituted (N,N-diarylamino)aryl group, and two aryl groups constituting the diarylamino moiety of the (N,N-diarylamino)aryl group may be bonded to each other. $X^1$ to $X$ and $Y^1$ to $Y^6$ each independently represent a carbon atom or a nitrogen atom. $n^1$, $n^2$, $p^1$, $p^2$, $q^1$ and $q^2$ each independently represent 0, 1 or 2.]

Examples of the compound include the following compounds.

[Chem. 89]

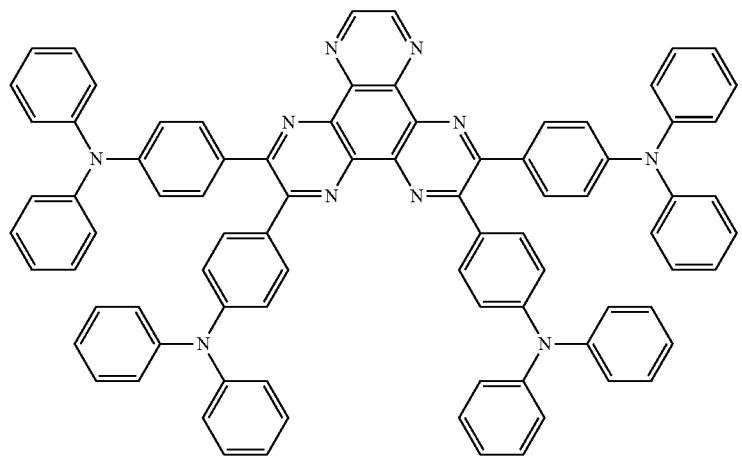

-continued
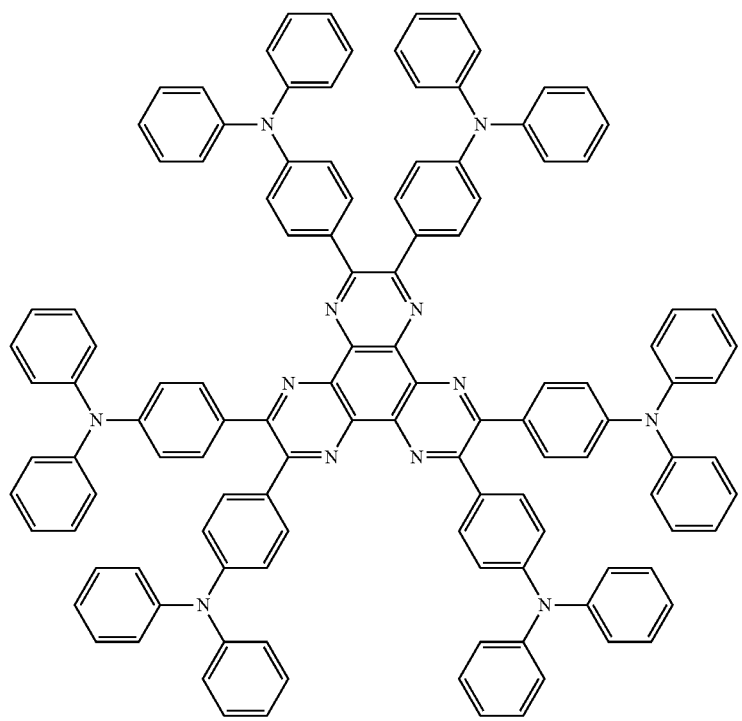
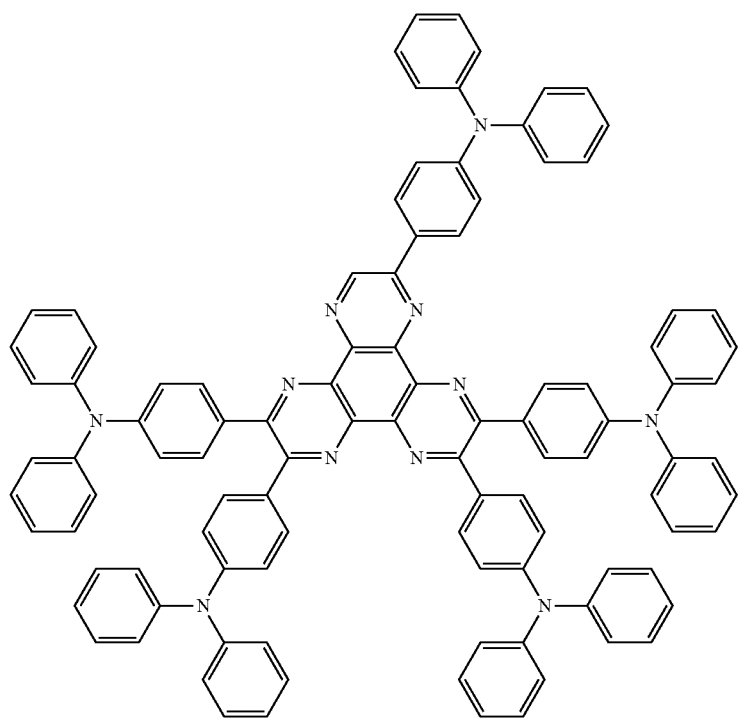

-continued
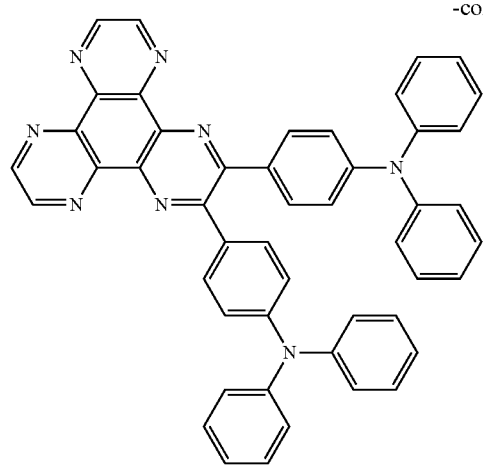
[Chem. 90]
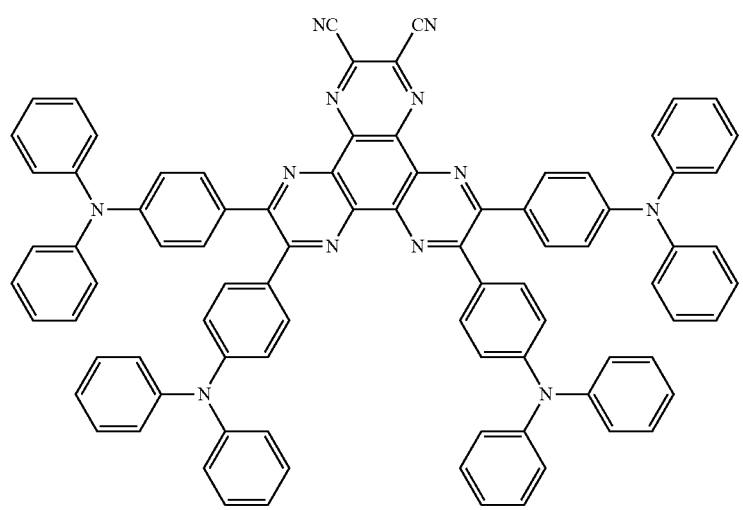
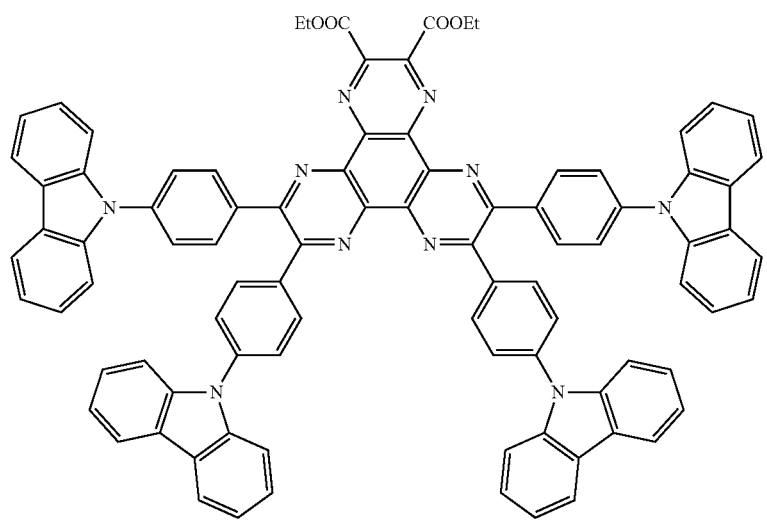

-continued
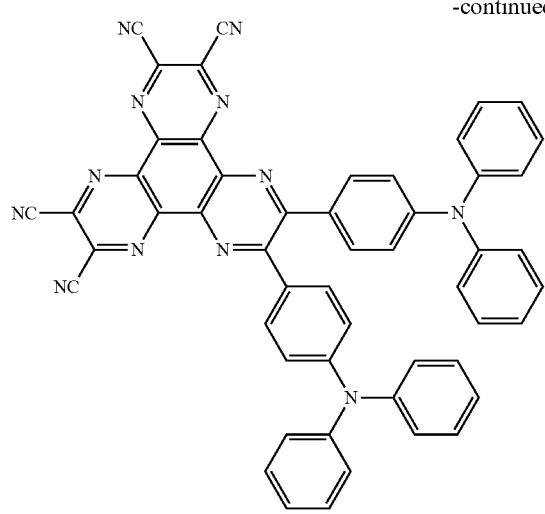
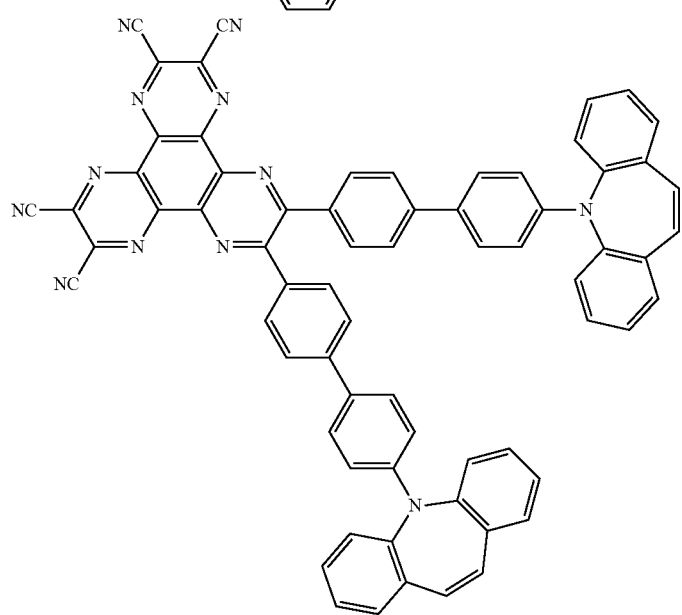
[Chem. 91]
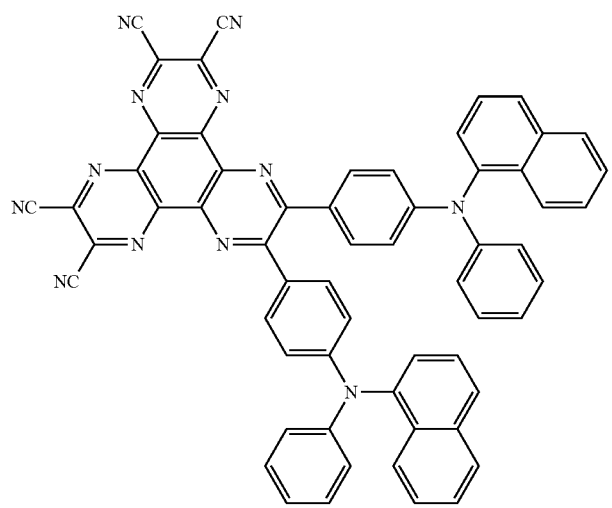

-continued
265
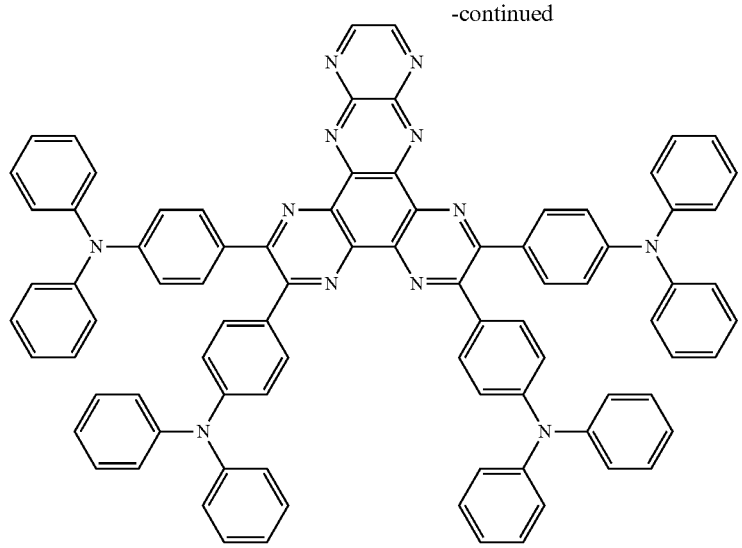
266
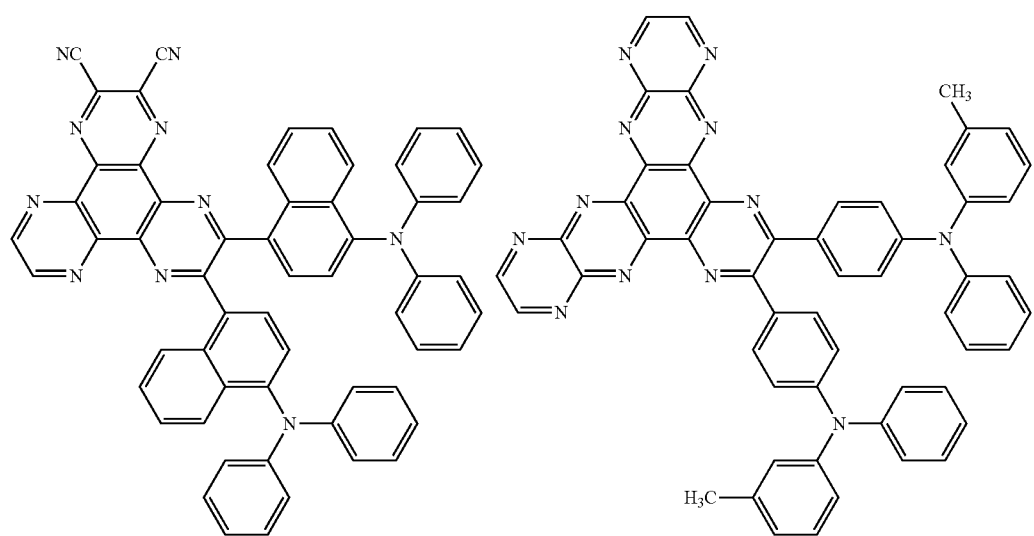

-continued
[Chem. 92]
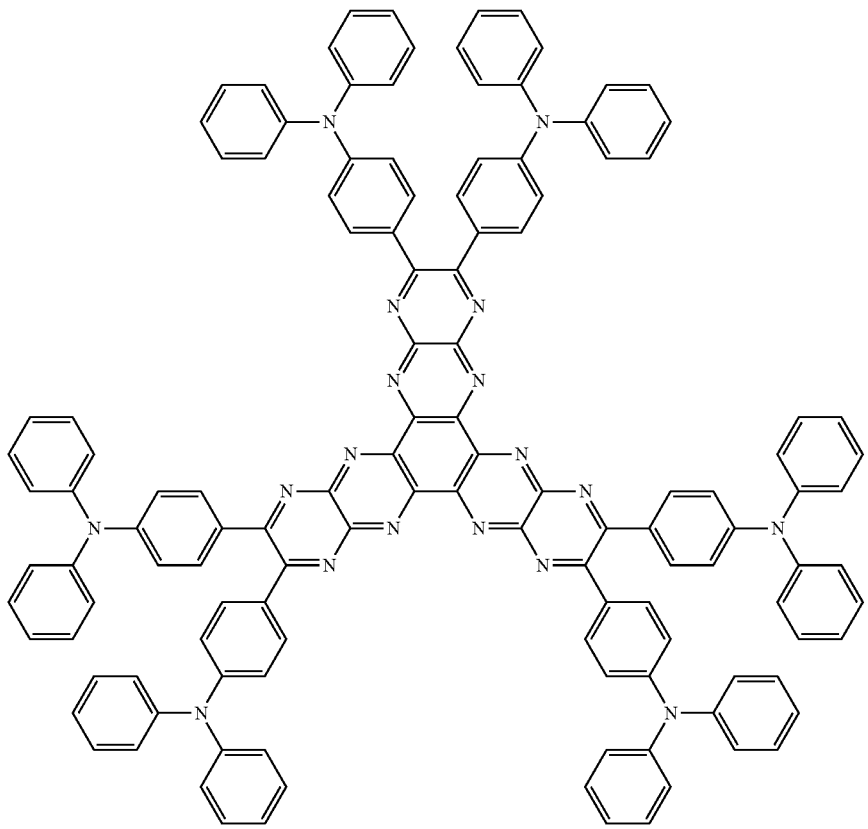
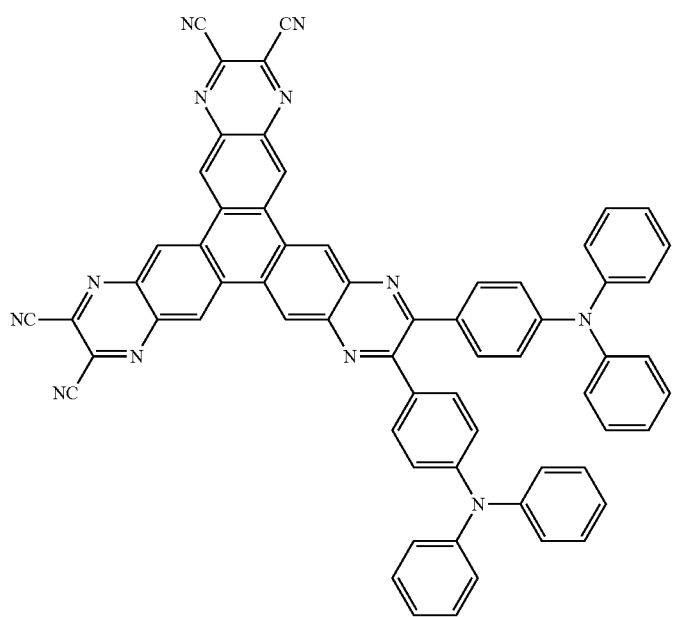

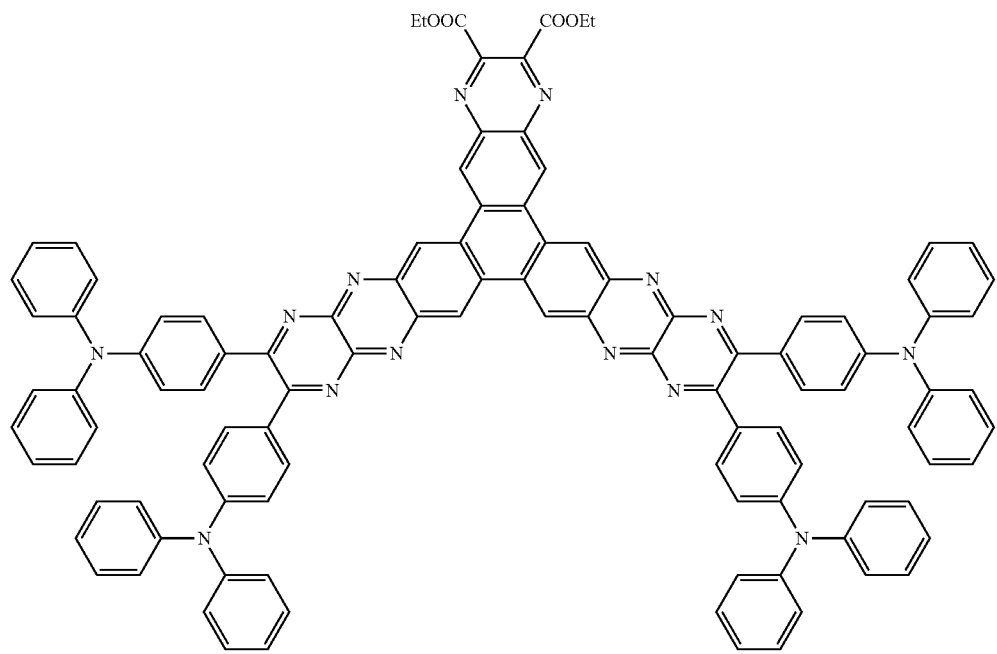
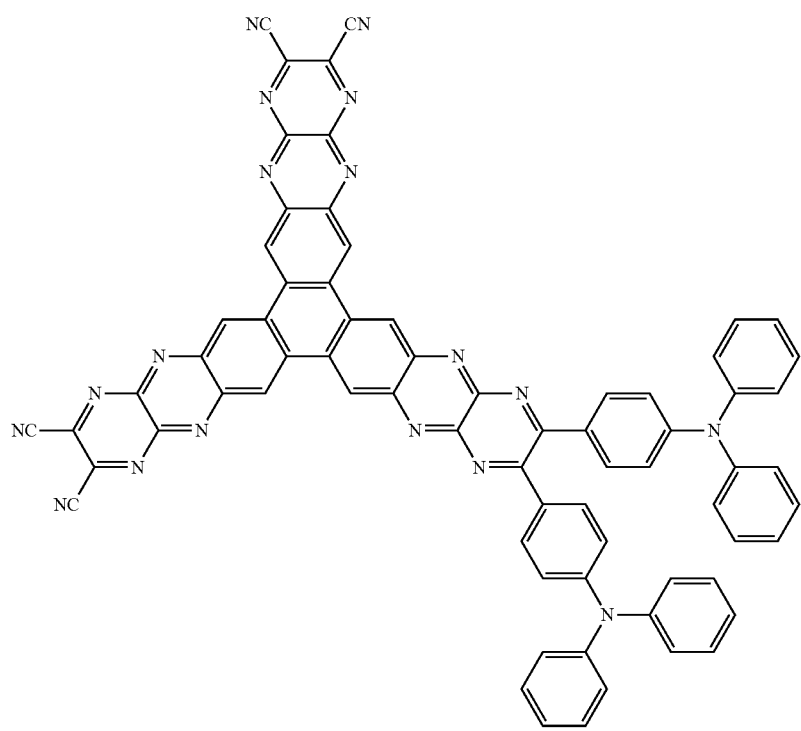

Preferred compounds for host materials that can be used together with the host material for delayed fluorescent materials of the present invention are mentioned below.
[Chem. 93]
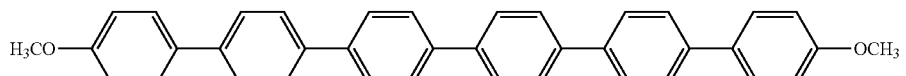
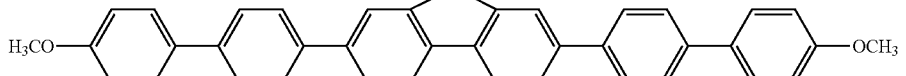
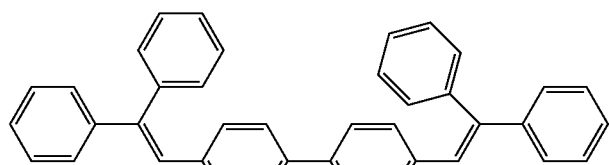
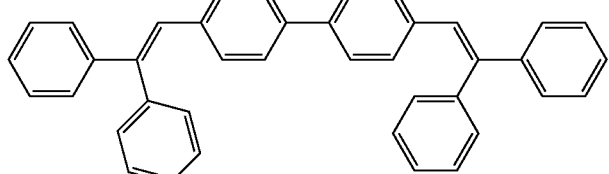
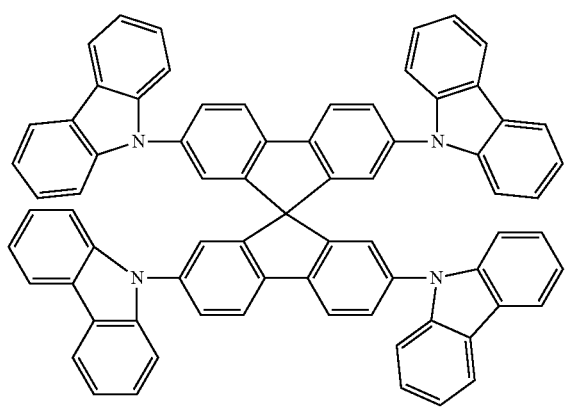
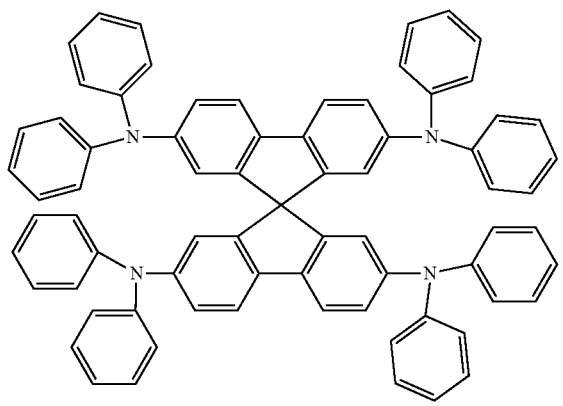

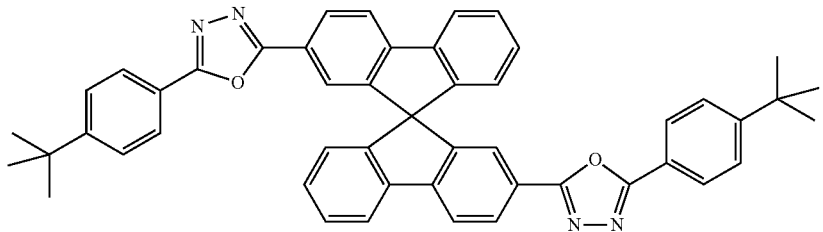
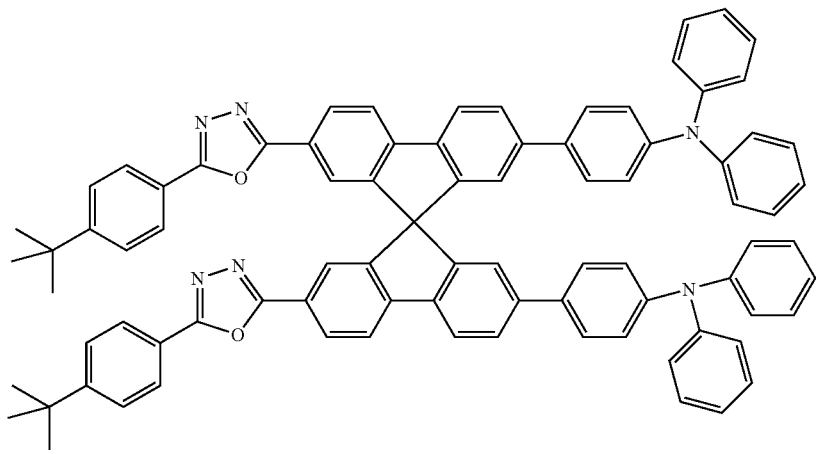
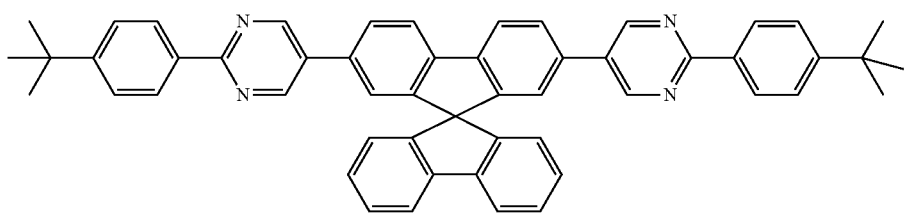
[Chem. 94]
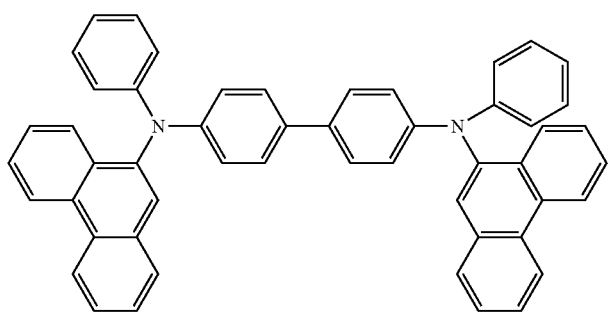
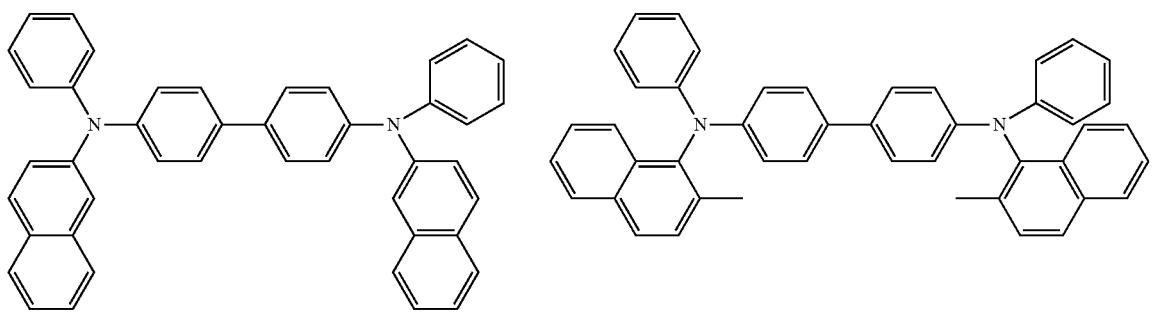

275
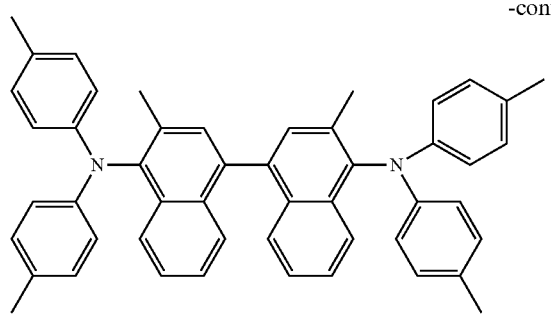
-continued
276
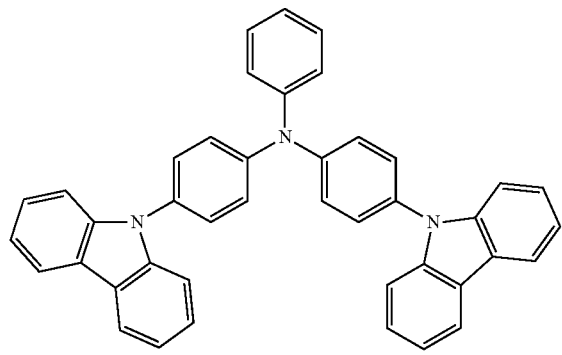
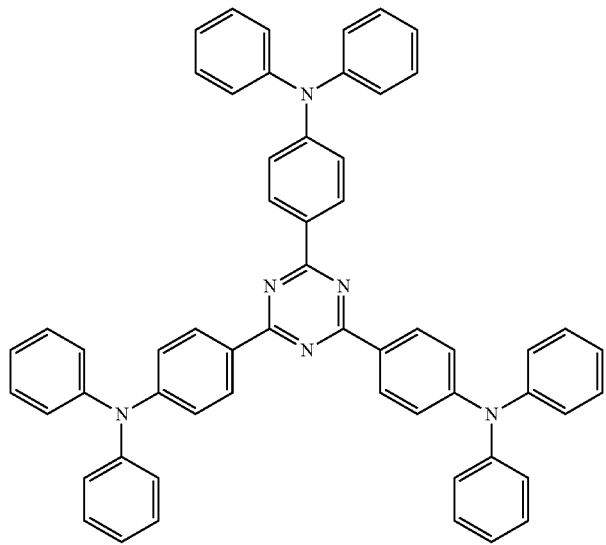
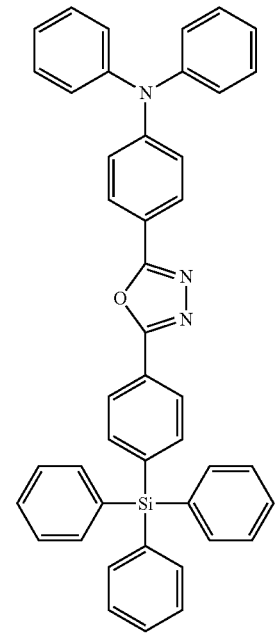

-continued
277
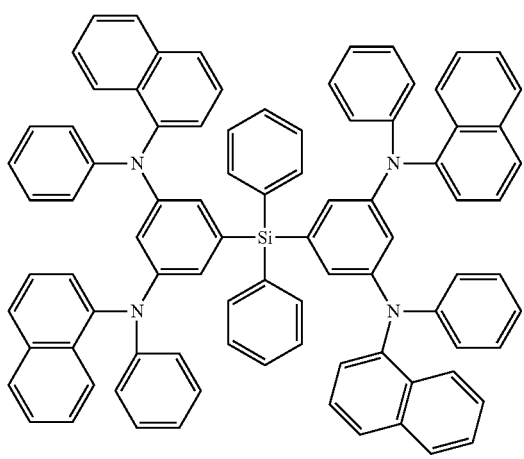
278
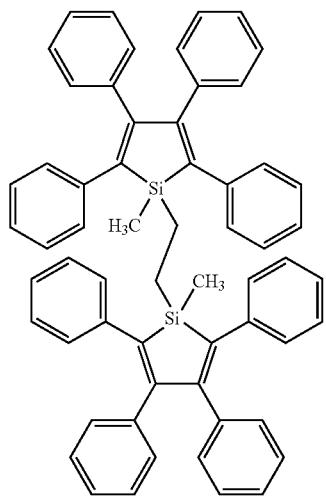
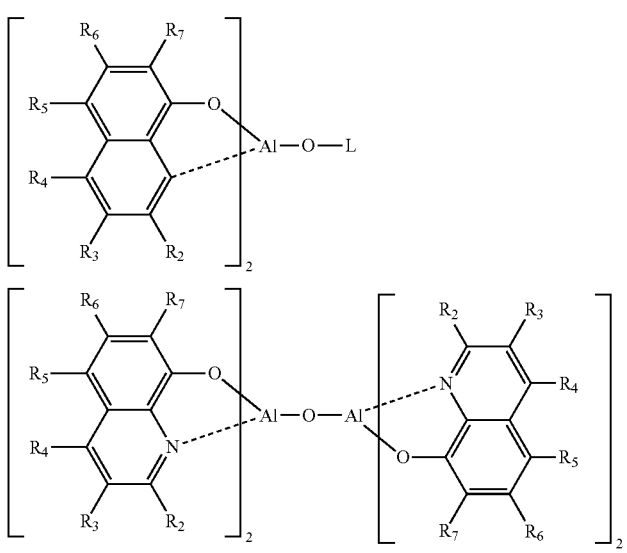
[Chem. 95]
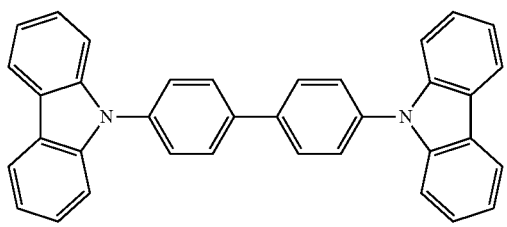
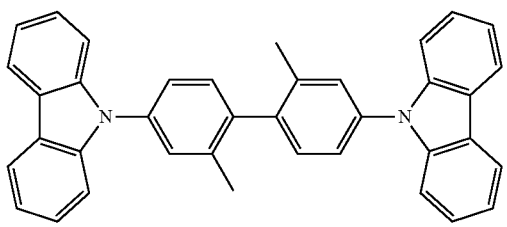
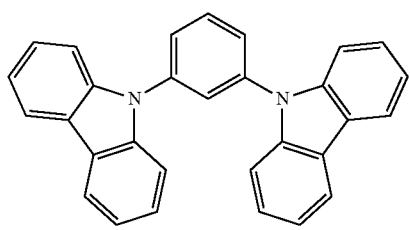
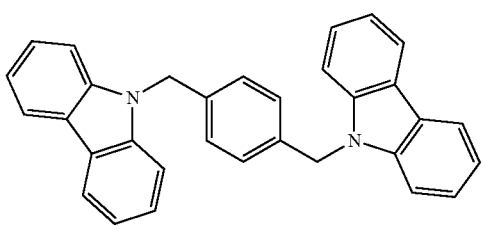

-continued
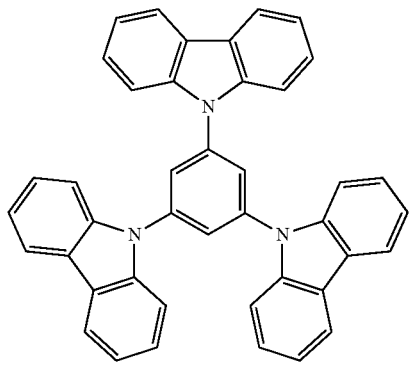
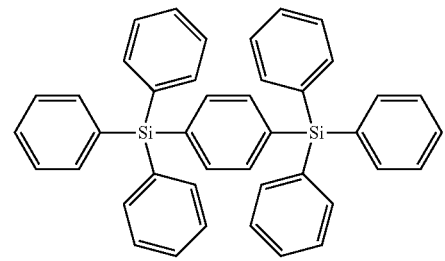
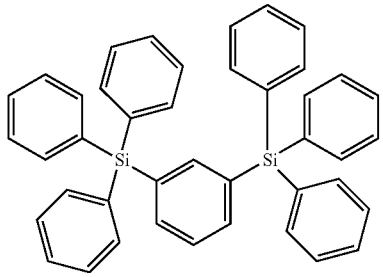
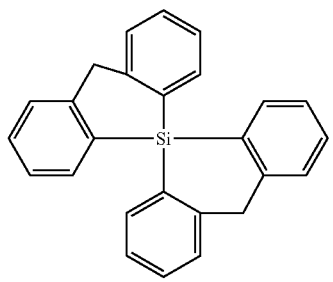
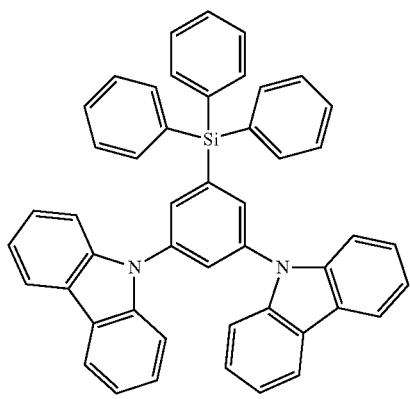
[Chem. 96]
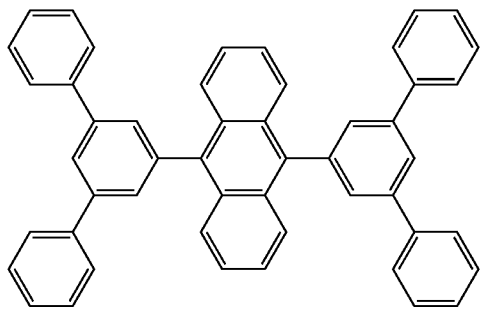
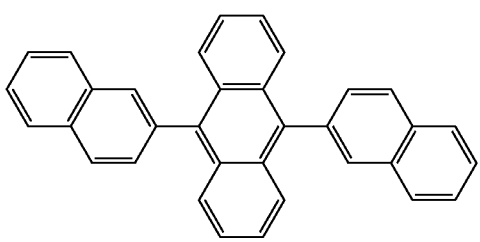
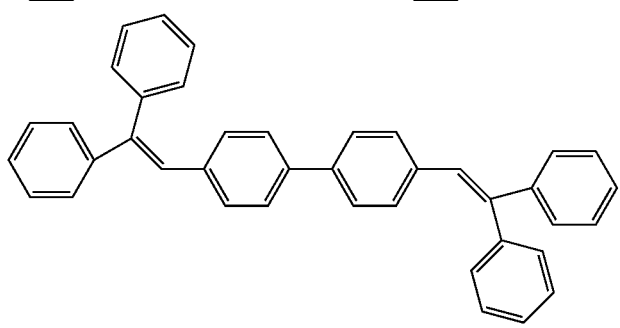

281
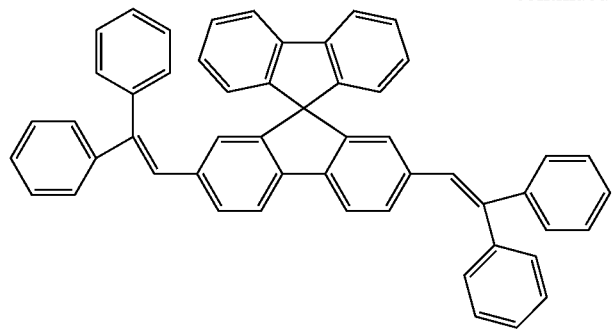
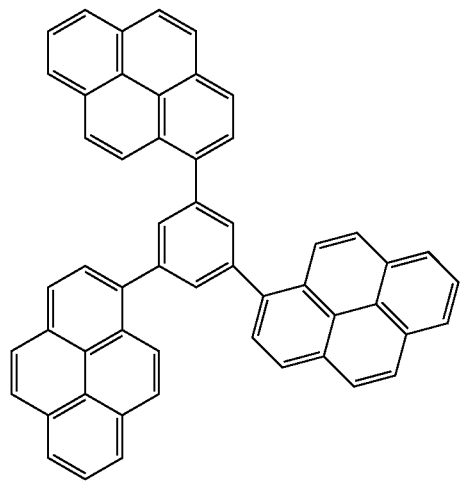
282
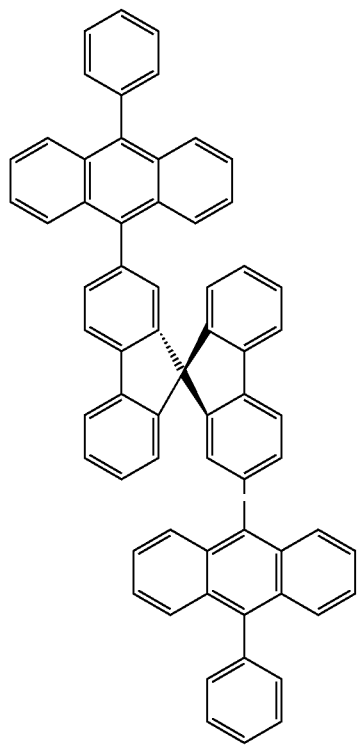
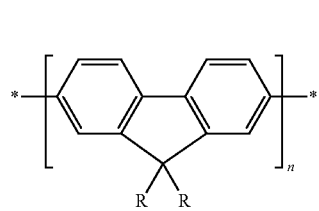
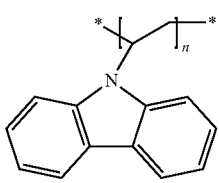
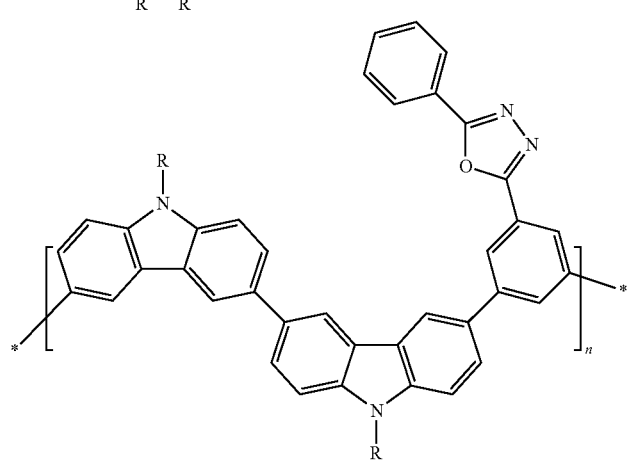

[Chem. 97]
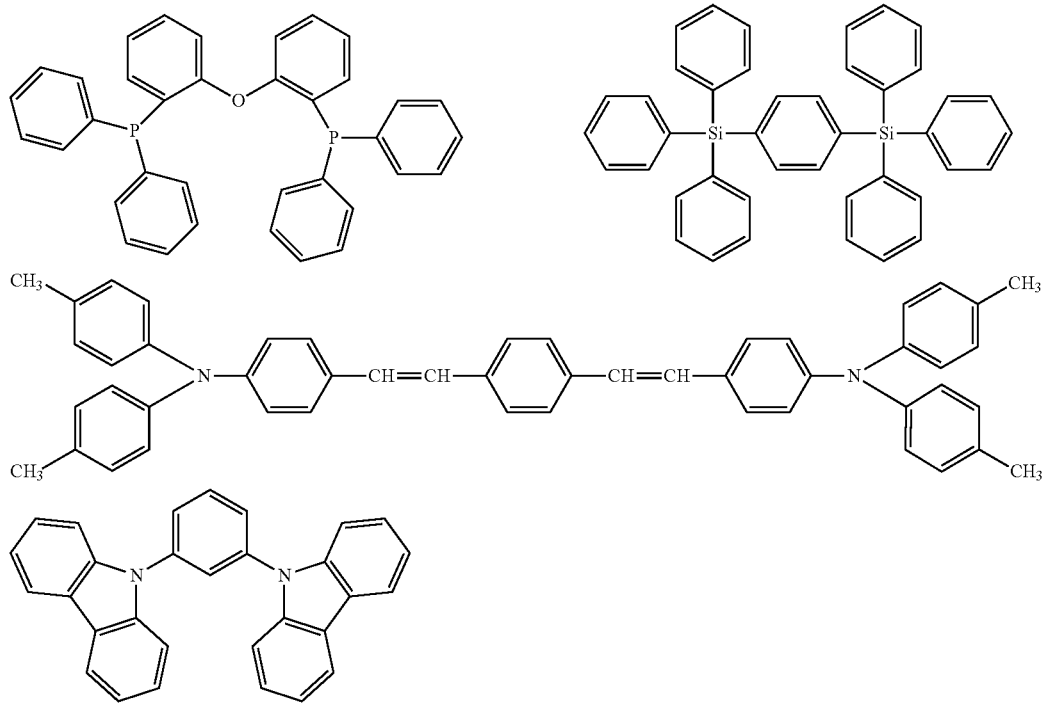
Preferred examples of compounds usable as a hole injection material are mentioned below.
[Chem. 98]
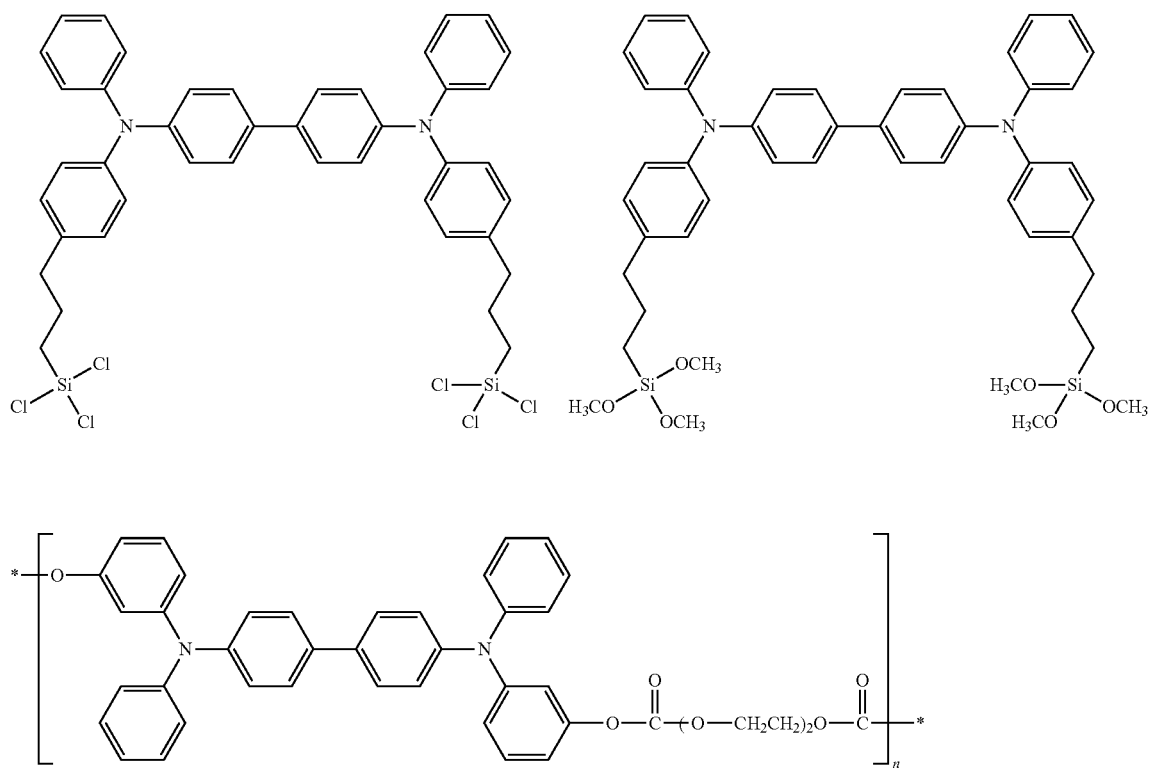

285
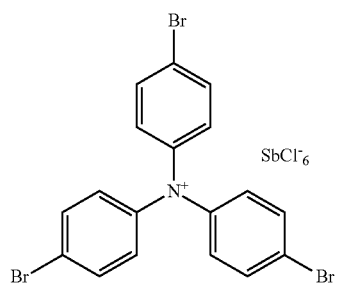
-continued
286
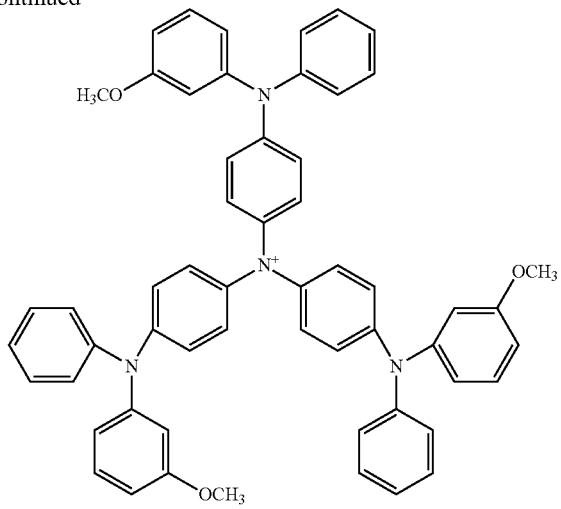
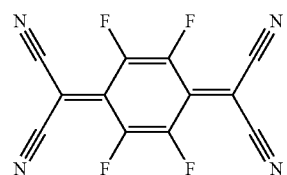
↓
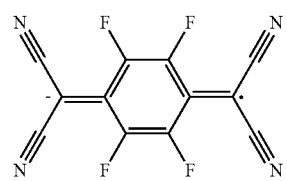
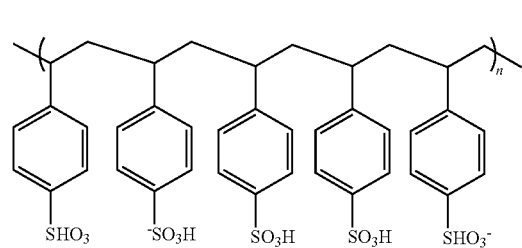
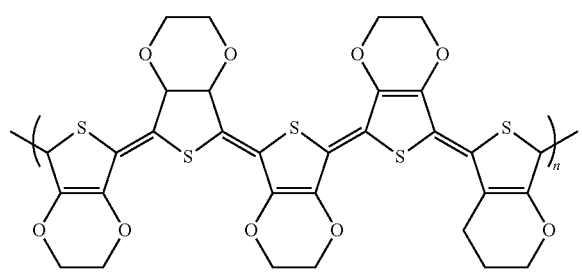

Next, preferred examples of compounds usable as a hole transport material are mentioned below.
[Chem. 99]
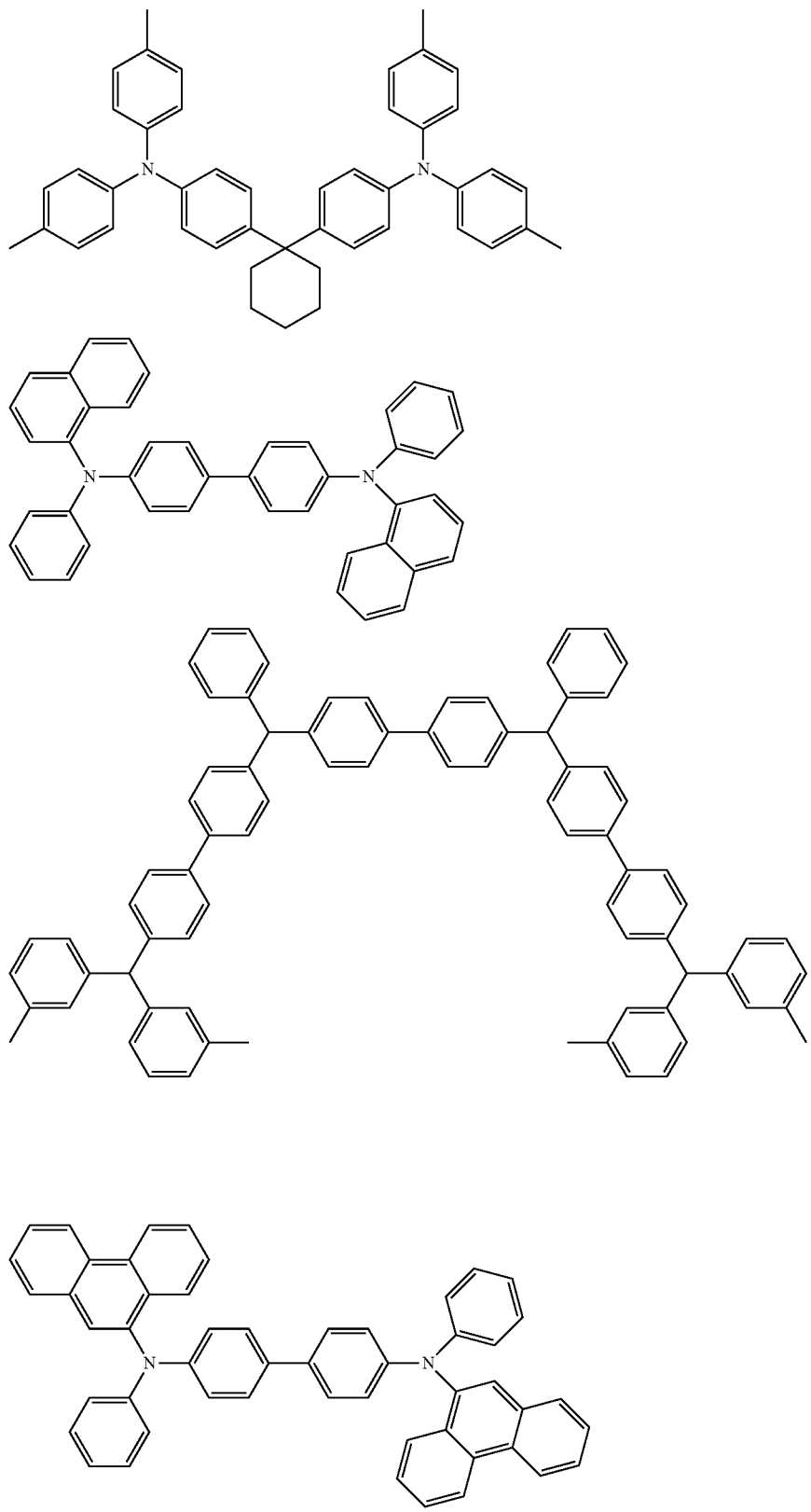

289
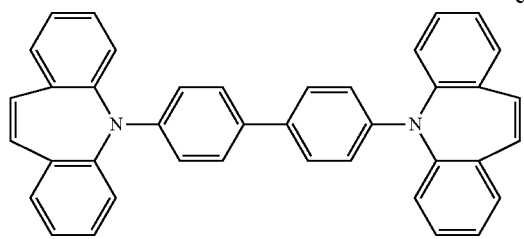
-continued
290
[Chem. 100]
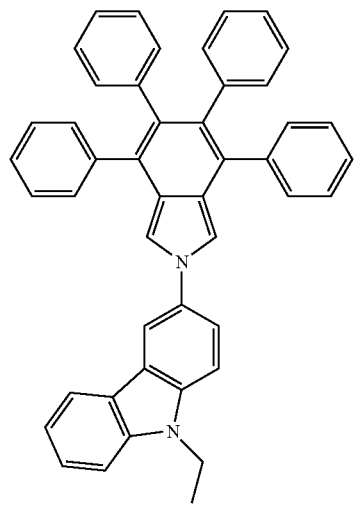
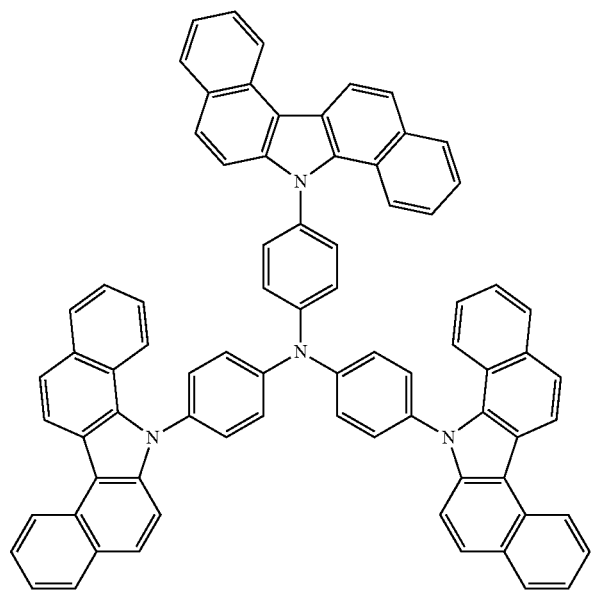
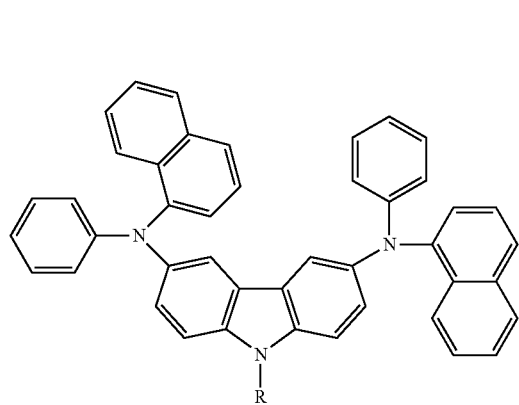
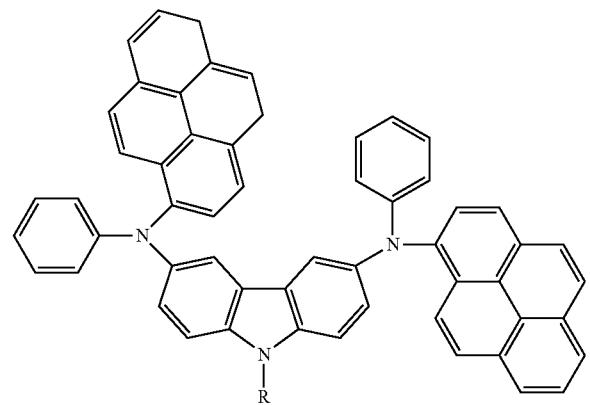

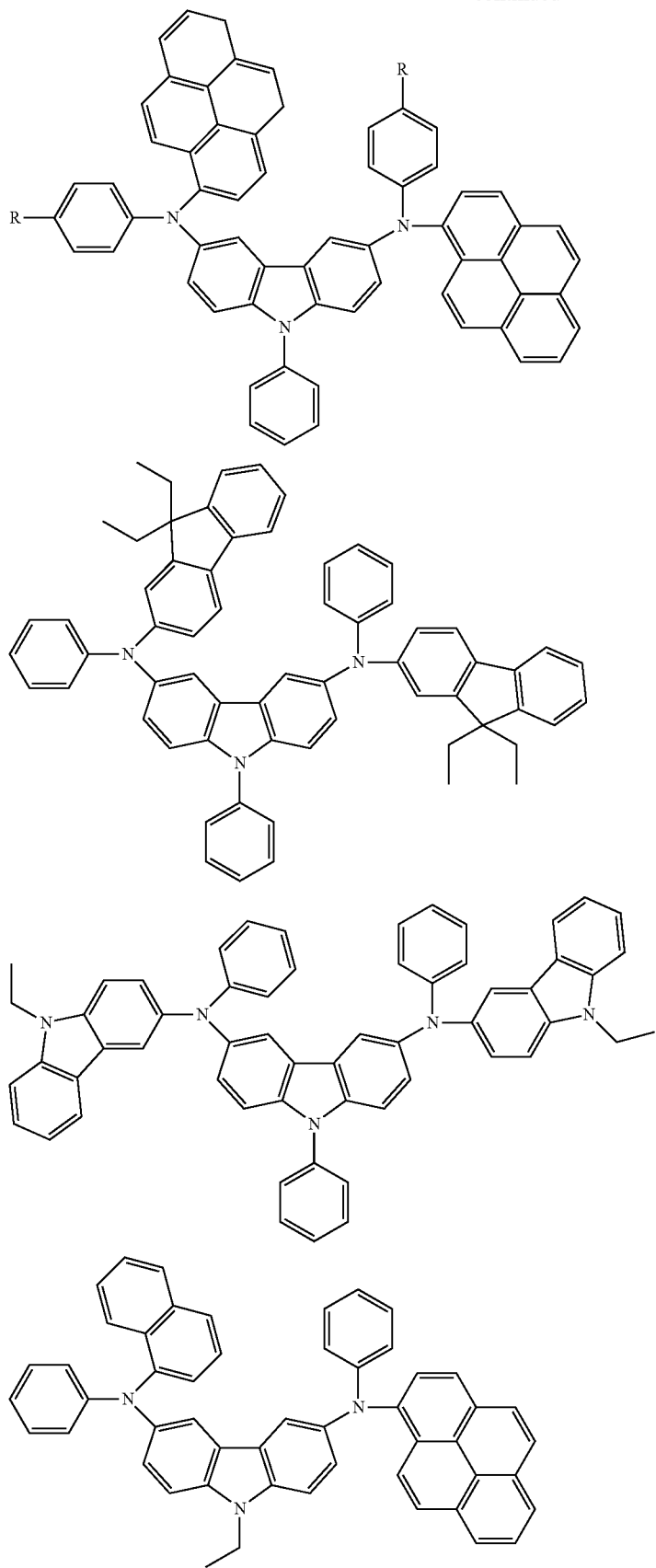

-continued
[Chem. 101]
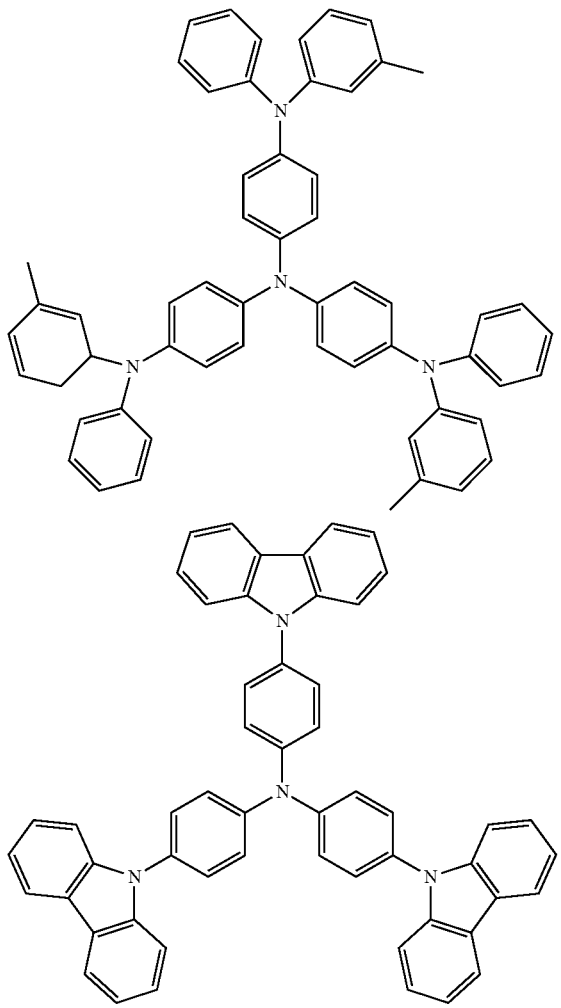
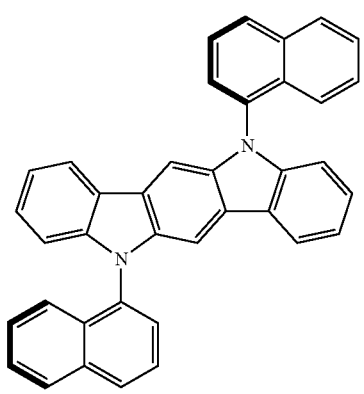
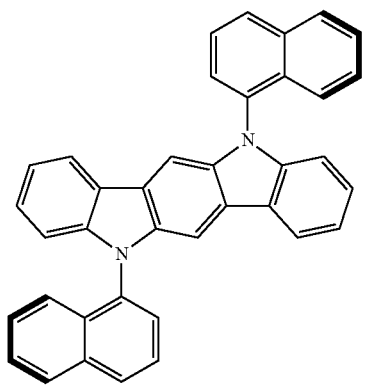
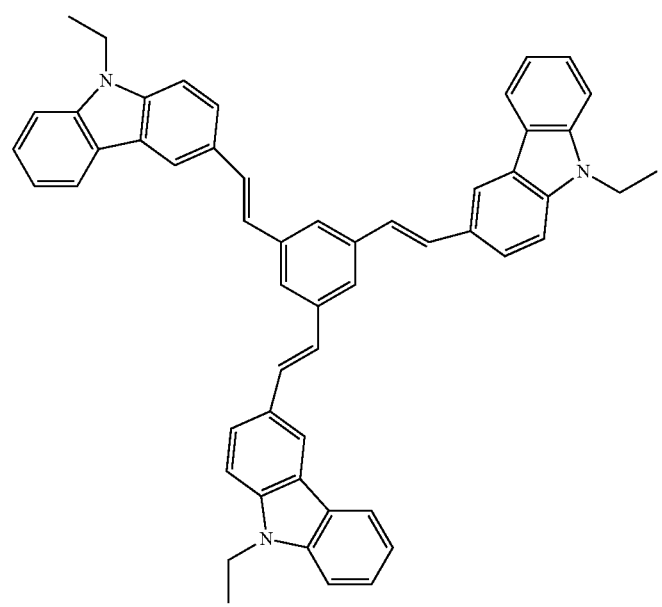

-continued
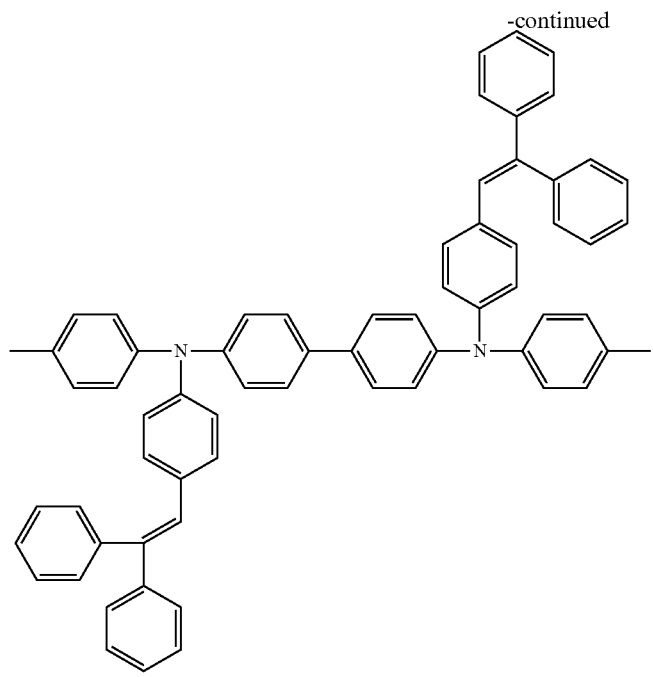
[Chem. 102]
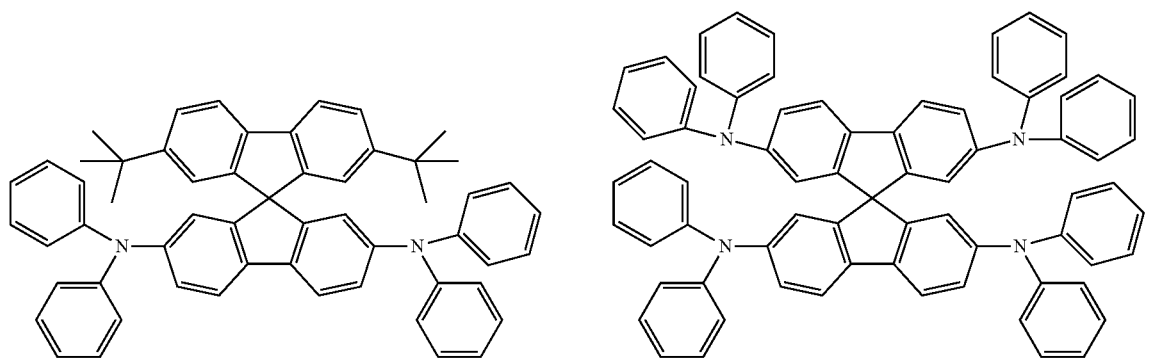
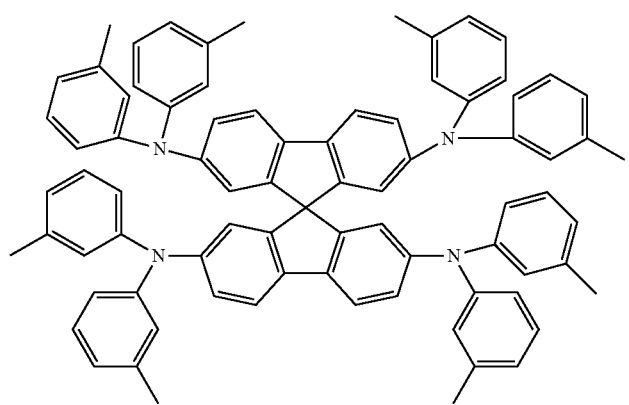

-continued
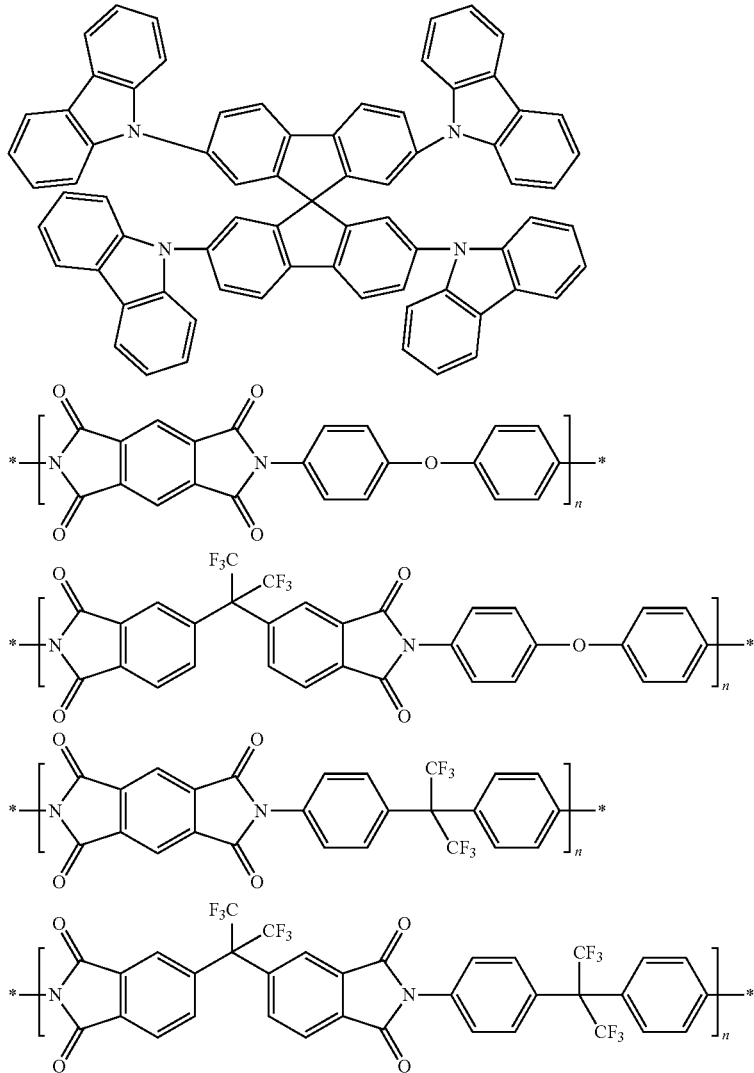
[Chem. 103]
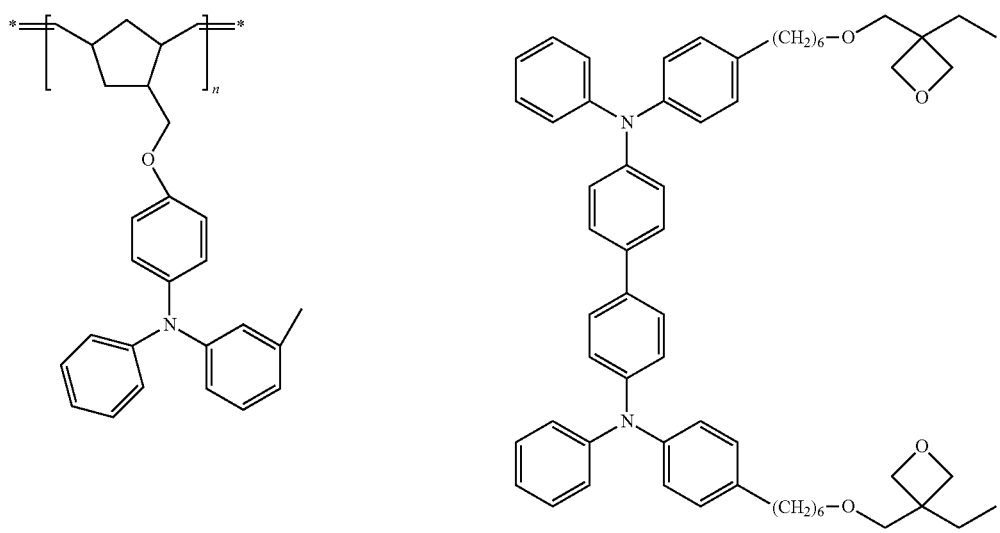

299
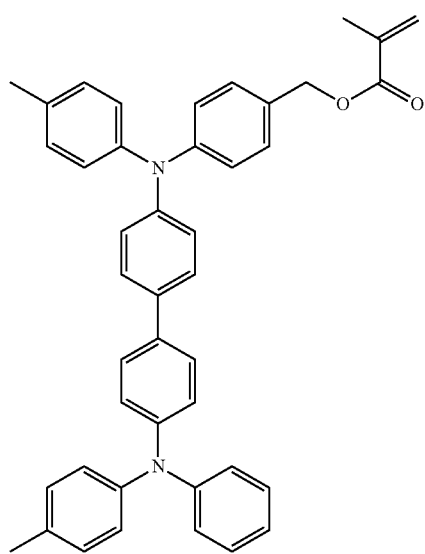
-continued
300
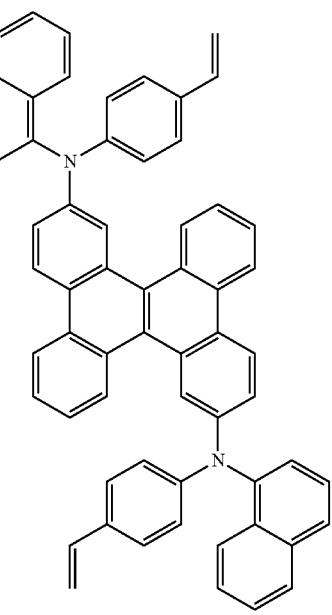
R =
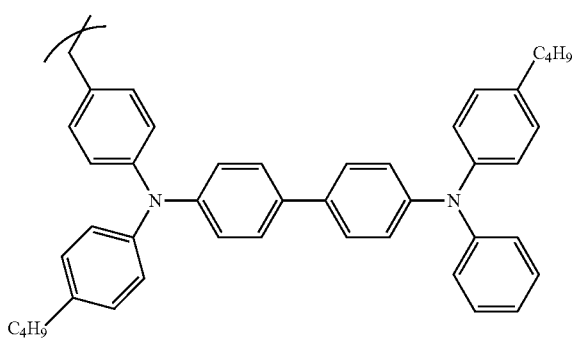
[Chem. 104]
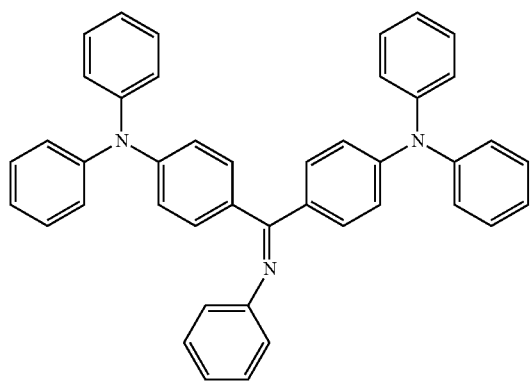

-continued
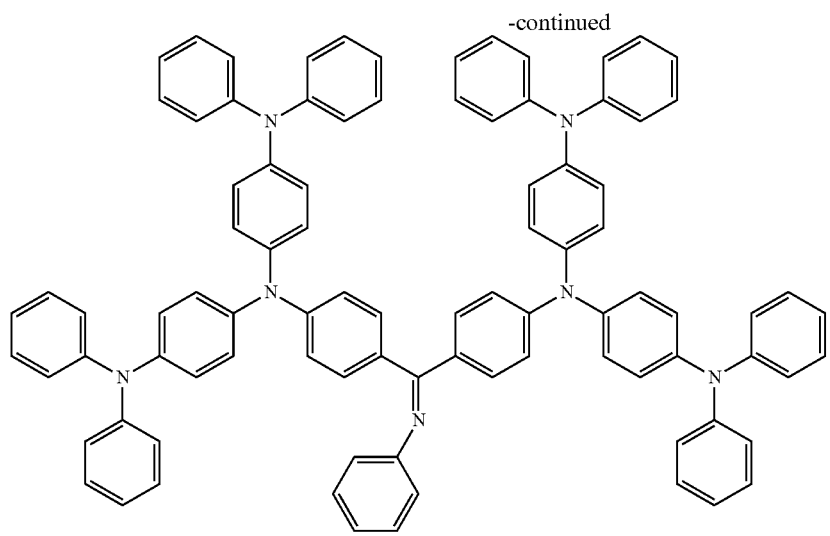
301
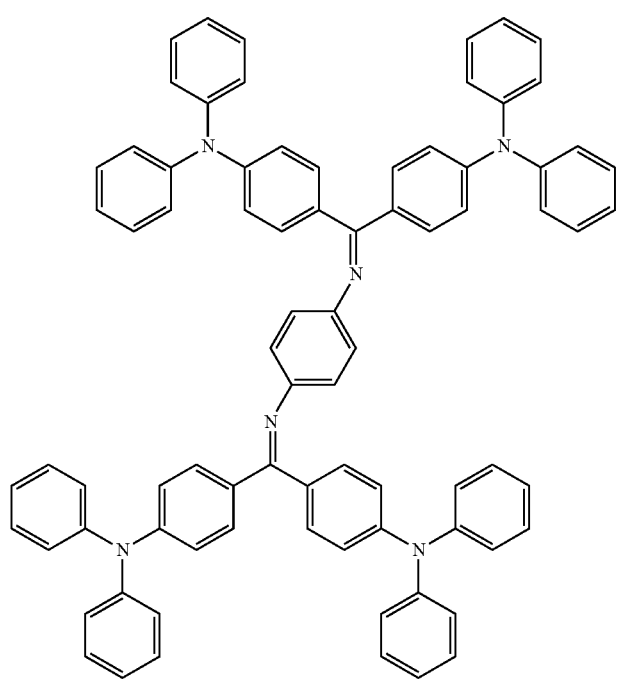
302

-continued
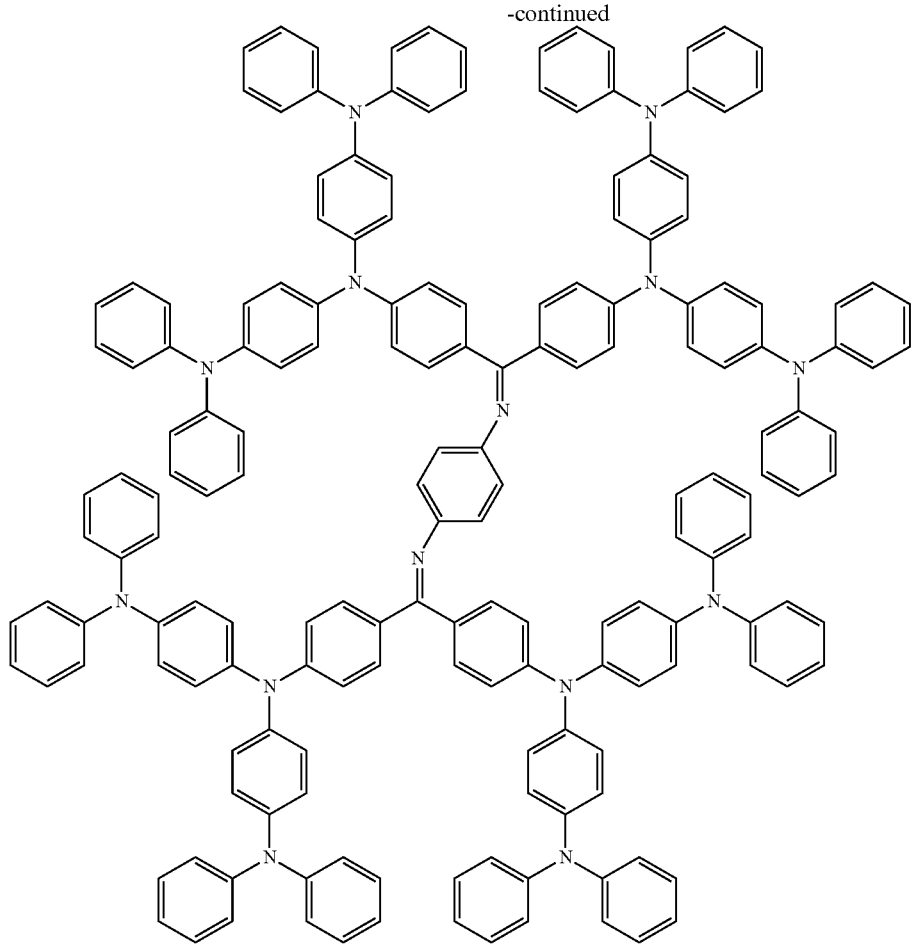
Next, preferred examples of compounds usable as a hole barrier material are mentioned below.
[Chem. 105]
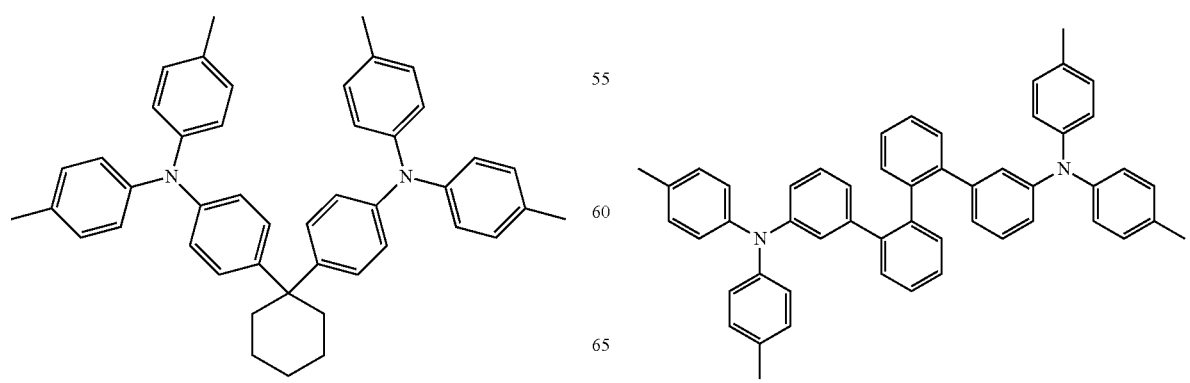

305
-continued
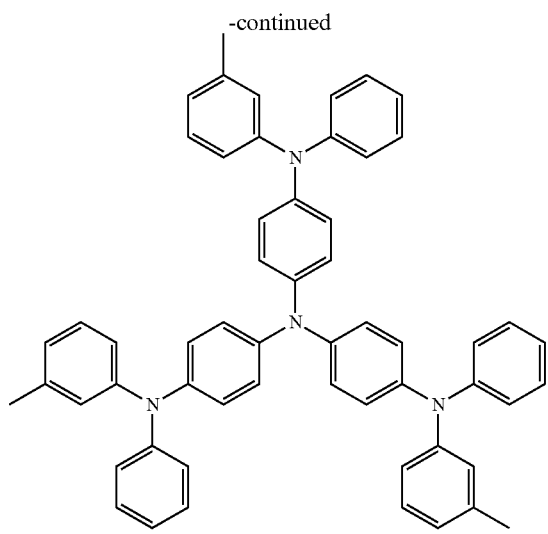
306
-continued
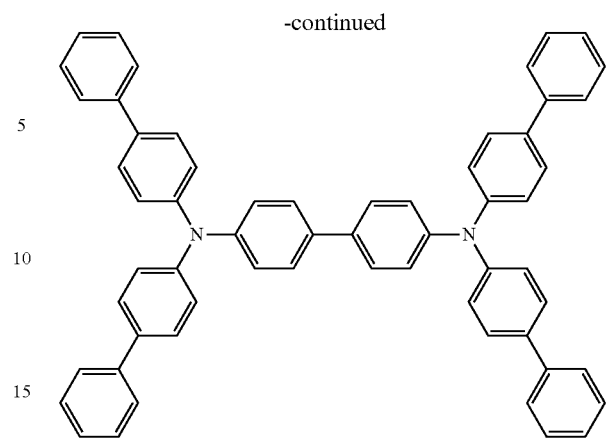
Next, preferred examples of compounds usable as a hole barrier material are mentioned below.
[Chem. 106]
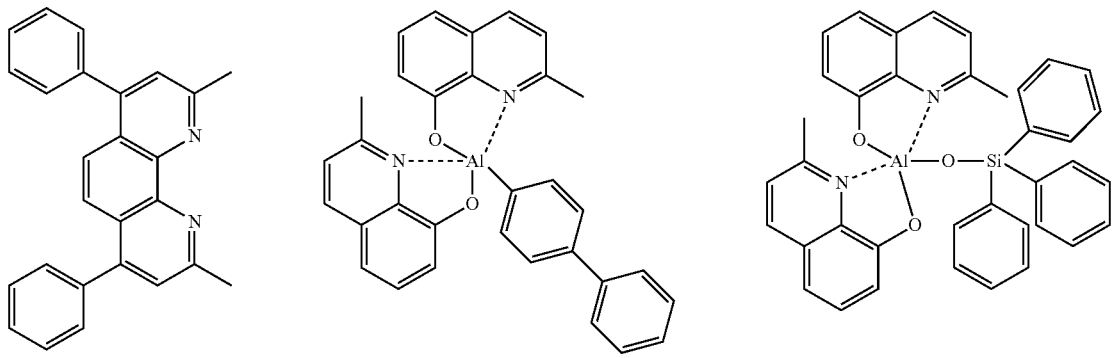
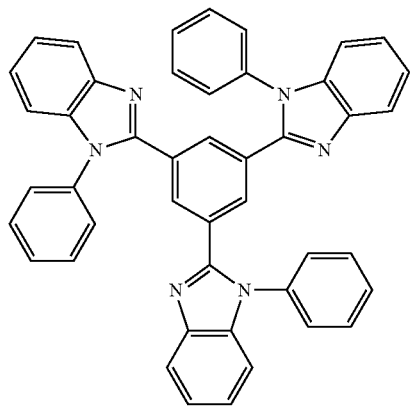
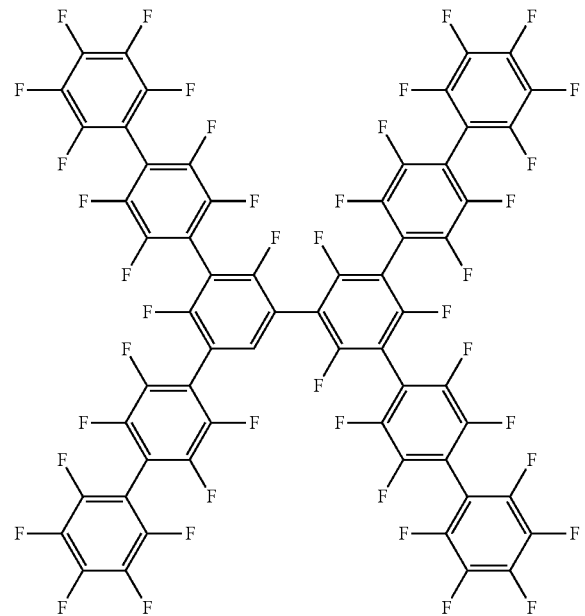

307
-continued
308
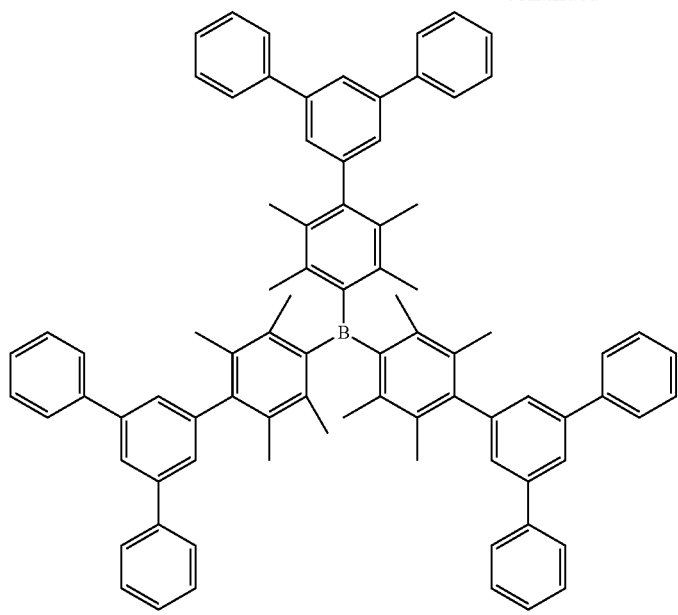
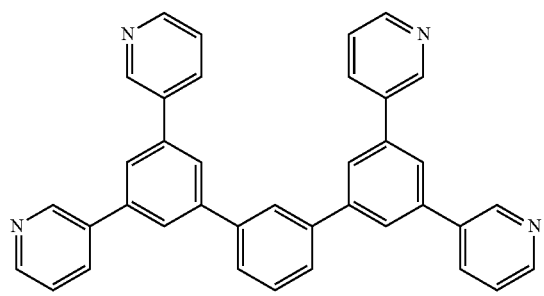
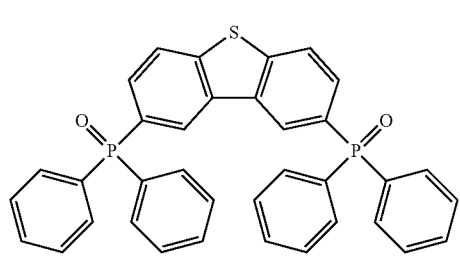
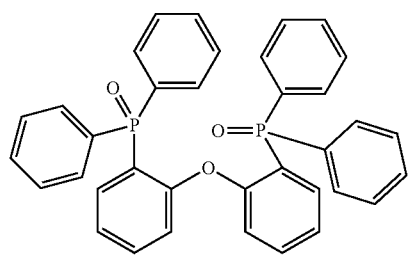

Next, preferred examples of compounds usable as a hole transport material are mentioned below.
[Chem. 107]
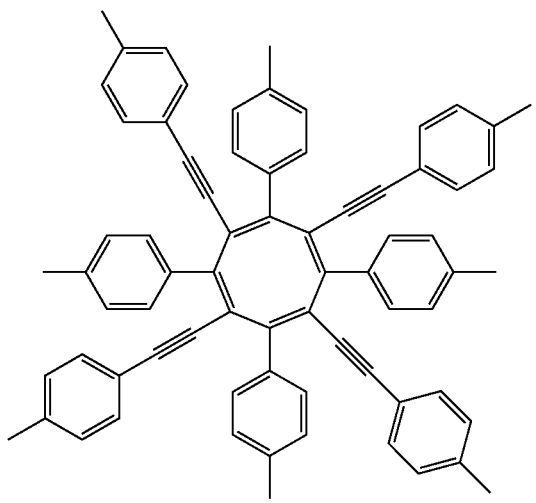
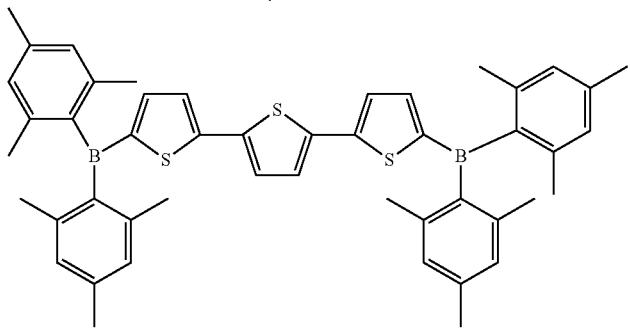
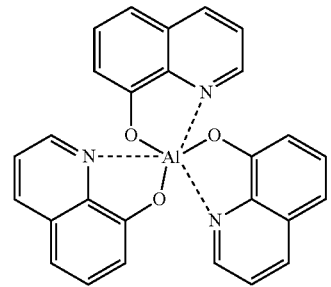
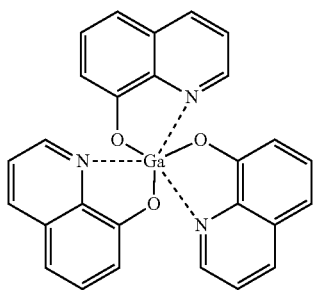
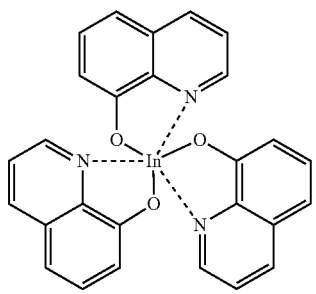
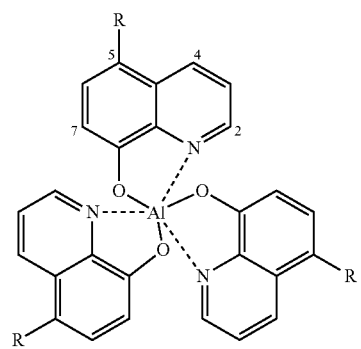
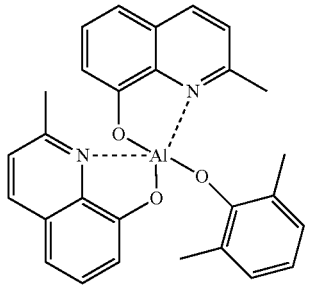
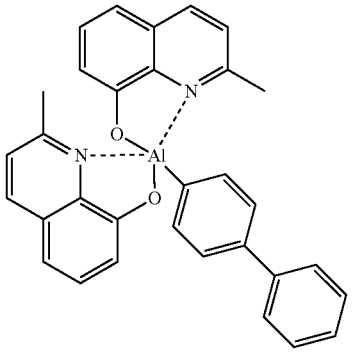

-continued
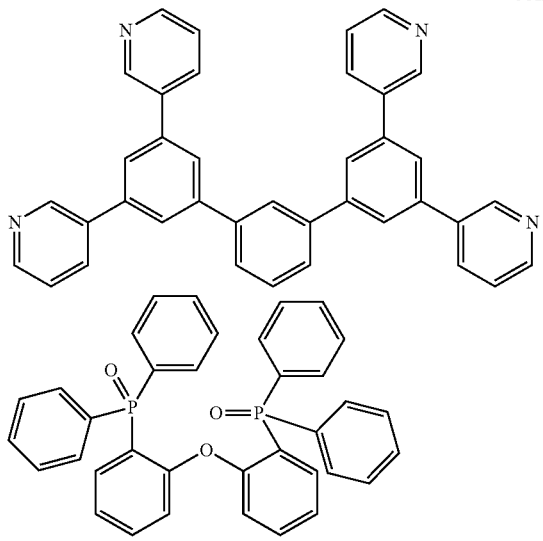
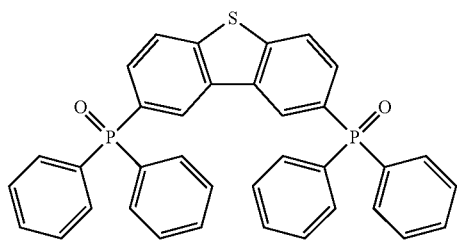
[Chem. 108]
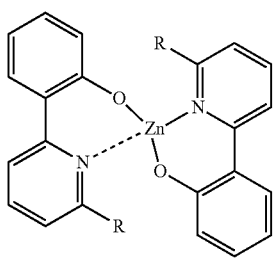
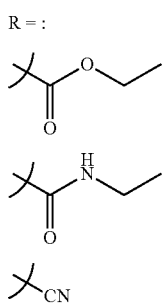
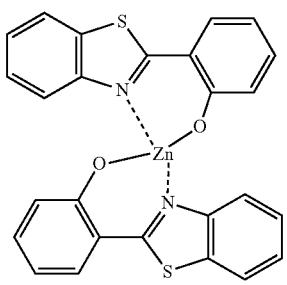
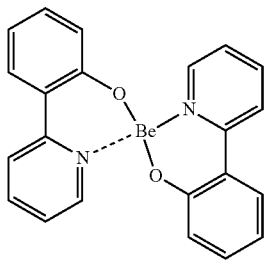
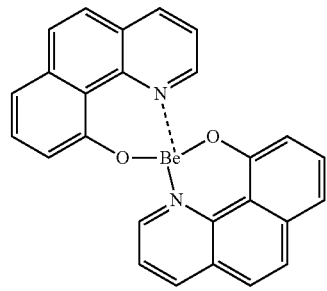
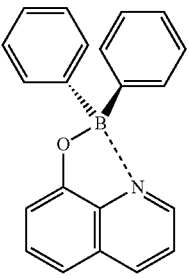
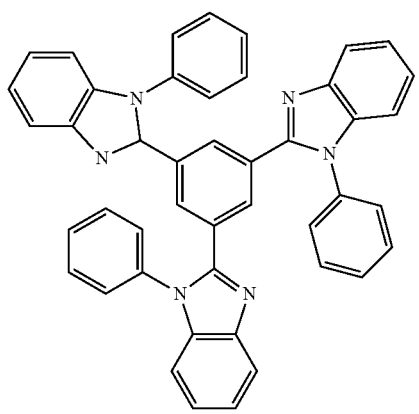

313                                    314
-continued
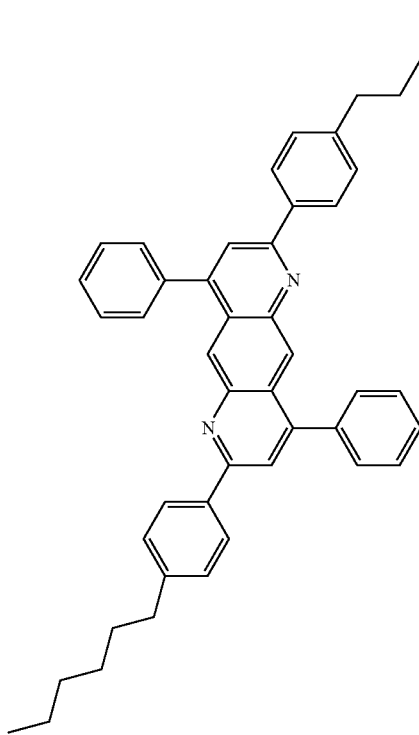
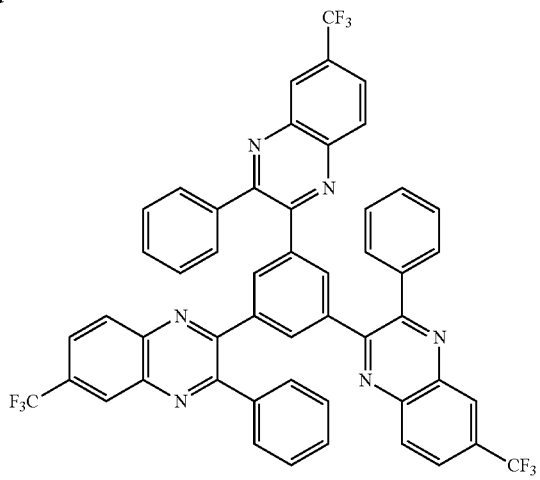
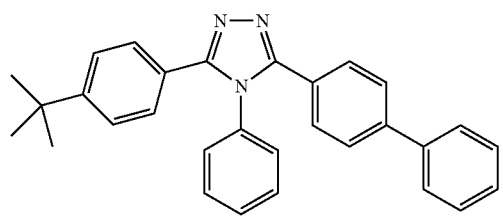
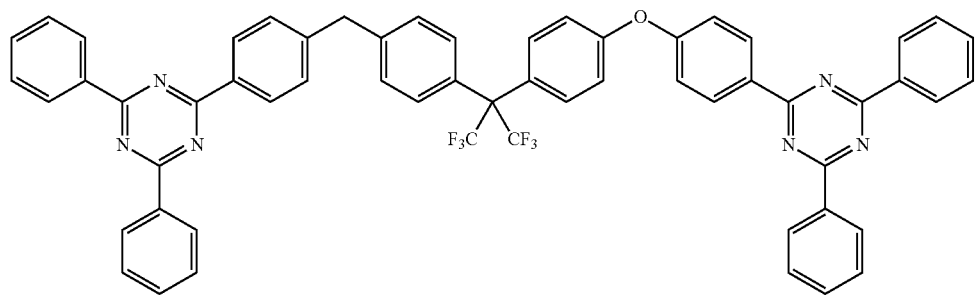
[Chem. 109]
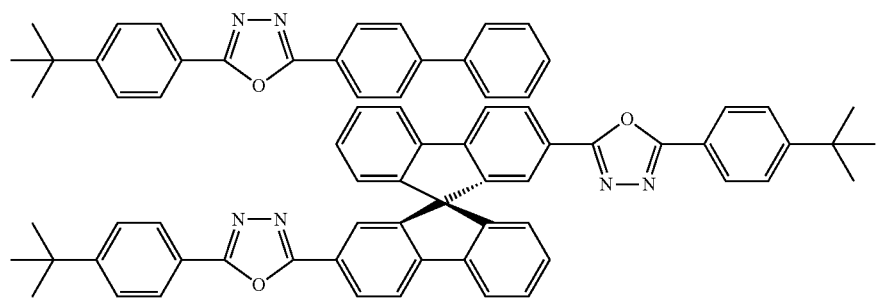

-continued
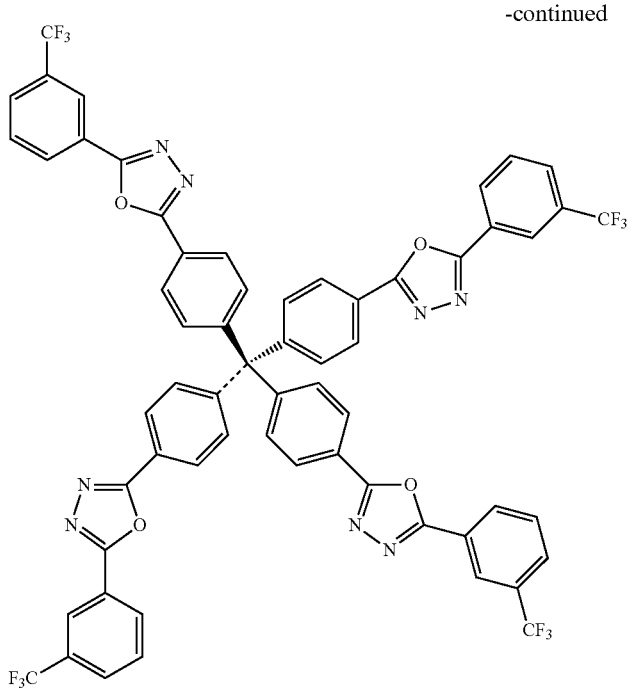
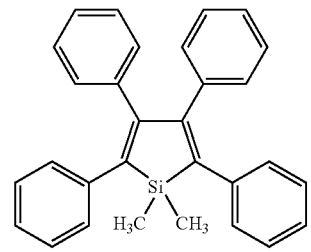
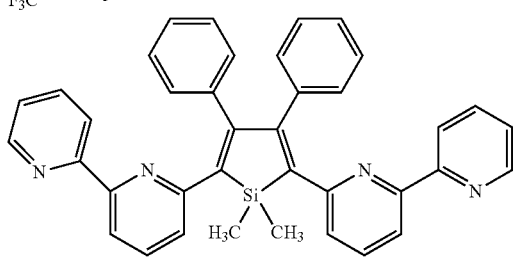
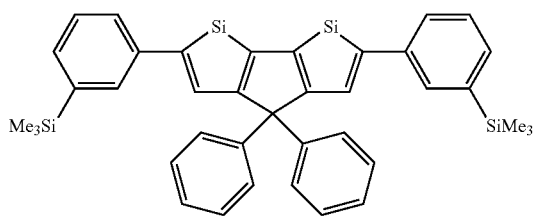
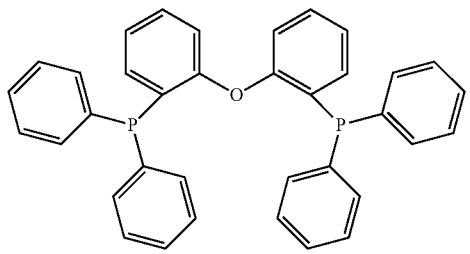
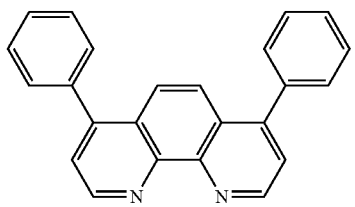
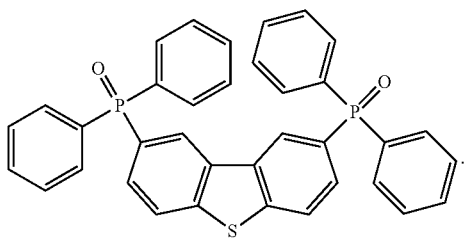

Next, preferred examples of compounds usable as an electron injection material are mentioned below.

[Chem. 110]

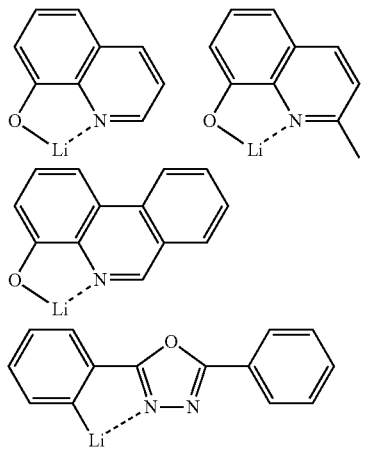

Further, preferred examples of additive compounds are mentioned below. For example, the compounds may be added as a stabilization material.

[Chem. 111]

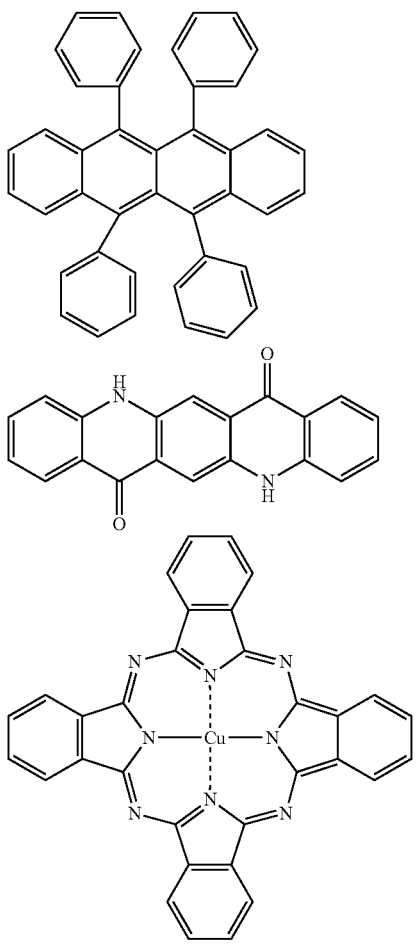

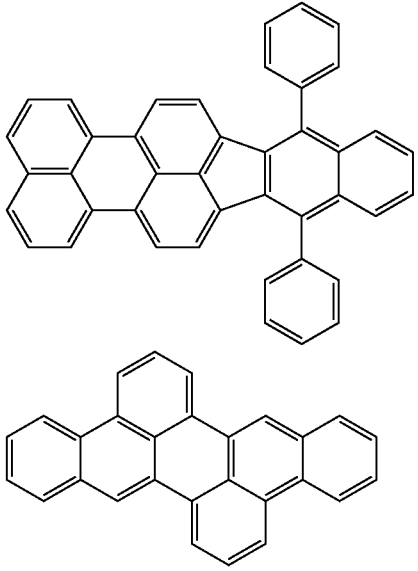

The organic electroluminescence device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

On the other hand, the phosphorescent light could not be substantially observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescence device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the compound represented by the general formula (1) to the light-emitting layer. The organic light-emitting device, such as the organic electroluminescence device, of the invention may be applied to a further wide range of purposes. For example, an organic electroluminescent display apparatus may be produced with the organic electroluminescence device of the invention, and for the details thereof, reference may be made to Seiji Tokito, Chihaya Adachi and Hideyuki Murata, "Yuki EL Display" (Organic EL Display) (Ohm-sha, Ltd.). In particular, the organic electroluminescence device of the invention may be applied to organic electroluminescent illumination and backlight which are highly demanded.

EXAMPLES

The features of the invention will be described more specifically with reference to Synthesis Examples and Examples below. The materials, processes, procedures and the like shown below may be appropriately modified unless they deviate from the substance of the invention. Accordingly, the scope of the invention is not construed as being limited to the specific examples shown below. The light emission characteristics were evaluated by using a source meter (2400 Series, produced by Keithley Instruments Inc.), a semiconductor parameter analyzer (E5273A, produced by Agilent Technologies, Inc.), an optical power meter (1930C, produced by Newport Corporation), an optical spectrometer (USB2000, produced by Ocean Optics, Inc.), a spectroradiometer (SR-3, produced by Topcon Corporation), and a streak camera (Model C4334, produced by Hamamatsu Photonics K.K.).

(Synthesis Example 1) Synthesis of Compound 4

[Chem. 112]

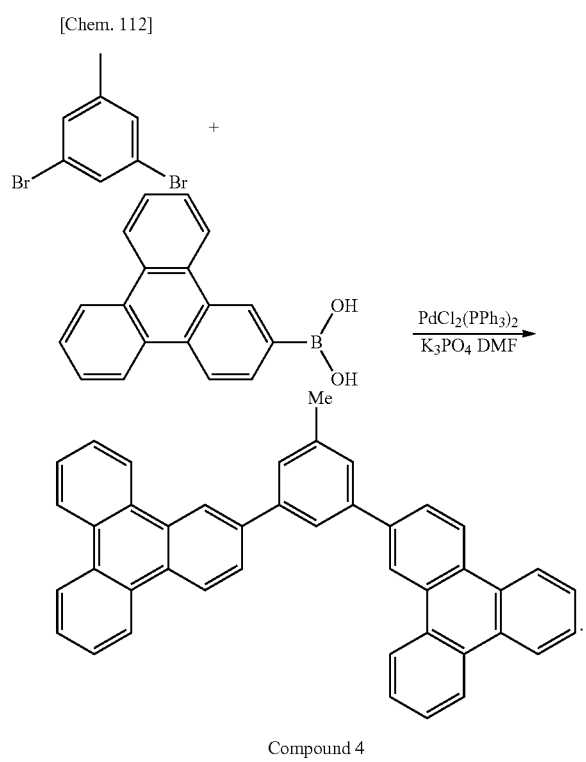

Compound 4

A commercial product, 3,5-dibromotoluene (2.50 g, 10 mmol) was dissolved in 80 ml of dimethylformamide, tripotassium phosphate (12.74 g, 60 mmol), $PdCl_2(PPh_3)_2$ (dichlorobis(triphenylphosphine) palladium(II): 0.35 g, 0.5 mmol) and triphenylenyl boronate (5.44 g, 20 mmol) were added, and stirred at room temperature for 24 hours, and then reacted at 60° C. for 24 hours. The reaction solution was left cooled, 100 ml of water was added, filtered, washed with 50 ml of acetone, and further washed with 80 ml of water and 80 ml of methanol to give the compound 4 with a yield of 4.90 g, 90%. The reaction product was purified by reduced-pressure sublimation. MS (70 eV, EI) m/z=544 (M+).

(Synthesis Example 2) Synthesis of Compound 9

[Chem. 113]

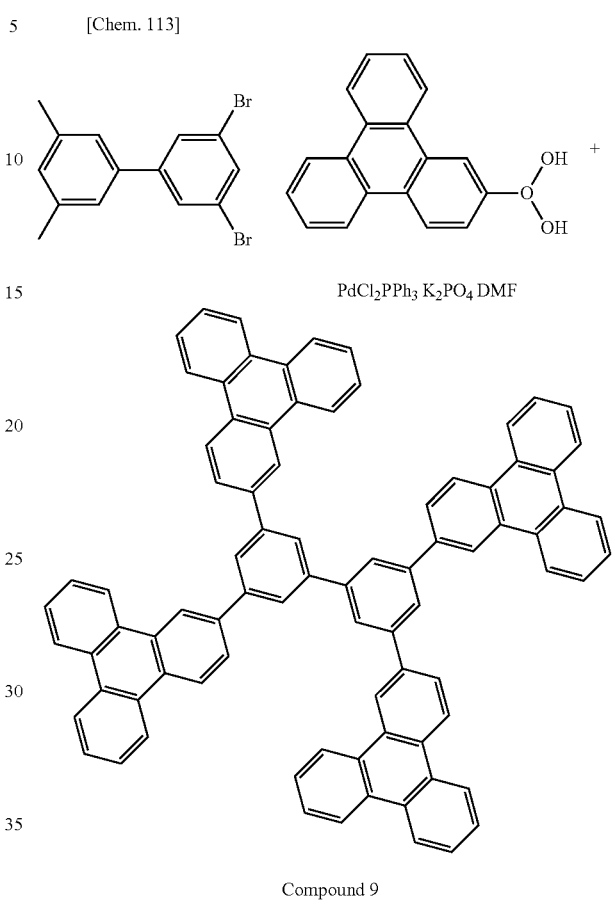

Compound 9

A commercial product, 3,3',5,5'-tetrabromobiphenyl (1.41 g, 3 mmol) was dissolved in 120 ml of dimethylformamide, tripotassium phosphate (7.64 g, 36 mmol), $PdCl_2(PPh_3)_2$ (0.11 g, 0.2 mmol) and triphenylenyl boronate (3.27 g, 12 mmol) were added, and stirred at room temperature for 24 hours, and then reacted at 80° C. for 24 hours. The reaction solution was left cooled, 240 ml of water was added, filtered, washed with 200 ml of acetone, and further washed with 100 ml of water and 200 ml of methanol to give the compound 9 with a yield, 2.45 g, 77%. The reaction product was purified by reduced-pressure sublimation.

MS (MALDI) m/z=1059 (M+1).

(Synthesis Example 3) Synthesis of Compound 10

[Chem. 114]

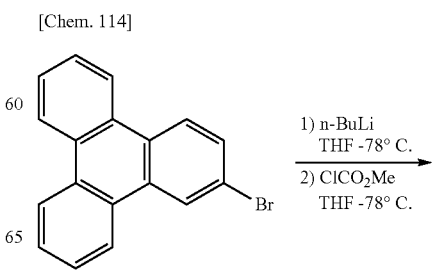

-continued

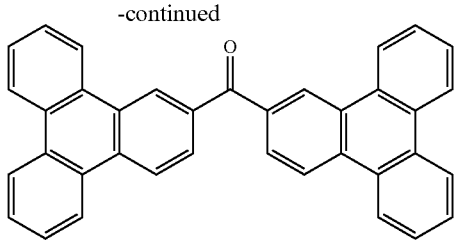

Compound 10

A commercial product, Br-triphenylene (3.07 g, 10 mmol) was dissolved in 80 ml of dewatered tetrahydrofuran in a nitrogen stream atmosphere, and kept at an internal temperature of −85° C. in an ethanol bath with liquid nitrogen. A hexane solution of n-butyl lithium (7.5 ml, 12 mmol) was gradually added to the solution, while kept at an internal temperature of −80° C. or lower. After 1 hour, a solution prepared by dissolving methyl chloroformate (1.42 g, 15 mmol) in 20 ml of dewatered tetrahydrofuran was added while kept at an internal temperature of −80° C. or lower, then kept at −85° C. for 1 hour, and thereafter stirred overnight at room temperature. 100 ml of water was gradually added to the reaction solution, filtered, and then washed with methanol and water to give the compound 10 with a yield of 1.21 g, 42%. The reaction product was purified by reduced-pressure sublimation.

MS (70 eV, EI) m/z=482 (M+).

(Example 1) Production and Evaluation of Organic Electroluminescence Device Using Compound 1

Figure 2:
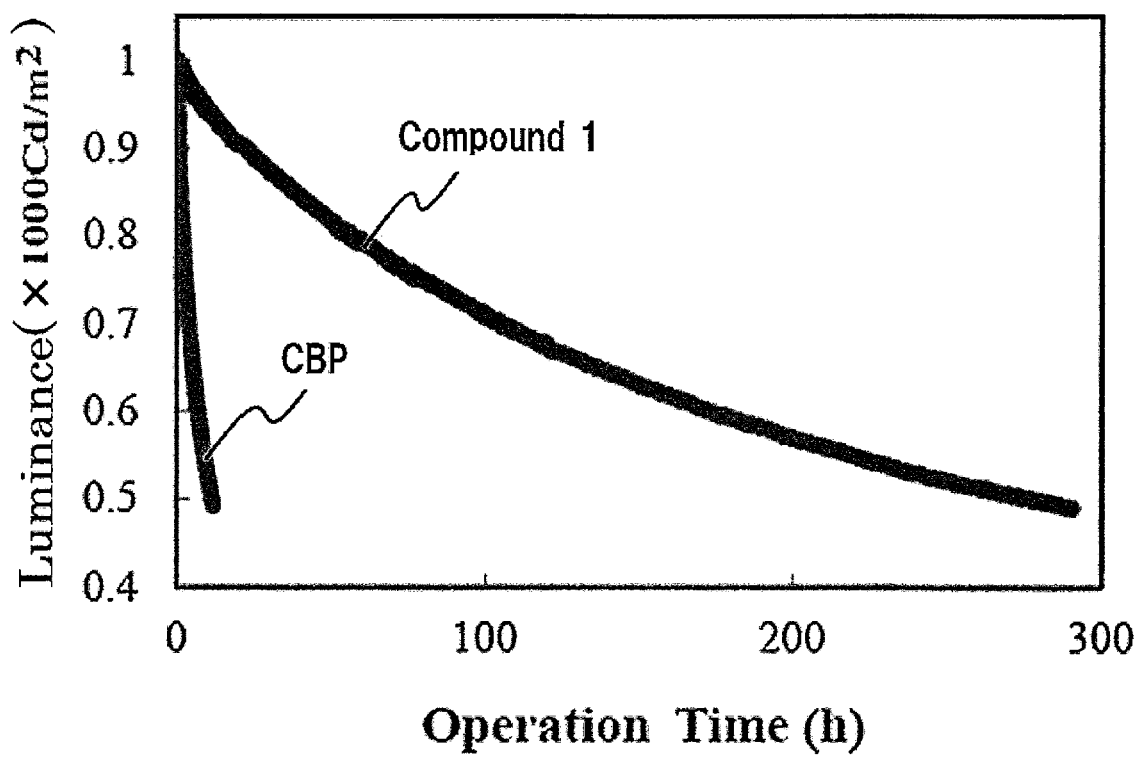
FIG. 2 This is a graph showing the lifetime characteristics of the organic electroluminescence device using the compound 1 of Example 1 and the organic electroluminescence device using the comparative compound A of Comparative Example 1.

On a glass substrate with an anode of indium-tin oxide (ITO) formed thereon to have a thickness of 100 nm, each thin film was laminated according to a vacuum evaporation method at a vacuum degree of $5.0 \times 10^{-4}$ Pa. First, HAT-CN was formed on ITO in a thickness of 10 nm, and then Tris-PCZ was formed thereon in a thickness of 30 nm. Next, a layer having a thickness of 30 nm was formed through co-evaporation with HK13 and the compound 1 from different evaporation sources, thereby forming a light-emitting layer. At this time, the concentration of HK13 was 6.0% by weight. Next, T2T was formed in a thickness of 10 nm, Bpy-TP2 was formed in a thickness of 40 nm, and further lithium fluoride (LiF) was deposited through vacuum evaporation in a thickness of 0.8 nm, and thereafter aluminum (Al) was deposited in a thickness of 100 nm, thereby forming a cathode to provide an organic electroluminescence device. The lifetime characteristic of the produced organic electroluminescence device, as measured at an initial brightness of 1000 Cd/m² and at a current density of 54.5 mA/cm², is shown in FIG. 2.

(Comparative Example 1) Production and Evaluation of Organic Electroluminescence Device Using Comparative Compound A (CBP)

An organic electroluminescence device was produced in the same manner as in Example 1 except that CBP was used to form a light-emitting layer in place of the compound 1. The lifetime characteristic of the produced organic electroluminescence device, as measured at an initial brightness of 1000 Cd/m² and at a current density of 54.5 mA/cm², is shown in FIG. 2.

The LT50 lifetime of the organic electroluminescence device using the comparative compound A was 12 days, but the LT50 lifetime of the organic electroluminescence device using the compound 1 was 277 days, that is, the latter device had a far longer lifetime.

[Chem. 115]

Comparative Compound A

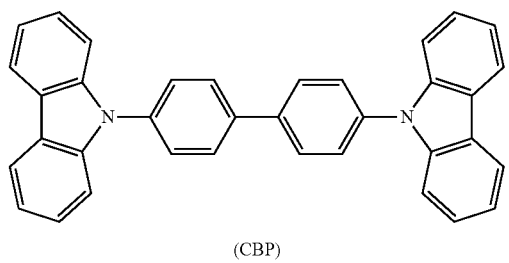

(CBP)

(Example 2) Production and Evaluation of Organic Electroluminescence Device Using Composite Host Material of Compound 10 and CBP An organic electroluminescence device was produced in the same manner as in Example 1 except that a light-emitting layer having a thickness of 30 nm was formed through co-deposition with HK13, the compound 10 and CBP from different evaporation sources, and the concentration of HK13 in the light-emitting layer was 1% by weight.

Figure 3:
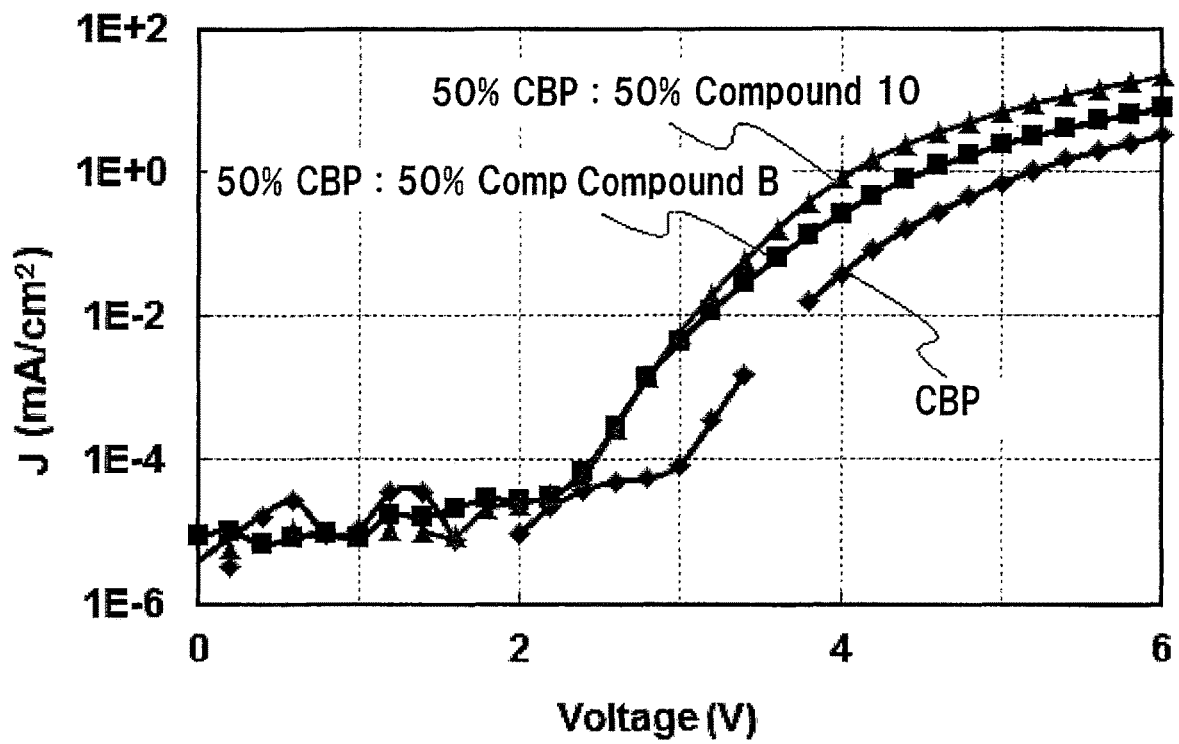
FIG. 3 This is a graph showing the voltage-current density characteristics of the organic electroluminescence device using the compound 10 and CBP of Example 2, the organic electroluminescence device using CBP of Comparative Example 2, and the organic electroluminescence device using the comparative compound B and CBP of Comparative Example 3.
Figure 4:
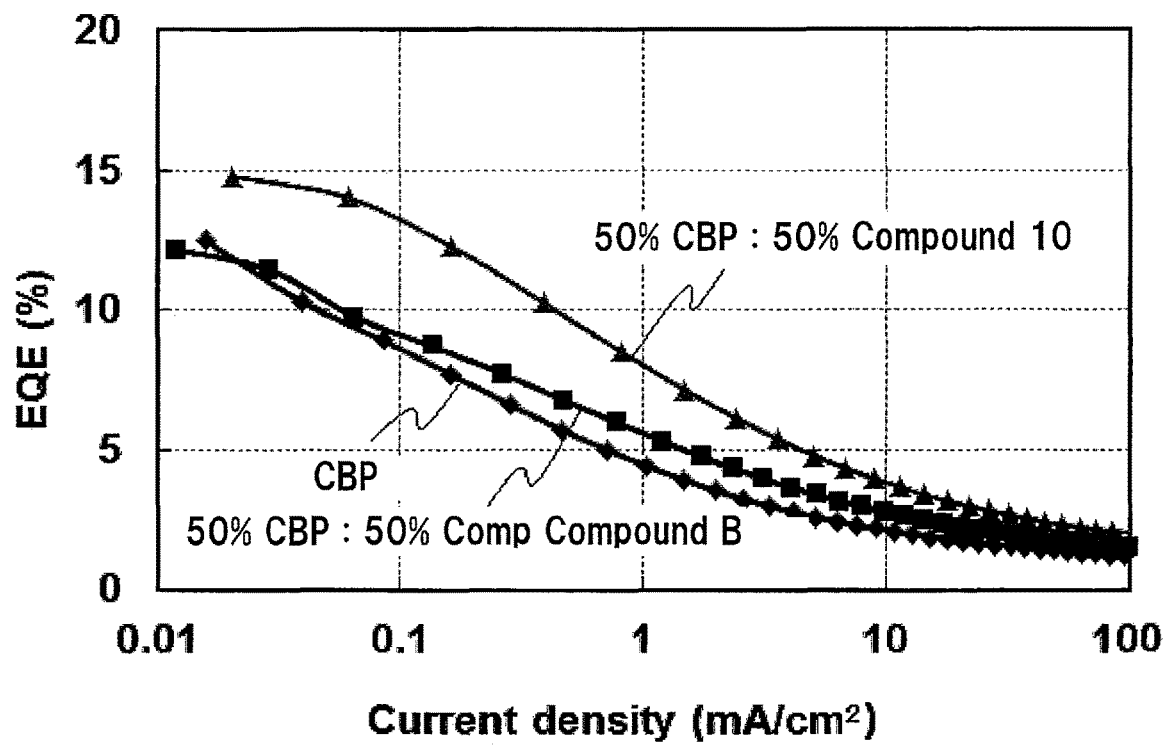
FIG. 4 This is a graph showing the current density-external quantum efficiency characteristics of the organic electroluminescence device using the compound 10 and CBP of Example 2, the organic electroluminescence device using CBP of Comparative Example 2, and the organic electroluminescence device using the comparative compound B and CBP of Comparative Example 3.
Figure 5:
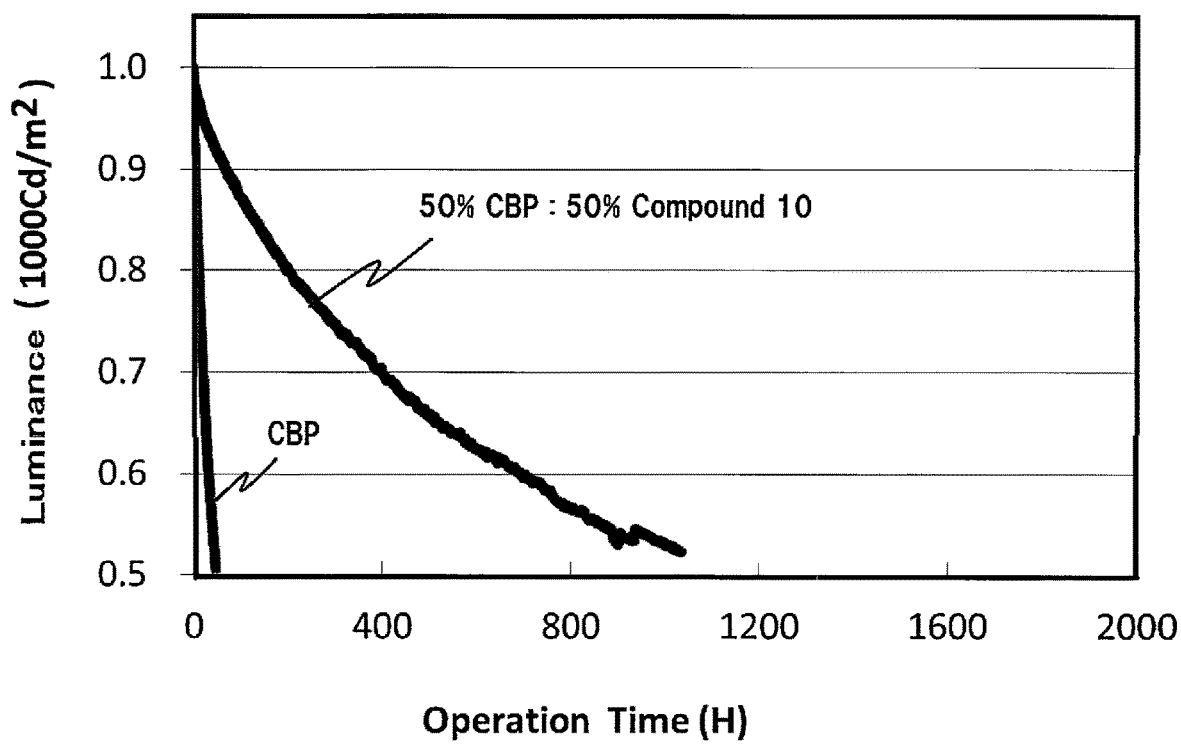
FIG. 5 This is a graph showing the lifetime characteristics of the organic electroluminescence device using the compound 10 and CBP of Example 2 and the organic electroluminescence device using CBP of Comparative Example 2.

The voltage-current density characteristic of the produced organic electroluminescent device is shown in FIG. 3, the current density-external quantum efficiency characteristic thereof is in FIG. 4, the lifetime characteristic thereof is in FIG. 5, and the characteristic values thereof measured at 1000 Cd/m² are shown in Table 22.

(Comparative Example 2) Production and Evaluation of Organic Electroluminescence Device Using Comparative Compound A (CBP)

An organic electroluminescence device was produced in the same manner as in Example 1 except that CBP was used in place of the compound 1 to form a light-emitting layer and the concentration of HK13 in the light-emitting layer was 1% by weight.

The voltage-current density characteristic of the produced organic electroluminescent device is shown in FIG. 3, the current density-external quantum efficiency characteristic thereof is in FIG. 4, the lifetime characteristic thereof is in FIG. 5, and the characteristic values thereof measured at 1000 Cd/m² are shown in Table 22.

(Comparative Example 3) Production and Evaluation of Organic Electroluminescence Device Using Composite Host Material of Comparative Compound B and CBP An organic electroluminescence device was produced in the same manner as in Example 1 except that a light-emitting layer having a thickness of 30 nm was formed through co-deposition with HK13, the comparative compound B and CBP from different evaporation sources, and the concentration of HK13 in the light-emitting layer was 1% by weight.

The voltage-current density characteristic of the produced organic electroluminescent device is shown in FIG. 3, the current density-external quantum efficiency characteristic thereof is in FIG. 4, and the characteristic values thereof measured at 1000 Cd/m² are shown in Table 22. The lifetime characteristic of the device was measured in the same manner as in Example 2, and LT50 thereof was 585 hours.

[Chem. 116]

Comparative Compound B

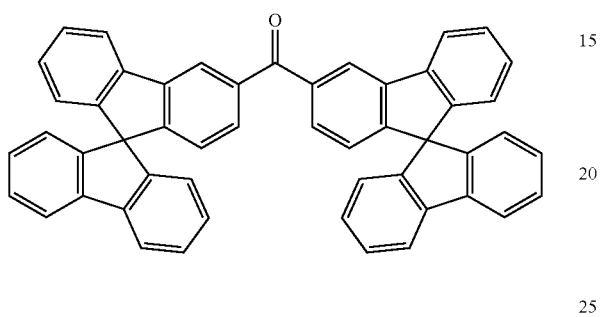

(Example 3) Production and Evaluation of Organic Electroluminescence Device Using Different Light-Emitting Material and Composite Host Material of Compound 10 and CBP An organic electroluminescence device was produced in the same manner as in Example 2 except that YH016 was used in place of HK13.

The characteristic values of the produced organic electroluminescence device, as measured at 1000 Cd/m², are shown in Table 22.

TABLE 22

| | Host Material | Light-Emitting Material | External Quantum Efficiency (%) | Current Density (mA/cm²) | Drive Voltage (V) | Current Efficiency (Cd/A) | Power Efficiency (lm/W) | CIE (x, y) | Maximum Emission Wavelength (nm) | LT50 Lifetime (H) | ΔV |
|---|---|---|---|---|---|---|---|---|---|---|---|
| Example 2 | 50% CBP:50% compound 10 | 1% HK13 | 3.4 | 15.2 | 5.6 | 6.7 | 3.8 | 0.55, 0.44 | 598 | 1050 | — |
| Comparative Example 2 | CBP | 1% HK13 | 1.6 | 29.6 | 8.5 | 3.3 | 1.3 | 0.53, 0.44 | 593 | 48 | 1.4 |
| Comparative Example 3 | 50% CBP:50% comparative compound B | 1% HK13 | 2.2 | 24.1 | 7.2 | 4.1 | 1.8 | 0.55, 0.44 | 599 | 585 | 0.84 |
| Example 3 | 50% CBP:50% compound 10 | 1% YH016 | 4.5 | 14.3 | 5.3 | 7.0 | 4.2 | 0.58, 0.42 | 616 | 1550 | — |

The organic electroluminescence device using a composite host material of the compound 10 and CBP has a remarkably longer LT50 lifetime, as compared with the organic electroluminescence device using the comparative compound A (CBP) and the organic electroluminescence device using a composite host material of the comparative compound B and CBP, and can operate at a low drive voltage, and the current efficiency, the power efficiency and the external quantum yield thereof are all high values.

[Chem. 117]
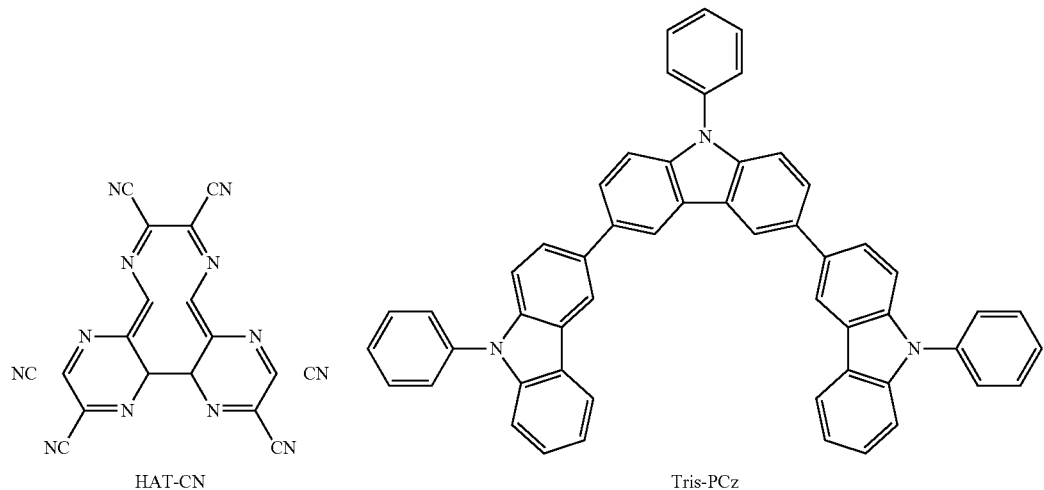
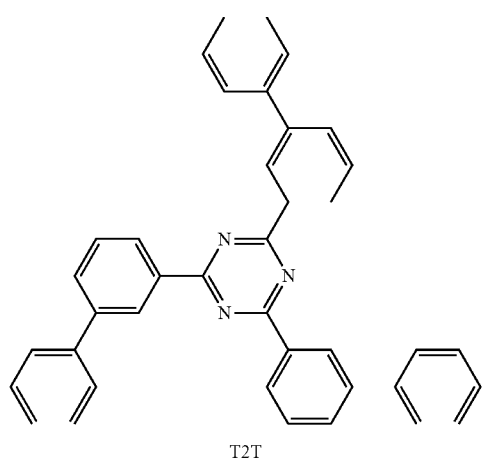
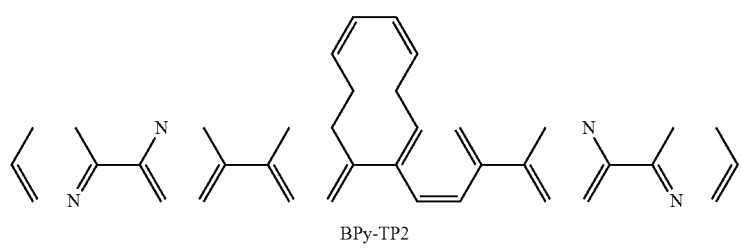
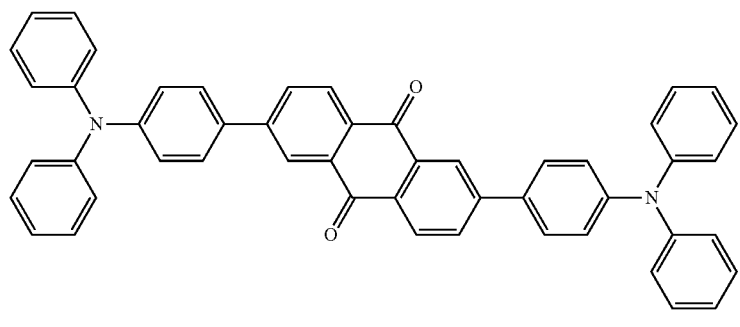

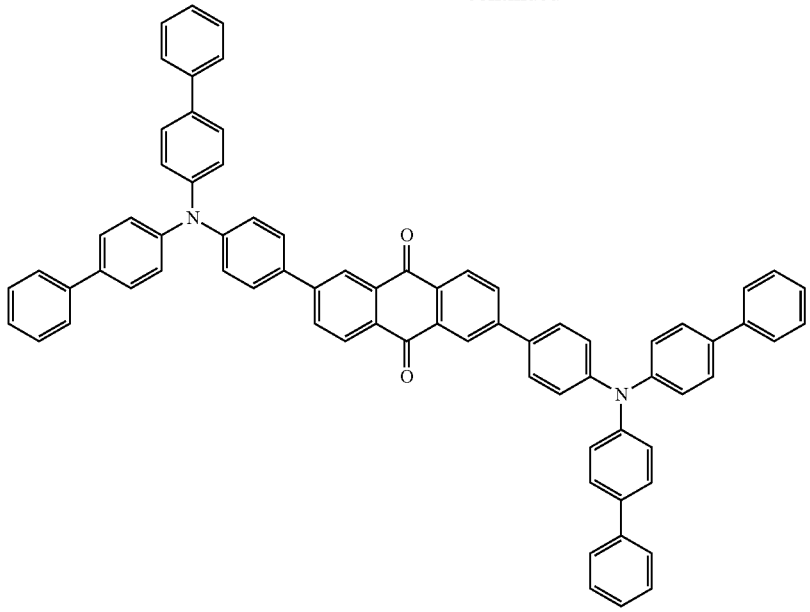

YH016

INDUSTRIAL APPLICABILITY

The compound of the invention is useful as a host material for delayed fluorescent materials. Accordingly, the compound of the invention may be effectively used as a host material for delayed fluorescent materials for organic light-emitting devices such as organic electroluminescence devices, etc. By using the host material for delayed fluorescent materials of the present invention, it is possible to provide an organic light-emitting device having a high efficiency, capable of operating at a low drive voltage and having a long lifetime. Thus, the invention has high industrial applicability.

REFERENCE SIGNS LIST

1 Substrate
2 Anode
3 Hole Injection Layer
4 Hole Transport Layer
5 Light-Emitting Layer
6 Electron Transport Layer
7 Cathode

The invention claimed is:
1. An organic light-emitting device comprising a layer that contains a delayed fluorescent material and a host material represented by the following general formula (1):

(Tr)$_n$-Z            General Formula (1)

wherein:
Tr represents a substituted or unsubstituted triphenylenyl group, and plural Tr's existing in the general formula (1) may be the same as or different from each other; Z represents a carbonyl group or a substituted or unsubstituted, n-valent aromatic hydrocarbon group; n represents an integer of 2 to 6, but when Z is a carbonyl group, then n is 2; and the substituted n-valent aromatic hydrocarbon group is a n-valent aromatic hydrocarbon group substituted by a hydroxy group, a halogen atom, a cyano group, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an acyl group having 2 to 20 carbon atoms, an aryl group having 6 to 40 carbon atoms, an alkenyl group having 2 to 10 carbon atoms, an alkynyl group having 2 to 10 carbon atoms, an alkoxycarbonyl group having 2 to 10 carbon atoms, an alkylsulfonyl group having 1 to 10 carbon atoms, a haloalkyl group having 1 to 10 carbon atoms, an amide group, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, a trialkylsilylalkynyl group having 5 to 20 carbon atoms, a nitro group, or a substituent represented by the following general formula (2):

Tr$^4$-CO—            General Formula (2)

wherein Tr$^4$ represents a substituted or unsubstituted triphenylenyl group,
provided that when Z is a substituted or unsubstituted, n-valent aromatic hydrocarbon group, then at least one of the following conditions is satisfied:
<1> at least one Tr is a substituted triphenylenyl group, and
<2> Z is the substituted aromatic hydrocarbon group, and provided that at least one of the following conditions is satisfied
<A> Z is an n-valent aromatic hydrocarbon group substituted with a substituted or unsubstituted alkyl group or a substituted or unsubstituted aryl group,
<B> Z is a carbonyl group,
<C> at least one Tr has a substituent represented by the following general formula (2):

Tr$^4$-CO—            General Formula (2)

wherein Tr$^4$ represents a substituted or unsubstituted triphenylenyl group, and <D> at least one Tr is a triphenylenyl group substituted with a substituted or unsubstituted alkyl group or a substituted or unsubstituted aryl group.

2. The organic light-emitting device according to claim 1, wherein Z is a substituted or unsubstituted, n-valent aromatic hydrocarbon group.

3. The organic light-emitting device according to claim 2, wherein Z is an n-valent benzene residue.

4. The organic light-emitting device according to claim 3, wherein Tr bonds to the 1-position and the 3-position of the benzene residue.

5. The organic light-emitting device according to claim 2, wherein Z is an n-valent biphenyl residue.

6. The organic light-emitting device according to claim 2, wherein Z is an n-valent aromatic hydrocarbon group substituted with a substituted or unsubstituted alkyl group or a substituted or unsubstituted aryl group.

7. The organic light-emitting device according to claim 1, wherein Z is a carbonyl group.

8. The organic light-emitting device according to claim 7, wherein at least one Tr has a substituent represented by the following general formula (2):

$Tr^4\text{-CO}-$  General Formula (2)

wherein $Tr^4$ represents a substituted or unsubstituted triphenylenyl group.

9. The organic light-emitting device according to claim 8, wherein two Tr's have, in total, 1 to 5 substituents each represented by the general formula (2).

10. The organic light-emitting device according to claim 7, which contains a partial structure with a carbonyl group bonding to the 2-position, the 3-position, the 6-position, the 7-position, the 10-position or the 11-position of the triphenylene ring inside the molecule.

11. The organic light-emitting device according to claim 10, wherein all the carbonyl groups bonding to the triphenylene ring existing inside the molecule bond to the 2-position, the 3-position, the 6-position, the 7-position, the 10-position or the 11-position of the triphenylene ring.

12. The organic light-emitting device according to claim 1, wherein at least one Tr in the general formula (1) is a triphenylenyl group substituted with a substituted or unsubstituted alkyl group or a substituted or unsubstituted aryl group.

13. The organic light-emitting device according to claim 1, which is an organic electroluminescence device.

14. A compound represented by the following general formula (3):

$Tr^1\text{-CO-}Tr^2$  General Formula (3)

wherein $Tr^1$ and $Tr^2$ each independently represent a substituted or unsubstituted triphenylenyl group, and $Tr^1$ and $Tr^2$ may be the same as or different from each other.

15. A compound represented by the following general formula (4):

$(Tr^3)_{n1}\text{-}Z^1$  General Formula (4)

wherein $Tr^3$ represents a substituted or unsubstituted triphenylenyl group, and plural $Tr^3$'s existing in the general formula (4) may be the same as or different from each other; $Z^1$ represents a substituted or unsubstituted n-valent aromatic hydrocarbon group; n1 represents an integer of 2 to 6; at least one of $Tr^3$ and $Z^1$ is substituted with a substituted or unsubstituted alkyl group or a substituted or unsubstituted aryl group; when $Tr^3$ is unsubstituted, then $Z^1$ is a benzene ring residue substituted with a phenyl group or a methyl group and bonds to $Tr^3$ at the 1-position and the 3-position, or is a biphenyl residue substituted with a phenyl group, provided that when $Tr^3$ is a substituted triphenylenyl group, the triphenylenyl is substituted at at least one of 6-, 7-, 10- and 11-positions by a hydroxy group, a halogen atom, a cyano group, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an acyl group having 2 to 20 carbon atoms, a heteroaryl group having 3 to 40 carbon atoms, an alkenyl group having 2 to 10 carbon atoms, an alkynyl group having 2 to 10 carbon atoms, an alkoxycarbonyl group having 2 to 10 carbon atoms, an alkylsulfonyl group having 1 to 10 carbon atoms, a haloalkyl group having 1 to 10 carbon atoms, an amide group, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, trialkylsilylalkynyl group having 5 to 20 carbon atoms, a nitro group, or a substituent represented by the following general formula (2):

$Tr^4\text{-CO}-$  General Formula (2)

wherein $Tr^4$ represents a substituted or unsubstituted triphenylenyl group.

* * * * *